US012139763B2

(12) United States Patent
Faruki et al.

(10) Patent No.: US 12,139,763 B2
(45) Date of Patent: *Nov. 12, 2024

(54) METHODS FOR SUBTYPING OF LUNG ADENOCARCINOMA

(71) Applicants: GeneCentric Therapeutics, Inc., Durham, NC (US); The University of North Carolina at Chapel Hill, Chapel Hill, NC (US)

(72) Inventors: Hawazin Faruki, Durham, NC (US); Myla Lai-Goldman, Durham, NC (US); Greg Mayhew, Durham, NC (US); Jonathan Serody, Duham, NC (US); Charles Perou, Carrboro, NC (US); David Neil Hayes, Chapel Hill, NC (US)

(73) Assignees: GeneCentric Therapeutics, Inc., Durham, NC (US); University of North Carolina at Chapel Hill, Chapel Hill, NC (US)

( * ) Notice: Subject to any disclaimer, the term of this patent is extended or adjusted under 35 U.S.C. 154(b) by 68 days.

This patent is subject to a terminal disclaimer.

(21) Appl. No.: 17/156,024

(22) Filed: Jan. 22, 2021

(65) Prior Publication Data

US 2021/0222254 A1 Jul. 22, 2021

Related U.S. Application Data

(63) Continuation of application No. 16/302,167, filed as application No. PCT/US2017/033110 on May 17, 2017, now Pat. No. 10,934,595.

(60) Provisional application No. 62/337,591, filed on May 17, 2016, provisional application No. 62/337,645, filed on May 17, 2016, provisional application No. 62/396,587, filed on Sep. 19, 2016, provisional application No. 62/420,836, filed on Nov. 11, 2016, provisional application No. 62/425,717, filed on Nov. 23, 2016.

(51) Int. Cl.
*C12Q 1/6886* (2018.01)

(52) U.S. Cl.
CPC ..... *C12Q 1/6886* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 4,683,202 A | 7/1987 | Mullis | |
| 4,843,155 A | 6/1989 | Chomczynski | |
| 5,384,261 A | 1/1995 | Winkler et al. | |
| 5,445,934 A | 8/1995 | Fodor et al. | |
| 5,677,195 A | 10/1997 | Winkler et al. | |
| 5,708,153 A | 1/1998 | Dower et al. | |
| 5,744,305 A | 4/1998 | Fodor et al. | |
| 5,770,358 A | 6/1998 | Dower et al. | |
| 5,770,722 A | 6/1998 | Lockhart et al. | |
| 5,789,162 A | 8/1998 | Dower et al. | |
| 5,800,992 A | 9/1998 | Fodor et al. | |
| 5,854,033 A | 12/1998 | Lizardi | |
| 5,856,174 A | 1/1999 | Lipshutz et al. | |
| 5,874,219 A | 2/1999 | Rava et al. | |
| 5,922,591 A | 7/1999 | Anderson et al. | |
| 6,020,135 A | 2/2000 | Levine et al. | |
| 6,033,860 A | 3/2000 | Lockhart et al. | |
| 6,040,138 A | 3/2000 | Lockhart et al. | |
| 6,040,193 A | 3/2000 | Winkler et al. | |
| 6,344,316 B1 | 2/2002 | Lockhart et al. | |
| 6,524,581 B1 | 2/2003 | Adamis | |
| 7,473,767 B2 | 1/2009 | Dimitrov | |
| 8,492,094 B2 | 7/2013 | Dimitrov et al. | |
| 10,829,819 B2 | 11/2020 | Faruki et al. | |
| 10,934,595 B2 | 3/2021 | Faruki et al. | |
| 11,041,214 B2 | 6/2021 | Faruki et al. | |
| 11,739,386 B2 * | 8/2023 | Lai-Goldman | C12Q 1/6886 435/6.14 |
| 2003/0092009 A1 | 5/2003 | Palm | |
| 2004/0009489 A1 | 1/2004 | Golub et al. | |
| 2006/0024692 A1 | 2/2006 | Nakamura et al. | |
| 2010/0233695 A1 | 9/2010 | Hayes et al. | |
| 2015/0057335 A1 | 2/2015 | Kohno et al. | |
| 2015/0140017 A1 | 5/2015 | Dhodapkar et al. | |
| 2015/0346208 A1 | 12/2015 | Couto et al. | |

(Continued)

FOREIGN PATENT DOCUMENTS

| | | |
|---|---|---|
| CN | 101509035 A | 8/2009 |
| JP | 2007006792 A | 1/2007 |

(Continued)

OTHER PUBLICATIONS

Shedden et al.Nature. 2008. 14(8): 822-827 and Supplemental Information p. 1-102 (Year: 2008).*

(Continued)

*Primary Examiner* — Carla J Myers
(74) *Attorney, Agent, or Firm* — COOLEY LLP

(57) ABSTRACT

Methods and compositions are provided for determining a subtype of lung adenocarcinoma (AD) of an individual by detecting the expression level of at least one classifier biomarker selected from a group of gene signatures for lung adenocarcinoma. Also provided herein are methods and compositions for determining the response of an individual with an adenocarcinoma subtype to a therapy such as immunotherapy.

5 Claims, 34 Drawing Sheets

Specification includes a Sequence Listing.

(56) References Cited

U.S. PATENT DOCUMENTS

| | | | |
|---|---|---|---|
| 2016/0109453 | A1 | 4/2016 | Weinhausel |
| 2017/0114416 | A1 | 4/2017 | Faruki et al. |
| 2019/0203296 | A1 | 7/2019 | Faruki et al. |
| 2019/0338365 | A1 | 11/2019 | Faruki et al. |
| 2019/0338366 | A1 | 11/2019 | Faruki et al. |
| 2021/0147948 | A1 | 5/2021 | Faruki et al. |
| 2021/0340631 | A1 | 11/2021 | Faruki et al. |
| 2022/0002820 | A1 | 1/2022 | Faruki et al. |
| 2022/0243283 | A1 | 8/2022 | Faruki et al. |

FOREIGN PATENT DOCUMENTS

| | | | |
|---|---|---|---|
| JP | 2010540672 | A | 12/2010 |
| JP | 2015521480 | A | 7/2015 |
| JP | 2017520520 | A | 7/2017 |
| JP | 2017536099 | A | 12/2017 |
| JP | 2018512160 | A | 5/2018 |
| WO | WO 2003/029273 | A2 | 4/2003 |
| WO | WO 2004/031413 | A2 | 4/2004 |
| WO | WO 2008/151110 | A2 | 12/2008 |
| WO | WO-2009146545 | A1 | 12/2009 |
| WO | WO 2015/184461 | | 6/2015 |
| WO | WO-2015173267 | A1 | 11/2015 |
| WO | WO-2016061142 | A1 | 4/2016 |
| WO | WO 2016/168446 | A1 | 10/2016 |
| WO | WO 2017/201164 | A1 | 11/2017 |
| WO | WO 2017/201165 | A1 | 11/2017 |

OTHER PUBLICATIONS

Sanchez-Palencia International J Cancer. 2010. 129:355-364 (Year: 2010).*

Anonymous, "New immunotherapy for lung cancer," Immunotherapy News Pick Up, [Online], Mar. 13, 2016, [Date of Retrieval: Apr. 14, 2021], https://web.archive.org/web/20160313081253/https://www.gan-info.jp/dendritic/newspickup/article02/, 21 pages including English translation.

"Rare lung cancers," Breathe (Sheffield, England), 11(4):323-330 (2015).

ALIMTA® (Pemetrexed disodium) Eli Lilly & Co., Indianapolis, IN prescribing information. http://pi.lilly.com/us/alimta-pi.pdf, 31 pages (2018).

American Cancer Society. Cancer Facts and Figures, retrieved Sep. 25, 2018 from https://www.cancer.org/research/cancer-facts-statistics/all-cancer-facts-figures/cancer-facts-figures-2014.html, 6 pages.

AVASTIN® (Bevacizumab) Genentech Inc, San Francisco, CA prescribing information (2018). Retrieved online Oct. 10, 2018 at https://www.gene.com/download/pdf/avastin_prescribing.pdf, 41 pages.

Barany, "Cloning, overexpression and nucleotide sequence of a thermostable DNA ligase-encoding gene," Proc. Natl. Acad. Sci. USA 88:189-193 (1991).

Bhattacharjee et al., Classification of Human Lung Carcinomas by mRNA Expression Profiling Reveals Distinct Adenocarcinoma Subclasses, PNAS 98(24):13790-13795 (2001).

Bibikova et al., "Quantitative gene expression profiling in formalin-fixed, paraffin-embedded tissues using universal bead arrays," Am J. Pathol 165:1799-1807 (2004).

Bild AH, Yao G, Chang JT, et al. Oncogenic pathway signatures in human cancers as a guide to targeted therapies. Nature 439(7074): 353-357 (2006).

Bindea et al., "Spatiotemporal dynamics of intratumoral immune cells reveal the immune landscape in human cancer," Immunity 39(4); 782-795 (2013).

Bolstad et al., "A comparison of normalization methods for high density oligonucleotide array data based on variance and bias," Bioinformatics Bioinformatics 19(2):185-193 (2003).

Brenner et al., "Gene expression analysis by massively parallel signature sequencing (MPSS) on microbead arrays," Nat. Biotech. 18:630-34, 2000.

Broomhead DS, Jones R, King GP., "Comment on Singular-value decomposition and embedding dimension," Phys Rev A Gen Phys. Jun. 15;37(12):5004-5005 (1988).

Calabrese et al., "Serpin B4 Isoform Overexpression is Associated with Aberrant Epithelial Proliferation and Lung Cancer in Idiopathic Pulmonary Fibrosis," Pathology 44(3):192-198 (2012).

Cancer Genome Atlas Research Network. "Comprehensive genomic characterization of squamous cell lung cancers." Nature 489.7417 (2012): 519-525.

Cao et al., "Role of LKBI-CRTCI on glycosylated COX-2 and response to COX-2 inhibition in lung cancer," JNatl Cancer Inst. 107(1):1-11 (2015).

Charych et al., Intra-tumoral immune 1 cell mobilization and anti-tumor activity after treatment with the engineered cytokine NKTR-214 in multiple preclinical mouse tumor models, European Journal of Cancer vol. 69, Jan. 1, 2016, Poster (Board P132), No. 306, 1 page.

Clark et al., "Suppression of nonspecific binding of avidin-biotin complex (ABC) to proteins electroblotted to nitrocellulose paper," J Histochem Cytochem 34:1509-1512 (1986).

Collisson E., et al., "Comprehensive Molecular Profiling of Lung Adenocarcinoma," Nature 511(7511):543-550 (2014).

Cronin et al., "Measurement of gene expression in archival paraffin-embedded tissues: development and performance of a 92-gene reverse transcriptase-polymerase chain reaction assay," Am. J Pathol. 164(1):35-42 (2004).

Dabney AR ClaNC: Point-and-click software for classifying microarrays to nearest centroids. Bioinformatics. 2006;22: 122-123.

Dabney, "Classification of microarrays to nearest centroids," Bioinformatics 21(22):4148-4154 (2005).

Ettinger et al., "Non-small cell lung cancer, version 2.2013." J Natl Compr Canc Netw. Jun. 1, 2013;11(6):645-53; quiz 653.

Extended European Search Report issued by the European Patent Office for Application No. 16780736.1, dated Nov. 9, 2018, 13 pages.

Extended European Search Report issued by the European Patent Office for Application No. 17800090.7, dated Jan. 27, 2020, 6pages.

Extended European Search Report issued by the European Patent Office for Application No. 17800091.5, dated Jan. 28, 2020, 7 pages.

Fan et al., "A Versatile Assay for High-Throughput Gene Expression Profiling on Universal Array Matrices," Genome Res. 14:878-885 (2004).

Faruki et al., "Lung Adenocarcinoma and Squamous Cell Carcinoma Gene Expression Subtypes Demonstrate Significant Differences in Tumor Immune Landscape," Journal of Thoracic Oncology 12(6):943-953 (2017).

Faruki H, et al., "Validation of the Lung Subtyping Panel in Multiple Fresh-Frozen and Formalin-Fixed, Paraffin-Embedded Lung Tumor Gene Expression Data Sets," Archives Path & Lab Med. Oct. 2015.

Fennell et al., "Association between Gene Expression Profile and Clinical Outcome of Pemetrexed-Based Treatment in Patients with Advanced Non-Small Cell Lung Cancer: Exploratory Results from a Phase II study," PLOS one 2014; Sep. 14 9(9): el07455, 8 pages.

Filosso et al., "Adenosquamous lung carcinomas: A histologic subtype with poor prognosis," Lung Cancer, 74(1):25-29 (2011).

Fishel and Kaufman et al., "Meta-analysis of gene expression data: a predictor-based approach," Bioinformatics 23(13): 1599-1606 (2007).

Forero et al., "Expression of the MHC class II pathway in triple negative breast cancer tumor cells is associated with a good prognosis and infiltrating lymphocytes," Cancer Immunol Res 4(5):390-399 2016.

Foundation Medicine Solid Tumor Mutation Panel accessed Oct. 2014, 2 pages.

Fox et al., "Formaldehyde Fixation," J Histochem Cytochem 33:845-853 (1985).

Friedman et al., "Regularization Paths for Generalized Linear Models via Coordinate Descent," Journal of statistical software 33(1): 1-22 (2010).

Geiss et al., "Direct multiplexed measurement of gene expression with color-coded probe pairs," Nat. Biotechnol. 26:317-325 (2008).

(56) References Cited

OTHER PUBLICATIONS

Grilley-Olson et al. Validation of interobserver agreement in lung cancer assessment: hematoxylin-eosin diagnostic reproducibility for non-small cell lung cancer. Arch Pathol Lab Med 2013; 137: 32-40.
Guatelli et al., "Isothermal, in vitro amplification of nucleic acids by a multienzyme reaction modeled after retroviral replication," Proc Natl Acad Sci U S A. 87(5):1874-1878 (1990).
Han et al., "RNA sequencing identifies novel markers of non-small cell lung cancer," Lung Cancer 84:229-23 (2014).
Hast et al., Cancer-derived mutations in KEAPI impair NRF2 degradation but not ubiquitination. Cancer Res 2014; 74(3): 808-817.
Hayes DN, Monti S, Parmigiani G, et al. Gene expression profiling reveals reproducible human lung adenocarcinoma subtypes in multiple independent patient cohorts. J Clin Oncol 24(31): 5079-5090 (2006).
Hou et al., "Gene Expression-Based Classification of Non-Small Cell Lung Carcinomas and Survival Prediction," PLoS ONE. 2010. 6(4): e10312, p. 1-12 (2010).
Hubbell, "Robust estimators for expression analysis," Bioinformatics (2002) 18(12):1585-1592.
International Search Report and Written Opinion issued by the International Searching Authority for Application No. PCT/US2015/033611, dated Sep. 14, 2015, 10 pages.
International Search Report and Written Opinion issued by the International Searching Authority for Application No. PCT/US2016/027503, dated Jul. 14, 2016, 10 pages.
International Search Report and Written Opinion issued by the International Searching Authority for Application No. PCT/US2017/033107, dated Oct. 23, 2017, 21 pages.
International Search Report and Written Opinion issued by the International Searching Authority for Application No. PCT/US2017/033110, dated Oct. 20, 2017, 21 pages.
Irizarry et al., "Exploration, normalization, and summaries of high-density oligonucleotide array probe level data," Biostatistics April 4(2): 249-64 (2003).
Koyama et al., STKI1/LKBI deficiency promotes neutrophil recruitment and proinflammatory cytokine production to suppress T-cell activity in the lung tumor microenvironment. Cancer Res 76(5): 999-1008 (2016).
Kratz JR, et al., "A practical molecular assay to predict survival in resected non-squamous, non-small-cell lung cancer: development and international validation studies," Lancet 379(9818):823-832 (2012).
Kuang et al., "The prognostic value of platelet endothelial cell adhesion molecule-I in non-small-cell lung cancer patients," Med. Oneal. 30:536 (2013).
Kwoh et al., "Transcription-based amplification system and detection of amplified human immunodeficiency virus type 1 with a bead-based sandwich hybridization format (TI RNA polymerase/in vitro nucleic acid amplification)," Proc. Natl. Acad. Sci. USA, 86:1173-1177 (1989).
Landegren et al., "A ligase-mediated gene detection technique," Science, 241(4869):1077-1080 (1988), retrieved from http://science.sciencemag.org/ on Oct. 29, 2018.
Lee ES, et al., "Prediction of recurrence-free survival in postoperative non-small cell lung cancer patients by using an integrated model of clinical information and gene expression." Clinical Cancer Research 14(22):7397-7404 (2008).
Lee et al., "Multiregion gene expression profiling reveals heterogeneity in molecular subtypes and immunotherapy response signatures in lung cancer," Modern Pathology, Nature Publishing Group, GB, 31(6):947-955 (2018).
Li and Dewey, "RSEM: accurate transcript quantification from RNA-Seq data with or without a reference genome," BMC Bioinformatics 2011 12:323, 16 pages.
McGhee and von Hippel, "Formaldehyde as a probe of DNA structure. II. Reaction with endocyclic imino groups of DNA bases," Biochemistry 14:1281-1296 (1975).
Mukhopadhyay S., "Utility of Small Biopsies for Diagnosis of Lung Nodules: Doing More with Less," Modern Pathology, 25(1): S43-S57 (2012).
Mullins et al., "Agreement in breast cancer classification between microarray and quantitative reverse transcription PCR from fresh-frozen and formalin-fixed, paraffin-embedded tissues," Clin Chem. 53(7):1273-1279 (2007).
Nielsen, "A comparison of PAM50 intrinsic subtyping with immunohistochemistry and clinical prognostic factors in tamoxifen-treated estrogen receptor-positive breast cancer," Clin Cancer Res. Nov. 1, 2010;16(21):5222-32. doi: 10.1158/1078-0432.CCR-10-1282. Epub Sep. 13, 2010, Downloaded from clincancerres.aacrjournals.org on Oct. 10, 2018.
Niki, T., et al., "Expression of Vascular Endothelial Growth Factors A, B. C, and D and Their Relationships to Lymph Node Status in Lung Adenocarcinoma," Clinical Cancer Research 6(6):2431-2439 (2000).
Paolillo et al., "Small molecule integrin antagonists in cancer therapy," Mini Rev Med Chem 12:1439-1446 (2009).
Parzen, "On Estimation of a Probability Density Function and Mode," Stanford University, 1065-1076 (1962).
Prasad et al., "Differential Expression of Degradome Components in Cutaneous Squamous Cell Carcinomas," Modern Pathology 27:495-957 (2014).
Quinlan, "Induction of Decision Trees," Machine Learning 1(1):81-106 (1986).
Raponi et al. "Gene expression signatures for predicting prognosis of squamous cell and adenocarcinomas of the lung," Cancer Res 66(7): 466-472 (2006).
Rekhtman et al., "Distinct profile of driver mutations and clinical features in immunomarker-defined subsets of pulmonary large-cell carcinoma," Mod Pathol 26(4): 511-22 (2013).
Rekhtman et al., "Immunnohistochemical algorithm for differentiation of lung adenocarcinoma and squamous cell carcinoma based on large series of whole-tissue sections with validation in small specimens," Modern Path. 24:1348-1359 (2011).
Ringnér, M., et al., "Prognostic and Chemotherapy Predictive Value of Gene-Expression Phenotypes in Primary Lung Adenocarcinoma," Clinical Cancer Research 22(1):218-229 (2015).
Robin et al., "pROC: an open source package for R and S+ to analyze and compare ROC curves," BMC bioinformatic 12:77 (2011), 8 pages.
Roepman P, et al. An immune response enriched 72-gene prognostic profile for early stage non-small-cell lung cancer. Clinical Cancer Research 15.1:284-290 (2009).
Rossi G, Mengoli MC, Cavazza A, et al. Large cell carcinoma of the lung: clinically oriented classification integrating immunohistochemistry and molecular biology. Virchows Arch. 2014; 464: 61-68. DOI 10.1007/s00428-013-1501-6.
Rouskin et al., "Genome-wide probing of RNA structure reveals active unfolding of mRNA structures in vivo," Nature 505, pp. 701-705 (2014).
Rousseaux S, et al. Ectopic activation of germline and placental genes identifies aggressive metastasis-prone lung cancers. Sci Transl Med. 5(186): 186ra66 (2013).
Rupp G and Locker J., University of Pittsburgh School of Medicine, "Purification and analysis of RNA from paraffin embedded tissues," BioTechniques 6(1):56-60 (1988).
Schabath et al., "Differential association of STKI1 and TP53 with KRAS mutation-associated gene expression, proliferation, and immune surveillance in lung adenocarcinoma," Oncogene 35(24):3209-3216, Author manuscript, 13 pages (2016).
Schafer, G., et al., *Homo sapiens* Vascular Endothelial Growth Factor D (FIGF) Gene, Promoter Region and 5' UTR. National Center for Biotechnology Information. Genbank Entry. Jan. 3, 2005 [retrieved on Sep. 27, 2017] Retrieved from the Internet: <URL: https://www.ncbi.nlm.nih.gov/nucleotide/58223364?report=genbank&log$=nuclalign&blast_rank=5&RID=WWYAJBVM015>; pp. 1-2.
Shedden K, Taylor JMG, Enkemann SA, et al. Gene expression-based survival prediction in lung adenocarcinoma: a multi-site, blinded validation study: director's challenge consortium for the molecular classification of lung adenocarcinoma. Nat Med 14(8): 822-827 (2008). doi: 10.1038/nm. I 790.

(56) References Cited

OTHER PUBLICATIONS

Skoulidis et al., "Co occuring genomic alterations define major subsets of KRAS-mutant lung adenocarcinoma with distinct biology, immune profiles, and therapeutic vulnerabilities," Cancer Discov 5(8): 860-77 (2015).
Smyth, G. K., Limma: linear models for microarray data. In: Bioinformatics and Computational Biology Solutions using Rand Bioconductor, R. Gentleman, V. Carey, S. Dudoit, R. Irizarry, W. Huber (eds.), Springer, New York, pp. 397-420 (2005).
Smyth, G. K., "Linear Models and Empirical Bayes Methods for Assessing Differential Expression in Microarray Experiments," Stat. Appi. Genet. Mol. Biol. 3: Article 3 (2004), 28 pages.
Statistical analyses R 3.2.0 software (http://www.R-project.org) retrieved online Jan. 7, 2019 at http://www.R-project.org, 3 pages.
Suykens JAK, Vandewalle J., "Least Squares Support Vector Machine Classifiers," Neural Processing Letters 9(3): 293-300 (1999).
Szumilas, "Explaining odds ratios," J. Can. Acad. Child Adolesc. Psychiatry 19(3): 227-229 (2010).
Tang et al., "Advances in lung adenocarcinoma classification: a summary of the new international multidisciplinary classification system (IASLC/ATS/ERS)," J Thorac Dis 2014; 6(S5): S489-S501.
The Clinical Lung Cancer Genome Project (CLCGP) and Network Genomic Medicine (NGM). A genomics-based classification of human lung tumors. Sci Transl Med 5, 209ral53, 28 pages (2013).
Thunnissen et al., "Reproducibility of histopathological subtypes and invasion in pulmonary adenocarcinoma. An international interobserver study," Mod Pathol 2012; 25(12):1574-1583. Doi: 10.1038/modpathol.2012.106 Epub Jul. 20, 2012.
Thunnissen et al., "Correlation of immunohistochemical staining p63 and TTF-1 with EGFR and K-ras mutational spectrum and diagnostic reproducibility in non-small cell lung carcinoma," Virchows Arch 2012; 46(6)1:629-38.
Thunnissen et al., "Reproducibility of histopathological diagnosis in poorly differentiated NSCLC: an international multiobserver study," J Thorac Oncol 2014; 9(9): 1354-1362.
Tibshirani et al., "Diagnosis of multiple cancer types by shrunken centroids of gene expression," Proc. Natl. Acad. Sci. USA 99(10):6576-6572 (2002).
Tomida S., et al., "Relapse-related molecular signature in lung adenocarcinomas identifies patients with dismal prognosis," J Clin Oncol 27(17): 2793-99 (2009).
Trapnell et al, "Transcript assembly and quantification by RNA-Seq reveals unannotated transcripts and isoform switching during cell differentiation," Nature biotechnology 28(5):511-515 (2010).
Trapnell et al., "TopHat: discovering splice junctions with RNA-Seq.," Bioinformatics 25(9):1105-11 (2009).
Travis et al., "Diagnosis of lung cancer in small biopsies and cytology: implications of the 2011 International Association for the Study of Lung Cancer/American Thoracic Society/European Respiratory Society classification," Arch Pathol Lab Med 2013; 137(5):668-84.
Travis and Rekhtman, "Pathological diagnosis and classification of lung cancer in small biopsies and cytology: strategic management of tissue for molecular testing," Sem Resp and Crit Care Med 32(1): 22-31 (2011).
Travis et al., "International Association for the study of lung cancer/American Thoracic Society/European Respiratory Society International multidisciplinary classification of lung adenocarcinoma," J Thorac Oncol, 6:244-285 (2011).
Travis et al., "New pathologic classification of lung cancer: relevance for clinical practice and clinical trials," J Clin Oncol 31:992-1001 (2013).
Velculescu et al., "Characterization of the yeast transcriptome," Cell 88(2):243-251 (1997).
Velculescu et al., "Serial analysis of gene expression," Science 270(5235):484-487 (1995), retrieved from http://science.sciencemag.org/ on Oct. 29, 2018.
Vermeulen, Pediatric Primitive Neuroectodermal Tumors of the Central Nervous System Differentially Express Granzyme Inhibitors. PLoS One. 11(3):1-8 (2016).
Wilkerson et al., Lung Squamous Cell Carcinoma mRNA Expression Subtypes are Reproducible, Clinically Important and Correspond to Different Normal Cell Types. Clinical Clin Cancer Res 16(19):4864-4875 (2010).
Wilkerson et al., "Differential pathogenesis of lung adenocarcinoma subtypes involving sequence mutations, copy number, chromosomal instability, and methylation," PLoS ONE. 2012; 7(5) e36530. Doi:10.1371/joumal.pone.0036530, 13 pages.
Wilkerson et al., "Prediction of lung cancer histological types by RT-qPCR gene expression in FFPE specimens," J Molec Diagn 15(4):485-497 (2013).
Wilkerson, M.D. et al. Supplemental Figure S2, Journal of Molecular Diagnostics 15(4):485 (Jul. 2013; online May 22, 2013), 1 page.
Wistuba et al., "Validation of a proliferation-based expression signature as prognostic marker in early stage lung adenocarcinoma," Clin Cancer Res 19(22):6261-6271 (2013), Downloaded from clincancerres.aacrjournals.org on Oct. 10, 2018.
Wold, et al., "Genome expression and mRNA maturation at late stages of productive adenovirus type 2 infection," J Virol. Nov. 1976;20(2):465-77.
Wu and Wallace, "The ligation amplification reaction (LAR)—amplification of specific DNA sequences using sequential rounds of template dependent ligation.," Genomics, 4(4):560-569 (1989).
Yang et al, "Normalization for cDNA microarray data: a robust composite method addressing single and multiple slide systematic variation," Feb. 15, 2002;30(4):e15, 10 pages.
Zhang et al., "Assessment of VEGF-D Expression Measured by Immunohistochemical Staining and F-18 FDG Uptake on PET as Biological Prognostic Factors for Recurrence in Patients with Surgically Resected Lung Adenocarcinoma," Annals of Nuclear Medicine. 24(7):533-540 (2010).
Zhu CQ, et al., "Prognostic and predictive gene signature for adjuvant chemotherapy in resected non-small-cell lung cancer," J Clin Oncol 28(29); 4417-4424 (2010).
Gene Expression Omnibus. NCBI Database, GEO Platform GPL29829 "[HG-U133A] Affymetrix Human Genome U133A" available via URL:<ncbi.nlm.nih.gov/geo/query/acc.cgi?acc=GPL29829>; Mar. 9, 2021, 194 pages.

* cited by examiner

FIG. 2

| Characteristic | TCGA[2] | Shedden[6] | Tomida[7] | UNC[1] | GeneCentric |
|---|---|---|---|---|---|
| Total # of samples | 515 | 442 | 117 | 116 | 88 |
| Tissue preservation | Fresh Frozen | Fresh Frozen | Fresh Frozen | Fresh Frozen | FFPE |
| Subtype | | | | | |
| bronchioid | 188 | 159 | 45 | 47 | 26 |
| magnoid | 154 | 161 | 40 | 40 | 29 |
| squamoid | 173 | 122 | 32 | 29 | 33 |
| Gender | | | | | |
| Female/Male/NA | 274/237/4 | 219/223/0 | 57/60/0 | 63/53/0 | |
| Age at diagnosis | | | | | |
| Median/(Range) | 66/(38-88) | 65/(33-87) | 61/(32-84) | 65/(41-90) | |
| Age not available | 35 | 0 | 0 | 0 | |
| Stage | | | | | |
| I | 276 | 276 | 79 | 73 | 42 |
| II | 123 | 95 | 13 | 21 | 7 |
| III | 84 | 68 | 25 | 19 | 15 |
| IV | 27 | 0 | 0 | 2 | 24 |
| Stage not available | 5 | 3 | 0 | 1 | 0 |
| Smoking ever | | | | | |
| yes | 346 | 300 | 61 | 82 | |
| no | 2 | 49 | 56 | 11 | |
| Smoking status not available | 167 | 93 | 0 | 23 | |

TCGA AD n=515

FIG. 5 (continued)
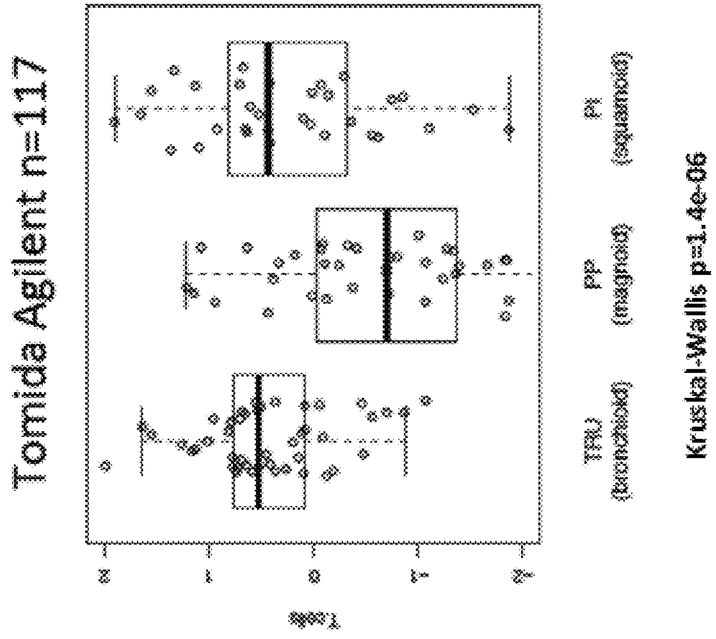
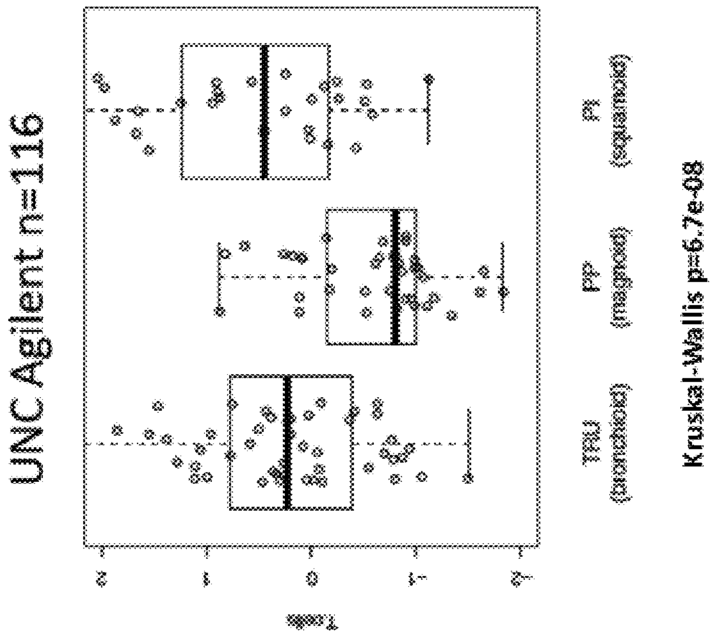

Kruskal-Wallis p=0.00026

FIG. 13

Gold standard (rows) vs clanc48 (columns)

| | | bronchioid | magnoid | squamoid |
|---|---|---|---|---|
| GeneCentric FFPE | bronchioid | 23 | 0 | 3 |
| | magnoid | 1 | 23 | 5 |
| | squamoid | 3 | 2 | 28 |
| shedden | bronchioid | 151 | 5 | 3 |
| | magnoid | 16 | 126 | 19 |
| | squamoid | 7 | 6 | 109 |
| tcga | bronchioid | 175 | 3 | 10 |
| | magnoid | 12 | 120 | 22 |
| | squamoid | 9 | 11 | 153 |
| tomida | bronchioid | 43 | 2 | 0 |
| | magnoid | 4 | 28 | 8 |
| | squamoid | 2 | 8 | 22 |
| unc | bronchioid | 44 | 3 | 0 |
| | magnoid | 0 | 38 | 2 |
| | squamoid | 1 | 3 | 25 |

Agreement

| | GeneCentric FFPE | shedden | tcga | tomida | unc |
|---|---|---|---|---|---|
| Agree | 0.84 | 0.87 | 0.87 | 0.79 | 0.92 |

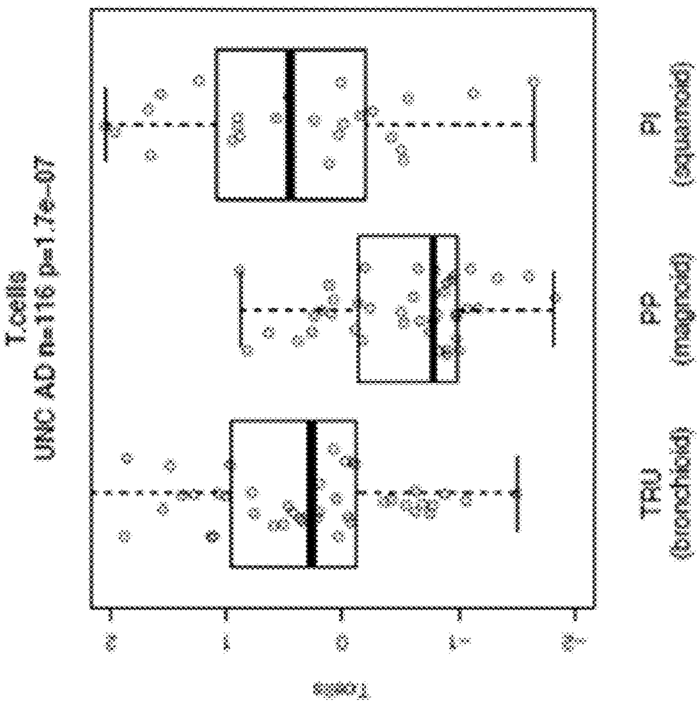
FIG. 15 (continued)
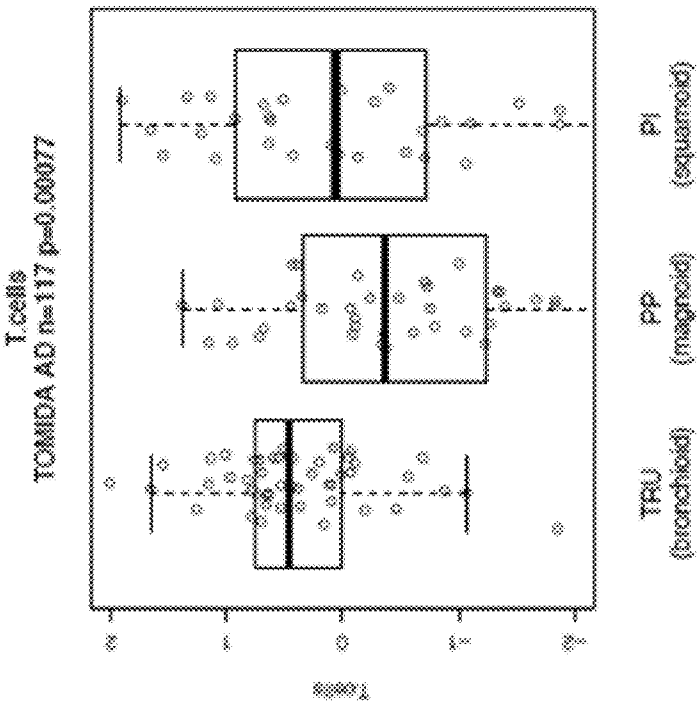

TCGA AD n=515

| | AD subtypes |
|---|---|
| Variable Expression | 203 |
| Similar Expression | 119 |

SEQUENCE LISTING

```
<160> NUMBER OF SEQ ID NOS: 48

<210> SEQ ID NO 1
<211> LENGTH: 2122
<212> TYPE: DNA
<213> ORGANISM: Homo sapiens

<400> SEQUENCE: 1

ctctagcttc tagcacaatg tctgtcattt aatgggcatt cagtacataa tagataggta     60

attgaatgaa tggatttaga tgcctgggtg ttttctttct acttgtattc tattccccac    120

atcctctcca aagatttcag catcatcaag acatattatc ctgtgtcttc cttctgaaga    180

tttaaattat agtgatcacc aaatccatgt tgatatgata acaatggtta agaagtttga    240

atatgttatt ttctctaagc aatacagttg tatattaatc agaatctccc agagaaagcc    300

ccttagagca ggcagttcca taaaaggaat gtcaggaact tctgcaggct ggatgaggac    360

atacactgag tgaacaagtc tgtcaactgc tctaaagaca ctgtcaatgc catataaaag    420
```

ctggccttgt tcatctagca gatcatgggg gtgagacagt ccagtgcctc tctgccccta 480
caatatatga agaaagggga agaaacacac attgcctcct ggtagattag gggaggactt 540
cttgtacatt tttagcaaaa tccgagttca gacccagcaa ttagacaaaa gggtcagcaa 600
actatggtcg atgggctaca tctgcccact gcatgttttt gtaaatgaag ttttattggg 660
acacagccat acctattcac ttttgcatta tctatggctg cttttgcact ttgatgaaag 720
agttgagtag ttgagacaga cactgtttga cccacaaaat ctaaaataca tactatctag 780
cccttcctag caaacatttg ccaaccccta gaaaactttt aaaaaatgat gctcttcgac 840
ttgaaatttt tataatcttc tgtttattgt caataggtgc tgctgatttt caaaaaatga 900
cttagaatcc tcaaataagt atacagcctt atatgctgct tagacaccaa agctatgata 960
agatttgtca gttctttgta tcagatgggt tcaattcttg acatcagcta atgttataaa 1020
aataactaca aaattggttg taatagaacc aaatctaaga ctctttttaa taaaaaagat 1080
caccattgct ggtgagaaac ctatactgaa tgggtgagat gccattgcat ttatctgaag 1140
tttcgtcttt ataatcaata atcatataca atcctagtca agaaactcat cttacagtcc 1200
ttggggattg aacactgtga aaataaactt ttactcttcg gatgtgcttg gattttgttt 1260
taaattaaga actacagaaa tatatatcat ttctagtggt agaggaaaat attgccaccc 1320
agaactttct gaatgtctct ttctgcccta ggtccatttg tgatgaacac caatgaagag 1380
atttctcaag ctattcttga tttcagaaac gcaaaaaatg ggtttgaaag ggccaaaacc 1440
tggaaatcaa agattgggaa ctagtggaaa gcggaagagc aggtcttgat gtgtcctaga 1500
attttgccat ttctgagatt gagccattga aggcattcca tttctaaagc ttatttagcc 1560
ggtgcttcta aagaattcca cactaacgtg ataacatggt ttttgtaaca ataaatgtag 1620
gatatttcct ggcacatgca aataaaccta atcattgttt ctttaaaaat cagtgttttt 1680
catttgagat acctaagtta ctaagcttct gtttaaaaag tcgttttgtg tatgtttgcc 1740 ttttttgca tgtatggatg gatgttttta ttatttttgt gcatgtgcag gttttaaaaa 1800
tcatatttga ttgctttctg tgtgtcattg gcagcagatg catgagcatc tgaggtccct 1860
tcttaagcaa tcccactgag atacaaaggt caaagctatg tgctggggtt tcatgttaca 1920
ggttatctgc tttaaaataa cggcagccct gaacatttga gtcagttctt aaaactgccc 1980
tgctattggt agggacgcaa caggattaca gccaagactt ctctgcattt tctgccaaaa 2040
tctgtgtcag atttaagaca catgcttctg caagcttcca tgaaggttgt gcaaaaaagt 2100
ttcaatccag agttgggttc ca 2122

<210> SEQ ID NO 2
<211> LENGTH: 1514
<212> TYPE: DNA
<213> ORGANISM: Homo sapiens

<400> SEQUENCE: 2
ttcgcgctcc cgccgctcct ccacgctcgt gccgctcccc ccccgcgctc ccagttgacg 60
ctctgggccg ccacctccgc ggaccctgag cgcaagagcc aagccgccag cgctgcgatg 120
tgggccacgc tgccgctgct ctgcgccggg gcctggctcc tgggagtccc cgtctgcggt 180
gccgccgaac tgtgcgtgaa ctccttagag aagtttcact tcaagtcatg gatgtctaag 240
caccgtaaga cctacagtac ggaggagtac caccacaggc tgcagacgtt tgccagcaac 300
tggaggaaga taaacgccca caacaatggg aaccacacat ttaaaatggc actgaaccaa 360

```
ttttcagaca tgagctttgc tgaaataaaa cacaagtatc tctggtcaga gcctcagaat    420
tgctcagcca ccaaaagtaa ctaccttcga ggtactggtc cctacccacc ttccgtggac    480
tggcggaaaa aaggaaattt tgtctcacct gtgaaaaatc agggtgcctg cggcagttgc    540
tggactttct ccaccactgg ggccctggag tctgcgatcg ccatcgcaac cggaaagatg    600
ctgtccttgg cggaacagca gctggtggac tgcgcccagg acttcaataa tcacggctgc    660
caagggggtc tccccagcca ggctttcgag tatatcctgt acaacaaggg gatcatgggt    720
gaagacacct acccctacca gggcaaggat ggttattgca agttccaacc tggaaaggcc    780
atcggctttg tcaaggatgt agccaacatc acaatctatg acgaggaagc gatggtggag    840
gctgtggccc tctacaaccc tgtgagcttt gcctttgagg tgactcagga cttcatgatg    900
tatagaacgg gcatctactc cagtacttcc tgccataaaa ctccagataa agtaaaccat    960
gcagtactgg ctgttgggta tggagaaaaa aatgggatcc cttactggat cgtgaaaaac   1020
tcttggggtc cccagtgggg aatgaacggg tacttcctca tcgagcgcgg aaagaacatg   1080
tgtggcctgg ctgcctgcgc ctcctacccc atccctctgg tgtgagccgt ggcagccgca   1140
gcgcagactg gcggagaagg agaggaacgg gcagcctggg cctgggtgga aatcctgccc   1200
tggaggaagt tgtggggaga tccactggga cccccaacat tctgccctca cctctgtgcc   1260
cagcctggaa acctacagac aaggaggagt tccaccatga gctcacccgt gtctatgacg   1320
caaagatcac cagccatgtg ccttagtgtc cttcttaaca gactcaaacc acatggacca   1380
cgaatattct ttctgtccag aagggctact ttccacatat agagctccag ggactgtctt   1440
ttctgtattc gctgttcaat aaacattgag tgagcacctc cccagatgga gcatgctggt   1500
cctggaaaaa aaaa                                                     1514
```

<210> SEQ ID NO 3
<211> LENGTH: 1833
<212> TYPE: DNA
<213> ORGANISM: Homo sapiens

<400> SEQUENCE: 3

```
aaagccgcgt cctgatcaat ggggcgggcg gcttagcgcg cgcggccacc tggtccgagg     60
aggagcagtc ccggggcccg ccgcaggtcg ggtggctcag ccatggctcc tcggggcgca    120
gcggccggcc ggagcccggg accctgcgcg gggcgctgag ctcccgagcg ggcagagggc    180
acgggcaggc ggacgtcggg gcgccctcgg ggaacgtgcg ggcaccatgc gtccccacct    240
gtcgccgccg ctgcagcagc tactactgcc ggtgctgctc gcctgcgccg cgcactcgac    300
tggagccctt ccccgactat gtgacgtgct acaagtgctg tgggaagagc aagaccagtg    360
cctgcaggaa ctctccagag agcagacagg agacctgggc acggagcagc cagtgccagg    420
ttgtgagggg atgtgggaca acataagctg ctggccctct tctgtgccgg gccggatggt    480
ggaggtggaa tgcccgagat tcctccggat gctcaccagc agaaatggtt ccttgttccg    540
aaactgcaca caggatggct ggtcagaaac cttccccagg cctaatctgg cctgtggcgt    600
taatgtgaac gactcttcca acgagaagcg gcactcctac ctgctgaagc tgaaagtcat    660
gtacaccgtg ggctacagct cctccctggt catgctcctg gtcgcccttg gcatcctctg    720
tgctttccgg aggctccact gcactcgcaa ctacatccac atgcacctgt tcgtgtcctt    780
catccttcgt gccctgtcca acttcatcaa ggacgccgtg ctcttctcct cagatgatgt    840
cacctactgc gatgcccaca gggcgggctg caagctggtc atggtgctgt tccagtactg    900
catcatggcc aactactcct ggctgctggt ggaaggcctc taccttcaca cactcctcgc    960
```

-continued

```
catctccttc ttctctgaaa gaaagtacct ccagggattt gtggcattcg gatggggttc   1020
tccagccatt tttgttgctt tgtgggctat tgccagacac tttctggaag atgttgggtg   1080
ctgggacatc aatgccaacg catccatctg gtggatcatt cgtggtcctg tgatcctctc   1140
catcctgatt aatttcatcc ttttcataaa cattctaaga atcctgatga gaaaacttag   1200
aacccaagaa acaagaggaa atgaagtcag ccattataag cgcctggcca ggtccactct   1260
cctgctgatc cccctctttg gcatccacta catcgtcttc gccttctccc cagaggacgc   1320
tatggagatc cagctgtttt ttgaactagc ccttggctca ttccagggac tggtggtggc   1380
cgtcctctac tgcttcctca atggggaggt gcagctggag gttcagaaga agtggcagca   1440
atggcacctc cgtgagttcc cactgcaccc cgtggcctcc ttcagcaaca gcaccaaggc   1500
cagccacttg gagcagagcc agggcacctg caggaccagc atcatctgag aggctggagc   1560
agggtcaccc acggacagag accaagagag gtcctgcgaa ggctgggcac tgctgtggga   1620
cagccagtct tcccagcaga caccctgtgt cctccttcag ctgaagatgc cctccccag    1680
gccttggact cttccgaagg gatgtgaggc actgtggggc aggacaaggg cctgggattt   1740
ggttcgtttg ctcttctggg aagagaagtt caggggtccc agaaagggac agggaaataa   1800
atggtgcctg ggatgagatt caaaaaaaaa aaa                                 1833
```

```
<210> SEQ ID NO 4
<211> LENGTH: 2128
<212> TYPE: DNA
<213> ORGANISM: Homo sapiens

<400> SEQUENCE: 4

aagatgcatg ggtccagagt ataaaggaac ccaggagcag ctgaaggcag gtcagatgaa     60
ggctaggtgg ctggaactgc aaccatggtg cccagcttcc tctccctgag cttctcctcc    120
ttgggcctgt gggcttctgg gctgatcttg gtcttaggct ttctcaagct catccacctg    180
ctgctgcgga ggcagacgtt ggctaaggct atggacaaat tcccagggcc tcccacccac    240
tggcttttg gacatgccct cgagatccag gagacgggga gcctggacaa agtggtgtcc     300
tgggcccacc agttcccgta tgcccaccca ctctggttcg gacagttcat tggcttcctg    360
aacatctatg agcctgacta tgccaaagct gtgtacagcc gtggggggag aggcctgctg    420
gttcttgagg ggcccaagtg gttgcagcac cgcaagctgc tcacacctgg ctttcattat    480
gatgtgctga agccctatgt ggccgtgttc actgagtcta cacgtatcat gctggacaag    540
tgggaagaga aagctcggga gggtaagtcc tttgacatct tctgcgatgt gggtcacatg    600
gcgctgaaca cactcatgaa gtgcaccttt ggaagaggag acaccggcct gggccacagc    660
agggacagca gctactacct tgcagtcagc gatctcactc tgttgatgca gcagcgcctt    720
gtgtccttcc agtaccataa tgacttcatc tactggctca ccccacatgg ccgccgcttc    780
ctgcgggcct gccaggtggc ccatgaccat acagaccagg tcatcaggga gcggaaggca    840
gccctgcagg atgagaaggt gcggaagaag atccagaacc ggaggcacct ggacttcctg    900
gacattctcc tgggtgcccg ggatgaagat gacatcaaac tgtcagatgc agacctccgg    960
gctgaagtgg acacattcat gtttgaaggc catgacacca ccaccagtgg tatctcctgg   1020
tttctctact gcatggccct gtaccctgag caccagcatc gttgtagaga ggaggtccgc   1080
gagatcctag ggaccagga cttcttccag tgggatgatc tgggcaaaat gacttatctg    1140
accatgtgca tcaaggagag cttccgcctc tacccacctg tgccccaggt gtaccgccag   1200
```

-continued

```
ctcagcaagc ctgtcacctt tgtggatggc cggtctctac ctgcaggaag cctgatctct   1260

atgcatatct atgccctcca taggaacagt gctgtatggc ccgaccctga ggtctttgac   1320

tctctgcgct tttccactga gaatgcatcc aaacgccatc cctttgcctt tatgcccttc   1380

tctgctgggc ccaggaactg cattgggcag cagtttgcca tgagtgagat gaaggtggtc   1440

acagccatgt gcttgctccg ctttgagttc tctctggacc cctcacggct gcccatcaag   1500

atgccccagc ttgtcctgcg ctccaagaat ggctttcacc tccacctgaa gccactgggc   1560

cctgggtctg ggaagtagct ctgatgagaa tggggtccca gatggctcag gctgtgacct   1620

ccctgggcac caccctcccc aggctgggtg tggaggagtt ggggccccct gccttcagga   1680

ggcttgtagt ttagaaggga agtaggcatt accatagacg actcctagag gacagtgcta   1740

tgtaaaaatg tgtgtctata aatgtttatc atgcatgtat tctagagctc attcatttat   1800

tcaacaaaca tttggtgagc acctatttcg ttcgagaaac ttcatttatc tcctataatt   1860

ggcaaactta aaaatgcagc agaaacttac attccaacct tagagactca tagtgagcac   1920

aaggaaagtt ttgccctgag attcatggtt atggctgggt accaccaaat agaagaatgg   1980

cttaggggag tgccccttca ctgagatgtg tttctttgtt gaactttgtg tgtgtgtgtt   2040

tagaatataa cagacataag aaaaaattac ctaaatgaag actgtacaaa ataataaata   2100

attctgaagc agaaaaaaaa aaaaaaaa                                      2128
```

<210> SEQ ID NO 5
<211> LENGTH: 3903
<212> TYPE: DNA
<213> ORGANISM: Homo sapiens

<400> SEQUENCE: 5

```
atgaaatccc caaggagaac cactttgtgc ctcatgttta ttgtgattta ttcttccaaa     60

gctgcactga actggaatta cgagtctact attcatcctt tgagtcttca tgaacatgaa    120

ccagctggtg aagaggcact gaggcaaaaa cgagcagttg ccacaaaaag tcctacggct    180

gaagaataca ctgttaatat tgagatcagt tttgaaaatg catccttcct ggatcctatc    240

aaagcctact tgaacagcct cagttttcca attcatggga ataacactga ccaaattacc    300

gacattttga gcataaatgt gacaacagtc tgcagacctg ctggaaatga aatctggtgc    360

tcctgcgaga caggttatgg gtggcctcgg gaaaggtgtc ttcacaatct catttgtcaa    420

gagcgtgacg tcttcctccc agggcaccat tgcagttgcc ttaaagaact gcctcccaat    480

ggaccttttt gcctgcttca ggaagatgtt accctgaaca tgagagtcag actaaatgta    540

ggctttcaag aagacctcat gaacacttcc tccgccctct ataggtccta caagaccgac    600

ttggaaacag cgttccggaa gggttacgga attttaccag gcttcaaggg cgtgactgtg    660

acagggttca agtctggaag tgtggttgtg acatatgaag tcaagactac accaccatca    720

cttgagttaa tacataaagc caatgaacaa gttgtacaga gcctcaatca gacctacaaa    780

atggactaca actcctttca agcagttact atcgaaagca atttctttgt cacaccagaa    840

atcatctttg aaggggacac agtcagtctg gtgtgtgaaa aggaagtttt gtcctccaat    900

gtgtcttggc gctatgaaga acagcagttg gaaatccaga acagcagcag attctcgatt    960

tacaccgcac ttttcaacaa catgacttcg gtgtccaagc tcaccatcca caacatcact   1020

ccaggtgatg caggtgaata tgtttgcaaa ctgatattag acatttttga atatgagtgc   1080

aagaagaaaa tagatgttat gcccatccaa attttggcaa atgaagaaat gaaggtgatg   1140

tgcgacaaca atcctgtatc tttgaactgc tgcagtcagg gtaatgttaa ttggagcaaa   1200
```

-continued

```
gtagaatgga agcaggaagg aaaaataaat attccaggaa cccctgagac agacatagat   1260
tctagctgca gcagatacac cctcaaggct gatggaaccc agtgcccaag cgggtcgtct   1320
ggaacaacag tcatctacac ttgtgagttc atcagtgcct atggagccag aggcagtgca   1380
aacataaaag tgacattcat ctctgtggcc aatctaacaa taaccccgga cccaatttct   1440
gtttctgagg gacaaaactt ttctataaaa tgcatcagtg atgtgagtaa ctatgatgag   1500
gtttattgga acacttctgc tggaattaaa atataccaaa gattttatac cacgaggagg   1560
tatcttgatg gagcagaatc agtactgaca gtcaagacct cgaccaggga gtggaatgga   1620
acctatcact gcatatttag atataagaat tcatacagta ttgcaaccaa agacgtcatt   1680
gttcacccgc tgcctctaaa gctgaacatc atggttgatc ctttggaagc tactgtttca   1740
tgcagtggtt cccatcacat caagtgctgc atagaggagg atggagacta caaagttact   1800
ttccatacgg gttcctcatc ccttcctgct gcaaaagaag ttaacaaaaa acaagtgtgc   1860
tacaaacaca atttcaatgc aagctcagtt tcctggtgtt caaaaactgt tgatgtgtgt   1920
tgtcacttta ccaatgctgc taataattca gtctggagcc catctatgaa gctgaatctg   1980
gttcctgggg aaaacatcac atgccaggat cccgtaatag gtgtcggaga gccggggaaa   2040
gtcatccaga agctatgccg gttctcaaac gttcccagca gccctgagag tcccattggc   2100
gggaccatca cttacaaatg tgtaggctcc cagtgggagg agaagagaaa tgactgcatc   2160
tctgccccaa taaacagtct gctccagatg gctaaggctt tgatcaagag cccctctcag   2220
gatgagatgc tccctacata cctgaaggat ctttctatta gcatagacaa agcggaacat   2280
gaaatcagct cttctcctgg gagtctggga gccattatta acatccttga tctgctctca   2340
acagttccaa cccaagtaaa ttcagaaatg atgacgcacg tgctctctac ggttaatgtc   2400
atccttggca agcccgtctt gaacacctgg aaggttttac aacagcaatg gaccaatcag   2460
agttcacagc tactacattc agtggaaaga ttttcccaag cattacagtc gggagatagc   2520
cctcctttgt ccttctccca aactaatgtg cagatgagca gcatggtaat caagtccagc   2580
cacccagaaa cctatcaaca gaggtttgtt ttcccatact ttgacctctg gggcaatgtg   2640
gtcattgaca agagctatct agaaaacttg cagtcggatt cgtctattgt caccatggct   2700
ttcccaactc tccaagccat ccttgcccag gatatccagg aaaataactt tgcagagagc   2760
ttagtgatga caaccactgt cagccacaat acaactatgc cattcaggat ttcaatgact   2820
tttaagaaca atagcccttc aggcggcgaa acgaagtgtg tcttctggaa cttcaggctt   2880
gccaacaaca caggggggtg ggacagcagt gggtgctatg tagaagaagg tgatggggac   2940
aatgtcacct gtatctgtga ccacctaaca tcattctcca tcctcatgtc ccctgactcc   3000
ccagatccta gttctctcct gggaatactc ctggatatta tttcttatgt tggggtgggc   3060
ttttccatct tgagcttggc agcctgtcta gttgtggaag ctgtggtgtg gaaatcggtg   3120
accaagaacc ggacttctta tatgcgccac acctgcatag tgaatatcgc tgcctccctt   3180
ctggtcgcca acacctggtt cattgtggtc gctgccatcc aggacaatcg ctacatactc   3240
tgcaagacag cctgtgtggc tgccaccttc ttcatccact tcttctacct cagcgtcttc   3300
ttctggatgc tgacactggg cctcatgctg ttctatcgcc tggttttcat tctgcatgaa   3360
acaagcaggt ccactcagaa agccattgcc ttctgtcttg gctatggctg cccacttgcc   3420
atctcggtca tcacgctggg agccacccag ccccgggaag tctatacgag gaagaatgtc   3480
tgttggctca actgggagga caccaaggcc ctgctggctt tcgccatccc agcactgatc   3540
```

```
attgtggtgg tgaacataac catcactatt gtggtcatca ccaagatcct gaggccttcc   3600

attggagaca agccatgcaa gcaggagaag agcagcctgt ttcagatcag caagagcatt   3660

ggggtcctca caccactctt gggcctcact tggggttttg gtctcaccac tgtgttccca   3720

gggaccaacc ttgtgttcca tatcatattt gccatcctca atgtcttcca gggattattc   3780

attttactct ttggatgcct ctgggatctg aagtcaacat ccctgggttc atccacacct   3840

gtgttttcta tgagttctcc aatatcaagg agatttaaca atttgtttgg taaaacaggt   3900

taa                                                                 3903
```

<210> SEQ ID NO 6
<211> LENGTH: 2829
<212> TYPE: DNA
<213> ORGANISM: Homo sapiens

<400> SEQUENCE: 6

```
acaagcaaac aaaataaata tctgtgcaat atatctgctt tatgcactca agcagagaag     60

aaatccacaa agactcacag tctgctggtg ggcagagaag acagaaacga catgagcaca    120

gcaggaaaag aaagttgtct gacagaagtt tgatgagagg aatttgactc agaagactga    180

aatatccttt aaccttacta taaaatatct tacaaaatac tcattgattt cacagcatta    240

gaatcatcaa ggtaatcaaa tgcaaagcag ctgtgctatg ggaggtaaag aaaccctttt    300

ccattgagga tgtggaggtt gcacctccta aggcttatga agttcgcatt aagatggtgg    360

ctgtaggaat ctgtcacaca gatgaccacg tggttagtgg caacctggtg acccccccttc    420

ctgtgatttt aggccatgag gcagccggca tcgtggagag tgttggagaa ggggtgacta    480

cagtcaaacc aggtgataaa gtcatcccgc tctttactcc tcagtgtgga aaatgcagag    540

tttgtaaaaa cccggagagc aactactgct tgaaaaatga tctaggcaat cctcgggggga    600

ccctgcagga tggcaccagg aggttcacct gcaggggggaa gcccattcac cacttccttg    660

gcaccagcac cttctcccag tacacggtgg tggatgagaa tgcagtggcc aaaattgatg    720

cagcctcgcc cctggagaaa gtctgcctca ttggctgtgg attctcgact ggttatgggt    780

ctgcagttaa cgttgccaag gtcaccccag gctctacctg tgctgtgttt ggcctgggag    840

gggtcggcct atctgctgtt atgggctgta aagcagctgg agcagccaga atcattgcgg    900

tggacatcaa caaggacaaa tttgcaaagg ccaaagagtt gggtgccact gaatgcatca    960

accctcaaga ctacaagaaa cccattcagg aagtgctaaa ggaaatgact gatggaggtg   1020

tggatttttc gtttgaagtc atcggtcggc ttgacaccat gatggcttcc ctgttatgtt   1080

gtcatgaggc atgtggcaca agcgtcatcg taggggtacc tcctgcttcc cagaacctct   1140

caataaaccc tatgctgcta ctgactggac gcacctggaa gggggctgtt tatggtggct   1200

ttaagagtaa agaaggtatc ccaaaacttg tggctgattt tatggctaag aagttttcac   1260

tggatgcgtt aataacccat gttttacctt ttgaaaaaat aaatgaagga tttgacctgc   1320

ttcactctgg gaaaagtatc cgtaccgtcc tgacgttttg aggcaataga gatgccttcc   1380

cctgtagcag tcttcagcct cctctaccct acaagatctg gagcaacagc taggaaatat   1440

cattaattca gctcttcaga gatgttatca ataaattaca catgggggct ttccaaagaa   1500

atggaaattg atgggaaatt atttttcagg aaaatttaaa attcaagtga gaagtaaata   1560

aagtgttgaa catcagctgg ggaattgaag ccaacaaacc ttccttctta accattctac   1620

tgtgtcacct ttgccattga ggaaaaatat tcctgtgact tcttgcattt ttggtatctt   1680

cataatcttt agtcatcgaa tcccagtgga ggggaccctt ttacttgccc tgaacataca   1740
```

catgctgggc cattgtgatt gaagtcttct aactctgtct cagttttcac tgtcgacatt 1800
ttcctttttc taataaaaat gtaccaaatc cctggggtaa aagctagggt aaggtaaagg 1860
atagactcac atttacaagt agtgaaggtc caagagttct aaatacagga aatttcttag 1920
gaactcaaat aaaatgcccc acattttact acagtaaatg gcagtgtttt tatgactttt 1980
atactatttc tttatggtcg atatacaatt gattttttaa aataatagca gatttcttgc 2040
ttcatatgac aaagcctcaa ttactaattg taaaaactga actattccca gaatcatgtt 2100
caaaaaatct gtaatttttg ctgatgaaag tgcttcattg actaaacagt attagtttgt 2160
ggctataaat gattatttag atgatgactg aaaatgtgta taaagtaatt aaaagtaata 2220
tggtggcttt aagtgtagag atgggatggc aaatgctgtg aatgcagaat gtaaaattgg 2280
taactaagaa atggcacaaa caccttaagc aatatatttt cctagtagat atatatatac 2340
acatacatat atacacatat acaaatgtat atttttgcaa aattgttttc aatctagaac 2400
ttttctatta actaccatgt cttaaaatca agtctataat cctagcatta gtttaatatt 2460
ttgaatatgt aaagacctgt gttaatgctt tgttaatgct tttcccactc tcatttgtta 2520
atgctttccc actctcaggg gaaggatttg cattttgagc tttatctcta aatgtgacat 2580
gcaaagatta ttcctggtaa aggaggtagc tgtctccaaa aatgctattg ttgcaatatc 2640
tacattctat ttcatattat gaaagacctt agacataaag taaaatagtt tatcatttac 2700
tgtgtgatct tcagtaagtc tctcaggctc tctgagcttg ttcatccttt gttttgaaaa 2760
aattactcaa ccaatccatt acagcttaac caagattaaa tgggatgatg ttaaaaaaaa 2820
aaaaaaaaa 2829

<210> SEQ ID NO 7
<211> LENGTH: 4081
<212> TYPE: DNA
<213> ORGANISM: Homo sapiens

<400> SEQUENCE: 7
ccgaggaaaa cgttgcgcag gttcaaaaat ggaacgtcgg cggcgtgagg gagcgcgagg 60
gggtgtgcgc gcgtgcgcgt gcgcgtgcgc gcccggacga gggtgacggg gaccccgcca 120
gccccagcat cgcgcgccgc agccgcggcc ccgcagctcc gcccccggcc cggcccggcc 180
ccgggcccgc tcgcccgccg ccccgcatgg agctgtcagc catcggcgag caggtgttcg 240
ccgtggagag catccggaag aagcgcgtgc ggaagggtaa agtcgagtat ctggtgaagt 300
ggaaaggatg gcccccaaag tacagcacgt gggagccaga agagcacatc ttggaccccc 360
gcctcgtcat ggcctacgag gagaaggagg agagagaccg agcatcgggg tataggaaga 420
gaggtccgaa acccaagcgg cttctgctgc agcggctgta cagcatggac ctgcggagct 480
cccacaaggc caagggcaag gagaagctct gcttctccct gacgtgccca ctcggcagcg 540
ggagccctga gggggtggtc aaggcggggg cacctgagct ggtggacaag ggcccccttgg 600 tgcccaccct gcccttcccg ctccgcaagc cccgaaaggc ccacaagtac ctgcggctct 660
cgcgcaagaa gttcccgccc cgcgggccca acctggagag ccacagccat cgacgggagc 720
tcttcctgca ggagccaccg gccccagacg tcctgcaggc ggctggcgag tgggagcctg 780
ctgcgcagcc ccctgaagag gaggcagatg ccgacctggc cgaggggccc cctccctgga 840
cacctgcgct cccctcaagt gaggtgaccg tgaccgacat caccgccaac tccatcaccg 900
tcaccttccg cgaggcccag gcagctgagg gcttcttccg agaccgcagt gggaagttct 960

-continued

```
gaatcaccgt ttttactctt cttaaactgt tttcttttgg gcttggggtg ggacttccag   1020
agatagggat gggttggggg cggggtaatt attttattta aaaaaatacc gagcagcaaa   1080
aggggagaag atcccactac tctcccacca cctgcccttt ctctgaggga cgtttaccac   1140
gaggcctcag gctggggatg gagagagttg ctctgggagt tggggtacca cccccagggc   1200
aggatgggga caggatcacc tgcccgggac accaccatta tcattctcct ctagtgacgc   1260
agcagctggt tctgggagtt aaaggagcat tggaaggccc aaaccctctc ccttgagtgg   1320
ccaccccagc ctggttggct ggttttcccc ttttctcttg tttcaattgg gtctttacct   1380
tgaactctcc tctctggctt tgcggtgggc tgtggaggct ggttttgacc aaaagtgagt   1440
ggggcgggag gaaggggcag gaggaagggt tgaggttact tggggcgagt cccttcccct   1500
tcagagaggc ttctatcctt cccagggagg aggcgccgct gagacccttc tgctgagagc   1560
tctgccctcc cctcatcacc tggcctgtgc agaaacgctc atgcacacct ggctgcacag   1620
gtgtgcacgc attacccttc gcgtgtacgt tcccatgtgc cccgtgaaag catgtgtggc   1680
tgcagacgtg tccacatggg ccttgcgaac ctgggttaga aaccctggcc aggcgaacgt   1740
ggggtgattc acagcacaaa agacctcacc accacacctg cactcacccc accttgcatg   1800
caccttgcta cctgcttgcg gctttcagtg gagggcaggg gtctggcaca ggtgcgatgg   1860
caccccatgc tccaggcata cagatgtggt ttctcggctg caccgggcca ggctgcgggt   1920
gtgcaggcgt ctgctaagtt gtgtgatgta tcagcacagg ctttgagacg tctggaccct   1980
gtccttcctc ccgtgagggg ttcttgttct ttctgactca ggtgactttt cagcccttcc   2040
aattcccctc tttttctgcc ctcccctcca actcagccaa cccaggtgtg ggcagtcagg   2100
gagggaggga gtgtcccacc acgttctcag ggcagccctt gactcctaag ccccttcctc   2160
cttccattct gcatcccctc cccatccaac ctaaatgcca cagctggggc tgagctgtat   2220
tcctgtggag ggacctctgc cgtgcctctc tgaggtcagg ctgtgctgtg tgatgggcag   2280
gctttgcccc agcccacccc tggcaaggtg cacttgtttt ctggtttgta caaggtgtcc   2340
tgggggcccg tggcttccct gccagtgagg agtgacttct ccctctcttc cagtcctgta   2400
ggggagacaa aaccagattg gggggcccaa ggggagcatg gaaaaggccg gctcccctgt   2460
ctttccttgg ctgtcagagt cagggtaaca cacaccaaga gtggagtgcg gccagcaagt   2520
ttgagacctg cccgccctcc tcgcagctct gctctgtgtc ctcaggaagt cacagagtct   2580
actgaggcaa ggagagggtg attctttccc caaatccctt cttccctggt tcccaaacca   2640
aagacagcct gcagcccttt ctgcatgggg tgctctgttg acaggcttcc cagatccctg   2700
agtctctctt tccttcctcc tcgatcttta gttgtccacg gtcaattcag tgcttccatt   2760
gggggacagt cccctccggg atgacctgat tcacctccag cccagggaat ggaatctaga   2820
ggaatacgtg gggtgggtct ggacaaggag cggcaggaat caccacccat ctccagctgt   2880
ggagccctgt ggaggggaag gggaagcttg gggttcagag gggactcttc caggagaggg   2940
gtgcccagcg gaggtaaaga tgatagaggg ttgtgggggg tctctagttg aatgttttgg   3000
cccatgactt tggaacatgg ctggcagctt ccagcagaag tcacgctccc catcccccag   3060
gggacatagg acctttttcc tgcttcctgg tcactttcaa agaactattt gcgcaatctg   3120
tgggtctgtg gattcacggg gctttctgtg tgggtgctgc agttgctttt gtctgcagca   3180
gcaggacaca tctttcctct tactcagccc tttatggccc atggggaact ccgtggctca   3240
gggagagctg aactccaggg gtgtgacctg ggacgggtgg gcctgaggtg cccagctcag   3300
ggcagccagg tggctcatgg gctgtagtga gccagctccc tgggggaaaa ggctgtgggc   3360
```

```
cgttaggacc atcctccagg acaggtgacc tctatgaggt cacctacggc tgtggccgtg   3420

caggcctcct tccagcccag agtggcccag tagagcaagg cagacagtga cctccacccc   3480

cgcagccctc ttaaaaggcc agtactcttg ggggtggggg gagggtttag aaagcatttg   3540

cccatctgcc tttctttccc ccagccccca cccgctttga atgtagagac ccgtgggcac   3600

ttttcctttt gtggtggggg gtgcggagga ggtacccccca ccccctggcac agccgcctgg   3660

aatgcaggac tgtcactgct gttcgggtga tgacctcgtt gccaagctcc tcctgtcccc   3720

ttgttctggg ggcaggcgct gtgcttctgt gaggtggttt agcttttgct ttcgaagtgg   3780

ccagctgcgg ccaccaggtc tcagcacaag agcgcttcct ttgcacagaa tgagcttcga   3840

gctttgttca gactaaatga atgtatctgg gaggggtcgg gggcacgagt tgattccaag   3900

cacatgcctt tgctgagtgt gtgtgtgctg ggagagtcag agtggatgta gagcgcggtt   3960

ttatttttgt actgacattg gtaagagact gtatagcatc tatttattta gatgatttat   4020

ctggtaaatg aggcaaaaaa attattaaaa atacattaaa gatgatttaa aaaaaagaaa   4080

a                                                                    4081
```

<210> SEQ ID NO 8
<211> LENGTH: 3865
<212> TYPE: DNA
<213> ORGANISM: Homo sapiens

<400> SEQUENCE: 8

```
tttttcaatt ttgaacattt tgcaaaacga ggggttcgag gcaggtgaga gcatcctgca     60

cgtcgccggg gagcccgcgg gcacttggcg cgctctcctg ggaccgtctg cactggaaac    120

ccgaaagttt ttttttaata tatattttta tgcagatgta tttataaaga tataagtaat    180

tttttcttc cctttttctcc accgccttga gagcgagtac ttttggcaaa ggacggagga    240

aaagctcagc aacattttag ggggcggttg tttctttctt tcttatttct tttttaaggg    300

gaaaaaattt gagtgcatcg cgatggagaa aatgtcccga ccgctccccc tgaatcccac    360

ctttatcccg cctccctacg gcgtgctcag gtccctgctg gagaacccgc tgaagctccc    420

ccttcaccac gaagacgcat ttagtaaaga taaagacaaa gaaaagaagc tggatgatga    480

gagtaacagc ccgacggtcc cccagtcggc attcctgggg cctaccttat gggacaaaac    540

ccttccctat gacggagata ctttccagtt ggaatacatg gacctggagg agtttttgtc    600

agaaaatggc attcccccca gcccatctca gcatgaccac agccctcacc ctcctgggct    660

gcagccagct tcctcggctg ccccctcggt catggacctc agcagccggg cctctgcacc    720

ccttcaccct ggcatcccat ctccgaactg tatgcagagc cccatcagac caggtcagct    780

gttgccagca aaccgcaata caccaagtcc cattgatcct gacaccatcc aggtcccagt    840

gggttatgag ccagacccag cagatcttgc cctttccagc atccctggcc aggaaatgtt    900

tgaccctcgc aaacgcaagt tctctgagga agaactgaag ccacagccca tgatcaagaa    960

agctcgcaaa gtcttcatcc ctgatgacct gaaggatgac aagtactggg caaggcgcag   1020

aaagaacaac atggcagcca agcgctcccg cgacgcccgg aggctgaaag agaaccagat   1080

cgccatccgg gcctcgttcc tggagaagga gaactcggcc ctccgccagg aggtggctga   1140

cttgaggaag gagctgggca aatgcaagaa catacttgcc aagtatgagg ccaggcacgg   1200

gcccctgtag gatggcattt ttgcaggctg gctttggaat agatggacag tttgtttcct   1260

gtctgatagc accacacgca aaccaacctt tctgacatca gcactttacc agaggcataa   1320
```

-continued

```
acacaactga ctcccatttt ggtgtgcatc tgtgtgtgtg tgcgtgtata tgtgcttgtg   1380
ctcatgtgtg tggtcagcgg tatgtgcgtg tgcgtgttcc tttgctcttg ccattttaag   1440
gtagccctct catcgtcttt tagttccaac aaagaaaggt gccatgtctt tactagactg   1500
aggagccctc tcgcgggtct cccatcccct ccctccttca ctcctgcctc ctcagctttg   1560
cttcatgttc gagcttacct actcttccag gactctctgc ttggattcac taaaaagggc   1620
cctggtaaaa tagtggatct cagtttttaa gagtacaagc tcttgtttct gtttagtccg   1680
taagttacca tgctaatgag gtgcacacaa taacttagca ctactccgca gctctagtcc   1740
tttataagtt gctttcctct tactttcagt tttggtgata atcgtcttca aattaaagtg   1800
ctgtttagat ttattagatc ccatatttac ttactgctat ctactaagtt tccttttaat   1860
tctaccaacc ccagataagt aagagtacta ttaatagaac acagagtgtg tttttgcact   1920
gtctgtacct aaagcaataa tcctattgta cgctagagca tgctgcctga gtattactag   1980
tggacgtagg atattttccc tacctaagaa tttcactgtc ttttaaaaaa caaaaagtaa   2040
agtaatgcat ttgagcatgg ccagactatt ccctaggaca aggaagcaga gggaaatggg   2100
aggtctaagg atgaggggtt aatttatcag tacatgagcc aaaaactgcg tcttggatta   2160
gcctttgaca ttgatgtgtt cggttttgtt gttccccttc cctcacaccc tgcctcgccc   2220
ccacttttct agttaacttt ttccatatcc ctcttgacat tcaaaacagt tacttaagat   2280
tcagttttcc cactttttgg taatatatat atttttgtga attatacttt gttgttttta   2340
aaaagaaaat cagttgatta agttaataag ttgatgtttt ctaaggccct ttttcctagt   2400
ggtgtcattt ttgaatgcct cataaattaa tgattctgaa gcttatgttt cttattctct   2460
gtttgctttt gaacgtatgt gctcttataa agtggacttc tgaaaaatga atgtaaaaga   2520
cactggtgta tctcagaagg ggatggtgtt gtcacaaact gtggttaatc caatcaattt   2580
aaatgtttac tatagaccaa aaggagagat tattaaatcg tttaatgttt atacagagta   2640
attataggaa gttctttttt gtacagtatt tttcagatat aaatactgac aatgtatttt   2700
ggaagacata tattatatat agaaaagagg agaggaaaac tattccatgt tttaaaatta   2760
tatagcaaag atatatattc accaatgttg tacagagaag aagtgcttgg gggtttttga   2820
agtctttaat attttaagcc ctatcactga cacatcagca tgttttctgc tttaaattaa   2880
aattttatga cagtatcgag gcttgtgatg acgaatcctg ctctaaaata cacaaggagc   2940
tttcttgttt cttattaggc ctcagaaaga agtcagttaa cgtcacccaa aagcacaaaa   3000
tggattttag tcaaatattt attggatgat acagtgtttt ttaggaaaag catctgccac   3060
aaaaatgttc acttcgaaat tctgagttcc tggaatggca cgttgctgcc agtgccccag   3120
acagttcttt tctaccctgc gggcccgcac gttttatgag gttgatatcg gtgctatgtg   3180
tttggtttat aatttgatag atgtttgact ttaaagatga ttgttctttt gtttcattaa   3240
gttgtaaaat gtcaagaaat tctgctgtta cgacaaagaa acattttacg ctagattaaa   3300
atatcctttc atcaatggga ttttctagtt tcctgccttc agagtatcta atcctttaat   3360
gatctggtgg tctcctcgtc aatccatcag caatgcttct ctcatagtgt catagacttg   3420
ggaaacccaa ccagtaggat atttctacaa ggtgttcatt ttgtcacaag ctgtagataa   3480
cagcaagaga tgggggtgta ttggaattgc aatacattgt tcaggtgaat aataaaatca   3540
aaaacttttg caatcttaag cagagataaa taaaagatag caatatgaga cacaggtgga   3600
cgtagagttg gcctttttac aggcaaagag gcgaattgta gaattgttag atggcaatag   3660
tcattaaaaa catagaaaaa tgatgtcttt aagtggagaa ttgtggaagg attgtaacat   3720
```

```
ggaccatcca aatttatggc cgtatcaaat ggtagctgaa aaaactatat ttgagcactg   3780

gtctctcttg gaattagatg tttatatcaa atgagcatct caaatgtttt ctgcagaaaa   3840

aaataaaaag attctaataa aaaaa                                         3865
```

<210> SEQ ID NO 9
<211> LENGTH: 2656
<212> TYPE: DNA
<213> ORGANISM: Homo sapiens

<400> SEQUENCE: 9

```
cacacctgat ggtgtgactc ggccgacgcg agcgccgcgc ttcgcttcag ctgctagctg     60

gcccaaggga ggcgaccgcg gagggtggcg aggggcggcc aggacccgca gccccggggc    120

cgggccggtc cggaccgcca gggagggcag gtcagtgggc agatcgcgtc cgcgggattc    180

aatctctgcc cgctctgata acagtccttt tccctggcgc tcacttcgtg cctggcaccc    240

ggctgggcgc ctcaagaccg ttgtctcttc gatcgcttct ttggacttgg cgaccatttc    300

agagatgtct tccagaagta ccaaagattt aattaaaagt aagtggggat cgaagcctag    360

taactccaaa tccgaaacta cattagaaaa attaaaggga gaaattgcac acttaaagac    420

atcagtggat gaaatcacaa gtgggaaagg aaagctgact gataaagaga gacacagact    480

tttggagaaa attcgagtcc ttgaggctga gaaggagaag aatgcttatc aactcacaga    540

gaaggacaaa gaaatacagc gactgagaga ccaactgaag gccagatata gtactaccgc    600

attgcttgaa cagctggaag agacaacgag agaaggagaa aggagggagc aggtgttgaa    660

agccttatct gaagagaaag acgtattgaa acaacagttg tctgctgcaa cctcacgaat    720

tgctgaactt gaaagcaaaa ccaatacact ccgtttatca cagactgtgg ctccaaactg    780

cttcaactca tcaataaata atattcatga aatggaaata cagctgaaag atgctctgga    840

gaaaaatcag cagtggctcg tgtatgatca gcagcgggaa gtctatgtaa aaggactttt    900

agcaaagatc tttgagttgg aaaagaaaac ggaaacagct gctcattcac tcccacagca    960

gacaaaaaag cctgaatcag aaggttatct tcaagaagag aagcagaaat gttacaacga   1020

tctcttggca agtgcaaaaa aagatcttga ggttgaacga caaaccataa ctcagctgag   1080

ttttgaactg agtgaatttc gaagaaaata tgaagaaacc caaaaagaag ttcacaattt   1140

aaatcagctg ttgtattcac aaagaagggc agatgtgcaa catctggaag atgataggca   1200

taaaacagag aagatacaaa aactcaggga agagaatgat attgctaggg gaaaacttga   1260

agaagagaag aagagatccg aagagctctt atctcaggtc cagtttcttt acacatctct   1320

gctaaagcag caagaagaac aaacaagggt agctctgttg gaacaacaga tgcaggcatg   1380

tactttagac tttgaaaatg aaaaactcga ccgtcaacat gtgcagcatc aattgcatgt   1440

aattcttaag gagctccgaa aagcaagaaa tcaaataaca cagttggaat ccttgaaaca   1500

gcttcatgag tttgccatca cagagccatt agtcactttc caaggagaga ctgaaaacag   1560

agaaaaagtt gccgcctcac caaaaagtcc cactgctgca ctcaatgaaa gcctggtgga   1620

atgtcccaag tgcaatatac agtatccagc cactgagcat cgcgatctgc ttgtccatgt   1680

ggaatactgt tcaaagtagc aaaataagta tttgttttga tattaaaaga ttcaatactg   1740

tattttctgt tagcttgtgg gcattttgaa ttatatattt cacattttgc ataaaactgc   1800

ctatctacct ttgacactcc agcatgctag tgaatcatgt atcttttagg ctgctgtgca   1860

tttctcttgg cagtgatacc tccctgacat ggttcatcat caggctgcaa tgacagaatg   1920
```

```
tggtgagcag cgtctactga gactactaac attttgcact gtcaaaatac ttggtgagga   1980

aaagatagct caggttattg ctaatgggtt aatgcaccag caagcaaaat attttatgtt   2040

ttgggggttt tgaaaaatca aagataatta accaaggatc ttaactgtgt tcgcattttt   2100

tatccaagca cttagaaaac ctacaatcct aattttgatg tccattgtta agaggtggtg   2160

atagatacta tttttttttt catattgtat agcggttatt agaaaagttg ggattttct    2220

tgatctttat tgctgcttac cattgaaact taacccagct gtgttcccca actctgttct   2280

gcgcacgaaa cagtatctgt ttgaggcata atcttaagtg gccacacaca atgttttctc   2340

ttatgttatc tggcagtaac tgtaacttga attacattag cacattctgc ttagctaaaa   2400

ttgttaaaat aaactttaat aaacccatgt agccctctca tttgattgac agtattttag   2460

ttatttttgg cattcttaaa gctgggcaat gtaatgatca gatctttgtt tgtctgaaca   2520

ggtattttta tacatgcttt ttgtaaacca aaaactttta aatttcttca ggtttctaa    2580

catgcttacc actgggctac tgtaaatgag aaaagaataa aattatttaa tgttttaaaa   2640

aaaaaaaaaa aaaaaa                                                   2656
```

<210> SEQ ID NO 10
<211> LENGTH: 3685
<212> TYPE: DNA
<213> ORGANISM: Homo sapiens

<400> SEQUENCE: 10

```
agtggactca cgcaggcgca ggagactaca cttcccagga actccgggcc gcgttgttcg     60

ctggtacctc cttctgactt ccggtattgc tgcggtctgt agggccaatc gggagcctgg    120

aattgctttc ccggcgctct gattggtgca ttcgactagg ctgcctgggt tcaaaatttc    180

aacgatactg aatgagtccc gcggcgggtt ggctcgcgct tcgttgtcag atctgaggcg    240

aggctaggtg agccgtggga agaaaagagg gagcagctag ggcgcgggtc tccctcctcc    300

cggagtttgg aacggctgaa gttcaccttc cagcccctag cgccgttcgc gccgctaggc    360

ctggcttctg aggcggttgc ggtgctcggt cgccgcctag gcggggcagg gtgcgagcag    420

gggcttcggg ccacgcttct cttggcgaca ggattttgct gtgaagtccg tccgggaaac    480

ggaggaaaaa aagagttgcg ggaggctgtc ggctaataac ggttcttgat acatatttgc    540

cagacttcaa gatttcagaa aaggggtgaa agagaagatt gcaactttga gtcagacctg    600

taggcctgat agactgatta aaccacagaa ggtgacctgc tgagaaaagt ggtacaaata    660

ctgggaaaaa cctgctcttc tgcgttaagt gggagacaat gtcacaagtt aaaagctctt    720

attcctatga tgccccctcg gatttcatca atttttcatc cttggatgat gaaggagata    780

ctcaaaacat agattcatgg tttgaggaga aggccaattt ggagaataag ttactgggga    840

agaatggaac tggagggctt tttcagggca aaactccttt gagaaaggct aatcttcagc    900

aagctattgt cacacctttg aaaccagttg acaacactta ctacaaagag gcagaaaaag    960

aaaatcttgt ggaacaatcc attccgtcaa atgcttgttc ttccctggaa gttgaggcag   1020

ccatatcaag aaaaactcca gcccagcctc agagaagatc tcttaggctt tctgctcaga   1080

aggatttgga acagaaagaa aagcatcatg taaaaatgaa agccaagaga tgtgccactc   1140

ctgtaatcat cgatgaaatt ctaccctcta agaaaatgaa agtttctaac aacaaaaaga   1200

agccagagga agaaggcagt gctcatcaag atactgctga aaagaatgca tcttccccag   1260

agaaagccaa gggtagacat actgtgcctt gtatgccacc tgcaaagcag aagtttctaa   1320

aaagtactga ggagcaagag ctggagaaga gtatgaaaat gcagcaagag gtggtggaga   1380
```

```
tgcggaaaaa gaatgaagaa ttcaagaaac ttgctctggc tggaataggg caacctgtga   1440
agaaatcagt gagccaggtc accaaatcag ttgacttcca cttccgcaca gatgagcgaa   1500
tcaaacaaca tcctaagaac caggaggaat ataaggaagt gaactttaca tctgaactac   1560
gaaagcatcc ttcatctcct gcccgagtga ctaagggatg taccattgtt aagcctttca   1620
acctgtccca aggaaagaaa agaacatttg atgaaacagt ttctacatat gtgccccttg   1680
cacagcaagt tgaagacttc cataaacgaa cccctaacag atatcatttg aggagcaaga   1740
aggatgatat taacctgtta ccctccaaat cttctgtgac caagatttgc agagacccac   1800
agactcctgt actgcaaacc aaacaccgtg cacgggctgt gacctgcaaa agtacagcag   1860
agctggaggc tgaggagctc gagaaattgc aacaatacaa attcaaagca cgtgaacttg   1920
atcccagaat acttgaaggt gggcccatct tgcccaagaa accacctgtg aaaccaccca   1980
ccgagcctat tggctttgat ttggaaattg agaaaagaat ccaggagcga gaatcaaaga   2040
agaaaacaga ggatgaacac tttgaatttc attccagacc ttgccctact aagattttgg   2100
aagatgttgt gggtgttcct gaaaagaagg tacttccaat caccgtcccc aagtcaccag   2160
cctttgcatt gaagaacaga attcgaatgc ccaccaaaga agatgaggaa gaggacgaac   2220
cggtagtgat aaaagctcaa cctgtgccac attatggggt gccttttaag ccccaaatcc   2280
cagaggcaag aactgtggaa atatgccctt tctcgtttga ttctcgagac aaagaacgtc   2340
agttacagaa ggagaagaaa ataaaagaac tgcagaaagg ggaggtgccc aagttcaagg   2400
cacttccctt gcctcatttt gacaccatta acctgccaga gaagaaggta aagaatgtga   2460
cccagattga acctttctgc ttggagactg acagaagagg tgctctgaag gcacagactt   2520
ggaagcacca gctggaagaa gaactgagac agcagaaaga agcagcttgt ttcaaggctc   2580
gtccaaacac cgtcatctct caggagccct ttgttcccaa gaaagagaag aaatcagttg   2640
ctgagggcct ttctggttct ctagttcagg aacctttca gctggctact gagaagagag    2700
ccaaagagcg gcaggagctg gagaagagaa tggctgaggt agaagcccag aaagcccagc   2760
agttggagga ggccagacta caggaggaag agcagaaaaa agaggagctg gccaggctac   2820
ggagagaact ggtgcataag gcaaatccaa tacgcaagta ccagggtctg gagataaagt   2880
caagtgacca gcctctgact gtgcctgtat ctcccaaatt ctccactcga ttccactgct   2940
aaactcagct gtgagctgcg gataccgccc ggcaatggga cctgctctta acctcaaacc   3000
taggaccgtc ttgctttgtc attgggcatg gagagaaccc atttctccag acttttacct   3060
acccgtgcct gagaaagcat acttgacaac tgtggactcc agttttgttg agaattgttt   3120
tcttacatta ctaaggctaa taatgagatg taactcatga atgtctcgat tagactccat   3180
gtagttactt cctttaaacc atcagccggc cttttatatg ggtcttcact ctgactagaa   3240
tttagtctct gtgtcagcac agtgtaatct ctattgctat tgccccttac gactctcacc   3300
ctctccccac ttttttaaa aattttaacc agaaaataaa gatagttaaa tcctaagata    3360
gagattaagt catggtttaa atgaggaaca atcagtaaat cagattctgt cctcttctct   3420
gcataccgtg aatttatagt taaggatccc tttgctgtga gggtagaaaa cctcaccaac   3480
tgcaccagtg aggaagaaga ctgcgtggat tcatggggag cctcacagca gccacgcagc   3540
aggctctggg tggggctgcc gttaaggcac gttctttcct tactggtgct gataacaaca   3600
gggaaccgtg cagtgtgcat tttaagacct ggcctggaat aaatacgttt tgtctttccc   3660
tcaaaaaaaa aaaaaaaaaa aaaaa                                          3685
```

<210> SEQ ID NO 11
<211> LENGTH: 3670
<212> TYPE: DNA
<213> ORGANISM: Homo sapiens

<400> SEQUENCE: 11

```
ccggtttgtt agggagtcgt gtacgtgcct tggtcgcttc tgtagctccg agggcaggtt     60
gcggaagaaa gcccaggcgg tctgtggccc agaggaaagg cctgcagcag gacgaggacc    120
tgagccagga atgcaggatg gcggcggtga agaaggaagg gggtgctctg agtgaagcca    180
tgtccctgga gggagatgaa tgggaactga gtaaagaaaa tgtacaacct ttaaggcaag    240
ggcggatcat gtccacgctt cagggagcac tggcacaaga atctgcctgt aacaatactc    300
ttcagcagca gaaacgggca tttgaatatg aaattcgatt ttacactgga aatgaccctc    360
tggatgtttg ggataggtat atcagctgga cagagcagaa ctatcctcaa ggtgggaagg    420
agagtaatat gtcaacgtta ttagaaagag ctgtagaagc actacaagga gaaaaacgat    480
attatagtga tcctcgattt ctcaatctct ggcttaaatt agggcgttta tgcaatgagc    540
ctttggatat gtacagttac ttgcacaacc aagggattgg tgtttcactt gctcagttct    600
atatctcatg ggcagaagaa tatgaagcta gagaaaactt taggaaagca gatgcgatat    660
ttcaggaagg gattcaacag aaggctgaac cactagaaag actacagtcc cagcaccgac    720
aattccaagc tcgagtgtct cggcaaactc tgttggcact tgagaaagaa gaagaggagg    780
aagtttttga gtcttctgta ccacaacgaa gcacactagc tgaactaaag agcaaaggga    840
aaaagacagc aagagctcca atcatccgtg taggaggtgc tctcaaggct ccaagccaga    900
acagaggact ccaaaatcca tttcctcaac agatgcaaaa taatagtaga attactgttt    960
ttgatgaaaa tgctgatgag gcttctacag cagagttgtc taagcctaca gtccagccat   1020
ggatagcacc ccccatgccc agggccaaag agaatgagct gcaagcaggc ccttggaaca   1080
caggcaggtc cttggaacac aggcctcgtg gcaatacagc ttcactgata gctgtacccg   1140
ctgtgcttcc cagtttcact ccatatgtgg aagagactgc acgacagcca gttatgacac   1200
catgtaaaat tgaacctagt ataaaccaca tcctaagcac cagaaagcct ggaaaggaag   1260
aaggagatcc tctacaaagg gttcagagcc atcagcaagc gtctgaggag aagaaagaga   1320
agatgatgta ttgtaaggag aagatttatg caggagtagg ggaattctcc tttgaagaaa   1380
ttcgggctga agttttccgg aagaaattaa aagagcaaag ggaagccgag ctattgacca   1440
gtgcagagaa gagagcagaa atgcagaaac agattgaaga gatggagaag aagctaaaag   1500
aaatccaaac tactcagcaa gaaagaacag gtgatcagca agaagagacg atgcctacaa   1560
aggagacaac taaactgcaa attgcttccg agtctcagaa aataccagga atgactctat   1620
ccagttctgt ttgtcaagta aactgttgtg ccagagaaac ttcacttgcg gagaacattt   1680
ggcaggaaca acctcattct aaaggtccca gtgtaccttt ctccattttt gatgagtttc   1740
ttctttcaga aaagaagaat aaaagtcctc ctgcagatcc cccacgagtt ttagctcaac   1800
gaagacccct tgcagttctc aaaacctcag aaagcatcac ctcaaatgaa gatgtgtctc   1860
cagatgtttg tgatgaattt acaggaattg aacccttgag cgaggatgcc attatcacag   1920
gcttcagaaa tgtaacaatt tgtcctaacc cagaagacac ttgtgacttt gccagagcag   1980
ctcgttttgt atccactcct tttcatgaga taatgtcctt gaaggatctc ccttctgatc   2040
ctgagagact gttaccggaa gaagatctag atgtaaagac ctctgaggac cagcagacag   2100
cttgtggcac tatctacagt cagactctca gcatcaagaa gctgagccca attattgaag   2160
```

```
acagtcgtga agccacacac tcctctggct tctctggttc ttctgcctcg gttgcaagca   2220
cctcctccat caaatgtctt caaattcctg agaaactaga acttactaat gagacttcag   2280
aaaaccctac tcagtcacca tggtgttcac agtatcgcag acagctactg aagtccctac   2340
cagagttaag tgcctctgca gagttgtgta tagaagacag accaatgcct aagttggaaa   2400
ttgagaagga aattgaatta ggtaatgagg attactgcat taaacgagaa tacctaatat   2460
gtgaagatta caagttattc tgggtggcgc caagaaactc tgcagaatta acagtaataa   2520
aggtatcttc tcaacctgtc ccatgggact tttatatcaa cctcaagtta aaggaacgtt   2580
taaatgaaga ttttgatcat tttgcagct gttatcaata tcaagatggc tgtattgttt   2640
ggcaccaata tataaactgc ttcacccttc aggatcttct ccaacacagt gaatatatta   2700
cccatgaaat aacagtgttg attatttata accttttgac aatagtggag atgctacaca   2760
aagcagaaat agtccatggt gacttgagtc caaggtgtct gattctcaga aacagaatcc   2820
acgatcccta tgattgtaac aagaacaatc aagctttgaa gatagtggac ttttcctaca   2880
gtgttgacct tagggtgcag ctggatgttt ttaccctcag cggctttcgg actgtacaga   2940
tcctggaagg acaaaagatc ctggctaact gttcttctcc ctaccaggta gacctgtttg   3000
gtatagcaga tttagcacat ttactattgt tcaaggaaca cctacaggtc ttctgggatg   3060
ggtccttctg gaaacttagc caaaatattt ctgagctaaa agatggtgaa ttgtggaata   3120
aattctttgt gcggattctg aatgccaatg atgaggccac agtgtctgtt cttggggagc   3180
ttgcagcaga aatgaatggg gtttttgaca ctacattcca aagtcacctg aacaaagcct   3240
tatggaaggt agggaagtta actagtcctg gggctttgct ctttcagtga gctaggcaat   3300
caagtctcac agattgctgc ctcagagcaa tggttgtatt gtggaacact gaaactgtat   3360
gtgctgtaat ttaatttagg acacatttag atgcactacc attgctgttc tactttttgg   3420
tacaggtata ttttgacgtc actgatattt tttatacagt gatatactta ctcatggcct   3480
tgtctaactt ttgtgaagaa ctattttatt ctaaacagac tcattacaaa tggttacctt   3540
gttatttaac ccatttgtct ctacttttcc ctgtactttt cccatttgta atttgtaaaa   3600
tgttctctta tgatcaccat gtattttgta aataataaaa tagtatctgt taaaaaaaaa   3660
aaaaaaaaaa                                                          3670
```

```
<210> SEQ ID NO 12
<211> LENGTH: 4504
<212> TYPE: DNA
<213> ORGANISM: Homo sapiens

<400> SEQUENCE: 12
```

```
gggcagtccg cactgcaatt ggttggcgtc tccgggacgg atttgaaact tggcggttaa     60
agctccggct gggacagggc ggcgggaggc ccagggagaa cggggaaggg acatttagtt    120
tgagacggtg ctgagatagg atcatgaagg aagaggtgaa gggaattcct gtaagagtgg    180
cgctgcgttg tcgccctctg gtccccaaag agattagcga gggctgccag atgtgccttt    240
ccttcgtgcc cggagagcct caggtggtgg ttggtacaga taaatccttc acctacgatt    300
ttgtatttga tccctctact gaacaggaag aagtcttcaa tacagcagta gcgccactca    360
taaaaggtgt atttaaagga tataatgcaa cggtcctggc ctatgggcag actggctctg    420
gaaaaaccta ttcaatggga ggtgcatata ctgcagagca agagaatgaa ccaacagttg    480
gggttattcc tagggtaata caactgctct tcaaagaaat tgataaaaag agtgactttg    540
```

-continued

```
aatttactct gaaagtgtct tacttagaga tttacaatga agaaattttg gatcttctat    600
gcccatctcg tgagaaagct caaataaata tacgagagga tcctaaggaa ggcataaaga    660
ttgtgggact cactgagaag actgttttgg ttgccttgga tactgtttcc tgtttggaac    720
agggcaacaa ctctaggact gtggcctcca cggctatgaa ctcccagtcg tcccgatctc    780
atgccatctt tacaatctcc ttagagcaaa gaaagaaaag tgacaagaat agcagctttc    840
gctccaagct gcatcttgta gacctcgctg gatcagaaag acagaagaaa accaaggctg    900
aaggggatcg tctaaaagag ggtattaata ttaaccgagg cctcctatgc ttgggaaatg    960
taatcagtgc tcttggagat gacaaaaagg gtggctttgt gccctacaga gattccaagt   1020
tgactcgact gcttcaagat tctctaggag gtaatagcca tactcttatg atagcctgtg   1080
tgagtcctgc tgactccaat ctagaggaaa cattaaatac ccttcgctat gctgacagag   1140
caagaaaaat caagaacaaa cctattgtta atattgatcc ccagacagct gaacttaatc   1200
atctaaagca acaggtacaa cagctacaag tcttgttgct acaggcccat ggaggtaccc   1260
tgcctggatc tataactgtg gaaccatcag agaatctaca atccctgatg gagaagaatc   1320
agtccctggt agaggagaat gaaaaattaa gtcgtggtct gagcgaggca gctggtcaga   1380
cagcccagat gttggagagg atcattttga cagagcaagc gaatgaaaaa atgaacgcca   1440
agctagaaga gctcaggcag catgcggcct gcaaactgga tcttcaaaag ctagtggaga   1500
ctttggaaga ccaggaattg aaagaaaatg tagagataat ttgtaacctg cagcaattga   1560
ttacccagtt atcggatgaa actgttgctt gcatggctgc agccattgat actgcggtgg   1620
agcaagaagc ccaagtagaa accagtccag agacgagcag gtcttctgac gcttttacca   1680
ctcagcatgc tctccgtcaa gcgcagatgt ctaaggagct ggttgagttg aataaagcgc   1740
ttgcactgaa agaggccctg gctaggaaga tgactcagaa tgacagccaa ctgcagccca   1800
ttcagtacca ataccaggat aacataaaag agctagaatt agaagtcatc aatctgcaaa   1860
aggaaaagga agaattggtt cttgaacttc agacagcaaa gaaggatgcc aaccaagcca   1920
agttgagtga gcgccgccgc aaacgtctcc aggagctgga gggtcaaatt gctgatctga   1980
agaagaaact gaatgagcag tccaaacttc tgaaactaaa ggaatccaca gagcgtactg   2040
tctccaaact gaaccaggag atacggatga tgaaaaacca gcgggtacag ttaatgcgtc   2100
aaatgaaaga agatgctgag aagtttagac agtggaagca gaaaaaagac aaagaagtaa   2160
tacagttaaa agaacgagac cgtaagaggc aatatgagct gctgaaactt gaaagaaact   2220
tccagaaaca atccaatgtg ctcagacgta aaacggagga ggcagcagct gccaacaagc   2280
gtctcaagga tgctctccag aaacaacggg aggttgcaga taagcggaaa gagactcaga   2340
gccgtggaat ggaaggcact gcagctcgag tgaagaattg gcttggaaac gaaattgagg   2400
ttatggtcag tactgaggaa gccaaacgcc atctgaatga cctccttgaa gatagaaaga   2460
tcctggctca agatgtggct caactcaaag aaaaaaagga atctggggag aatccacctc   2520
ctaaactccg gaggcgtaca ttctccctta ctgaagtgcg tggtcaagtt tcggagtcag   2580
aagattctat tacaaagcag attgaaagcc tagagactga aatggaattc aggagtgctc   2640
agattgctga cctacagcag aagctgctgg atgcagaaag tgaagacaga ccaaaacaac   2700
gctgggagaa tattgccacc attctggaag ccaagtgtgc cctgaaatat ttgattggag   2760
agctggtctc ctccaaaata caggtcagca aacttgaaag cagcctgaaa cagagcaaga   2820
ccagctgtgc tgacatgcag aagatgctgt ttgaggaacg aaatcatttt gccgagatag   2880
agacagagtt acaagctgag ctggtcagaa tggagcaaca gcaccaagag aaggtgctgt   2940
```

```
accttctcag ccagctgcag caaagccaaa tggcagagaa gcagttagag gaatcagtca   3000
gtgaaaagga acagcagctg ctgagcacac tgaagtgtca ggatgaagaa cttgagaaaa   3060
tgcgagaagt gtgtgagcaa aatcagcagc ttctccgaga gaatgaaatc atcaagcaga   3120
aactgaccct cctccaggta gccagcagac agaaacatct tcctaaggat acccttctat   3180
ctccagactc ttcttttgaa tatgtcccac ctaagccaaa accttctcgt gttaaagaaa   3240
agttcctgga gcaaagcatg gacatcgagg atctaaaata ttgttcagag cattctgtga   3300
atgagcatga ggatggtgat ggtgatgatg atgaggggga tgacgaggaa tggaagccaa   3360
caaaattagt taaggtgtcc aggaagaaca tccaagggtg ttcctgcaag ggctggtgtg   3420
gaaacaagca gtgtgggtgc aggaagcaaa agtcagactg tggtgtggac tgttgctgtg   3480
accccacaaa gtgtcggaac cgccagcaag gcaaggatag cttgggcact gttgaacgga   3540
cccaggattc cgaaggctcc ttcaaactgg aggatcctac cgaggtgacc ccaggattga   3600
gcttctttaa tcccgtctgt gccacccccca atagcaagat cctgaaagag atgtgcgatg   3660
tggagcaggt gctgtcaaag aagactcccc cagctccctc ccttttgac ctcccagagt    3720
tgaaacatgt agcaacagaa taccaagaaa acaaggctcc agggaagaaa aagaaacggg   3780
ctctggccag caacaccagc ttcttctctg gctgctcccc tatcgaagaa gaggcccact   3840
gaagttggag tcatcatctc tacccccagt ctggcttggg agatgctttc aggttgcagc   3900
cagaaggggt tttttaaatg acttctctgg atttcaggtt tcttgctgtt gaaaaaagga   3960
acaaagcgtt actgaaaaga aggtaacctt tgttggatgt gggccttagc ctccaggtcc   4020
agactactac tctatgttct ccagaagggt gctaagtcac ctactgaaga gagaaccaac   4080
tgactttcct attgactcat caggaaccag tcctcagtct ggtcaagttg tttcttattt   4140
gtgagcagtt caggctatct cctgatgggg atgaggccaa ggctttctta tcttttggtt   4200
gtctctgctt aatggaggag cctggcctag gatggaggcc tggcttagat ctttcattcc   4260
acctcaggaa tgaggttgtg atctttcctg tcctgaccct ctctgaatta tgtttcaata   4320
gtactcttga ttgtctgcca tgttgttgaa gcaaatgaat tatttttaaa tgttaagtaa   4380
gtaaataaac cttagcccgt ctactgtttg ggaagatcct tctgtgctag agggagaaat   4440
aaaatttcaa cctgtgttcc tcagcccctg aggaagctat taaggggatt cattacaagt   4500
aaaa                                                                4504
```

<210> SEQ ID NO 13
<211> LENGTH: 1566
<212> TYPE: DNA
<213> ORGANISM: Homo sapiens

<400> SEQUENCE: 13

```
gggccgccca atggggcgca agcgacgcgg tatttgaatc ctggaacaag gctacagcgt     60
cgaagatccc cagcgctgcg ggctcggaga gcagtcctaa cggcgcctcg tacgctagtg    120
tcctcccttt tcagtccgcg tccctccctg ggccgggctg gcactcttgc cttccccgtc    180
cctcatggcg ctgctccgac gcccgacggt gtccagtgat ttggagaata ttgacacagg    240
agttaattct aaagttaaga gtcatgtgac tattaggcga actgttttag aagaaattgg    300
aaatagagtt acaaccagag cagcacaagt agctaagaaa gctcagaaca ccaaagttcc    360
agttcaaccc accaaaacaa caaatgtcaa caaacaactg aaacctactg cttctgtcaa    420
accagtacag atggaaaagt tggctccaaa gggtccttct cccacacctg aggatgtctc    480
```

-continued

```
catgaaggaa gagaatctct gccaagcttt ttctgatgcc ttgctctgca aaatcgagga    540
cattgataac gaagattggg agaaccctca gctctgcagt gactacgtta aggatatcta    600
tcagtatctc aggcagctgg aggttttgca gtccataaac ccacatttct tagatggaag    660
agatataaat ggacgcatgc gtgccatcct agtggattgg ctggtacaag tccactccaa    720
gtttaggctt ctgcaggaga ctctgtacat gtgcgttggc attatggatc gatttttaca    780
ggttcagcca gtttcccgga agaagcttca attagttggg attactgctc tgctcttggc    840
ttccaagtat gaggagatgt tttctccaaa tattgaagac tttgtttaca tcacagacaa    900
tgcttatacc agttcccaaa tccgagaaat ggaaactcta attttgaaag aattgaaatt    960
tgagttgggt cgacccttgc cactacactt cttaaggcga gcatcaaaag ccggggaggt   1020
tgatgttgaa cagcacactt tagccaagta tttgatggag ctgactctca tcgactatga   1080
tatggtgcat tatcatcctt ctaaggtagc agcagctgct tcctgcttgt ctcagaaggt   1140
tctaggacaa ggaaaatgga acttaaagca gcagtattac acaggataca cagagaatga   1200
agtattggaa gtcatgcagc acatggccaa gaatgtggtg aaagtaaatg aaaacttaac   1260
taaattcatc gccatcaaga ataagtatgc aagcagcaaa ctcctgaaga tcagcatgat   1320
ccctcagctg aactcaaaag ccgtcaaaga ccttgcctcc ccactgatag gaaggtccta   1380
ggctgccgtg gcccctgggg atgtgtgctt cattgtgccc tttttcttat tggtttagaa   1440
ctcttgattt tgtacatagt cctctggtct atctcatgaa acctcttctc agaccagttt   1500
tctaaacata tattgaggaa aaataaagcg attggttttt cttaaggtaa aaaaaaaaaa   1560
aaaaaa                                                               1566
```

<210> SEQ ID NO 14
<211> LENGTH: 7293
<212> TYPE: DNA
<213> ORGANISM: Homo sapiens

<400> SEQUENCE: 14

```
ctggggagcc ggcgctggag gtggtgagtg gcgtggggac tgtgtcgagg gggtccccaa     60
ggtgccggac cctgcggagg ggcgaagttt cggcactggg gagggcgtgc ggacgctttc    120
cctacaggcg accactgctc tgcgggcggg tggtcttagc tccagtcccc cattcagttc    180
ctcagcattc caggtcggcg gcgaaggggt ccccgaacga agggcgcaag gcagcgtctc    240
tgctgggacc gggaagccgg acttcagggc ctctcggccc gtgggcttct ccccgagtct    300
ccccgagtcg gttggcatta agagtttagc agatactttc agaaatggat acataagaaa    360
tggctggaaa tcaaatgaat gtccaaagaa gagcttaggg tcttagtaac attctttttt    420
aaaataactg tctgccaaaa tgtcattaca cagtactcat aatagaaata acagcggtga    480
tattcttgat attccttctt cccaaaatag ttcatcactg aatgccctca cccacagtag    540
ccgacttaag ctgcatttga agtcggatat gtcagaatgt gaaaatgatg atccattatt    600
gagatctgca ggtaaagtca gagacataaa tagaacttat gttatttctg ccagtagaaa    660
aacagcagac atgcccctta cccctaatcc tgtaggtaga ttggcacttc agaggagaac    720
tacaaggaac aaagaatcat ctttgcttgt tagtgagttg gaagacacaa ctgaaaaaac    780
agcagaaaca cgtcttacat tacaacgtcg tgctaaaaca gattctgcag aaaagtggaa    840
aacagctgaa atagattctg tcaaaatgac actgaatgtg ggaggtgaaa cagaaaataa    900
tggtgtttct aaggaaagta gaacaaatgt aaggattgta aataatgcta aaaactcttt    960
tgttgcctct tctgtacctt tagatgaaga tccacaggtc attgaaatga tggctgataa   1020
```

gaaatacaaa gaaacatttt ctgcccccag tagagcaaat gaaaatgttg cacttaagta 1080
ctcaagtaat agaccaccca ttgcttccct gagtcagact gaagttgtta gatcaggaca 1140
cttgacaacg aaacctactc agagcaagtt ggatatcaaa gtgttgggaa caggaaactt 1200
gtatcataga agtattggga aggaaattgc aaaaacttca aataaatttg ggagcttaga 1260
aaaaagaaca cctacaaaat gtacaacaga acacaaactg acaacaaagt gcagcctgcc 1320
tcagcttaag agcccagctc catcaatact gaagaataga atgtctaacc ttcaagttaa 1380
acaaagacca aaaagttcct ttcttgcaaa taaacaggaa agatccgcag aaaatacaat 1440
tcttcccgaa gaagaaactg tagttcagaa cacctctgca ggaaaagacc ccttaaaagt 1500
agagaatagt caagtgacag tggcagtacg cgtaagacct ttcaccaaga gagagaagat 1560
tgaaaaagca tcccaggtag tcttcatgag tgggaaagaa ataactgtgg aacaccctga 1620
cacgaaacaa gtttataatt ttatttatga tgtttcattc tggtcttttg atgaatgtca 1680
tcctcactac gctagccaga caactgtcta tgagaagcta gcagcaccac tcctagaaag 1740
agccttcgaa ggcttcaata cctgtctttt tgcttatggt cagactggct ctggaaaatc 1800
atatacgatg atgggattta gtgaagaacc aggaataatt ccaagatttt gtgaagatct 1860
tttttctcaa gtagccagaa aacaaaccca agaggtcagc tatcacattg aaatgagctt 1920
ctttgaagta tataatgaaa aaattcacga ccttctggtt tgtaaagatg aaaatgggca 1980
gagaaagcaa ccactgagag tgagggaaca tcctgtttat ggaccatatg ttgaagcact 2040
gtcaatgaac attgtcagtt cttacgctga tatccagagt tggctagaat tgggaaataa 2100
acaaagagct actgctgcta ctggtatgaa tgataaaagt tcccgatctc attcagtttt 2160
caccctggtg atgacccaga ccaagacaga atttgtggaa ggggaagaac acgatcacag 2220
aataacaagt cgaattaacc taatagatct ggcaggcagt gagcgctgct ctacggctca 2280
cactaatgga gatcgactaa aggaaggtgt gagtattaat aagtccttgc taactttggg 2340
aaaagttata tctgcacttt cggaacaagc aaaccaaagg agtgttttta ttccttatcg 2400
tgaatctgtt cttacatggc tgttaaaaga aagtctgggt ggaaattcaa aaactgcaat 2460
gattgctacg attagtcccg ctgccagcaa catagaagaa acattaagca cacttagata 2520
tgctaaccaa gcccgtttaa tagtcaacat tgctaaagta aatgaagata tgaacgctaa 2580
gttaattaga gaattgaagg cagaaattgc aaagctaaaa gctgctcaga gaaacagtcg 2640
gaatattgac cctgaacgat acaggctctg tcggcaagaa ataacatcct taagaatgaa 2700
actgcatcaa caggagagag acatggcaga aatgcaaaga gtgtggaaag aaaagtttga 2760
acaagctgaa aaaagaaaac ttcaagaaac aaaagagtta cagaaagcag gaattatgtt 2820
tcaaatggac aatcatttac caaaccttgt taatctgaat gaagatccac aactatctga 2880
gatgctgcta tatatgataa aagaaggaac aactacagtt ggaaagtata aaccaaactc 2940
aagccatgat attcagttat ctggggtgct gattgctgat gatcattgta ctatcaaaaa 3000
ttttggtggg acagtgagta ttatcccagt tggggaagca aagacatatg taaatggaaa 3060
acatattttg gaaatcacag tattacgtca tggtgatcga gtgattcttg gtggagatca 3120
ttattttaga tttaatcatc cagtagaagt ccagaaagga aaaaggccat ctggaagaga 3180
tactcctata agtgagggtc caaaagactt tgaatttgca aaaaatgagt tgctcatggc 3240
acagagatca caacttgaag cagaaataaa agaggctcag ttgaaggcaa aggaagaaat 3300
gatgcaagga atccagattg caaaagaaat ggctcagcaa gagctttctt ctcaaaaagc 3360

```
tgcatatgaa agcaaaataa aagcactgga agcagaactg agagaagagt ctcaaaggaa   3420
aaaaatgcag gaaataaata accagaaggc taatcacaaa attgaggaat tagaaaaggc   3480
aaagcagcat cttgaacagg aaatatatgt caacaaaaag cgattagaaa tggaaacatt   3540
ggctacaaaa caggctttag aagaccatag catccgccat gcaagaattc tggaagcttt   3600
agaaactgaa aagcaaaaaa ttgctaaaga agtacaaatt ctacagcaga atcggaataa   3660
tagggataaa acttttacag tgcagacaac ttggagctct atgaaactct caatgatgat   3720
tcaggaagcc aatgctatca gcagcaaatt gaaaacatac tatgtttttg gcagacatga   3780
tatatcagat aaaagtagtt ctgacacttc tattcgggtt cgtaacctga aactaggaat   3840
ctcaacattc tggagtctgg aaaagtttga atctaaactt gcagcaatga aagaacttta   3900
tgagagtaat ggtagtaaca ggggtgaaga tgccttttgt gatcctgaag atgaatggga   3960
acccgacatt acagatgcac cagtttcttc actttctaga aggaggagta ggagtttgat   4020
gaagaacaga agaatttctg gttgtttaca tgacatacaa gtccatccaa ttaagaattt   4080
gcattcttca cattcatcag gtttaatgga caaatcaagc actatttact caaattcagc   4140
agagtccttt cttcctggaa tttgcaaaga attgattggt tcttcgttag atttttttgg   4200
acagagttat gatgaagaaa gaactatagc agacagccta attaatagtt ttcttaaaat   4260
ttataatggg ctatttgcca tttccaaggc tcatgaagaa caagatgaag aaagtcaaga   4320
taacttgttt tcttctgatc gagcaatcca gtcacttact attcagactg catgtgcttt   4380
tgagcagcta gtagtgctaa tgaaacactg gctgagtgat ttactgcctt gtaccaacat   4440
agcaagactt gaggatgagt tgagacaaga agttaaaaaa ctgggaggct acttacagtt   4500
atttttgcag ggatgctgtt tggatatttc atcaatgata aaagaggctc aaaagaatgc   4560
aatccaaatt gtacaacaag ctgtaaagta tgtggggcag ttagcagttc tgaaagggag   4620
caagctacat tttctagaaa acggtaacaa taaagctgcc agtgtccagg aggaattcat   4680
ggatgctgtt tgtgatggtg taggcttagg aatgaagatt ttattagatt ctggactgga   4740
aaaagcaaaa gaacttcagc atgaactctt taggcagtgt acaaaaaatg aggttaccaa   4800
agaaatgaaa actaatgcca tgggattgat tagatctctt gaaaacatct ttgctgaatc   4860
gaaaattaaa agtttcagaa ggcaagtaca agaagaaaac tttgaatacc aagatttcaa   4920
gaggatggtt aatcgtgctc cagaattctt aaagttaaaa cattgcttag agaaagctat   4980
tgaaattatt atttctgcac tgaaaggatg ccatagtgat ataaatcttc tccagacttg   5040
tgttgaaagt attcgcaact tggccagtga tttttacagt gacttcagtg tgccttctac   5100
ttctgttggc agctatgaga gtagagtaac tcacattgtc caccaggaac tagaatctct   5160
agctaagtct ctcctctttt gttttgaatc tgaagaaagc cctgatttgt tgaaaccctg   5220
ggaaacttat aatcaaaata ccaaagaaga acaccaacaa tctaaatcaa gcgggattga   5280
cggcagtaag aataaaggtg taccaaagcg tgtctatgag ctccatggct catccccagc   5340
agtgagctca gaggaatgca cacccagtag gattcagtgg gtgtgaatac tgatgtgtag   5400
gcacttttat gaccacccat gaaagaaaaa gaacacttgc tcggtaattt tctttatgca   5460
ggagagttta agagaaatca gcacagatat ttcaaaaaag tccatgtctt tttatcttta   5520
aaatatctat ttatcaaagg ccagacacag tggctcacgc ctgtaatccc agcactttgg   5580
gaggcgggca gatcacaagg tcaggagttt gagaccggcc tggccaacat ggcgaaaccc   5640
cgtctctact aaaaatacaa aaatttgctg ggcatggtgg cgcgtgcctg taatcccagc   5700
tactaggggg gctgaggcag gaggatcgct tgaacctgag aggcagaggt tgcagtgagc   5760
```

```
caagatcatg ccactttact ccagtctgag caacagaacg agacttagtc aaaataaata   5820
aataaataaa taaataaata aataaataaa taaataaaat atatttttat ctttaaagtg   5880
tttaacattg gtatactgtc tgtagttggt tcattagtcg tttataaagg gttatttttct   5940
catgagtgga aacctgaaca atcagttacc tttgtgccta tgccttctct ctcctcagac   6000
agctgggatg tttatggtga aatggcctgt acaagtttaa ctaagacaac ttaacttgca   6060
ttgttaatca aaaattcttt tctcaaaggg ttaactggtt gccattttga atagtatgtt   6120
caagggtgta gcttcctgtt tctttccaaa ttataagtag ctacctaaat atagtataat   6180
tatatattaa taatatggct tgctggcaca gtagtttacc ctgttatctg tgtttcataa   6240
tgggggctgt atgaatatta tttaaaacta ataaaatgtt gccagaatta tactaaactg   6300
ttggatgaga ttaggagatc agaggctgga ccttctcttg ataatgcttg ttttgttaaa   6360
ggtataatga aataatttgt atatgatttg atgaagatta aagaccctta ttttccacag   6420
ctttaaaaaa aaaccttat ttatgatcaa gtaataaaga taatattcta cttgtgggat   6480
cttacattac ggaaatagtt tgacgttttt gacctcaaga gtatgtataa tttgaagaga   6540
tactttgtaa ctatgcttgg gtgatattga gcagttccta aagaataatt catttaaaaa   6600
aaaagaagaa aaaaaaagaa gaattcattt aaataacctg atcctttcat ttgccctttt   6660
cgaatttaca gatactactt gtacatttgg cataactagt tgaaattggc cattcgtacc   6720
atgaataaat ctgatagttt ccttgttagg aagagattgt aagtaaatac agtcattgca   6780
gtcagaacag tattagtgaa ccttgtgtgg tgttttcaag ctctttaaaa tggtacaatg   6840
tagcacattt gctttcattt cttttttat ttttggcatt tgaccttgta ttctttctga   6900
agctctatat gtgtttttat tagtcaataa tctggcaagt agcactttgc ctgtgcagtt   6960
tgctggagtg tagatgtaca tatgaggatt tcccgggagg tgcacttctt tgaagaactt   7020
cctaaagtac ctgtatagta gttttcatct taatattcag tatttaatct tcagtttgtg   7080
ctttgtaaac tcatgactta attggtcaga aactttttag tgtctttata aaattttgta   7140
tacatattta tactaaacac attgtgatac tgtatttgaa tgaatggtga aaaaatattt   7200
gctattggaa ttatgtgcac tgacaagaaa tgttataaag agaatgcctt taataaatct   7260
tttcagcatt agaattgaaa aaaaaaaaaa aaa                                7293
```

```
<210> SEQ ID NO 15
<211> LENGTH: 2486
<212> TYPE: DNA
<213> ORGANISM: Homo sapiens

<400> SEQUENCE: 15

gagatttgat tcccttggcg ggcggaagcg gccacaaccc ggcgatcgaa aagattctta     60
ggaacgccgt accagccgcg tctctcagga cagcaggccc ctgtccttct gtcgggcgcc    120
gctcagccgt gccctccgcc cctcaggttc tttttctaat tccaaataaa cttgcaagag    180
gactatgaaa gattatgatg aacttctcaa atattatgaa ttacatgaaa ctattgggac    240
aggtggcttt gcaaaggtca aacttgcctg ccatatcctt actggagaga tggtagctat    300
aaaaatcatg gataaaaaca cactagggag tgatttgccc cggatcaaaa cggagattga    360
ggccttgaag aacctgagac atcagcatat atgtcaactc taccatgtgc tagagacagc    420
caacaaaata ttcatggttc ttgagtactg ccctggagga gagctgtttg actatataat    480
ttcccaggat cgcctgtcag aagaggagac ccgggttgtc ttccgtcaga tagtatctgc    540
```

tgttgcttat gtgcacagcc agggctatgc tcacagggac ctcaagccag aaaatttgct 600
gtttgatgaa tatcataaat taaagctgat tgactttggt ctctgtgcaa aacccaaggg 660
taacaaggat taccatctac agacatgctg tgggagtctg gcttatgcag cacctgagtt 720
aatacaaggc aaatcatatc ttggatcaga ggcagatgtt tggagcatgg gcatactgtt 780
atatgttctt atgtgtggat ttctaccatt tgatgatgat aatgtaatgg ctttatacaa 840
gaagattatg agaggaaaat atgatgttcc caagtggctc tctcccagta gcattctgct 900
tcttcaacaa atgctgcagg tggacccaaa gaaacggatt tctatgaaaa atctattgaa 960
ccatccctgg atcatgcaag attacaacta tcctgttgag tggcaaagca agaatccttt 1020
tattcacctc gatgatgatt gcgtaacaga actttctgta catcacagaa acaacaggca 1080
aacaatggag gatttaattt cactgtggca gtatgatcac ctcacggcta cctatcttct 1140
gcttctagcc aagaaggctc ggggaaaacc agttcgttta aggctttctt ctttctcctg 1200
tggacaagcc agtgctaccc cattcacaga catcaagtca aataattgga gtctggaaga 1260
tgtgaccgca agtgataaaa attatgtggc gggattaata gactatgatt ggtgtgaaga 1320
tgatttatca acaggtgctg ctactccccg aacatcacag tttaccaagt actggacaga 1380
atcaaatggg gtggaatcta aatcattaac tccagcctta tgcagaacac ctgcaaataa 1440
attaaagaac aaagaaaatg tatatactcc taagtctgct gtaaagaatg aagagtactt 1500
tatgtttcct gagccaaaga ctccagttaa taagaaccag cataagagag aaatactcac 1560
tacgccaaat cgttacacta caccctcaaa agctagaaac cagtgcctga aagaaactcc 1620
aattaaaata ccagtaaatt caacaggaac agacaagtta atgacaggtg tcattagccc 1680
tgagaggcgg tgccgctcag tggaattgga tctcaaccaa gcacatatgg aggagactcc 1740
aaaaagaaag ggagccaaag tgtttgggag ccttgaaagg gggttggata aggttatcac 1800
tgtgctcacc aggagcaaaa ggaagggttc tgccagagac gggcccagaa gactaaagct 1860
tcactataac gtgactacaa ctagattagt gaatccagat caactgttga atgaaataat 1920
gtctattctt ccaaagaagc atgttgactt tgtacaaaag ggttatacac tgaagtgtca 1980
aacacagtca gattttggga aagtgacaat gcaatttgaa ttagaagtgt gccagcttca 2040
aaaacccgat gtggtgggta tcaggaggca gcggcttaag ggcgatgcct gggtttacaa 2100
aagattagtg gaagacatcc tatctagctg caaggtataa ttgatggatt cttccatcct 2160
gccggatgag tgtgggtgtg atacagccta cataaagact gttatgatcg ctttgatttt 2220
aaagttcatt ggaactacca acttgtttct aaagagctat cttaagacca atatctcttt 2280
gtttttaaac aaaagatatt attttgtgta tgaatctaaa tcaagcccat ctgtcattat 2340
gttactgtct tttttaatca tgtggttttg tatattaata attgttgact ttcttagatt 2400
cacttccata tgtgaatgta agctcttaac tatgtctctt tgtaatgtgt aatttctttc 2460
tgaaataaaa ccatttgtga atatag 2486

<210> SEQ ID NO 16
<211> LENGTH: 5101
<212> TYPE: DNA
<213> ORGANISM: Homo sapiens

<400> SEQUENCE: 16
agcgcagcca ttggtccggc tactctgtct ctttttcaaa ttgaggcgcc gagtcgttgc 60
ttagtttctg gggattcggg cggagacgag attagtgatt tggcggctcc gactggcgcg 120
ggacaaacgc cacggccaga gtaccgggta gagagcgggg acgccgacct gcgtgcgtcg 180

-continued

```
gtcctccagg ccacgccagc gcccgagagg gaccagggag actccggccc ctgtcggccg    240
ccaagcccct ccgcccctca cagcgcccag gtccgcggcc gggccttgat tttttggcgg    300
ggaccgtcat ggcgtcgcag ccaaattcgt ctgcgaagaa gaaagaggag aaggggaaga    360
acatccaggt ggtggtgaga tgcagaccat ttaatttggc agagcggaaa gctagcgccc    420
attcaatagt agaatgtgat cctgtacgaa aagaagttag tgtacgaact ggaggattgg    480
ctgacaagag ctcaaggaaa acatacactt ttgatatggt gtttggagca tctactaaac    540
agattgatgt ttaccgaagt gttgtttgtc caattctgga tgaagttatt atgggctata    600
attgcactat ctttgcgtat ggccaaactg gcactggaaa aacttttaca atggaaggtg    660
aaaggtcacc taatgaagag tatacctggg aagaggatcc cttggctggt ataattccac    720
gtacccttca tcaaattttt gagaaactta ctgataatgg tactgaattt tcagtcaaag    780
tgtctctgtt ggagatctat aatgaagagc tttttgatct tcttaatcca tcatctgatg    840
tttctgagag actacagatg tttgatgatc cccgtaacaa gagaggagtg ataattaaag    900
gtttagaaga aattacagta cacaacaagg atgaagtcta tcaaatttta gaaaaggggg    960
cagcaaaaag gacaactgca gctactctga tgaatgcata ctctagtcgt tcccactcag   1020
ttttctctgt tacaatacat atgaaagaaa ctacgattga tggagaagag cttgttaaaa   1080
tcggaaagtt gaacttggtt gatcttgcag gaagtgaaaa cattggccgt tctggagctg   1140
ttgataagag agctcgggaa gctggaaata taaatcaatc cctgttgact ttgggaaggg   1200
tcattactgc ccttgtagaa agaacacctc atgttcctta tcgagaatct aaactaacta   1260
gaatcctcca ggattctctt ggagggcgta caagaacatc tataattgca acaatttctc   1320
ctgcatctct caatcttgag gaaactctga gtacattgga atatgctcat agagcaaaga   1380
acatattgaa taagcctgaa gtgaatcaga aactcaccaa aaaagctctt attaaggagt   1440
atacggagga gatagaacgt ttaaaacgag atcttgctgc agcccgtgag aaaaatggag   1500
tgtatatttc tgaagaaaat tttagagtca tgagtggaaa attaactgtt caagaagagc   1560
agattgtaga attgattgaa aaaattggtg ctgttgagga ggagctgaat agggttacag   1620
agttgtttat ggataataaa aatgaacttg accagtgtaa atctgacctg caaaataaaa   1680
cacaagaact tgaaaccact caaaaacatt tgcaagaaac taaattacaa cttgttaaag   1740
aagaatatat cacatcagct ttggaaagta ctgaggagaa acttcatgat gctgccagca   1800
agctgcttaa cacagttgaa gaaactacaa aagatgtatc tggtctccat tccaaactgg   1860
atcgtaagaa ggcagttgac caacacaatg cagaagctca ggatattttt ggcaaaaacc   1920
tgaatagtct gtttaataat atggaagaat taattaagga tggcagctca aagcaaaagg   1980
ccatgctaga agtacataag accttatttg gtaatctgct gtcttccagt gtctctgcat   2040
tagataccat tactacagta gcacttggat ctctcacatc tattccagaa aatgtgtcta   2100
ctcatgtttc tcagattttt aatatgatac taaaagaaca atcattagca gcagaaagta   2160
aaactgtact acaggaattg attaatgtac tcaagactga tcttctaagt tcactggaaa   2220
tgattttatc cccaactgtg gtgtctatac tgaaaatcaa tagtcaacta aagcatattt   2280
tcaagacttc attgacagtg gccgataaga tagaagatca aaaaaaggaa ctagatggct   2340
ttctcagtat actgtgtaac aatctacatg aactacaaga aaataccatt tgttccttgg   2400
ttgagtcaca aaagcaatgt ggaaacctaa ctgaagacct gaagacaata aagcagaccc   2460
attcccagga actttgcaag ttaatgaatc tttggacaga gagattctgt gctttggagg   2520
```

-continued

```
aaaagtgtga aaatatacag aaaccactta gtagtgtcca ggaaaatata cagcagaaat   2580
ctaaggatat agtcaacaaa atgacttttc acagtcaaaa attttgtgct gattctgatg   2640
gcttctcaca ggaactcaga aattttaacc aagaaggtac aaaattggtt gaagaatctg   2700
tgaaacactc tgataaactc aatggcaacc tggaaaaaat atctcaagag actgaacaga   2760
gatgtgaatc tctgaacaca agaacagttt atttttctga acagtgggta tcttccttaa   2820
atgaaaggga acaggaactt cacaacttat tggaggttgt aagccaatgt tgtgaggctt   2880
caagttcaga catcactgag aaatcagatg gacgtaaggc agctcatgag aaacagcata   2940
acatttttct tgatcagatg actattgatg aagataaatt gatagcacaa aatctagaac   3000
ttaatgaaac cataaaaatt ggtttgacta agcttaattg ctttctggaa caggatctga   3060
aactggatat cccaacaggt acgacaccac agaggaaaag ttatttatac ccatcaacac   3120
tggtaagaac tgaaccacgt gaacatctcc ttgatcagct gaaaaggaaa cagcctgagc   3180
tgttaatgat gctaaactgt tcagaaaaca acaaagaaga gacaattccg gatgtggatg   3240
tagaagaggc agttctgggg cagtatactg aagaacctct aagtcaagag ccatctgtag   3300
atgctggtgt ggattgttca tcaattggcg gggttccatt tttccagcat aaaaaatcac   3360
atggaaaaga caaagaaaac agaggcatta acacactgga gaggtctaaa gtggaagaaa   3420
ctacagagca cttggttaca aagagcagat tacctctgcg agcccagatc aacctttaat   3480
tcacttgggg gttggcaatt ttatttttaa agaaaactta aaaataaaac ctgaaacccc   3540
agaacttgag ccttgtgtat agattttaaa agaatatata tatcagccgg gcgcggtggc   3600
tcatgcctgt aatcccagca ctttgggagg ctgaggcggg tggattgctt gagcccagga   3660
gtttgagacc agcctggcca acgtggcaaa acctcgtctc tgttaaaaat tagccgggcg   3720
tggtggcaca ctcctgtaat cccagctact ggggaggctg aggcacgaga atcacttgaa   3780
cccaggaagc ggggttgcag tgagccaaag gtacaccact acactccagc ctgggcaaca   3840
gagcaagact cggtctcaaa aacaaaattt aaaaaagata taaggcagta ctgtaaattc   3900
agttgaattt tgatatctac ccatttttct gtcatcccta tagttcactt tgtattaaat   3960
tgggtttcat ttgggatttg caatgtaaat acgtatttct agttttcata taaagtagtt   4020
cttttataac aaatgaaaag tatttttctt gtatattatt aagtaatgaa tatataagaa   4080
ctgtactctt ctcagcttga gcttacatag gtaaatatca ccaacatctg tccttagaaa   4140
ggaccatctc atgttttttt tcttgctatg acttgtgtat tttcttgcat cctccctaga   4200
cttccctatt tcgctttctc ctcggctcac tttctccctt tttatttttc accaaaccat   4260
ttgtagagct acaaaaggta tcctttctta ttttcagtag tcagaatttt atctagaaat   4320
cttttaacac ctttttagtg gttatttcta aaatcactgt caacaataaa tctaacccta   4380
gttgtatccc tcctttcagt atttttcact tgttgcccca aatgtgaaag catttcattc   4440
ctttaagagg cctaactcat tcaccctgac agagttcaca aaaagcccac ttaagagtat   4500
acattgctat tatgggagac cacccagaca tctgactaat ggctctgtgc ccacactcca   4560
agacctgtgc cttttagaga agctcacaat gatttaagga ctgtttgaaa cttccaatta   4620
tgtctataat ttatattctt ttgtttacat gatgaaactt tttgttgttg cttgtttgta   4680
tataatacaa tgtgtacatg tatctttttc tcgattcaaa tcttaaccct taggactctg   4740
gtatttttga tctggcaacc atatttctgg aagttgagat gtttcagctt gaagaaccaa   4800
aacagaagga atatgtacaa agaataaatt ttctgctcac gatgagttta gtgtgtaaag   4860
tttagagaca tctgactttg atagctaaat taaaccaaac cctattgaag aattgaatat   4920
```

```
atgctacttc aagaaactaa attgatctcg tagaattatc ttaataaaat aatggctata   4980

atttctctgc aaaatcagat gtcagcataa gcgatggata atacctaata aactgccctc   5040

agtaaatcca tggttaataa atgtggtttc tacattaaaa aaaaaaaaaa aaaaaaaaaa   5100

a                                                                   5101
```

<210> SEQ ID NO 17
<211> LENGTH: 1285
<212> TYPE: DNA
<213> ORGANISM: Homo sapiens

<400> SEQUENCE: 17

```
aattacaaat tcccaatgca gttacaggat cctgggaagc agagtgtctg gatggaacct     60

gagctgggtc tctgactcac ttctgacttt agttttttca agggggaaca tggcaaaggt    120

gttcagtttc atccttgtta ccaccgctct gacaatgggc agggaaattt cggcgctcga    180

ggactgtgcc caggagcaga tgcggctcag agcccaggtg cgcctgcttg agacccgggt    240

caaacagcaa caggtcaaga tcaagcagct tttgcaggag aatgaagtcc agttccttga    300

taaaggagat gagaatactg tcattgatct tggaagcaag aggcagtatg cagattgttc    360

agagattttc aatgatgggt ataagctcag tggattttac aaaatcaaac ctctccagag    420

cccagcagaa ttttctgttt attgtgacat gtccgatgga ggaggatgga ctgtaattca    480

gagacgatct gatggcagtg aaaactttaa cagaggatgg aaagactatg aaaatggctt    540

tggaaatttt gtccaaaaac atggtgaata ttggctgggc aataaaaatc ttcacttctt    600

gaccactcaa gaagactaca ctttaaaaat cgaccttgca gattttgaaa aaaatagccg    660

ttatgcacaa tataagaatt tcaaagttgg agatgaaaag aatttctacg agttgaatat    720

tggggaatat tctggaacag ctggagattc ccttgcgggg aattttcatc ctgaggtgca    780

gtggtgggct agtcaccaaa gaatgaaatt cagcacgtgg gacagagatc atgacaacta    840

tgaagggaac tgcgcagaag aagatcagtc tggctggtgg tttaacaggt gtcactctgc    900

aaacctgaat ggtgtatact acagcggccc ctacacggct aaaacagaca atgggattgt    960

ctggtacacc tggcatgggt ggtggtattc tctgaaatct gtggttatga aaattaggcc   1020

aaatgatttt attccaaatg taatttaatt gctgctgttg ggctttcgtt tctgcaattc   1080

agctttgttt aaagtgattt gaaaaatact cattctgaac atatccatgc gcaatcatga   1140

taactgttgt gagtagtgct tttcattctt ctcacttgcc tttgttactt aatgtgcttt   1200

cagtacagca gatatgcaat attcaccaaa taaatgtaga ctgtgttaaa aaaaaaaaaa   1260

aaaaaaaaaa aaaaaaaaaa aaaaa                                         1285
```

<210> SEQ ID NO 18
<211> LENGTH: 2127
<212> TYPE: DNA
<213> ORGANISM: Homo sapiens

<400> SEQUENCE: 18

```
ataatcacga cacattcaac acagatgtga gcgtttggag agagcttcag ccttcagcac     60

aggcaactgt gttctattca ccgggctgtg ctcctcggaa gggctggtgg ttcctgtaaa    120

agtttgtgct ccccgcgcct ttccttcctt ccctcgtctt tggcgcctgc gggcaccggg    180

agtcctggga gagggaggag gaacggcgaa tcggcggggc gtgtccttca cgccgccccg    240

tagctcgggg ccgaagctgg cgcagcgcgc gactttttga aagccaggag ggttcgaatt    300
```

-continued

```
gcaacggcag ctgccgggcg tatgtgttgg tgctagaggc agctgcaggg tctcgctggg    360
ggccgctcgg gaccaatttt gaagaggtac ttggccacga cttattttca cctccgacct    420
ttccttccag gcggtgagac tctggactga gagtggcttt cacaatggaa gggatcagta    480
atttcaagac accaagcaaa ttatcagaaa aaaagaaatc tgtattatgt tcaactccaa    540
ctataaatat cccggcctct ccgtttatgc agaagcttgg ctttggtact ggggtaaatg    600
tgtacctaat gaaaagatct ccaagaggtt tgtctcattc tccttgggct gtaaaaaaga    660
ttaatcctat atgtaatgat cattatcgaa gtgtgtatca aaagagacta atggatgaag    720
ctaagatttt gaaaagcctt catcatccaa acattgttgg ttatcgtgct tttactgaag    780
ccaatgatgg cagtctgtgt cttgctatgg aatatggagg tgaaaagtct ctaaatgact    840
taatagaaga acgatataaa gccagccaag atccttttcc agcagccata attttaaaag    900
ttgctttgaa tatggcaaga gggttaaagt atctgcacca agaaaagaaa ctgcttcatg    960
gagacataaa gtcttcaaat gttgtaatta aaggcgattt tgaaacaatt aaaatctgtg   1020
atgtaggagt ctctctacca ctggatgaaa atatgactgt gactgaccct gaggcttgtt   1080
acattggcac agagccatgg aaacccaaag aagctgtgga ggagaatggt gttattactg   1140
acaaggcaga catatttgcc tttggcctta ctttgtggga aatgatgact ttatcgattc   1200
cacacattaa tctttcaaat gatgatgatg atgaagataa aacttttgat gaaagtgatt   1260
ttgatgatga agcatactat gcagcgttgg gaactaggcc acctattaat atggaagaac   1320
tggatgaatc ataccagaaa gtaattgaac tcttctctgt atgcactaat gaagacccta   1380
aagatcgtcc ttctgctgca cacattgttg aagctctgga aacagatgtc tagtgatcat   1440
ctcagctgaa gtgtggcttg cgtaaataac tgtttattcc aaaatattta catagttact   1500
atcagtagtt attagactct aaaattggca tatttgagga ccatagtttc ttgttaacat   1560
atggataact atttctaata tgaaatatgc ttatattggc tataagcact tggaattgta   1620
ctgggttttc tgtaaagttt tagaaactag ctacataagt actttgatac tgctcatgct   1680
gacttaaaac actagcagta aaacgctgta aactgtaaca ttaaattgaa tgaccattac   1740
ttttattaat gatctttctt aaatattcta tattttaatg gatctactga cattagcact   1800
ttgtacagta caaaataaag tctacatttg tttaaaacac tgaacctttt gctgatgtgt   1860
ttatcaaatg ataactggaa gctgaggaga atatgcctca aaaagagtag ctccttggat   1920
acttcagact ctggttacag attgtcttga tctcttggat ctcctcagat ctttggtttt   1980
tgctttaatt tattaaatgt attttccata ctgagtttaa aatttattaa tttgtacctt   2040
aagcatttcc cagctgtgta aaaacaataa aactcaaata ggatgataaa gaataaagga   2100
cactttgggt accagaaaaa aaaaaaa                                       2127
```

<210> SEQ ID NO 19
<211> LENGTH: 2339
<212> TYPE: DNA
<213> ORGANISM: Homo sapiens

<400> SEQUENCE: 19

```
acgcggtgcc gcggggcggg agtagaggcg gagggagggg acacgggctc attgcggtgt     60
gcgccctgca ctctgtccct cactcgccgc cgacgacctg tctcgccgag cgcacgcctt    120
gccgccgccc cgcagaaatg cttcggttac ccacagtctt tcgccagatg agaccggtgt    180
ccagggtact ggctcctcat ctcactcggg cttatgccaa agatgtaaaa tttggtgcag    240
atgcccgagc cttaatgctt caaggtgtag accttttagc cgatgctgtg gccgttacaa    300
```

```
tggggccaaa gggaagaaca gtgattattg agcagagttg gggaagtccc aaagtaacaa    360

aagatggtgt gactgttgca aagtcaattg acttaaaaga taaatacaaa aacattggag    420

ctaaacttgt tcaagatgtt gccaataaca caaatgaaga agctggggat ggcactacca    480

ctgctactgt actggcacgc tctatagcca aggaaggctt cgagaagatt agcaaaggtg    540

ctaatccagt ggaaatcagg agaggtgtga tgttagctgt tgatgctgta attgctgaac    600

ttaaaaagca gtctaaacct gtgaccaccc ctgaagaaat tgcacaggtt gctacgattt    660

ctgcaaacgg agacaaagaa attggcaata tcatctctga tgcaatgaaa aaagttggaa    720

gaaagggtgt catcacagta aaggatggaa aaacactgaa tgatgaatta gaaattattg    780

aaggcatgaa gtttgatcga ggctatattt ctccatactt tattaataca tcaaaaggtc    840

agaaatgtga attccaggat gcctatgttc tgttgagtga aaagaaaatt tctagtatcc    900

agtccattgt acctgctctt gaaattgcca atgctcaccg taagcctttg gtcataatcg    960

ctgaagatgt tgatggagaa gctctaagta cactcgtctt gaataggcta aaggttggtc   1020

ttcaggttgt ggcagtcaag gctccagggt ttggtgacaa tagaaagaac cagcttaaag   1080

atatggctat tgctactggt ggtgcagtgt ttggagaaga gggattgacc ctgaatcttg   1140

aagacgttca gcctcatgac ttaggaaaag ttggagaggt cattgtgacc aaagacgatg   1200

ccatgctctt aaaaggaaaa ggtgacaagg ctcaaattga aaaacgtatt caagaaatca   1260

ttgagcagtt agatgtcaca actagtgaat atgaaaagga aaaactgaat gaacggcttg   1320

caaaactttc agatggagtg gctgtgctga aggttggtgg gacaagtgat gttgaagtga   1380

atgaaaagaa agacagagtt acagatgccc ttaatgctac aagagctgct gttgaagaag   1440

gcattgtttt gggagggggt tgtgccctcc ttcgatgcat tccagccttg gactcattga   1500

ctccagctaa tgaagatcaa aaaattggta tagaaattat taaaagaaca ctcaaaattc   1560

cagcaatgac cattgctaag aatgcaggtg ttgaaggatc tttgatagtt gagaaaatta   1620

tgcaaagttc ctcagaagtt ggttatgatg ctatggctgg agattttgtg aatatggtgg   1680

aaaaaggaat cattgaccca acaaaggttg tgagaactgc tttattggat gctgctggtg   1740

tggcctctct gttaactaca gcagaagttg tagtcacaga aattcctaaa gaagagaagg   1800

accctggaat gggtgcaatg ggtggaatgg gaggtggtat gggaggtggc atgttctaac   1860

tcctagacta gtgctttacc tttattaatg aactgtgaca ggaagcccaa ggcagtgttc   1920

ctcaccaata acttcagaga agtcagttgg agaaaatgaa gaaaaaggct ggctgaaaat   1980

cactataacc atcagttact ggtttcagtt gacaaaatat ataatggttt actgctgtca   2040

ttgtccatgc ctacagataa tttattttgt atttttgaat aaaaaacatt tgtacattcc   2100

tgatactggg tacaagagcc atgtaccagt gtactgcttt caacttaaat cactgaggca   2160

tttttactac tattctgtta aaatcaggat tttagtgctt gccaccacca gatgagaagt   2220

taagcagcct ttctgtggag agtgagaata attgtgtaca aagtagagaa gtatccaatt   2280

atgtgacaac ctttgtgtaa taaaaatttg tttaaagtta aaaaaaaaaa aaaaaaaaa    2339
```

<210> SEQ ID NO 20
<211> LENGTH: 3251
<212> TYPE: DNA
<213> ORGANISM: Homo sapiens

<400> SEQUENCE: 20

```
gatttggctc cgaggaggcg gaagtgcagc acagaaaggg ggtccgtggg ggacggtaga     60
```

-continued

```
agcctggagg aggagcttga gtccagccac tgtctgggta ctgccagcca tcgggcccag    120
gtctctgggg ttgtcttacc gcagtgagta ccacgcggta ctacagagac cggctgcccg    180
tgtgcccggc aggtggagcc gcccgcatca gcggcctcgg ggaatggaag cggagaacgc    240
gggcagctat tcccttcagc aagctcaagc tttttatacg tttccatttc aacaactgat    300
ggctgaagct cctaatatgg cagttgtgaa tgaacagcaa atgccagaag aagttccagc    360
cccagctcct gctcaggaac cagtgcaaga ggctccaaaa ggaagaaaaa gaaaacccag    420
aacaacagaa ccaaaacaac cagtggaacc caaaaaacct gttgagtcaa aaaaatctgg    480
caagtctgca aaatcaaaag aaaaacaaga aaaaattaca gacacattta aagtaaaaag    540
aaaagtagac cgttttaatg gtgtttcaga agctgaactt ctgaccaaga ctctccccga    600
tattttgacc ttcaatctgg acattgtcat tattggcata aacccgggac taatggctgc    660
ttacaaaggg catcattacc ctggacctgg aaaccatttt tggaagtgtt tgtttatgtc    720
agggctcagt gaggtccagc tgaaccatat ggatgatcac actctaccag ggaagtatgg    780
tattggattt accaacatgg tggaaaggac cacgcccggc agcaaagatc tctccagtaa    840
agaatttcgt gaaggaggac gtattctagt acagaaatta cagaaatatc agccacgaat    900
agcagtgttt aatggaaaat gtatttatga aatttttagt aaagaagttt ttggagtaaa    960
ggttaagaac ttggaatttg ggcttcagcc ccataagatt ccagacacag aaactctctg   1020
ctatgttatg ccatcatcca gtgcaagatg tgctcagttt cctcgagccc aagacaaagt   1080
tcattactac ataaaactga aggacttaag agatcagttg aaaggcattg aacgaaatat   1140
ggacgttcaa gaggtgcaat atacatttga cctacagctt gcccaagagg atgcaaagaa   1200
gatggctgtt aaggaagaaa aatatgatcc aggttatgag gcagcatatg gtggtgctta   1260
cggagaaaat ccatgcagca gtgaaccttg tggcttctct tcaaatgggc taattgagag   1320
cgtggagtta agaggagaat cagctttcag tggcattcct aatgggcagt ggatgaccca   1380
gtcatttaca gaccaaattc cttcctttag taatcactgt ggaacacaag aacaggaaga   1440
agaaagccat gcttaagaat ggtgcttctc agctctgctt aaatgctgca gttttaatgc   1500
agttgtcaac aagtagaacc tcagtttgct aactgaagtg ttttattagt attttactct   1560
agtggtgtaa ttgtaatgta gaacagttgt gtggtagtgt gaaccgtatg aacctaagta   1620
gtttggaaga aaaagtaggg tttttgtata ctagcttttg tatttgaatt aattatcatt   1680
ccagcttttt atatactata tttcatttat gaagaaattg attttctttt gggagtcact   1740
tttaatctgt aattttaaaa tacaagtctg aatatttata gttgattctt aactgcataa   1800
acctagatat accattatcc cttttatacc taagaagggc atgctaataa ttaccactgt   1860
caaagaggca aaggtgttga tttttgtata tgaagttaag cctcagtgga gtctcatttg   1920
ttagttttta gtggtaacta agggtaaact cagggttccc tgagctatat gcacactcag   1980
acctctttgc tttaccagtg gtgtttgtga gttgctcagt agtaaaaact ggcccttacc   2040
tgacagagcc ctggctttga cctgctcagc cctgtgtgtt aatcctctag tagccaatta   2100
actactctgg ggtggcaggt tccagagaat gcagtagacc ttttgccact catctgtgtt   2160
ttacttgaga catgtaaata tgatagggaa ggaactgaat ttctccattc atatttataa   2220
ccattctagt tttatcttcc ttggctttaa gagtgtgcca tggaaagtga taagaaatga   2280
acttctaggc taagcaaaaa gatgctggag atatttgata ctctcattta aactggtgct   2340
ttatgtacat gagatgtact aaaataagta atatagaatt tttcttgcta ggtaaatcca   2400
gtaagccaat aattttaaag attctttatc tgcatcattg ctgtttgtta ctataaatta   2460
```

```
aatgaacctc atggaaaggt tgaggtgtat acctttgtga ttttctaatg agttttccat   2520

ggtgctacaa ataatccaga ctaccaggtc tggtagatat taaagctggg tactaagaaa   2580

tgttatttgc atcctctcag ttactcctga atattctgat ttcatacgta cccagggagc   2640

atgctgtttt gtcaatcaat ataaaatatt tatgaggtct cccccacccc caggaggtta   2700

tatgattgct cttctcttta taataagaga aacaaattct tattgtgaat cttaacatgc   2760

tttttagctg tggctatgat ggattttatt ttttcctagg tcaagctgtg taaaagtcat   2820

ttatgttatt taaatgatgt actgtactgc tgtttacatg gacgttttgt gcgggtgctt   2880

tgaagtgcct tgcatcaggg attaggagca attaaattat tttttcacgg gactgtgtaa   2940

agcatgtaac taggtattgc tttggtatat aactattgta gctttacaag agattgtttt   3000

atttgaatgg ggaaaatacc ctttaaatta tgacggacat ccactagaga tgggtttgag   3060

gattttccaa gcgtgtaata atgatgtttt tcctaacatg acagatgagt agtaaatgtt   3120

gatatatcct atacatgaca gtgtgagact ttttcattaa ataatattga aagattttaa   3180

aattcatttg aaagtctgat ggcttttaca ataaaagata ttaagaattg ttatccttaa   3240

cttaaaaaaa a                                                        3251
```

<210> SEQ ID NO 21
<211> LENGTH: 3207
<212> TYPE: DNA
<213> ORGANISM: Homo sapiens

<400> SEQUENCE: 21

```
gattgcgcac ccgcgacttc agcccgaggg gcggggattt tcttggagcg acgggacgcg     60

acgccaatcg cgacgaggct tcgccccgtg gcgcggtttg aaattttgcg gggctcaacg    120

gctcgcggag cggctacgcg gagtgacatc gccggtgttt gcgggtggtt gttgctctcg    180

gggccgtgtg gagtaggtct ggacctggac tcacggctgc ttggagcgtc cgccatgagg    240

agaagtgagg tgctggcgga ggagtccata gtatgtctgc agaaagccct aaatcacctt    300

cgggaaatat gggagctaat tggggattcca gaggaccagc ggttacaaag aactgaggtg    360

gtaaagaagc atatcaagga actcctggat atgatgattg ctgaagagga aagcctgaag    420

gaaagactca tcaaaagcat atccgtctgt cagaaagagc tgaacactct gtgcagcgag    480

ttacatgttg agccatttca ggaagaagga gagacgacca tcttgcaact agaaaaagat    540

ttgcgcaccc aagtggaatt gatgcgaaaa cagaaaaagg agagaaaaca ggaactgaag    600

ctacttcaag agcaagatca agaactgtgc gaaattcttt gtatgcccca ctatgatatt    660

gacagtgcct cagtgcccag cttagaagag ctgaaccagt tcaggcaaca tgtgacaact    720

ttgagggaaa caaaggcttc taggcgtgag gagtttgtca gtataaagag acagatcata    780

ctgtgtatgg aagaattaga ccacacccca gacacaagct ttgaaagaga tgtggtgtgt    840

gaagacgaag atgccttttg tttgtctttg gagaatattg caacactaca aaagttgcta    900

cggcagctgg aaatgcagaa atcacaaaat gaagcagtgt gtgaggggct gcgtactcaa    960

atccgagagc tctgggacag gttgcaaata cctgaagaag aaagagaagc tgtggccacc   1020

attatgtctg ggtcaaaggc caaggtccgg aaagcgctgc aattagaagt ggatcggttg   1080

gaagaactga aaatgcaaaa catgaagaaa gtgattgagg caattcgagt ggagctggtt   1140

cagtactggg accagtgctt ttatagccag gagcagagac aagcttttgc ccctttctgt   1200

gctgaggact acacagaaag tctgctccag ctccacgatg ctgagattgt gcggttaaaa   1260
```

```
aactactatg aagttcacaa ggaactcttt gaaggtgtcc agaagtggga agaaacctgg   1320

aggcttttct tagagtttga gagaaaagct tcagatccaa atcgatttac aaaccgagga   1380

ggaaatcttc taaaagaaga aaaacaacga gccaagctcc agaaaatgct gcccaagctg   1440

gaagaagagt tgaaggcacg aattgaattg tgggaacagg aacattcaaa ggcatttatg   1500

gtgaatgggc agaaattcat ggagtatgtg gcagaacaat gggagatgca tcgattggag   1560

aaagagagag ccaagcagga aagacaactg aagaacaaaa aacagacaga gacagagatg   1620

ctgtatggca gcgctcctcg aacacctagc aagcggcgag gactggctcc caatacaccg   1680

ggcaaagcac gtaagctgaa cactaccacc atgtccaatg ctacggccaa tagtagcatt   1740

cggcctatct ttggagggac agtctaccac tcccccgtgt ctcgacttcc tccttctggc   1800

agcaagccag tcgctgcttc cacctgttca gggaagaaaa caccccgtac tggcaggcat   1860

ggagccaaca aggagaacct ggagctcaac ggcagcatcc tgagtggtgg gtaccctggc   1920

tcggcccccc tccagcgcaa cttcagcatt aattctgttg ccagcaccta ttctgagttt   1980

gcgaaggatc cgtccctctc tgacagttcc actgttgggc ttcagcgaga actttcaaag   2040

gcttccaaat ctgatgctac ttctggaatc ctcaattcaa ccaacatcca gtcctgagaa   2100

gccctgatca gtcaaccagc tgtggcttcc tgtgcctaga ctggacctaa ttatatgggg   2160

gtgactttag tttttcttca gcttaggcgt gcttgaaacc ttggccaggt tccatgacca   2220

tgggcctaac ttaaagatgt gaatgagtgt tacagttgaa agcccatcat aggtttagtg   2280

gtcctaggag acttggtttt gacttatata catgaaaagt ttatggcaag aagtgcaaat   2340

tttagcatat ggggcctgac ttctctacca cataattcta cttgctgaag catgatcaaa   2400

gcttgtttta tttcaccact gtaggaaaat gattgactat gcccatccct gggggtaatt   2460

ttggcatgta tacctgtaac tagtaattaa catctttttt gtttaggcat gttcaattaa   2520

tgctgtagct atcatagctt tgctcttacc tgaagccttg tccccaccac acaggacagc   2580

cttcctcctg aagagaatgt ctttgtgtgt ccgaagttga gatggcctgc cctactgcca   2640

aagaggtgac aggaaggctg ggagcagctt tgttaaattg tgttcagttc tgttacacag   2700

tgcattgccc tttgttgggg gtatgcatgt atgaacacac atgcttgtcg gaacgctttc   2760

tcggcgtttg tcccttggct ctcatctccc ccattcctgt gcctactttg cctgagttct   2820

tctacccccg cagttgccag ccacattggg agtctgtttg ttccaatggg ttgagctgtc   2880

tttgtcgtgg agatctggaa ctttgcacat gtcactactg gggaggtgtt cctgctctag   2940

cttccacgat gaggcgccct ctttacctat cctctcaatc actactcttc ttgaagcact   3000

attatttatt cttccgctgt ctgcctgcag cagtactact gtcaacatag tgtaaatggt   3060

tctcaaaagc ttaccagtgt ggacttggtg ttagccacgc tgtttactca tacagtacgt   3120

gtcctgtttt taaaatatac aattattctt aaaaataaat taaaatctgt atacttacat   3180

ttcaaaaaga aaaaaaaaaa aaaaaaa                                       3207
```

<210> SEQ ID NO 22
<211> LENGTH: 5625
<212> TYPE: DNA
<213> ORGANISM: Homo sapiens

<400> SEQUENCE: 22

```
acctagcgcc ccctcccccg ggagcgcgga ggagcattaa taaacctcta agccgaggag     60

aaaactctgg ctggggcagt gcgctgagcg ccggaggagc gtaggcaggg cagcgctggc    120

gccagtggcg acaggagccg cgcgaccggc aaaaatacac gggaggccgt cgccgaaaag    180
```

-continued

```
agtccgcggt cctctctcgt aaacacactc tcctccaccg gcgcctcccc ctccgctctg    240
cgcgccgccc ggctgggcgc ccgaggccgc tccgactgct atgtgaccgc gaggctgcgg    300
gaggaagggg acagggaaga agaggctctc ccgcgggagc ccttgaggac caagtttgcg    360
gccacttctg caggcgtccc ttcttagctc tcgcccgccc ctttctgcag cctaggcggc    420
ccgggttctc ttctcttcct cgcgcgccca gccgcctcgg ttcccggcga ccatggtgac    480
gatggaggag ctgcgggaga tggactgcag tgtgctcaaa aggctgatga accgggacga    540
gaatggcggc ggcgcgggcg gcagcggcag ccacggcacc ctggggctgc cgagcggcgg    600
caagtgcctg ctgctggact gcagaccgtt cctggcgcac agcgcgggct acatcctagg    660
ttcggtcaac gtgcgctgta acaccatcgt gcggcggcgg gctaagggct ccgtgagcct    720
ggagcagatc ctgcccgccg aggaggaggt acgcgcccgc ttgcgctccg gcctctactc    780
ggcggtcatc gtctacgacg agcgcagccc gcgcgccgag agcctccgcg aggacagcac    840
cgtgtcgctg gtggtgcagg cgctgcgccg caacgccgag cgcaccgaca tctgcctgct    900
caaaggcggc tatgagaggt tttcctccga gtacccagaa ttctgttcta aaaccaaggc    960
cctggcagcc atcccacccc cggttccccc cagtgccaca gagcccttgg acctgggctg   1020
cagctcctgt gggaccccac tacacgacca gggggggtcct gtggagatcc ttcccttcct   1080
ctacctcggc agtgcctacc atgctgcccg gagagacatg ctggacgccc tgggcatcac   1140
ggctctgttg aatgtctcct cggactgccc aaaccacttt gaaggacact atcagtacaa   1200
gtgcatccca gtggaagata accacaaggc cgacatcagc tcctggttca tggaagccat   1260
agagtacatc gatgccgtga aggactgccg tgggcgcgtg ctggtgcact gccaggcggg   1320
catctcgcgg tcggccacca tctgcctggc ctacctgatg atgaagaaac gggtgaggct   1380
ggaggaggcc ttcgagttcg ttaagcagcg ccgcagcatc atctcgccca acttcagctt   1440
catggggcag ctgctgcagt tcgagtccca ggtgctggcc acgtcctgtg ctgcggaggc   1500
tgctagcccc tcgggacccc tgcgggagcg gggcaagacc cccgccaccc ccacctcgca   1560
gttcgtcttc agctttccgg tctccgtggg cgtgcactcg gcccccagca gcctgcccta   1620
cctgcacagc cccatcacca cctctcccag ctgttagagc cgccctgggg gccccagaac   1680
cagagctggc tcccagcaag ggtaggacgg gccgcatgcg ggcagaaagt tgggactgag   1740
cagctgggag caggcgaccg agctccttcc ccatcatttc tccttggcca acgacgaggc   1800
cagccagaat ggcaataagg actccgaata cataataaaa gcaaacagaa cactccaact   1860
tagagcaata acggctgccg cagcagccag ggaagacctt ggtttggttt atgtgtcagt   1920
ttcacttttc cgatagaaat ttcttacctc attttttaa gcagtaaggc ttgaagtgat   1980
gaaacccaca gatcctagca aatgtgccca accagcttta ctaaaggggg aggaagggag   2040
ggcaaaggga tgagaagaca agtttcccag aagtgcctgg ttctgtgtac ttgtcccttt   2100
gttgtcgttg ttgtagttaa aggaatttca tttttaaaa gaaatcttcg aaggtgtggt   2160
tttcatttct cagtcaccaa cagatgaata attatgctta ataataaagt atttattaag   2220
actttcttca gagtatgaaa gtacaaaaag tctagttaca gtggatttag aatatattta   2280
tgttgatgtc aaacagctga gcaccgtagc atgcagatgt caaggcagtt aggaagtaaa   2340
tggtgtcttg tagatatgtg caaggtagca tgatgagcaa cttgagtttg ttgccactga   2400
gaagcaggcg ggttgggtgg gaggaggaag aaagggaaga attaggtttg aattgctttt   2460
taaaaaaaaa agaaaagaaa aagacagcat ctcactatgt tgccaaggct catcttgaga   2520
```

-continued

```
agcaggcggg ttgggtggga ggaggaagaa agggaagaat taggtttgaa ttgctttttt   2580
aaaaaaaaag aaaagaaaaa aaaagacagc atctcactat gttgccaagg ctcatctcaa   2640
gctcttgggc tcaagagatc ctcccacctc ggcctcctga gtagctggga ctgcaggtgt   2700
gtgtcatcat gaccaatgtg aattgctttt gaagctggtt catgggcatg taggccaccg   2760
aagcaatttt agaccacagt aagtcaagct tttttccctc cgatgatcac tgggtggttg   2820
cagcattttt tgcataaacc tgcctaagac ttgtctatcg tctgtgatca atatgccata   2880
ttacactaag gtgctcctgg aaaattgggt gcagttcaaa ttttcctaca gcaaatcatt   2940
tggcaaggcc agccattggg gaaaccagac aactagagat aaccctgaaa tgaatccttt   3000
tgtaaattga agcaccatct tttctttttt tgcataaatt ggaggtttta attttagggc   3060
agttacctga agtgaaatat accaacaatt tcttgtgttc tttaaattcc tagttaggtg   3120
aatatttttg aaggtcctct tttgaataaa gaggggaatg gacaccacat ttcaggtctt   3180
ctcgaagtgt ggaagggcaa gagagcatca gtgagctgat ggtggattgc ttacatcgga   3240
ttccattggt atgaatttcc caaactggaa atcaaagcgc cagggtgggg ttggggctga   3300
ctgctggtga gggggctggc cgctggctcc cgtgacgtgc gtcatgggca cgcaggcgcc   3360
attttgaatc tatcgtcggc acgtgggtgc cattttgaat ccttagttgg gcctttctaa   3420
atggagaatg gctttggagg gagacacgtt ttctgtgggg agggtttggg ggggagggag   3480
gagggaacaa gctacatgct attttgtttg tagtattgtg gaacagtctt gttatggagt   3540
gccagcttag aggttgttgc aaacttgtct agaagtgaga gcatggtttt ttttagccct   3600
ttgagagtct acatctaatg aacattcttg ctcacccata aataacgtca agcctcaatg   3660
tcaccgtcac gttgggatac tctttctcat ctggcatcct agacaggaca aggttggtta   3720
cctttccttc catgaaccat gaacctgtga cggcatcatt catcctgact tcaccaagct   3780
ccgcctgtgg gtgaggccag agctcccact ggcaattttt agaagagcca gaggctccct   3840
gcttcctcta gaaataacag ttcagggtga agcatggagg gtttcagttc ccagacaatg   3900
gaaccattta gagacaacac agttggacat ttccactttt tccttgattc ctggaagtcc   3960
agtgggttct gcagctgaaa aagccctggg tcccagcagc agagagacag gacagagggg   4020
atgcttgggc ggggagggac ggtaacctgc agaacagatt ccatttttat agaacgagta   4080
cacgtttgct aaaacagtcc tgctttccca gactggattc ccaccacagg gacagtcgga   4140
actcaggact agctccagcg acatctttcc tccgaattca agccttctat cacaatgtca   4200
aaacagctat ttataaagcc attttcattg tacttgataa cagcacgagt cccaaaactt   4260
ttagaaataa aataggacat tggcttgatt gaaaagaggg actttttaaa aattgttctt   4320
tcgtcagaag ccttttggat gacttacaat agctctgatg aagataccac cccagcgtca   4380
gtccaatagg tcagtgagtt tcaacaggca tccatccctc ccatgaaggg attctggtga   4440
tgggaagttt ctgtaatgac aggaaagcat tgaccctcat tgattgtcaa ctttggtatt   4500
agccatgaaa gacaggatgc tcattgggtg ttctgtagag tgaggaatgc tgcctattcc   4560
ctcccagaac gtctgaccca ggggtgtgtg ttgaggagcc ctgggggaaa tggaccaagt   4620
tttcccacag agcagtatta ggctgaagag caggtgactg gtaggcccca gctcccatca   4680
ttccctccca aagccatttt gttcagttgc tcatccacgc tggattccag agagttttcc   4740
aatttgggaa gccatgagaa aggtttttaa atcttgggaa gatggagaga gggacatagg   4800
atagttgact ccaacatgac aggaagaggc tggagattgg gaattggcca tcaaccaagc   4860
ctgtagtagt aaagccatgg tcccgcattg gaattacttg ggaacttatt acagttctga   4920
```

tacccaggct ctcctagacc agttcaacca attctaggtg ggggactcag gcatcagtgt 4980
gtttcgtagc tccccgggtg ttttccctgt gcagccgagc ttgggaaact gccatgcttt 5040
ttggatgtca aggcgctgtt ggaggctggg tgtgacagca cagagccagg ttgtcttgtg 5100
gaaaccacag ccacgggttt gccactggct cagcatggcc tcactgccag tcccagcctg 5160
gctgagggac aagatggttt ctcttgggag ttcctgagtg gagcaccctt ccaggctttt 5220
tgaaagccag ctgatctgtg gagccttgtt aagggactca atacggtgtt tggatattga 5280
tgtttttcct tgagactgtc ttgtccatca ataaagatgg aggatgtctc ctctttgaac 5340
cccgcttccc caccagtact ctctctccct tagagtttat gagttattca aggaggagac 5400
ttcttaaaga cagcaacgca attcttgtaa cttgtgtaaa tagccccatc tttcagagtg 5460
ataccatttc tacatttgat aatgcctgta ttcctgtagg atgtatatag tttaggggat 5520
tttttttttg tttggttttg ttttttagaa gtcaatatgt ctggttttat ttattgcttg 5580
aaaaagatca tttgaaaaaa ataaatacat tttcaaccac taaaa 5625

<210> SEQ ID NO 23
<211> LENGTH: 2537
<212> TYPE: DNA
<213> ORGANISM: Homo sapiens

<400> SEQUENCE: 23
ggaagtccca cctgcgcccg acggcggaag ttccgggagt gccaagtacc cgcgtgcata 60
cggctgccgg catggcacat tacaacttca agaaaattac ggtggtgccg tccgccaagg 120
acttcataga cctcacgttg tcgaagactc aacgaaagac tccaaccgtt attcataaac 180
attaccaaat acatcgcatt agacattttt acatgagaaa agtcaaattt actcaacaga 240
attaccatga tagactttca caaattctaa cagatttccc caaattggat gatattcatc 300
cgttctatgc tgatttgatg aatattctct acgacaagga tcattacaag ttggctctgg 360
ggcaaataaa tattgccaaa aatttagtgg acaatgttgc taaagattat gtgcgactga 420
tgaagtatgg cgactctctc taccgctgca aacagctgaa gcgtgcggcc ctgggacgga 480
tgtgcacagt gatcaagagg cagaagcaga gtttggagta tttggagcaa gtgcgtcagc 540
atttatcccg tttgccaacc attgatccga ataccaggac cctgcttttg tgtgggtacc 600
caaatgttgg gaagtccagc ttcatcaaca aggtgacgag agcagacgtg gatgtccagc 660
cctatgcgtt cacaaccaag tctctgtttg ttgggcacat ggattataag tatctacgtt 720
ggcaggttgt agacactcct gggatcctgg accaccctct ggaggatagg aacaccatcg 780
agatgcaggc catcactgcc ctggcccacc tccgtgctgc ggtcctgtat gtgatggatt 840
tgtctgagca gtgtgggcat gggctgaggg agcagctaga actcttccag aacatcagac 900
ctctcttcat caacaagcct ctcatagttg tagccaacaa atgtgatgtg aagagaatag 960
ctgaactttc tgaagatgat cagaaaatat ttacagattt gcagtctgaa ggattccctg 1020
taatagagac cagcaccctg actgaggaag gtgttattaa agttaaaaca gaggcttgcg 1080
ataggctttt ggctcatcga gtggaaacca aaatgaaggg aaataaagtg aatgaggtgc 1140
tgaatagact gcacctggct atcccaacca ggagggacga taaggagagg ccccctttca 1200
tccctgaagg agtggtggct cgcaggaaga ggatggaaac tgaggagtcc aggaagaaga 1260
gggaacgaga tcttgagctg gaaatgggag atgattatat tttggatctt cagaagtact 1320
gggatttaat gaatttgtct gaaaaacatg ataagatacc agaaatctgg gaaggccata 1380

```
atatagctga ttatattgat ccagccatca tgaagaaatt ggaagaatta gaaaaagaag   1440
aagagctgag aacagctgct ggagagtatg acagtgtatc tgagagtgaa gacgaagaga   1500
tgctggaaat ccgacagctg gcaaagcaaa ttcgagagaa aaagaagttg aaaattctgg   1560
agtccaaaga aaagaataca cagggaccca ggatgccgcg aactgctaag aaggttcaga   1620
ggacagtttt ggagaaggag atgcgtagtc ttggtgttga catggacgat aaagacgatg   1680
cccattacgc agtccaggca agaagatccc ggagcatcac taggaaaaga aagcgggaag   1740
actctgctcc cccgtcctct gtggcccgga gtgggagttg ctctcgaact ccacgtgacg   1800
tttctggtct tagggatgtc aagatggtga agaaagccaa gactatgatg aagaatgctc   1860
agaagaagat gaatcggttg ggaagaaag gggaggcgga tagacacgtg tttgatatga   1920
agcccaagca cttgctgtct gggaagagga aagctggtaa aaaggacagg agatagtatc   1980
cgtttggttg gcgtggcttc gctagagtgt tgctgtttat ttcctggttt ggcacagtat   2040
ggtttcatga aattggagct ctgtataaac tgaaaaagac aaaataagta aagcacttgt   2100
tgctttgctg aaaactatgg ttaaccctat ataggtgtgg gaaatttttg tcactgcata   2160
atattacaaa tattttgagt agacagtgtt tccacattta atggagtatc agttgcttca   2220
gattttcaga actgggaaga tttactggtg taactgggtt gtttttgatg gagaaaaacc   2280
ttattttctt ttgtaagagc tgggagcaaa cacgtttatg agtgtgtcgg aatcccgtgc   2340
ttaaaatacg ctcttaaatt attttctagt cttattttac aatgtctcat tgtagtctgt   2400
cttcaactat tttatccaaa ataaacctcc agaagaaagt agttttcatt tacttagctc   2460
atgttttggt ttagttatag tcgctatgga tttggccaaa taaaaaggca aacaacaaaa   2520
aaaaaaaaaa aaaaaaa                                                  2537
```

<210> SEQ ID NO 24
<211> LENGTH: 1687
<212> TYPE: DNA
<213> ORGANISM: Homo sapiens

<400> SEQUENCE: 24

```
gattgtggga aggcagctga actcggcgcc tggaaagatg gaggcagcgg agacagaggc     60
ggaagctgca gccctagagg tcctggctga ggtggcaggc atcttggaac ctgtaggcct    120
gcaggaggag gcagaactgc cagccaagat cctggttgag tttgtggtgg actctcagaa    180
gaaagacaag ctgctctgca gccagcttca ggtagcggat ttcctgcaga acatcctggc    240
tcaggaggac actgctaagg gtctcgaccc cttggcttct gaagacacga gccgacagaa    300
ggcaattgca gctaaggaac aatggaaaga gctgaaggcc acctacaggg agcacgtaga    360
ggccatcaaa attggcctca ccaaggccct gactcagatg gaggaagccc agaggaaacg    420
gacacaactc cgggaagcct ttgagcagct ccaggccaag aaacaaatgg ccatggagaa    480
acgcagagca gtccagaacc agtggcagct acaacaggag aagcatctgc agcatctggc    540
ggaggtttct gcagaggtga gggagcgtaa gacagggact cagcaggagc ttgacagggt    600
gtttcagaaa cttggaaacc tgaagcagca ggcagaacag gagcgggaca agctgcagag    660
gtatcagacc ttcctccagc ttctgtatac cctgcagggt aagctgttgt tccctgaggc    720
tgaggctgag gcagagaatc ttccagatga taaaccccag cagccgactc gaccccagga    780
gcagagtaca ggagacacca tggggagaga ccctggtgtg tccttcaagg ctgttggtct    840
acaacctgct ggagatgtaa atttgccatg acttcctgga ggacagcagc atggagaaag    900
atcctagaaa aggcctctga cttccctcac ctcccaacca tcattacagg aaagactgtg    960
```

aactcctgag ttcagcttga tttctgacta catcccagca agctctggca tctgtggatt 1020
aaaatccctg gatctctctc agttgtgtat ttgttcatct tcatatgctg gcaggaacaa 1080
ctattaatac agatactcag aagccaataa catgacagga gctgggactg gtttgaacac 1140
agggtgtgca gatggggagg gggtactggc cttgggcctc ctatgatgca gacatggtga 1200
atttaattca aggaggagga gaatgtttta ggcaggtggt tatatgtggg aagataattt 1260
tattcatgga tccaaatgtt tgttgagtcc tttctttgtg ctaaggttct tgcggtgaac 1320
cagaattata acagtgagct catctgactg ttttaggatg tacagcctag tgttaacatt 1380
cttggtatct ttttgtgcct tatctaaaac atttctcgat cactggtttc agatgttcat 1440
ttattatatt cttttcaaag attcagagat tggcttttgt catccactat tgtatgtttt 1500
gtttcattga cctctagtga taccttgatc tttcccactt tctgttttcg gattggagaa 1560
gatgtacctt ttttgtcaac tcttactttt atcagatgat caactcacgt atttggatct 1620
ttatttgttt tctcaaataa atatttaagg ttatacattt aaaaaaaaaa aaaaaaaaaa 1680
aaaaaaa 1687

<210> SEQ ID NO 25
<211> LENGTH: 3849
<212> TYPE: DNA
<213> ORGANISM: Homo sapiens

<400> SEQUENCE: 25
cccttttgct tacttcctag tcccgggcag gccggctcgg aggcagcgag aaagcgcagc 60
caggcggctg ctcggcgttc tctcaggtga ctgctcggag ttctcccagt gtttggtgtt 120
gcaagcagga tccaaaggag acctatagtg actcccagga gctcttagtg accaagtgaa 180
ggcaggaaga cagggttctg atggtgtgag tctccttcaa ctcagcaaac caccttggtc 240
tgcctcgagt ttccaacacc cctcctgcct gctagtgata ggtgtgaggc aggttgatga 300
acatggaact tttttctttt ggtcccaaag catgctactc ctggagtttc attcagtgaa 360
tgagaactat agtttggttc tgtgagatct ctatgaatca aggcggccac tgaagcggag 420
aaaagaaatg cttaaatgtt aagaaagttt gaagtgcaga aaaaggttga agcactggac 480
aatgccacat actttgtgga tggtgtgggt cttgggggtc atcatcagcc tctccaagga 540
agaatcctcc aatcaggctt ctctgtcttg tgaccgcaat ggtatctgca agggcagctc 600
aggatcttta aactccattc cctcagggct cacagaagct gtaaaaagcc ttgacctgtc 660
caacaacagg atcacctaca ttagcaacag tgacctacag aggtgtgtga acctccaggc 720
tctggtgctg acatccaatg gaattaacac aatagaggaa gattcttttt cttccctggg 780
cagtcttgaa catttagact tatcctataa ttacttatct aatttatcgt cttcctggtt 840
caagcccctt tcttctttaa cattcttaaa cttactggga aatccttaca aaccctagg 900
ggaaacatct ctttttctc atctcacaaa attgcaaatc ctgagagtgg gaaatatgga 960
caccttcact aagattcaaa gaaaagattt tgctggactt accttccttg aggaacttga 1020
gattgatgct tcagatctac agagctatga gccaaaaagt ttgaagtcaa ttcagaatgt 1080
aagtcatctg atccttcata tgaagcagca tattttactg ctggagattt ttgtagatgt 1140
tacaagttcc gtggaatgtt tggaactgcg agatactgat ttggacactt tccattttc 1200
agaactatcc actggtgaaa caaattcatt gattaaaaag tttacattta gaaatgtgaa 1260
aatcaccgat gaaagtttgt ttcaggttat gaaacttttg aatcagattt ctggattgtt 1320
agaattagag tttgatgact gtacccttaa tggagttggt aattttagag catctgataa 1380
tgacagagtt atagatccag gtaaagtgga aacgttaaca atccggaggc tgcatattcc 1440
aaggttttac ttattttatg atctgagcac tttatattca cttacagaaa gagttaaaag 1500
aatcacagta gaaaacagta aagtttttct ggttccttgt ttactttcac aacatttaaa 1560
atcattagaa tacttggatc tcagtgaaaa tttgatggtt gaagaatact tgaaaaattc 1620
agcctgtgag gatgcctggc cctctctaca aactttaatt ttaaggcaaa atcatttggc 1680
atcattggaa aaaaccggag agactttgct cactctgaaa aacttgacta acattgatat 1740
cagtaagaat agtttttcatt ctatgcctga aacttgtcag tggccagaaa agatgaaata 1800
tttgaactta tccagcacac gaatacacag tgtaacaggc tgcattccca agacactgga 1860
aattttagat gttagcaaca acaatctcaa tttattttct ttgaatttgc cgcaactcaa 1920
agaactttat atttccagaa ataagttgat gactctacca gatgcctccc tcttacccat 1980
gttactagta ttgaaaatca gtaggaatgc aataactacg ttttctaagg agcaacttga 2040
ctcatttcac acactgaaga ctttggaagc tggtggcaat aacttcattt gctcctgtga 2100
attcctctcc ttcactcagg agcagcaagc actggccaaa gtcttgattg attggccagc 2160
aaattacctg tgtgactctc catcccatgt gcgtggccag caggttcagg atgtccgcct 2220
ctcggtgtcg gaatgtcaca ggacagcact ggtgtctggc atgtgctgtg ctctgttcct 2280
gctgatcctg ctcacggggg tcctgtgcca ccgtttccat ggcctgtggt atatgaaaat 2340
gatgtgggcc tggctccagg ccaaaaggaa gcccaggaaa gctcccagca ggaacatctg 2400
ctatgatgca tttgtttctt acagtgagcg ggatgcctac tgggtggaga accttatggt 2460
ccaggagctg gagaacttca atcccccctt caagttgtgt cttcataagc gggacttcat 2520
tcctggcaag tggatcattg acaatatcat tgactccatt gaaaagagcc acaaaactgt 2580
ctttgtgctt tctgaaaact ttgtgaagag tgagtggtgc aagtatgaac tggacttctc 2640
ccatttccgt ctttttgatg agaacaatga tgctgccatt ctcattcttc tggagcccat 2700
tgagaaaaaa gccattcccc agcgcttctg caagctgcgg aagataatga acaccaagac 2760
ctacctggag tggcccatgg acgaggctca gcgggaagga ttttgggtaa atctgagagc 2820
tgcgataaag tcctaggttc ccatatttaa gaccagtctt tgtctagttg ggatctttat 2880
gtcactagtt atagttaagt tcattcagac ataattatat aaaaactacg tggatgtacc 2940
gtcatttgag gacttgctta ctaaaactac aaaacttcaa attttgtctg gggtgctgtt 3000
ttataaacat atgccagatt taaaaattgg tttttggttt ttcttttttc tatgagataa 3060
ccatgatcat aagtctatta ctgatatctg aatatagtcc cttggtatcc aagggaattg 3120
gttgcaggat cctcgtggat atcaaaattc atagatgatc aagtccctta taagagtggc 3180
atagtatttg catataacct gtgtacattc tcctgtatac tttaaatcat ctctagatta 3240
cttatgatac ccaatacaat gtaaatacta tgtaaatagt tgtactgtct ttttatttat 3300
attattattg ttattttttta ttttcaaaat ttttaaaaca tacttttgat ccacagttgg 3360
ttgacttcat ggatgcagaa cccatggata tagagggcca actgtaatct gtagcaactg 3420
gcttagttca ttaggaaaca gcacaaatga acttaagatt ctcaatgact gtgtcattct 3480
ttcttcctgc taagagactc ctctgtggcc acaaaaggca ttctctgtcc tacctagctg 3540
tcacttctct gtgcagctga tctcaagagc aacaaggcaa agtatttggg gcactcccca 3600
aaacttgttg ctattcctag aaaaaagtgc tgtgtatttc ctattaaact ttacaggatg 3660
agaaatacta gagggtgtat tttcatgtga tctggatctg tctttctggc tattagatag 3720
gtttctccag ccatagttac ttgagagagt gagtacacag tgcaaggtac agtaaattat 3780
gtatttctgt aatttaacaa aataaatact cagtttagga gaatttgaaa gacaaaaaaa 3840
aaaaaaaaa 3849

<210> SEQ ID NO 26
<211> LENGTH: 1698
<212> TYPE: DNA
<213> ORGANISM: Homo sapiens

<400> SEQUENCE: 26
ctgcctgggg agcccccccg ccccacatcc tgccccgcaa aaggcagctt caccaaagtg 60
gggtatttcc agcctttgta gctttcactt ccacatctac caagtgggcg gagtggcctt 120
ctgtggacga atcagattcc tctccagcac cgactttaag aggcgagccg gggggtcagg 180
gtcccagatg cacaggagga gaagcaggag ctgtcgggaa gatcagaagc cagtcatgga 240
tgaccagcgc gaccttatct ccaacaatga gcaactgccc atgctgggcc ggcgccctgg 300
ggccccggag agcaagtgca gccgcggagc cctgtacaca ggcttttcca tcctggtgac 360
tctgctcctc gctggccagg ccaccaccgc ctacttcctg taccagcagc agggccggct 420
ggacaaactg acagtcacct cccagaacct gcagctggag aacctgcgca tgaagcttcc 480
caagcctccc aagcctgtga gcaagatgcg catggccacc ccgctgctga tgcaggcgct 540
gcccatggga gccctgcccc aggggcccat gcagaatgcc accaagtatg gcaacatgac 600
agaggaccat gtgatgcacc tgctccagaa tgctgacccc ctgaaggtgt acccgccact 660
gaaggggagc ttcccggaga acctgagaca ccttaagaac accatggaga ccatagactg 720
gaaggtcttt gagagctgga tgcaccattg gctcctgttt gaaatgagca ggcactcctt 780
ggagcaaaag cccactgacg ctccaccgaa agtactgacc aagtgccagg aagaggtcag 840
ccacatccct gctgtccacc cgggttcatt caggcccaag tgcgacgaga acggcaacta 900
tctgccactc cagtgctatg ggagcatcgg ctactgctgg tgtgtcttcc ccaacggcac 960
ggaggtcccc aacaccagaa gccgcgggca ccataactgc agtgagtcac tggaactgga 1020
ggacccgtct tctgggctgg gtgtgaccaa gcaggatctg ggcccagtcc ccatgtgaga 1080
gcagcagagg cggtcttcaa catcctgcca gccccacaca gctacagctt tcttgctccc 1140
ttcagccccc agcccctccc ccatctccca ccctgtacct catcccatga gaccctggtg 1200
cctggctctt tcgtcaccct tggacaagac aaaccaagtc ggaacagcag ataacaatgc 1260
agcaaggccc tgctgcccaa tctccatctg tcaacagggg cgtgaggtcc caggaagtgg 1320
ccaaaagcta gacagatccc cgttcctgac atcacagcag cctccaacac aaggctccaa 1380
gacctaggct catggacgag atgggaaggc acagggagaa gggataaccc tacacccaga 1440
ccccaggctg gacatgctga ctgtcctctc ccctccagcc tttggccttg gcttttctag 1500
cctatttacc tgcaggctga gccactctct tccctttccc cagcatcact ccccaaggaa 1560
gagccaatgt tttccaccca taatcctttc tgccgacccc tagttccctc tgctcagcca 1620
agcttgttat cagctttcag ggccatggtt cacattagaa taaaaggtag taattagaac 1680
aaaaaaaaaa aaaaaaaa 1698

<210> SEQ ID NO 27
<211> LENGTH: 1501
<212> TYPE: DNA
<213> ORGANISM: Homo sapiens

<400> SEQUENCE: 27
agcgagtcct tcttttcctg actgcagctc ttttcatttt gccatccttc tccagctcca 60
tgatggttct gcaggtttct gcggcccccc ggacagtggc tctgacggcg ttactgatgg 120
tgctgctcac atctgtggtc cagggcaggg ccactccaga gaattacgtg taccagggac 180
ggcaggaatg ctacgcgttt aatgggacac agcgcttcct ggagagatac atctacaacc 240
gggaggagta cgcgcgcttc gacagcgacg tgggggagtt ccgggcggtg acggagctgg 300
ggcggcctgc tgcggagtac tggaacagcc agaaggacat cctggaggag aagcgggcag 360
tgccggacag ggtatgcaga cacaactacg agctggacga ggccgtgacc ctgcagcgcc 420
gagtccagcc taaggtgaac gtttccccct ccaagaaggg gcccctgcag caccacaacc 480
tgcttgtctg ccacgtgaca gatttctacc caggcagcat tcaagtccga tggttcctga 540
atggacagga ggaaacagct ggggtcgtgt ccaccaacct gatccgtaat ggagactgga 600
ccttccagat cctggtgatg ctggaaatga ccccccagca gggagacgtc tacatctgcc 660
aagtggagca caccagcctg gacagtcctg tcaccgtgga gtggaaggca cagtctgatt 720
ctgcccagag taagacattg acgggagctg ggggcttcgt gctggggctc atcatctgtg 780
gagtgggcat cttcatgcac aggaggagca agaaagttca acgaggatct gcataaacag 840
ggttcctgac ctcaccgaaa agactaatgt gccttagaac aagcatttgc tgtgttttgt 900
taacacctgg ttccaggaca gaccctcagc ttcccaagag gatactgctg ccaagaagtt 960
gctctgaagt cagtttctat cgttctgctc tttgattcaa agcactgttt ctctcactgg 1020
gcctccaacc atgttccctt cttcttagca ccacaaataa tcaaaaccca acataagtgt 1080
ttgctttcct ttaaaaatat gcatcaaatc gtctctcatt acttttctct gagggtttta 1140
gtaaacagta ggagttaata aagaagttca ttttggttta cacgtaggaa agaagagaag 1200
catcaaagtg gagatatgtt aactattgta taatgtggcc tgttatacat gacactcttc 1260
tgaattgact gtatttcagt gagctgcccc caaatcaagt ttagtgccct catccattta 1320
tgtctcagac cgctattctt aactattcaa tggtgagcag actgcaaatc tgcctgatag 1380
gacccatatt cccacagcac taattcaaca tatatcttac tgagagcatg ttttatcatt 1440
accattaaga agttaaatga acatcagaat ttaaaatcat aaatataatc taatacactt 1500
t 1501

<210> SEQ ID NO 28
<211> LENGTH: 1697
<212> TYPE: DNA
<213> ORGANISM: Homo sapiens

<400> SEQUENCE: 28
atttccagtg ctagaggccc acagtttcag tctcatctgc ctccactcgg cctcagttcc 60
tcatcactgt tcctgtgctc acagtcatca attatagacc ccacaacatg cgccctgaag 120
acagaatgtt ccatatcaga gctgtgatct tgagagccct ctccttggct ttcctgctga 180
gtctccgagg agctggggcc atcaaggcgg accatgtgtc aacttatgcc gcgtttgtac 240
agacgcatag accaacaggg gagtttatgt ttgaatttga tgaagatgag atgttctatg 300
tggatctgga caagaaggag accgtctggc atctggagga gtttggccaa gccttttcct 360
ttgaggctca gggcgggctg gctaacattg ctatattgaa caacaacttg aataccttga 420
tccagcgttc caaccacact caggccacca acgatccccc tgaggtgacc gtgtttccca 480
aggagcctgt ggagctgggc cagcccaaca ccctcatctg ccacattgac aagttcttcc 540
caccagtgct caacgtcacg tggctgtgca acggggagct ggtcactgag ggtgtcgctg 600
agagcctctt cctgcccaga acagattaca gcttccacaa gttccattac ctgacctttg 660
tgccctcagc agaggacttc tatgactgca gggtggagca ctggggcttg gaccagccgc 720
tcctcaagca ctgggaggcc caagagccaa tccagatgcc tgagacaacg gagactgtgc 780
tctgtgccct gggcctggtg ctgggcctag tcggcatcat cgtgggcacc gtcctcatca 840
taaagtctct gcgttctggc catgaccccc gggcccaggg gaccctgtga aatactgtaa 900
aggtgacaaa atatctgaac agaagaggac ttaggagaga tctgaactcc agctgcccta 960
caaactccat ctcagctttt cttctcactt catgtgaaaa ctactccagt ggctgactga 1020
attgctgacc cttcaagctc tgtccttatc cattacctca aagcagtcat tccttagtaa 1080
agtttccaac aaatagaaat taatgacact ttggtagcac taatatggag attatccttt 1140
cattgagcct tttatcctct gttctccttt gaagaacccc tcactgtcac cttcccgaga 1200
ataccctaag accaataaat acttcagtat ttcagagcgg ggagactctg agtcattctt 1260
actggaagtc taggaccagg tcacatgtga atactatttc ttgaaggtgt ggtttcaacc 1320
tctgttgccg atgtggttac taaaggttct gatcccactt gaacggaaag gtctgaggat 1380
attgattcag tcctgggttt ttccctaact acaggatagg gtggggtaga gaaaggatat 1440
ttgggggaaa ttttacttgg atgaagattt tcttggatgt agtttgaaga ctgcagtgtt 1500
tgaagtctct gagggaagag atttggtctg tctggatcaa gatttcaggc agattaggat 1560
tccattcaca gcccctgagc ttccttccca aggctgtatt gtaattatag caatatttca 1620
tggaggattt ttctacatga taaactaaga gccaagaaat aaaattttta aaatgcccta 1680
aaaaaaaaaa aaaaaaa 1697

<210> SEQ ID NO 29
<211> LENGTH: 1312
<212> TYPE: DNA
<213> ORGANISM: Homo sapiens

<400> SEQUENCE: 29
ttttaatggt cagactctat tacaccccac attctctttt cttttattct tgtctgttct 60
gcctcactcc cgagctctac tgactcccaa cagagcgccc aagaagaaaa tggccataag 120
tggagtccct gtgctaggat ttttcatcat agctgtgctg atgagcgctc aggaatcatg 180
ggctatcaaa gaagaacatg tgatcatcca ggccgagttc tatctgaatc ctgaccaatc 240
aggcgagttt atgtttgact ttgatggtga tgagattttc catgtggata tggcaaagaa 300
ggagacggtc tggcggcttg aagaatttgg acgatttgcc agctttgagg ctcaaggtgc 360
attggccaac atagctgtgg acaaagccaa cctggaaatc atgacaaagc gctccaacta 420
tactccgatc accaatgtac ctccagaggt aactgtgctc acaaacagcc ctgtggaact 480
gagagagccc aacgtcctca tctgtttcat agacaagttc accccaccag tggtcaatgt 540
cacgtggctt cgaaatggaa aacctgtcac cacaggagtg tcagagacag tcttcctgcc 600
cagggaagac cacctttcc gcaagttcca ctatctcccc ttcctgccct caactgagga 660
cgtttacgac tgcagggtgg agcactgggg cttggatgag cctcttctca agcactggga 720
gtttgatgct ccaagccctc tcccagagac tacagagaac gtggtgtgtg ccctgggcct 780
gactgtgggt ctggtgggca tcattattgg gaccatcttc atcatcaagg gattgcgcaa 840
aagcaatgca gcagaacgca gggggcctct gtaaggcaca tggaggtgat ggtgtttctt 900

```
agagagaaga tcactgaaga aacttctgct ttaatggctt tacaaagctg gcaatattac     960
aatccttgac ctcagtgaaa gcagtcatct tcagcatttt ccagccctat agccacccca    1020
agtgtggata tgcctcttcg attgctccgt actctaacat ctagctggct tccctgtcta    1080
ttgcctttc ctgtatctat tttcctctat ttcctatcat tttattatca ccatgcaatg     1140
cctctggaat aaaacataca ggagtctgtc tctgctatgg aatgccccat ggggcatctc    1200
ttgtgtactt attgtttaag gtttcctcaa actgtgattt ttctgaacac aataaactat    1260
tttgatgatc ttgggtggaa aaaaaaaaaa aaaaaaaaaa aaaaaaaaaa aa            1312

<210> SEQ ID NO 30
<211> LENGTH: 2973
<212> TYPE: DNA
<213> ORGANISM: Homo sapiens

<400> SEQUENCE: 30

gggccgctct ctgacatcag agctgctgta gagcggagag gggcaggggt gaagggccac      60
ggtggtgcaa cccaccactt cctccaagga ggagctgaga ggaacaggaa gtgtcaggac     120
tttacgaccc gcgcctccag ctgaggtttc tagacgtgac ccagggcaga ctggtagcaa     180
agcccccacg cccagccagg agcaccgccg aggactccag cacaccgagg gacatgctgg     240
gcctgcgccc cccactgctc gccctggtgg ggctgctctc cctcgggtgc gtcctctctc     300
aggagtgcac gaagttcaag gtcagcagct gccgggaatg catcgagtcg gggcccggct     360
gcacctggtg ccagaagctg aacttcacag ggccgggga tcctgactcc attcgctgcg      420
acacccggcc acagctgctc atgaggggct gtgcggctga cgacatcatg gaccccacaa     480
gcctcgctga aacccaggaa gaccacaatg gggccagaa gcagctgtcc ccacaaaaag      540
tgacgcttta cctgcgacca ggccaggcag cagcgttcaa cgtgaccttc cggcgggcca     600
agggctaccc catcgacctg tactatctga tggacctctc ctactccatg cttgatgacc     660
tcaggaatgt caagaagcta ggtggcgacc tgctccgggc cctcaacgag atcaccgagt     720
ccggccgcat tggcttcggg tccttcgtgg acaagaccgt gctgccgttc gtgaacacgc     780
accctgataa gctgcgaaac ccatgcccca acaaggagaa agagtgccag cccccgtttg     840
ccttcaggca cgtgctgaag ctgaccaaca actccaacca gtttcagacc gaggtcggga     900
agcagctgat ttccggaaac ctggatgcac ccgagggtgg gctggacgcc atgatgcagg     960
tcgccgcctg cccggaggaa atcggctggc gcaacgtcac gcggctgctg gtgtttgcca    1020
ctgatgacgg cttccatttc gcgggcgacg ggaagctggg cgccatcctg acccccaacg    1080
acggccgctg tcacctggag gacaacttgt acaagaggag caacgaattc gactacccat    1140
cggtgggcca gctggcgcac aagctggctg aaaacaacat ccagcccatc ttcgcggtga    1200
ccagtaggat ggtgaagacc tacgagaaac tcaccgagat catccccaag tcagccgtgg    1260
gggagctgtc tgaggactcc agcaatgtgg tccatctcat taagaatgct tacaataaac    1320
tctcctccag ggtcttcctg gatcacaacg ccctccccga caccctgaaa gtcacctacg    1380
actccttctg cagcaatgga gtgacgcaca ggaaccagcc cagaggtgac tgtgatggcg    1440
tgcagatcaa tgtcccgatc accttccagg tgaaggtcac ggccacagag tgcatccagg    1500
agcagtcgtt tgtcatccgg gcgctgggct tcacggacat agtgaccgtg caggttcttc    1560
cccagtgtga gtgccggtgc cgggaccaga gcagagaccg cagcctctgc catggcaagg    1620
gcttcttgga gtgcggcatc tgcaggtgtg acactggcta cattgggaaa aactgtgagt    1680
gccagacaca gggccggagc agccaggagc tggaaggaag ctgccggaag gacaacaact    1740
```

ccatcatctg ctcagggctg ggggactgtg tctgcgggca gtgcctgtgc cacaccagcg 1800
acgtccccgg caagctgata tacgggcagt actgcgagtg tgacaccatc aactgtgagc 1860
gctacaacgg ccaggtctgc ggcggcccgg ggagggggct ctgcttctgc gggaagtgcc 1920
gctgccaccc gggctttgag ggctcagcgt gccagtgcga gaggaccact gagggctgcc 1980
tgaacccgcg gcgtgttgag tgtagtggtc gtggccggtg ccgctgcaac gtatgcgagt 2040
gccattcagg ctaccagctg cctctgtgcc aggagtgccc cggctgcccc tcaccctgtg 2100
gcaagtacat ctcctgcgcc gagtgcctga agttcgaaaa gggccccttt gggaagaact 2160
gcagcgcggc gtgtccgggc ctgcagctgt cgaacaaccc cgtgaagggc aggacctgca 2220
aggagaggga ctcagagggc tgctgggtgg cctacacgct ggagcagcag gacgggatgg 2280
accgctacct catctatgtg gatgagagcc gagagtgtgt ggcaggcccc aacatcgccg 2340
ccatcgtcgg gggcaccgtg gcaggcatcg tgctgatcgg cattctcctg ctggtcatct 2400
ggaaggctct gatccacctg agcgacctcc gggagtacag gcgctttgag aaggagaagc 2460
tcaagtccca gtggaacaat gataatcccc ttttcaagag cgccaccacg acggtcatga 2520
accccaagtt tgctgagagt taggagcact tggtgaagac aaggccgtca ggacccacca 2580
tgtctgcccc atcacgcggc cgagacatgg cttgccacag ctcttgagga tgtcaccaat 2640
taaccagaaa tccagttatt ttccgccctc aaaatgacag ccatggccgg ccgggtgctt 2700
ctgggggctc gtcgggggga cagctccact ctgactggca cagtctttgc atggagactt 2760
gaggagggag ggcttgaggt tggtgaggtt aggtgcgtgt ttcctgtgca agtcaggaca 2820
tcagtctgat taaaggtggt gccaatttat ttacatttaa acttgtcagg gtataaaatg 2880
acatcccatt aattatattg ttaatcaatc acgtgtatag aaaaaaaata aaacttcaat 2940
acaggctgtc catggaaaaa aaaaaaaaaa aaa 2973

<210> SEQ ID NO 31
<211> LENGTH: 2755
<212> TYPE: DNA
<213> ORGANISM: Homo sapiens

<400> SEQUENCE: 31
cctacccgcg cgcaggccaa gttgctgaat caatggagcc ctccccaacc cgggcgttcc 60
ccagcgaggc ttccttccca tcctcctgac caccggggct tttcgtgagc tcgtctctga 120
tctcgcgcaa gagtgacaca caggtgttca aagacgcttc tggggagtga gggaagcggt 180
ttacgagtga cttggctgga gcctcagggg cgggcactgg cacggaacac accctgaggc 240
cagccctggc tgcccaggcg gagctgcctc ttctcccgcg ggttggtgga cccgctcagt 300
acggagttgg ggaagctctt tcacttcgga ggattgctca acaaccatgc tgggcatctg 360
gaccctccta cctctggttc ttacgtctgt tgctagatta tcgtccaaaa gtgttaatgc 420
ccaagtgact gacatcaact ccaagggatt ggaattgagg aagactgtta ctacagttga 480
gactcagaac ttggaaggcc tgcatcatga tggccaattc tgccataagc cctgtcctcc 540
aggtgaaagg aaagctaggg actgcacagt caatggggat gaaccagact gcgtgccctg 600
ccaagaaggg aaggagtaca cagacaaagc ccatttttct tccaaatgca gaagatgtag 660
attgtgtgat gaaggacatg gcttagaagt ggaaataaac tgcacccgga cccagaatac 720
caagtgcaga tgtaaaccaa acttttttg taactctact gtatgtgaac actgtgaccc 780
ttgcaccaaa tgtgaacatg gaatcatcaa ggaatgcaca ctcaccagca acaccaagtg 840

-continued

```
caaagaggaa ggatccagat ctaacttggg gtggctttgt cttcttcttt tgccaattcc    900
actaattgtt tgggtgaaga gaaaggaagt acagaaaaca tgcagaaagc acagaaagga    960
aaaccaaggt tctcatgaat ctccaacttt aaatcctgaa acagtggcaa taaatttatc   1020
tgatgttgac ttgagtaaat atatcaccac tattgctgga gtcatgacac taagtcaagt   1080
taaaggcttt gttcgaaaga atggtgtcaa tgaagccaaa ataggtgaga tcaagaatga   1140
caatgtccaa gacacagcag aacagaaagt tcaactgctt cgtaattggc atcaacttca   1200
tggaaagaaa gaagcgtatg acacattgat taaagatctc aaaaaagcca atctttgtac   1260
tcttgcagag aaaattcaga ctatcatcct caaggacatt actagtgact cagaaaattc   1320
aaacttcaga aatgaaatcc aaagcttggt ctagagtgaa aaacaacaaa ttcagttctg   1380
agtatatgca attagtgttt gaaaagattc ttaatagctg gctgtaaata ctgcttggtt   1440
ttttactggg tacattttat catttattag cgctgaagag ccaacatatt tgtagatttt   1500
taatatctca tgattctgcc tccaaggatg tttaaaatct agttgggaaa acaaacttca   1560
tcaagagtaa atgcagtggc atgctaagta cccaaatagg agtgtatgca gaggatgaaa   1620
gattaagatt atgctctggc atctaacata tgattctgta gtatgaatgt aatcagtgta   1680
tgttagtaca aatgtctatc cacaggctaa ccccactcta tgaatcaata gaagaagcta   1740
tgacctttttg ctgaaatatc agttactgaa caggcaggcc actttgcctc taaattacct   1800
ctgataattc tagagatttt accatatttc taaactttgt ttataactct gagaagatca   1860
tatttatgta aagtatatgt atttgagtgc agaatttaaa taaggctcta cctcaaagac   1920
ctttgcacag tttattggtg tcatattata caatatttca attgtgaatt cacatagaaa   1980
acattaaatt ataatgtttg actattatat atgtgtatgc attttactgg ctcaaaacta   2040
cctacttctt tctcaggcat caaaagcatt ttgagcagga gagtattact agagctttgc   2100
cacctctcca tttttgcctt ggtgctcatc ttaatggcct aatgcacccc caaacatgga   2160
aatatcacca aaaaatactt aatagtccac caaaaggcaa gactgccctt agaaattcta   2220
gcctggtttg gagatactaa ctgctctcag agaaagtagc tttgtgacat gtcatgaacc   2280
catgtttgca atcaaagatg ataaaataga ttcttatttt tcccccaccc ccgaaaatgt   2340
tcaataatgt cccatgtaaa acctgctaca aatggcagct tatacatagc aatggtaaaa   2400
tcatcatctg gatttaggaa ttgctcttgt catacccccca agtttctaag atttaagatt   2460
ctccttacta ctatcctacg tttaaatatc tttgaaagtt tgtattaaat gtgaatttta   2520
agaaataata tttatatttc tgtaaatgta aactgtgaag atagttataa actgaagcag   2580
atacctggaa ccacctaaag aacttccatt tatggaggat ttttttgccc cttgtgtttg   2640
gaattataaa atataggtaa aagtacgtaa ttaaataatg tttttggtaa aaaaaaaaaa   2700
aaaaaaaaaa aaaaaaaaaa aaaaaaaaaa aaaaaaaaaa aaaaaaaaaa aaaaa        2755
```

<210> SEQ ID NO 32
<211> LENGTH: 1280
<212> TYPE: DNA
<213> ORGANISM: Homo sapiens

<400> SEQUENCE: 32

```
cctataactt ggaatgtggg tggaggggtt catagttctc cctgagtgag acttgcctgc     60
ttctctggcc cctggtcctg tcctgttctc cagcatggtg tgtctgaagc tccctggagg    120
ctcctgcatg acagcgctga cagtgacact gatggtgctg agctccccac tggctttgtc    180
tggggacacc cgaccacgtt tcctgtggca gcctaagagg gagtgtcatt tcttcaatgg    240
```

```
gacggagcgg gtgcggttcc tggacagata cttctataac caggaggagt ccgtgcgctt    300
cgacagcgac gtgggggagt tccgggcggt gacggagctg gggcggcctg acgctgagta    360
ctggaacagc cagaaggaca tcctggagca ggcgcgggcc gcggtggaca cctactgcag    420
acacaactac ggggttgtgg agagcttcac agtgcagcgg cgagtccaac ctaaggtgac    480
tgtatatcct tcaaagaccc agcccctgca gcaccacaac ctcctggtct gctctgtgag    540
tggtttctat ccaggcagca ttgaagtcag gtggttcctg aacggccagg aagagaaggc    600
tgggatggtg tccacaggcc tgatccagaa tggagactgg accttccaga ccctggtgat    660
gctggaaaca gttcctcgaa gtggagaggt ttacacctgc caagtggagc acccaagcgt    720
gacaagccct ctcacagtgg aatggagagc acggtctgaa tctgcacaga gcaagatgct    780
gagtggagtc gggggctttg tgctgggcct gctcttcctt ggggccgggc tgttcatcta    840
cttcaggaat cagaaaggac actctggact tcagccaaca ggattcctga gctgaaatgc    900
agatgaccac attcaaggaa gaactttctg ccccggcttt gcaggatgaa aagctttcct    960
gcttggcagt tattcttcca caagagaggg ctttctcagg acctggttgc tactggttcg   1020
gcaactgcag aaaatgtcct cccttgtggc ttcctcagct cctgcccttg gcctgaagtc   1080
ccagcattga tggcagcgcc tcatcttcaa cttttgtgct cccctttgcc taaaccgtat   1140
ggcctcccgt gcatctgtat tcaccctgta tgacaaacac attacattat taaatgtttc   1200
tcaaagatgg agttaaaaaa aaaaaaaaaa aaaaaaaaaa aaaaaaaaaa aaaaaaaaaa   1260
aaaaaaaaaa aaaaaaaaaa                                               1280
```

<210> SEQ ID NO 33
<211> LENGTH: 2398
<212> TYPE: DNA
<213> ORGANISM: Homo sapiens

<400> SEQUENCE: 33

```
ctgatataga gcaggcgccg cgggtcgcag cacagtgcgg agaccgcagc cccggagccc     60
gggccagggt ccacctgtcc ccgcagcgcc ggctcgcgcc ctcctgccgc agccaccgag    120
ccgccgtcta gcgccccgac ctcgccacca tgagagccct gctggcgcgc ctgcttctct    180
gcgtcctggt cgtgagcgac tccaaaggca gcaatgaact tcatcaagtt ccatcgaact    240
gtgactgtct aaatggagga acatgtgtgt ccaacaagta cttctccaac attcactggt    300
gcaactgccc aaagaaattc ggagggcagc actgtgaaat agataagtca aaaacctgct    360
atgaggggaa tggtcacttt taccgaggaa aggccagcac tgacaccatg ggccggccct    420
gcctgccctg gaactctgcc actgtccttc agcaaacgta ccatgcccac agatctgatg    480
ctcttcagct gggcctgggg aaacataatt actgcaggaa cccagacaac cggaggcgac    540
cctggtgcta tgtgcaggtg ggcctaaagc cgcttgtcca agagtgcatg gtgcatgact    600
gcgcagatgg aaaaaagccc tcctctcctc cagaagaatt aaaatttcag tgtggccaaa    660
agactctgag gccccgcttt aagattattg gggagaatt caccaccatc gagaaccagc     720
cctggtttgc ggccatctac aggaggcacc ggggggctc tgtcacctac gtgtgtggag     780
gcagcctcat cagcccttgc tgggtgatca gcgccacaca ctgcttcatt gattacccaa    840
agaaggagga ctacatcgtc tacctgggtc gctcaaggct taactccaac acgcaagggg    900
agatgaagtt tgaggtggaa aacctcatcc tacacaagga ctacagcgct gacacgcttg    960
ctcaccacaa cgacattgcc ttgctgaaga tccgttccaa ggagggcagg tgtgcgcagc   1020
```

```
catcccggac tatacagacc atctgcctgc cctcgatgta taacgatccc cagtttggca   1080
caagctgtga gatcactggc tttggaaaag agaattctac cgactatctc tatccggagc   1140
agctgaaaat gactgttgtg aagctgattt cccaccggga gtgtcagcag ccccactact   1200
acggctctga agtcaccacc aaaatgctgt gtgctgctga cccacagtgg aaaacagatt   1260
cctgccaggg agactcaggg ggacccctcg tctgttccct ccaaggccgc atgactttga   1320
ctggaattgt gagctggggc cgtggatgtg ccctgaagga caagccaggc gtctacacga   1380
gagtctcaca cttcttaccc tggatccgca gtcacaccaa ggaagagaat ggcctggccc   1440
tctgagggtc cccagggagg aaacgggcac cacccgcttt cttgctggtt gtcatttttg   1500
cagtagagtc atctccatca gctgtaagaa gagactggga agataggctc tgcacagatg   1560
gatttgcctg tgccacccac cagggcgaac gacaatagct ttaccctcag gcataggcct   1620
gggtgctggc tgcccagacc cctctggcca ggatggaggg gtggtcctga ctcaacatgt   1680
tactgaccag caacttgtct tttctggac tgaagcctgc aggagttaaa aagggcaggg   1740
catctcctgt gcatgggtga agggagagcc agctcccccg acggtgggca tttgtgaggc   1800
ccatggttga gaaatgaata atttcccaat taggaagtgt aacagctgag gtctcttgag   1860
ggagcttagc caatgtggga gcagcggttt ggggagcaga gacactaacg acttcagggc   1920
agggctctga tattccatga atgtatcagg aaatatatat gtgtgtgtat gtttgcacac   1980
ttgtgtgtgg gctgtgagtg taagtgtgag taagagctgg tgtctgattg ttaagtctaa   2040
atatttcctt aaactgtgtg gactgtgatg ccacacagag tggtctttct ggagaggtta   2100
taggtcactc ctggggcctc ttgggtcccc cacgtgacag tgcctgggaa tgtattattc   2160
tgcagcatga cctgtgacca gcactgtctc agtttcactt tcacatagat gtccctttct   2220
tggccagtta tcccttcctt ttagcctagt tcatccaatc ctcactgggt ggggtgagga   2280
ccactcctgt acactgaata tttatatttc actattttta tttatatttt tgtaatttta   2340
aataaaagtg atcaataaaa tgtgattttt ctgatgacaa aaaaaaaaaa aaaaaaaa     2398
```

<210> SEQ ID NO 34
<211> LENGTH: 3050
<212> TYPE: DNA
<213> ORGANISM: Homo sapiens

<400> SEQUENCE: 34

```
ggagtcagtg atttgaacga agtactttca gtttcatatt actctaaatc cattacaaat     60
ctgcttagct tctaaatatt tcatcaatga ggaaatccca gccctacaac ttcggaacag    120
tgaaatatta gtccagggat ccagtgagag acacagaagt gctagaagcc agtgctcgtg    180
aactaaggag aaaaagaaca gacaagggaa cagcctggac atggcatcag agatccacat    240
gacaggccca atgtgcctca ttgagaacac taatgggcga ctgatggcga atccagaagc    300
tctgaagatc ctttctgcca ttacacagcc tatggtggtg gtggcaattg tgggcctcta    360
ccgcacaggc aaatcctacc tgatgaacaa gctggctgga aagaaaaagg gcttctctct    420
gggctccacg gtgcagtctc acactaaagg aatctggatg tggtgtgtgc ccaccccaa     480
gaagccaggc cacatcctag ttctgctgga caccgagggt ctgggagatg tagagaaggg    540
tgacaaccag aatgactcct ggatcttcgc cctggccgtc ctcctgagca gcaccttcgt    600
gtacaatagc ataggaacca tcaaccagca ggctatggac caactgtact atgtgacaga    660
gctgacacat agaatccgat caaaatcctc acctgatgag aatgagaatg aggttgagga    720
ttcagctgac tttgtgagct tcttcccaga ctttgtgtgg acactgagag atttctccct    780
```

-continued

```
ggacttggaa gcagatggac aacccctcac accagatgag tacctgacat actccctgaa    840
gctgaagaaa ggtaccagtc aaaaagatga aacttttaac ctgcccagac tctgtatccg    900
gaaattcttc ccaaagaaaa aatgctttgt ctttgatcgg cccgttcacc gcaggaagct    960
tgcccagctc gagaaactac aagatgaaga gctggacccc gaatttgtgc aacaagtagc   1020
agacttctgt tcctacatct ttagtaattc caaaactaaa actctttcag gaggcatcca   1080
ggtcaacggg cctcgtctag agagcctggt gctgacctac gtcaatgcca tcagcagtgg   1140
ggatctgccg tgcatggaga acgcagtcct ggccttggcc cagatagaga actcagctgc   1200
agtgcaaaag gctattgccc actatgaaca gcagatgggc cagaaggtgc agctgcccac   1260
agaaaccctc caggagctgc tggacctgca cagggacagt gagagagagg ccattgaagt   1320
cttcatcagg agttccttca aagatgtgga ccatctattt caaaaggagt tagcggccca   1380
gctagaaaaa aagcgggatg acttttgtaa acagaatcag gaagcatcat cagatcgttg   1440
ctcagcttta cttcaggtca ttttcagtcc tctagaagaa gaagtgaagg cgggaattta   1500
ttcgaaacca gggggctatc gtctctttgt tcagaagcta caagacctga agaaaaagta   1560
ctatgaggaa ccgaggaagg ggatacaggc tgaagagatt ctgcagacat acttgaaatc   1620
caaggagtct atgactgatg caattctcca gacagaccag actctcacag aaaaagaaaa   1680
ggagattgaa gtggaacgtg tgaaagctga gtctgcacag gcttcagcaa aaatgttgca   1740
ggaaatgcaa agaaagaatg agcagatgat ggaacagaag gagaggagtt atcaggaaca   1800
cttgaaacaa ctgactgaga agatggagaa cgacagggtc cagttgctga aagagcaaga   1860
gaggaccctc gctcttaaac ttcaggaaca ggagcaacta ctaaaagagg gatttcaaaa   1920
agaaagcaga ataatgaaaa atgagataca ggatctccag acgaaaatga gacgacgaaa   1980
ggcatgtacc ataagctaaa gaccagagcc ttcctgtcac ccctaaccaa ggcataattg   2040
aaacaatttt agaatttgga acaagcgtca ctacatttga taataattag atcttgcatc   2100
ataacaccaa aagtttataa aggcatgtgg tacaatgatc aaaatcatgt tttttcttaa   2160
aaaaaaaaaa agactgtaaa ttgtgcaaca aagatgcatt tacctctgta tcaactcagg   2220
aaatctcata agctggtacc actcaggaga agtttattct tccagatgac cagcagtaga   2280
caaatggata ctgagcagag tcttaggtaa aagtcttggg aaatatttgg gcattggtct   2340
ggccaagtct acaatgtccc aatatcaagg acaaccaccc tagcttctta gtgaagacaa   2400
tgtacagtta tccgttagat caagactaca cggtctatga gcaataatgt gatttctgga   2460
cattgcccat gtataatcct cactgatgat ttcaagctaa agcaaaccac cttatacaga   2520
gatctagaat ctctttatgt tctccagagg aaggtggaag aaaccatggg caggagtagg   2580
aattgagtga taaacaattg ggctaatgaa gaaaacttct cttattgttc agttcatcca   2640
gattataact tcaatgggac actttagacc attagacaat tgacactgga ttaaacaaat   2700
tcacataatg ccaaatacac aatgtattta tagcaacgta taatttgcaa agatggactt   2760
taaaagatgc tgtgtaacta aactgaaata attcaattac ttattattta gaatgttaaa   2820
gcttatgata gtcttttcta actcttaaca ctcatacttg aaaactttct gagtttcccc   2880
agaagagaat atgggatttt ttttgacatt tttgactcat ttaataatgc tcttgtgttt   2940
acctagtata tgtagacttt gtcttatgtg tgaaaagtcc taggaaagtg gttgatgttt   3000
cttatagcaa ttaaaaatta tttttgaact gaaaatacaa tgtatttcac              3050
```

<210> SEQ ID NO 35

<211> LENGTH: 4146
<212> TYPE: DNA
<213> ORGANISM: Homo sapiens

<400> SEQUENCE: 35
cggagcctca gcgcccgccg cgtccctccc tccgcccctt tcgcccacac ctacccgccc 60
ccgccggccc ggctctcagt agcgtcgccc gaggctgcag cagcgcatcc cggggcatgg 120
cgcggcgggg gcgcggaggg ctcggttcgg agggggccgg gagcccgggc gccctggagt 180
gaggaggacc gggagctggc tctggaggct gcggaggcga cgccggagag aacgaagcct 240
cggctgggag cggatctttc gaagatggtt tggctgcctt ggagatttgg agatctgatg 300
ccacgatgag gactcacaca cggggggctc ccagtgtgtt tttcatatat ttgctttgct 360
ttgtgtcagc ctacatcacc gacgagaacc cagaagttat gattcccttc accaatgcca 420
actacgacag ccatcccatg ctgtacttct ccagggcaga agtggcggag ctgcagctca 480
gggctgccag ctcgcacgag cacattgcag cccgcctcac ggaggctgtg cacacgatgc 540
tgtccagccc cttggaatac ctccctccct gggatcccaa ggactacagt gcccgctgga 600
atgaaatttt tggaaacaac ttgggtgcct tggcaatgtt ctgtgtgctg tatcctgaga 660
acattgaagc ccgagacatg gccaaagact acatggagag gatggcagcg cagcctagtt 720
ggttggtgaa agatgctcct tgggatgagg tcccgcttgc tcactccctg gttggttttg 780
ccactgctta tgacttcttg tacaactacc tgagcaagac acaacaggag aagtttcttg 840
aagtgattgc caatgcctca gggtatatgt atgaaacttc atacaggaga ggatggggat 900
ttcaatacct gcacaatcat cagcccacca actgtatggc tttgctcacg ggaagcctag 960
tcctgatgaa tcaaggatat cttcaagaag cctacttatg gaccaaacaa gttctgacca 1020
tcatggagaa atctctggtc ttgctcaggg aggtgacgga tggctccctc tatgaaggag 1080
ttgcgtatgg cagctacacc actagatcac tcttccaata catgtttctc gtccagaggc 1140
acttcaacat caaccacttt ggccatccgt ggcttaaaca acactttgca tttatgtata 1200
gaaccatcct gccagggttt caaaggactg tggctattgc ggactcaaat tacaactggt 1260
tttatggtcc agaaagccaa ttagtgttcc ttgataaatt tgtcatgcgt aatggcagtg 1320
gtaactggct agctgaccaa atcagaagga accgtgtggt ggaaggtcca ggaacaccat 1380
ccaaagggca gcgctggtgc actctgcaca cagaatttct ctggtatgat ggcagcttga 1440
aatcggttcc tcctccagac tttggcaccc ctacactgca ttattttgaa gactggggtg 1500
tcgtgactta tggaagtgca ctacctgcag aaatcaatag atctttcctt tccttcaagt 1560
ctggaaaact gggggggacgt gcaatatatg acattgtcca cagaaacaaa tacaaagatt 1620
ggatcaaagg atggagaaat tttaatgcag ggcatgaaca tcctgatcaa aactcattta 1680
cttttgctcc caatggtgtg cctttcatta ctgaggctct gtacgggcca aagtacacct 1740
tcttcaacaa tgttttgatg ttttccccag ctgtgtcaaa gagctgcttt tctccctggg 1800
tgggtcaggt cacagaagac tgctcatcaa aatggtctaa atacaagcat gacctggcag 1860
ctagttgtca ggggagggtg gttgcagcag aggagaaaaa tggggtggtt ttcatccgag 1920
gagaaggtgt gggagcttat aacccccagc tcaacctgaa gaatgttcag aggaatctca 1980
tcctcctaca tccacagctg cttctccttg tagaccaaat acacctggga gaggagagtc 2040
ccttggagac agcagcgagc ttcttccata atgtggatgt tcctttttgag gagactgtgg 2100 tagatggtgt ccatggggct ttcatcaggc agagagatgg tctctataaa atgtactgga 2160
tggacgatac tggctacagc gagaaagcaa cctttgcctc agtgacatat cctcggggct 2220

```
atccctacaa cgggacaaac tatgtgaatg tcaccatgca cctccgaagt cccatcacca   2280
gggcagctta cctcttcata gggccatcta tagatgttca gagcttcact gtccacggag   2340
actctcagca actggatgtg ttcatagcca ccagcaaaca tgcctacgcc acatacctgt   2400
ggacaggtga ggccacagga cagtctgcct ttgcacaggt cattgctgat cgtcacaaaa   2460
ttctgtttga ccggaattca gccatcaaga gcagcattgt ccctgaggtg aaggactatg   2520
ctgctattgt ggaacagaac ttgcagcatt ttaaaccagt gtttcagctg ctggagaagc   2580
agatactgtc ccgagtccgg aacacagcta gctttaggaa gactgctgaa cgcctgctga   2640
gattttcaga taagagacag actgaggagg ccattgacag gatttttgcc atatcacagc   2700
aacagcagca gcaaagcaag tcaaagaaaa accgaagggc aggcaaacgc tataaatttg   2760
tggatgctgt ccctgatatt tttgcacaga ttgaagtcaa tgagaaaaag attagacaga   2820
aagctcagat tttggcacag aaagaactac ccatagatga agatgaagaa atgaaagacc   2880
ttttagattt tgcagatgta acatacgaga aacataaaaa tggggggcttg attaaaggcc   2940
ggtttggaca ggcacggatg gtgacaacta cacacagcag ggccccatca ctgtctgctt   3000
cctataccag gttgttcctg attctgaaca ttgctatttt ctttgtcatg ttggcaatgc   3060
aactgactta tttccagagg gcccagagcc tacatggcca aagatgtctt tatgcagttc   3120
ttctcataga tagctgtatt ttattatggt tgtactcttc ttgttcccaa tcacagtgtt   3180
agcactgaag ctataaatta cctggtcatt ttgtgatcac aagagtctat gcaaaaaaaa   3240
aaatttcttt accccagatt atcagatttt tttccctcag attcatttta acaaattaag   3300
ggaagatatt ttgacacaag aaagcaggaa cgtggagaaa ttggagcagg aaaagaaatt   3360
atcaaagcaa tagaaatagc ttggtggtcc tatggtgttt ttggaagtat ttggcattgc   3420
taattgagca gtccatatag tactactttt agaagaaaca aaaagtctat tttttaaagt   3480
aatgtttttt cttatgagaa aaaggtttag atagaattgg gttttattaa tattaattta   3540
atgctattag caatttccat atactatatt gtggaaaaga ctgaagaata caattctgag   3600
aaatataaaa aaattttaat ggtatactca tgttgaaaga taaatgttgc taagtcctgg   3660
tatgatggtg tgagcttcct tggggaagta cttcttgagt tatgtaacta acaggatgtt   3720
ttactacaga tctggatggc tattcagata acatggcaaa aaatgatagc agaagatcat   3780
taaaaactta aaatatattt tattagaaaa catttatcta tgaatgaata tttccttgat   3840
gctggtctct gcacacatat gcttggttac ttgcatgcat tcattggttg ttcaataagt   3900
gagatgatta cagataatac tgtattttcc ttatatggaa aaccgttata gacccaataa   3960
caactaaacc tttcaaaaga aaatattttc tattatgaat gttgattttc ataccaaaga   4020
agatggagag tctaaaattt ggatatgatt cttatgtttt tttaatagaa aaccttcttc   4080
aagtttattt tcctaaataa acatcataat tgtgaatttt ctctagtaaa aaaaaaaaaa   4140
aaaaaa                                                              4146
```

<210> SEQ ID NO 36
<211> LENGTH: 1236
<212> TYPE: DNA
<213> ORGANISM: Homo sapiens

<400> SEQUENCE: 36

```
caggcgctga cgaggagccc ggctgaggga ggatgcgccg ctgacgcctg cgggagccgc     60
gcgcctgggg cgggaggatg ctccagaggg gcctctggcc gtggcgcacg cggctgctgc    120
```

-continued

```
cgacccctgg cacctggcgc ccagcgcgcc cgtggccgct gccgcctccg ccccaggttt    180

tgcgtgtgaa gctgtgtgga aatgtgaaat actaccagtc acaccattat agtaccgtgg    240

tgccacctga tgaaataaca gttatttata gacatggcct tcccttggta acacttacct    300

tgccatctag aaaagaacgt tgtcaattcg tagtcaaacc aatgttgtca acagttggtt    360

cattccttca ggacctacaa aatgaagata agggtatcaa aactgcagcc atcttcacag    420

cagatggcaa catgatttca gcttctacct tgatggatat tttgctaatg aatgatttta    480

aacttgtcat taataaaata gcatatgatg tgcagtgtcc aaagagagaa aaaccaagta    540

atgagcacac tgctgagatg gaacacatga aatccttggt tcacagacta tttacaatct    600

tgcatttaga agagtctcag aaaaagagag agcaccattt actggagaaa attgaccacc    660

tgaaggaaca gctgcagccc cttgaacagg tgaaagctgg aatagaagct cattcggaag    720

ccaaaaccag tggactcctg tgggctggat tggcactgct gtccattcag ggtggggcac    780

tggcctggct cacgtggtgg gtgtactcct gggatatcat ggagccagtt acatacttca    840

tcacatttgc aaattctatg gtctttttttg catactttat agtcactcga caggattata    900

cttactcagc tgttaagagt aggcaatttc ttcagttctt ccacaagaaa tcaaagcaac    960

agcactttga tgtgcagcaa tacaacaagt taaaagaaga ccttgctaag gctaaagaat   1020

ccctgaaaca ggcgcgtcat tctctctgtt tgcaaatgca agtagaagaa ctcaatgaaa   1080

agaattaatc ttacagtttt aaatgtcgtc agattttcca ttatgtattg attttgcaac   1140

ttaggatgtt tttgagtccc atggttcatt ttgattgttt aatctttgtt attaaattct   1200

tgtaaaacag aaaaaaaaaa aaaaaaaaaa aaaaaa                              1236
```

<210> SEQ ID NO 37
<211> LENGTH: 2805
<212> TYPE: DNA
<213> ORGANISM: Homo sapiens

<400> SEQUENCE: 37

```
ctccttgcac gggccggccc agcttccccg cccctggcgt ccgctccctc ccgctcgcag     60

cttacttaac ctggcccggg cggcggaggc gctctcactt ccctggagcc gcccgcttgc    120

ccgtcggtcg ctagctcgct cggtgcgcgt cgtcccgctc catggcgctc ttcgtgcggc    180

tgctggctct cgccctggct ctggccctgg gccccgccgc gaccctggcg ggtcccgcca    240

agtcgcccta ccagctggtg ctgcagcaca gcaggctccg gggccgccag cacggcccca    300

acgtgtgtgc tgtgcagaag gttattggca ctaataggaa gtacttcacc aactgcaagc    360

agtggtacca aaggaaaatc tgtggcaaat caacagtcat cagctacgag tgctgtcctg    420

gatatgaaaa ggtccctggg gagaagggct gtccagcagc cctaccactc tcaaaccttt    480

acgagaccct gggagtcgtt ggatccacca ccactcagct gtacacggac cgcacggaga    540

agctgaggcc tgagatggag gggcccggca gcttcaccat cttcgcccct agcaacgagg    600

cctgggcctc cttgccagct gaagtgctgg actccctggt cagcaatgtc aacattgagc    660

tgctcaatgc cctccgctac catatggtgg gcaggcgagt cctgactgat gagctgaaac    720

acggcatgac cctcacctct atgtaccaga attccaacat ccagatccac cactatccta    780

atgggattgt aactgtgaac tgtgcccggc tgctgaaagc cgaccaccat gcaaccaacg    840

ggggtggtgca cctcatcgat aaggtcatct ccaccatcac caacaacatc cagcagatca    900

ttgagatcga ggacaccttt gagacccttc gggctgctgt ggctgcatca gggctcaaca    960

cgatgcttga aggtaacggc cagtacacgc ttttggcccc gaccaatgag gccttcgaga   1020
```

```
agatccctag tgagactttg aaccgtatcc tgggcgaccc agaagccctg agagacctgc   1080
tgaacaacca catcttgaag tcagctatgt gtgctgaagc catcgttgcg ggctgtctg    1140
tagagaccct ggagggcacg acactggagg tgggctgcag cggggacatg ctcactatca   1200
acgggaaggc gatcatctcc aataaagaca tcctagccac caacggggtg atccactaca   1260
ttgatgagct actcatccca gactcagcca agacactatt tgaattggct gcagagtctg   1320
atgtgtccac agccattgac cttttcagac aagccggcct cggcaatcat ctctctggaa   1380
gtgagcggtt gaccctcctg gctcccctga attctgtatt caaagatgga acccctccaa   1440
ttgatgccca tacaaggaat ttgcttcgga accacataat taaagaccag ctggcctcta   1500
agtatctgta ccatggacag accctggaaa ctctgggcgg caaaaaactg agagtttttg   1560
tttatcgtaa tagcctctgc attgagaaca gctgcatcgc ggcccacgac aagaggggga   1620
ggtacgggac cctgttcacg atggaccggg tgctgacccc cccaatgggg actgtcatgg   1680
atgtcctgaa gggagacaat cgctttagca tgctggtagc tgccatccag tctgcaggac   1740
tgacggagac cctcaaccgg gaaggagtct acacagtctt tgctcccaca aatgaagcct   1800
tccgagccct gccaccaaga gaacggagca gactcttggg agatgccaag gaacttgcca   1860
acatcctgaa ataccacatt ggtgatgaaa tcctggttag cggaggcatc ggggccctgg   1920
tgcggctaaa gtctctccaa ggtgacaagc tggaagtcag cttgaaaaac aatgtggtga   1980
gtgtcaacaa ggagcctgtt gccgagcctg acatcatggc cacaaatggc gtggtccatg   2040
tcatcaccaa tgttctgcag cctccagcca acagacctca ggaaagaggg gatgaacttg   2100
cagactctgc gcttgagatc ttcaaacaag catcagcgtt ttccagggct tcccagaggt   2160
ctgtgcgact agcccctgtc tatcaaaagt tattagagag gatgaagcat tagcttgaag   2220
cactacagga ggaatgcacc acggcagctc tccgccaatt tctctcagat ttccacagag   2280
actgtttgaa tgttttcaaa accaagtatc acactttaat gtacatgggc cgcaccataa   2340
tgagatgtga gccttgtgca tgtgggggag gagggagaga gatgtacttt ttaaatcatg   2400
ttccccctaa acatggctgt taacccactg catgcagaaa cttggatgtc actgcctgac   2460
attcacttcc agagaggacc tatcccaaat gtggaattga ctgcctatgc caagtccctg   2520
gaaaaggagc ttcagtattg tggggctcat aaaacatgaa tcaagcaatc cagcctcatg   2580
ggaagtcctg gcacagtttt tgtaaagccc ttgcacagct ggagaaatgg catcattata   2640
agctatgagt tgaaatgttc tgtcaaatgt gtctcacatc tacacgtggc ttggaggctt   2700
ttatggggcc ctgtccaggt agaaaagaaa tggtatgtag agcttagatt tccctattgt   2760
gacagagcca tggtgtgttt gtaataataa aaccaaagaa acata                   2805
```

<210> SEQ ID NO 38
<211> LENGTH: 1227
<212> TYPE: DNA
<213> ORGANISM: Homo sapiens

<400> SEQUENCE: 38

```
ctttgcagat aaatatggca cactagcccc acgttttctg agacattcct caattgctta     60
gacatattct gagcctacag cagaggaacc tccagtctca gcaccatgaa tcaaactgcc    120
attctgattt gctgccttat ctttctgact ctaagtggca ttcaaggagt acctctctct    180
agaactgtac gctgtacctg catcagcatt agtaatcaac ctgttaatcc aaggtcttta    240
gaaaaacttg aaattattcc tgcaagccaa ttttgtccac gtgttgagat cattgctaca    300
```

```
atgaaaaaga agggtgagaa gagatgtctg aatccagaat cgaaggccat caagaattta    360

ctgaaagcag ttagcaagga aaggtctaaa agatctcctt aaaaccagag gggagcaaaa    420

tcgatgcagt gcttccaagg atggaccaca cagaggctgc ctctcccatc acttccctac    480

atggagtata tgtcaagcca taattgttct tagtttgcag ttacactaaa aggtgaccaa    540

tgatggtcac caaatcagct gctactactc ctgtaggaag gttaatgttc atcatcctaa    600

gctattcagt aataactcta ccctggcact ataatgtaag ctctactgag gtgctatgtt    660

cttagtggat gttctgaccc tgcttcaaat atttccctca cctttcccat cttccaaggg    720

tactaaggaa tctttctgct ttggggttta tcagaattct cagaatctca aataactaaa    780

aggtatgcaa tcaaatctgc tttttaaaga atgctcttta cttcatggac ttccactgcc    840

atcctcccaa ggggcccaaa ttctttcagt ggctacctac atacaattcc aaacacatac    900

aggaaggtag aaatatctga aaatgtatgt gtaagtattc ttatttaatg aaagactgta    960

caaagtagaa gtcttagatg tatatatttc ctatattgtt ttcagtgtac atggaataac   1020

atgtaattaa gtactatgta tcaatgagta acaggaaaat tttaaaaata cagatagata   1080

tatgctctgc atgttacata agataaatgt gctgaatggt tttcaaaata aaaatgaggt   1140

actctcctgg aaatattaag aaagactatc taaatgttga aagatcaaaa ggttaataaa   1200

gtaattataa ctaagaaaaa aaaaaaa                                       1227
```

<210> SEQ ID NO 39
<211> LENGTH: 586
<212> TYPE: DNA
<213> ORGANISM: Homo sapiens

<400> SEQUENCE: 39

```
agttaaaagg gtgggagcgt ccgggggccc atctctctcg ggtggagtct tctgacagct     60

ggtgcgcctg cccgggaaca tcctcctgga ctcaatcatg gcttgtggtc tggtcgccag    120

caacctgaat ctcaaacctg gagagtgcct tcgagtgcga ggcgaggtgg ctcctgacgc    180

taagagcttc gtgctgaacc tgggcaaaga cagcaacaac ctgtgcctgc acttcaaccc    240

tcgcttcaac gcccacggcg acgccaacac catcgtgtgc aacagcaagg acggcggggc    300

ctgggggacc gagcagcggg aggctgtctt tcccttccag cctggaagtg ttgcagaggt    360

gtgcatcacc ttcgaccagg ccaacctgac cgtcaagctg ccagatggat acgaattcaa    420

gttccccaac cgcctcaacc tggaggccat caactacatg gcagctgacg gtgacttcaa    480

gatcaaatgt gtggcctttg actgaaatca gccagcccat ggcccccaat aaaggcagct    540

gcctctgctc cctctgaaaa aaaaaaaaaa aaaaaaaaaa aaaaaa                   586
```

<210> SEQ ID NO 40
<211> LENGTH: 2078
<212> TYPE: DNA
<213> ORGANISM: Homo sapiens

<400> SEQUENCE: 40

```
ttttccgccc ggctcccggc aagggtcccc cgactggcgc ccgcgcgtcc tccctcggct     60

gctgcaggcc gggccgcggc gtcgagcggg ggcggcgggg cggggcccgc agccattggc    120

gagcggcggg gcgggggcgg gggcgcggag ggtcggcccc gggacgcgcg cagccggccc    180

gcagttgccg ctgtcgtccg cagagccagt tcctagcgca gagccgcgcc cgccatgagg    240

gagatcgtgc acatccaggc gggccagtgc gggaaccaga tcggcaccaa gttttgggaa    300

gtgatcagcg atgagcacgg catcgacccg gccggaggct acgtgggaga ctcggcgctg    360
```

cagctggaga gaatcaacgt ctactacaat gagtcatcgt ctcagaaata tgtgcccagg 420
gccgccctgg tggacttaga gccaggcacc atggacagcg tgcggtctgg gccttttggg 480
cagcttttcc ggcctgacaa cttcatcttt ggccagacgg gtgcagggaa caactgggcg 540
aaagggcact acacggaggg cgcggagctg gtggacgcag tgctggacgt ggtgcggaag 600
gagtgcgagc actgcgactg cctgcagggc ttccagctca cgcactcgct gggcggcggc 660
acgggctcag gcatgggcac gctgctcatc agcaagatcc gtgaggagtt cccggaccgc 720
atcatgaaca ccttcagcgt catgccctcg cccaaggtgt cggacacggt ggtggagccc 780
tacaatgcca cactgtcggt gcaccagctg gtggagaata cagacgagac ctactgcatc 840
gacaacgagg cgctctatga catctgcttc cgcactctga agctgacaac gcccacctac 900
ggggacctca accacctggt gtccgccacc atgagtgggg tcaccacctc gctgcgcttc 960
ccgggccagc tcaatgctga cctgcgcaag ctggcggtga acatggtgcc cttcccgcgc 1020
ctgcacttct tcatgcctgg cttcgcgccg ctcaccagcc gcggcagcca gcagtaccgg 1080
gccctgaccg tgcccgagct cacccagcag atgttcgacg ccaggaacat gatggccgcc 1140
tgcgatccgc gccatggccg ctacctgacc gtggccaccg tgttccgcgg gcccatgtcc 1200
atgaaggagg tggacgagca gatgctggcc atccagagta agaacagcag ctacttcgtg 1260
gagtggattc ccaacaacgt gaaggtggcc gtgtgcgaca tcccgccccg cggcctgaag 1320
atggcctcca ccttcatcgg caacagcacg gccatccagg agctgttcaa gcgcatctcc 1380
gagcagttct cagccatgtt ccggcgcaag gccttcctgc actggttcac gggtgagggc 1440
atggatgaaa tggagttcac cgaggcggag agcaacatga acgacctggt atccgagtac 1500
cagcagtacc aggatgccac cgccaatgac ggggaggaag cttttgagga tgaggaagag 1560
gagatcgatg gatagtcgga atagagccgc cccaactcag atcctacaac acgcaagttc 1620
cttcttgaac cctggtgcct cctaccctat ggccctgaat ggtgcactgg tttaattgtg 1680
ttggtgtcgg cccctcacaa atgcagccaa gtcatgtaat tagtcatctg gaacaaagac 1740
taaaaacagc agagaattgc gggttctacc cagtcagaag atcacaccat ggagactttc 1800
tactagagga cttgaaagag aactgagggg ccacaaaata aacttcacct tccattaagt 1860
gttcaagcat gtctgcaaat taggagggag ttagaaacag tctttttcat cctttgtgat 1920
gaagcctgaa attgtgccgt gttgccttat atgaatatgc agtatgggac tttgaaataa 1980
tgattcataa taaaatacta aacgtgtgtc ttcatctctc tagccatgtg cataaatgac 2040
gtaagttact ttgtatggtt aaaaaaaaaa aaaaaaaa 2078

<210> SEQ ID NO 41
<211> LENGTH: 1623
<212> TYPE: DNA
<213> ORGANISM: Homo sapiens

<400> SEQUENCE: 41
ctggtggcat agggcagaca cgcctgcaga cattctctgg gaaagggcag cagcagccag 60
gtgtggcagt gacagggagg tgtgaatgag gcaggatgaa ctggacaggt ttgtacacct 120
tgctcagtgg cgtgaaccgg cattctactg ccattggccg agtatggctc tcggtcatct 180
tcatcttcag aatcatggtg ctggtggtgg ctgcagagag tgtgtggggt gatgagaaat 240
cttccttcat ctgcaacaca ctccagcctg gctgcaacag cgtttgctat gaccaattct 300
tccccatctc ccatgtgcgg ctgtggtccc tgcagctcat cctagtttcc accccagctc 360

```
tcctcgtggc catgcacgtg gctcaccagc aacacataga gaagaaaatg ctacggcttg    420

agggccatgg ggacccccta cacctggagg aggtgaagag gcacaaggtc cacatctcag    480

ggacactgtg gtggacctat gtcatcagcg tggtgttccg gctgttgttt gaggccgtct    540

tcatgtatgt cttttatctg ctctaccctg gctatgccat ggtgcggctg gtcaagtgcg    600

acgtctaccc ctgccccaac acagtggact gcttcgtgtc ccgccccacc gagaaaaccg    660

tcttcaccgt cttcatgcta gctgcctctg gcatctgcat catcctcaat gtggccgagg    720

tggtgtacct catcatccgg gcctgtgccc gccgagccca gcgccgctcc aatccacctt    780

cccgcaaggg ctcgggcttc ggccaccgcc tctcacctga atacaagcag aatgagatca    840

acaagctgct gagtgagcag gatggctccc tgaaagacat actgcgccgc agccctggca    900

ccggggctgg gctggctgaa aagagcgacc gctgctcggc ctgctgatgc cacataccag    960

gcaacctccc atcccacccc cgaccctgcc ctgggcgagc ccctccttct cccctgccgg   1020

tgcacaggcc tctgcctgct ggggattact cgatcaaaac cttccttccc tggctacttc   1080

ccttcctccc ggggccttcc ttttgaggag ctggaggggt ggggagctag aggccaccta   1140

tgccagtgct caaggttact gggagtgtgg gctgcccttg ttgcctgcac ccttccctct   1200

tccctctccc tctctctggg accactgggt acaagagatg ggatgctccg acagcgtctc   1260

caattatgaa actaatctta accctgtgct gtcagatacc ctgtttctgg agtcacatca   1320

gtgaggaggg atgtgggtaa gaggagcaga gggcaggggt gctgtggaca tgtgggtgga   1380

gaagggaggg tggccagcac tagtaaagga ggaatagtgc ttgctggcca caaggaaaag   1440

gaggaggtgt ctggggtgag ggagttaggg agagagaagc aggcagataa gttggagcag   1500

gggttggtca aggccacctc tgcctctagt ccccaaggcc tctctctgcc tgaaatgtta   1560

cacattaaac aggattttac agtaaatgaa gaggtggctt gtgaaaaaaa aaaaaaaaaa   1620

aaa                                                                 1623


<210> SEQ ID NO 42
<211> LENGTH: 3310
<212> TYPE: DNA
<213> ORGANISM: Homo sapiens

<400> SEQUENCE: 42

gcgcgggccg ggccgggcgg cggcggcggc accatgagcg gccggaagcg cagcttcacc     60

ttcggggcct acggcggggt ggacaagtcc ttcacttctc gccggagtgt gtggaggagc    120

gatgggcaga accagcactt ccctcaggca ctagacctgt cacgagtgaa cttagttccc    180

tcctatactc cttcactcta ccctaagaac acagatctat ttgagatgat tgagaagatg    240

cagggaagca ggatggatga acaacgctgc tccttcccgc cgcccctcaa aacagaggag    300

gactacattc catacccgag cgtgcacgag gtcttggggc gagaaggacc cttccccctc    360

atcctgctgc cccagtttgg gggctactgg attgagggca ccaaccacga aatcaccagc    420

atccccgaga cagagccact gcagtcgccc acaaccaagg tgaagctcga gtgcaacccc    480

acagcccgca tctaccggaa gcactttctc ggcaaggagc atttcaatta ctactcactg    540

gacgctgccc tcggccacct tgtcttctca ctcaagtacg atgtcatcgg ggaccaagag    600

cacctgcggc tgctgctcag gaccaagtgc cggacatacc atgatgtcat ccccatctcc    660

tgcctcaccg agttccctaa tgttgtccag atggcaaagt tggtgtgtga agacgtcaat    720

gtggatcggt tctatcctgt gctctacccc aaggcttccc ggctcatcgt cacctttgac    780

gagcatgtca tcagcaataa cttcaagttt ggcgtcattt atcagaagct tgggcagacc    840
```

-continued

```
tccgaggaag aactcttcag caccaatgag gaaagtcccg ctttcgtgga gttccttgaa    900
tttcttggcc agaaggtcaa actgcaggac tttaaggggt tccgaggagg cctggacgtg    960
acccacgggc agacggggac cgaatctgtg tactgcaact tccgcaacaa ggagatcatg   1020
tttcacgtgt ccaccaagct gccatacacg gaaggggacg cccagcagtt gcagcggaag   1080
cggcacatcg ggaacgacat cgtggctgtg gtcttccagg atgagaacac tcctttcgtg   1140
cccgacatga tcgcgtccaa cttcctgcat gcctacgtcg tggtgcaggc tgagggcggg   1200
ggccctgatg gcccccctcta caaggtctct gtcactgcaa gagatgatgt gcccttcttt   1260
ggacccccccc tcccggaccc cgctgtgttc aggaaggggc ctgagttcca ggaattttg   1320
ctgacaaagc tgatcaatgc tgaatatgcc tgctacaagg cagagaagtt tgccaaactg   1380
gaggagcgga cgcgggccgc cctcctggag acgctctatg aggaactaca catccacagc   1440
cagtccatga tgggcttggg cggcgacgag gacaagatgg agaatggcag tgggggcggc   1500
ggcttctttg agtctttcaa gcgggtcatc cggagccgca gccagtccat ggatgccatg   1560
gggctgagca acaagaagcc caacaccgtg tccaccagcc acagcgggag cttcgcgccc   1620
aacaaccccg acctggccaa ggcggctgga atatcactga ttgtccctgg gaagagcccc   1680
acgaggaaga agtcgggccc gttcggctcc cgccgcagca gcgccattgg catcgagaac   1740
atacaggagg tgcaggagaa gagggagagc cctccggctg gtcagaagac cccagacagc   1800
gggcacgtct cacaggagcc caagtcggag aactcatcca ctcagagctc cccagagatg   1860
cccacgacca agaacagagc ggagaccgca gcgcagagag cagaggcgct caaggacttc   1920
tcccgctcct cgtccagtgc cagcagcttc gccagcgtgg tggaggagac ggagggtgtg   1980
gacggagagg acacaggcct ggagagcgtg tcatcctcag gaacacccca caagcgggac   2040
tccttcatct atagcacgtg gctggaggac agtgtcagca ccactagtgg gggcagctcc   2100
ccaggcccct ctcgatcacc ccacccagac gccggcaagt tgggggaccc tgcgtgtccc   2160
gagatcaaga tccagctgga agcatctgag cagcacatgc cccagctggg ctgttagccg   2220
ggccaccccc tctgaaggtg aaactgagca gatgaggcca cagaagcaca aggggaaggt   2280
gccgtgtcaa gcccaggcag acgagacctc tgccctgaag accaacacca gcccgtgggc   2340
tgccccctgc ctccccaccc tccccatggc ccacccatct gggctgtctc tgcagggcag   2400
agccgtccag acctgggatc agggaagctg ctggcatcgt ccccaccccc agcctggggg   2460
tctgggctgg ggcagggatt gctcagtgga agcaggactg gggtctggc ttgcccccctc   2520
cctgggcctc catcacccct gagcatccct ctggactcag agggaacaag gtgggagaga   2580
gagtttgaga cagctccgtg tggagagctt agcccctgga ggcagcacaa ggaggatgtg   2640
atatgtgggg gagtgagcac tgggttggga gccgggtcct ggtttccaat ttgggttctg   2700
ctgtgtgact ctgggcaagt cactctccct ctctgggcat gtctgctaca aatggacaag   2760
attatttcag aggtcactga agactgtgat tacatgcacc tgccttagaa ggtaggattt   2820
tcttcccagg gacctcctat caccctaccc tgcttcttga ggtccctgga gccccaggtg   2880
ggctgagggg cagggagccg gctgtgccca gtatgcctcc tggaccctcc agttctgcca   2940
caggtctgcc gatgccctgt ccactgccta cacatgacag acaagtaacc ccctcatggg   3000
ggatggggac ctacctggct cctcagccag cacccagctt aacccctgcc atcccatgct   3060
gggccctcca ggccaagagt ctcagctggc cgagagtcca ggccttgcct cccccgaccg   3120
ccatggaggg ggcagcccgg cacagctgct gggagccctt gtgtgtctgg tcacactttt   3180
```

taggcgtcac gccaaaggcc agcctcctgg ccccaatacc cattttggaa gcccctgtgg 3240
ccgtgtggat gtcggtaaca gttgtataaa ataaattcta tttatcgcta ttgtaaaaaa 3300
aaaaaaaaaa 3310

<210> SEQ ID NO 43
<211> LENGTH: 5665
<212> TYPE: DNA
<213> ORGANISM: Homo sapiens

<400> SEQUENCE: 43
gcgcagcccg cagaggcgct gcggcccgtg cagccccgga ggcccctcgc ggagaaggcg 60
gcggcggagg agaggccgag ttaccgcccg ccgcccgcgc ccccccaacc ccgccgccgc 120
cgccgccgcc gccactgccc cccctccccg cggcgccgca tcttgaatgg aaacatggcg 180
gtgccggctc ggacctgcgg cgcctctcgg cccggcccag cgcggactgc gcgcccctgg 240
cccggctgcg gcccccaccc tggccccggc acccggcgcc cgacgtccgg gcccccgcgc 300
ccgctgtggc tgctgctgcc gcttctaccg ctgctcgccg cccccggcgc ctctgcctac 360
agcttccccc agcagcacac gatgcagcac tgggcccggc gtctggagca ggaggtcgac 420
ggcgtgatgc ggatttttgg aggcgtccag cagctccgtg agatttacaa ggacaaccgg 480
aacctgttcg aggtacagga gaatgagcct cagaagttgg tggagaaggt ggcaggggac 540
attgagagcc ttctggacag gaaggtgcag gccctgaaga gactggctga tgctgcagag 600
aacttccaga aagcacaccg ctggcaggac aacatcaagg aggaagacat cgtgtactat 660
gacgccaagg ctgacgctga gctggacgac cctgagagtg aggatgtgga aaggggggtct 720 aaggccagca ccctaaggct ggacttcatc gaggacccaa acttcaagaa caaggtcaac 780
tattcatacg cggctgtaca gatccctacg gacatctaca aaggctccac tgtcatcctc 840
aatgagctca actggacaga ggccctggag aatgtgttca tggaaaaccg cagacaagac 900
cccacactgc tgtggcaggt cttcggcagc gccacaggag tcactcgcta ctacccggcc 960
accccgtggc gagcccccaa gaagatcgac ctgtacgatg tccgaaggag accctggtat 1020
atccaggggg cctcgtcacc caaagacatg gtcatcatcg tggatgtgag tggcagtgtg 1080
agcggcctga ccctgaagct gatgaagaca tctgtctgcg agatgctgga cacgctgtct 1140
gatgatgact atgtgaatgt ggcctcgttc aacgagaagg cacagcctgt gtcatgcttc 1200
acacacctgg tgcaggccaa tgtgcgcaac aagaaggtgt tcaaggaagc tgtgcagggc 1260
atggtggcca agggcaccac aggctacaag gccggctttg agtatgcctt tgaccagctg 1320
cagaactcca acatcactcg ggccaactgc aacaagatga tcatgatgtt cacggatggt 1380
ggtgaggacc gcgtgcagga cgtctttgag aagtacaatt ggccaaaccg gacggtgcgc 1440
gtgtttactt tctccgtggg gcagcataac tatgacgtca caccgctgca gtggatggcc 1500
tgtgccaaca aaggctacta ttttgagatc ccttccatcg gagccatccg catcaacaca 1560
caggaatatc tagatgtgtt gggcaggccc atggtgctgg caggcaagga ggccaagcag 1620
gtgcagtgga ccaacgtgta tgaggatgca ctgggactgg ggttggtggt aacagggacc 1680
ctccctgttt tcaacctgac acaggatggc cctggggaaa agaagaacca gctgatcctg 1740
ggcgtgatgg gcattgacgt ggctctgaat gacatcaaga ggctgacccc caactacacg 1800
cttggagcca acggctatgt gtttgccatt gacctgaacg gctacgtgtt gctgcacccc 1860
aatctcaagc cccagaccac caacttccgg gagcctgtga ctctggactt cctggatgcg 1920
gagctagagg atgagaacaa ggaagagatc cgtcggagca tgattgatgg caacaagggc 1980

-continued

```
cacaagcaga tcagaacgtt ggtcaagtcc ctggatgaga ggtacataga tgaggtgaca   2040
cggaactaca cctgggtgcc tataaggagc actaactaca gcctggggct ggtgctccca   2100
ccctacagca ccttctacct ccaagccaat ctcagtgacc agatcctgca ggtcaagtat   2160
tttgagttcc tgctccccag cagctttgag tctgaaggac acgttttcat tgctcccaga   2220
gagtactgca aggacctgaa tgcctcagac aacaacaccg agttcctgaa aaactttatt   2280
gagctcatgg agaaagtgac tccagactcc aagcagtgca acaacttcct tctgcacaac   2340
ctgatcttgg acacgggcat cacgcagcag ctggtagagc gtgtgtggag ggaccaggat   2400
ctcaacacgt acagcctact ggccgtgttc gctgccacag acggtggcat cacccgagtc   2460
ttccccaaca aggcagctga ggactggaca gagaaccctg agcccttcaa tgccagcttc   2520
taccgccgca gcctggataa ccacggttat gtcttcaagc cccacacca ggatgccctg   2580
ttaaggccgc tggagctgga gaatgacact gtgggcatcc tcgtcagcac agctgtggag   2640
ctcagcctag gcaggcgcac actgaggcca gcagtggtgg gcgtcaagct ggacctagag   2700
gcttgggctg agaagttcaa ggtgctagcc agcaaccgta cccaccaaga ccagcctcag   2760
aagtgcggcc ccaacagcca ctgtgagatg gactgcgagg ttaacaatga ggacttactc   2820
tgtgtcctca ttgatgatgg aggattcctg gtgctgtcaa accagaacca tcagtgggac   2880
caggtgggca ggttcttcag tgaggtggat gccaacctga tgctggcact ctacaataac   2940
tccttctaca cccgcaagga gtcctatgac tatcaggcag cctgtgcccc tcagccccct   3000
ggcaacctgg gtgctgcacc ccggggtgtc tttgtgccca ccgttgcaga tttccttaac   3060
ctggcctggt ggacctctgc tgccgcctgg tccctgttcc agcagcttct ctacggcctc   3120
atctaccaca gctggttcca agcagacccc gcggaggccg aggggagccc cgagacgcgc   3180
gagagcagct gcgtcatgaa acagacccag tactacttcg gctcggtaaa cgcctcctac   3240
aacgccatca tcgactgcgg aaactgctcc aggctgttcc acgcgcagag actgaccaac   3300
accaatcttc tctttgtggt ggccgagaag ccgctgtgca gccagtgcga ggctggccgg   3360
ctgctgcaga aggagacgca ctgcccagcg gacggcccgg agcagtgtga gctagtgcag   3420
agaccgcgat accggagagg cccgcacatc tgcttcgact acaacgcgac agaagatacc   3480
tcagactgtg gccgcggggc ctccttcccg ccgtcgctgg gcgtcctggt ctccctgcaa   3540
ctgctgctcc tcctgggcct gccgccccgg ccgcagcctc aagtcctcgt ccacgcctct   3600
cgccgcctct gagcaccctg ccccacccca cctccactcc cacctcaccc ggcctcttcg   3660
cctttcccac cctcctgccc cacactcccc gccttagagc ctcgtccctc cctcactgaa   3720
ggacctgagc tggccaggcc ctgagagtct ggtctgcgcc ttgggatggg gagtcccaaa   3780
gcgggacgcc gcaggtgttt ggcacccaaa tcacatctca cctccgaact gttcaagtgt   3840
ccccagaccc ttcttgcctg ctgggctccc cccagtggga tgggacaggg aggccacacg   3900
cactggtgcc aaaaccaggc ctctgctgcc gcccttcctg gaggctgcct atgttggggg   3960
ggaccctgcc tcagctgacc cggcctctct gccccaccca agcccaaact tggtttctgt   4020
gagaatagtg gaggaaggtg agatggccag tttgaagcct gtgcctccca gcttaaatcc   4080
tagcaggaga gaggctctgg ggcagccccc atgggctcct gcccctttca ggcctacagc   4140
cacatcccca agcccaccag gtgtcaggat agtcacagtg ataccagttc agacactacc   4200
ccatatacac ctggaacatt gaggatggaa actggactca cattcgacat accccactgg   4260
gcacacgcac aaacacacac actatggggt ggggtgggtg taggggctta caaagcctta   4320
```

-continued cacagggcga ggggttggtg ggagggttgg cacctgcaca ctccatctcc tgctcaccac 4380
ctgcctctaa tctgagctgc agcctggctg gtcctcccat ttctaaagct gaatgtcaaa 4440
cagtgccaaa tgctggggca gggggtgaag aaccctctgt cccaccccta gccaccagtg 4500
tcctccaagt gccccctcac ctctccaggt gctcattgta accatttctc actagtgtca 4560
ggcccccagt gggaccacat gccactgcct gcacctttcg gcagaggaac ccccaccaga 4620
catcaccctt tgccttagca ggggtgactt tgtctctcct ggctgggcca tccttccgcc 4680
aatctggccc ttacacactc aggcctgtgc ccactcccta tctccttccc accccctacac 4740 acacactccc tgcttgcagg aggccaaact gtccctccct tgctgaacac acacacacac 4800
acacacacac aggtggggac tgggcacagc tcttcacacc attcattctg gtcatttccc 4860
ccaaaggcat cccagcctgg gggccagtgg ggaactgagg gcaaggggat atagtgatgg 4920
ggctcagatg gactgggagg agggggaggg tgatgcatta attaatggct tcgttaatta 4980
atgtcatgtt gcttgtcgct ttctcagtgt gtgtgtgtgg tccatgccca ctgctggtgc 5040
cagggtgggt gtccatgtgc acccggcctg gatgccagct gtgtccttcg ggggcgtgcg 5100
tgtaactgta gtgtagtcag gtgctcaatg gagaatataa acatatacag aaaaatatat 5160
attttaagtt taaaaaacag aaaaacagac aaaacaatcc ccatcaggta gctgtctaac 5220
ccccagctgg gtctaatcct tctcattacc cacccgacct ggctgcccct caccttgggc 5280
tgggggactg gggggccatt tccttttctc tgcccttttt ttgttgttct attttgtaca 5340
gacaagttgg aaaaacaaca gcgacaaaaa agtcaagaaa ctttgtaaaa tatcgtgtgt 5400
gtgattcctt gtaaaatatt ttcaaatggt ttattacaga agatcagtta ttaaataatg 5460
ttcatatttt cacttcaaat ggttcccatc cactgtatca gcttgggggt gaggactggg 5520
tagctatgaa gacagttggc caagacctca gagtcccact tagtgctctg caggggggtga 5580 agaccatggt agcccaggtc cctgtcaacc acagggcatg gcacttgctt ccaccagtta 5640
taataggtgc caggcccttg acata 5665

<210> SEQ ID NO 44
<211> LENGTH: 1768
<212> TYPE: DNA
<213> ORGANISM: Homo sapiens

<400> SEQUENCE: 44
tataaattcc ctcccttcgc tccttccccg gaacagcggc ctctgacacc agcacagcaa 60
acccgccggg atcaaagtgt accagtcggc agcatggcta cgaaatgtgg gaattgtgga 120
cccggctact ccacccctct ggaggccatg aaaggaccca gggaagagat cgtctacctg 180
ccctgcattt accgaaacac aggcactgag gccccagatt atctggccac tgtggatgtt 240
gaccccaagt ctccccagta ttgccaggtc atccaccggc tgcccatgcc caacctgaag 300
gacgagctgc atcactcagg atggaacacc tgcagcagct gcttcggtga tagcaccaag 360
tcgcgcacca agctggtgct gcccagtctc atctcctctc gcatctatgt ggtggacgtg 420
ggctctgagc cccgggcccc aaagctgcac aaggtcattg agcccaagga catccatgcc 480
aagtgcgaac tggcctttct ccacaccagc cactgcctgg ccagcgggga agtgatgatc 540
agctccctgg gagacgtcaa gggcaatggc aaagggggtt ttgtgctgct ggatggggag 600
acgttcgagg tgaaggggac atgggagaga cctgggggtg ctgcaccgtt gggctatgac 660
ttctggtacc agcctcgaca caatgtcatg atcagcactg agtgggcagc tcccaatgtc 720
ttacgagatg gcttcaaccc cgctgatgtg gaggctggac tgtacgggag ccacttatat 780
gtatgggact ggcagcgcca tgagattgtg cagaccctgt ctctaaaaga tgggcttatt 840
cccttggaga tccgcttcct gcacaaccca gacgctgccc aaggctttgt gggctgcgca 900
ctcagctcca ccatccagcg cttctacaag aacgagggag gtacatggtc agtggagaag 960
gtgatccagg tgccccccaa gaaagtgaag ggctggctgc tgcccgaaat gccaggcctg 1020
atcaccgaca tcctgctctc cctggacgac cgcttcctct acttcagcaa ctggctgcat 1080
ggggacctga ggcagtatga catctctgac ccacagagac cccgcctcac aggacagctc 1140
ttcctcggag gcagcattgt taagggaggc cctgtgcaag tgctggagga cgaggaacta 1200
aagtcccagc cagagcccct agtggtcaag ggaaaacggg tggctggagg ccctcagatg 1260
atccagctca gcctggatgg gaagcgcctc tacatcacca cgtcgctgta cagtgcctgg 1320
gacaagcagt tttaccctga tctcatcagg gaaggctctg tgatgctgca ggttgatgta 1380
gacacagtaa aaggagggct gaagttgaac cccaacttcc tggtggactt cgggaaggag 1440
ccccttggcc cagcccttgc ccatgagctc cgctaccctg gggggcgattg tagctctgac 1500 atctggattt gaactccacc ctcatcaccc acactcccta ttttgggccc tcacttcctt 1560
ggggacctgg cttcattctg ctctctcttg gcacccgacc cttggcagca tgtaccacac 1620
agccaagctg agactgtggc aatgtgttga gtcatataca tttactgacc actgttgctt 1680
gttgctcact gtgctgcttt tccatgagct cttggaggca ccaagaaata aactcgtaac 1740
cctgtccttc agaaaaaaaa aaaaaaaa 1768

<210> SEQ ID NO 45
<211> LENGTH: 9306
<212> TYPE: DNA
<213> ORGANISM: Homo sapiens

<400> SEQUENCE: 45
gggttcggag cgcgaagccg ccgctgggtc ctcggcgcgc cccgcgtctg cgcttgctgc 60
cgcgccccgg tcggcgcgct gggagttcca gccatgctct tctggcacac gcagcccgag 120
cactacaacc agcacaactc cggcagctac ctgcgtgatg tgctcgctct gcccatcttc 180
aagcaggagg aaccccagct gtcccccgag aacgaggccc gcctgccacc cctgcaatat 240
gtgttgtgtg ctgccacgtc cccagccgtg aagctgcatg aagagacgct gacctacctc 300
aaccaaggtc agtcttatga aatccgacta ctggagaatc ggaagctggg agactttcaa 360
gatctgaaca caaaatatgt caagagcatc atccgtgtgg tcttccatga ccgccggctg 420
cagtatacgg agcaccagca gctggagggc tggcggtgga gtcggccagg ggaccggatc 480
ctggacatcg atattccact gtctgttggt atcttggacc ccagggccag cccgacccag 540
ctgaatgcag tcgagttttt gtgggaccct gcgaagagag cttctgcatt cattcaggta 600
cactgcatca gcacagaatt cacccccagg aagcacgggg gcgagaaggg agtgcccttt 660
cgagtccaga ttgacacgtt taagcagaac gagaatgggg agtacacgga gcacctgcac 720
tcagccagct gccagatcaa ggtgttcaag ccgaagggag ccgatcggaa acagaagact 780
gaccgggaga agatggagaa aagaactgcc caagagaagg agaaatacca gccgtcctat 840
gaaaccacca tcctcacaga gtgctctcca tggcccgacg tggcctacca ggtgaacagc 900
gccccgtccc caagctacaa tggttctcca aacagctttg gcctcggcga aggcaacgcc 960
tctccgaccc acccggtgga ggccctgccc gtgggcagtg accacctgct cccatcagct 1020
tcgatccagg atgcccagca gtggcttcac cgcaacaggt tctcgcagtt ctgccggctc 1080

-continued

```
tttgccagct tctcaggtgc tgacttgctg aagatgtccc gagatgattt ggtccagatc   1140

tgtggtcccg cagatgggat ccggctcttc aacgccatca aaggccggaa tgtgaggcca   1200

aagatgacca tttatgtctg tcaggagctg gagcagaatc gagtgcccct gcagcagaag   1260

cgggacggca gtggagacag caacctgtct gtgtaccacg ccatcttcct ggaagagctg   1320

accaccttgg agctgattga gaagatcgcc aacctgtaca gcatctcccc ccagcacatc   1380

caccgagtct accggcaggg ccccacgggc atccatgtgg tggtgagcaa cgagatggtg   1440

cagaacttcc aagatgaatc ctgttttgtc ctcagcacaa ttaaagctga gagcaatgat   1500

ggctaccaca tcatcctgaa atgtggactc tgagcagcag tggacctcat acctgtctcc   1560

agctcccagc cctgtggatc cccgtggatg tagacattgc cccactgtaa gctgtggcct   1620

caccaggcaa gctgaggcca ggagggaccc tgcccagtct gtgaaagcta cagagcacca   1680

accagcagaa gcctgtggac accaagtacg gtgtacagaa agccagtggc tcctttctcc   1740

cttcctcttg gcctccagat tttgaatggt tccttgttct tttctattgg tccaaccctg   1800

acgttctaaa agggcaaaca gtggagacgt ctgctctgaa atccctcatc ccttagttgg   1860

aagctgattg ggtatcttgg tgctgcctgt attggtccct tctgaccact ctcctgcctc   1920

cagagaaagc tctgcttcac cctggaagct ggtaccttta cctcctcctc tgggagttgg   1980

ctgcatggcc agcactgccg acttgatggg agcagtttgc cctcattctc ctgtttcagg   2040

tttgcttccc ttctcagtga ccctggtgag catccgcctt tcctgttctt ggatgaattg   2100

atgggagtgg ggctattctg tgccttctac ctctttcttc tctacgttgt ttctaaggat   2160

ctgctgctgc ggaacccaaa gatgtgctcc tgtctctgca ctggcgcatt ggcatggtag   2220

atgccacaat gtatgtgcac ggcctttctc agagacatta gttctgaggc cctttgtggg   2280

gaggttaggg ggatggtaat agaaaaagac tattttattt cctggcaatc acgggtaagg   2340

aggattagga atgagtattc cattcctagg tgtcatcaga tgaccttgac caccacaata   2400

ccaggccctc ttggatggac ttatagaaag ttagagaaga ccttgttgaa ccgctgctaa   2460

acttgccaca ggagcgatgt gttttctctg agtgcccctc acttacatgt ttatctttgt   2520

ttgtagaggc tatgtttagg atattttgcc tgcatcagaa tgggtgcatc atctttctta   2580

atggcctaac tatcgggaaa tttgagtgtc agtaactgtg gtagactcag aaattcgtct   2640

ttgtcttgcc tctggttcct gggatccagt gatctctact ggcccagggc ttcagctctt   2700

ggttaattta ggttcatggg gaaccctctg accacctgaa tgggatgtca tagcttctaa   2760

atggagcttc tgtggaatga agtgctagac tgaaggacta ccagaataaa acagggtcta   2820

caatggggag aacttgtttt atagatgagg aaaccaaggc tcagaggggc aaagtcacct   2880

gcatggtagc acatagtgat agggtagcga tataaattta tcatataaac caggacatct   2940

cggaataaaa ggggctctgt tagtcattat gttgggtaat agccgtggca ttcctacaga   3000

acagagtgag gacaggctcc tgattcctct tccttcttta gaggagaagc ggggagtggg   3060

ttaactaaca gctttattga gatgtcattc acatgccatt cagtttaccc attgctagtg   3120

tccaattgta ttcacagaac caccatcaat tcacagaatt acagtcaacg ttggtacatt   3180

ttcatcaccc ccagtaaaac cccgtaccct tggtctgtca ctcctgcttt cctaactcct   3240

gcagtccaag gcagccatga atctactttc tatgtaagat taacctactc tggacatttc   3300

atatatctgg aatcatgtga tatctctttt gtgactggct tcttccactg aatgttttct   3360

agggccgtcc aagttgagga tgtatcagta cttcattctt ttgtattgct gaataatact   3420

tcattgtata gatagaccac atttgtttat tgattcatca gttgatggac atttgtgtgt   3480
```

-continued ttttactttt tggctactct gaatgatgct gctatgaaca tatttctaca agattttgtg 3540
tggacatatg ttttcatttc ttttagcaat atacatagga gtggaattgc taggtcttac 3600
agtaactccg tgttttaact ttttgagaaa ctgccagact gttttctata gcagctgtac 3660
cattttacat tcccaccagc aatgtatcca ggtttcaatt tgtctacatc ctcatcaaca 3720
cttgctatta tctgtctttt tgcttttagc atcctaatga gtatgaaatg ctatcttgtg 3780
gttttgattt gcattcccct gatggcaact gatgctgagt gtcttttcct gtgcttacgg 3840
gccatgcgta tttctttgga gaaaggtcta tccaggtcct ttgcctattt ttaattgagt 3900
tgtctttttt tttttaagtt ttctgttttc ctaaccacta gactaccagg gatgagcctt 3960
ctttttatta ttgagttggg tgagctattt gtatattcta gacgccagtc ttttatcagg 4020
tatatgactg gtaaaaatgt tctccccttc tgtggattgt tttcagtttc ttgttggtgt 4080
cctttgagac acaaaacttt ttaactttga tgatttccaa gatacgtatt ttttttctat 4140
tgtcacttgt gcttttggtg ccatatctag aaaaccattg cctaatccaa ggtcaagaag 4200
attaatgcct gtgttttctt ctaagaacta tacttttagt tctcacaatg gtctttgatc 4260
catttcgagt atatttttat atatgatgtg atgtaggggt ccagcttcat tcttttgctt 4320
gtggatctcc acttgtccca ctgctgatta ttgagaaaaa tatcctttct ccacggaatt 4380
gtcttggcat ccttgctaaa ggcctctgct tcttactgga tcttctttcc tgggacatgg 4440
tgtcgttggg aagcttacct tttttttttt tttacttagt ctgtgtttgg ttccaccagt 4500
tttatgctgc ctttctactc tgttcttgct gtctccctct ttacctgagt caacggtact 4560
gagtcctatc tctctctgat gttccccagt cttccttggt gcatgttcta gctccacaca 4620
ctagtccttg gaggaaggtt gagaccaatg atttcctgtt atgagtcatg aggaaactga 4680
atcacctaga agtggaataa tgtgctcagg gtcaccatag cccattagtg gaaggaccag 4740
gactagacct ttagtcttct gaggtccagc cccttaggct gtctgtcatc actgtaccca 4800
agtgatgtca ctaccaaggc caaatgatgg tgggctaaat tttaattctc aaaagtgtag 4860
gaggctaata ttgtcttcta agttccaaaa gaagatgtaa taaaagtctg ttaccttaag 4920
tgtgctatta gtagagtctt ccatttttct ggcatgcccc tggcatctgc tcttcttacc 4980
ttctcgtggt tgtagttaaa gcttatagct tatgaaagaa tagaaaataa taaataccaa 5040
aaaaaagtac acatggtaat ttggtaccaa aatatctcag ctgcctaatt tagcagctca 5100
tcccttccac aggggtcaga tgagctaaag ctccaggttt tatttttcat ttgattgaca 5160
tacagaaaag ccatagccct tcccacagct gtccagggtc tttcctgtga gtccggaggt 5220
gctggcctat tgagcaggac agctcttccc agggcattcc caccaacctg tggcttctga 5280
actgtagctt ctttttacag tgaaccccag agggaaataa gacagacaca tgtgctcagg 5340
ccaccatctt gaactggaag cccaaagctg agttccttac tcttaggtcg tcacggtttt 5400
tgcggggtat ctgcaaggtt gagataaacc ctttcctgtt taccaggttg tcctttctgg 5460
atgaagggac agaggctgtt gaatggagga ataataggtt tgctggagga ggggcatggt 5520
atgcctgtgg aaaggacagg atggggtggg gaggtcgagg ctttgacttg gggtcctaaa 5580
caaaggtcag gtgttgccct agtgacctct tgcccagaca gcccagagcc ccttacacag 5640
agctattaac ctagggaagg ctttaccagc agtggactgg agccagccag ggtcacaagt 5700
ttccaagtcc agcattgctt caggggctgg cctgagtaac tgaagatctg aaaatcatta 5760
acaagtcgat gaaataaacg gaaaagcctc ttaggctgtt gtcagtggag cagagggaga 5820

-continued

```
aagtccctag gcgctcagag ggggtgagaa agcagtggat gattgggcgg gggtggggga   5880
ttagatgttg acactgcctg ggtgtagga agaggaacag agaacccaga gtcagggtcc    5940
tagatcccag accctcgctc agtatgagtc tctttgcctc tctgggtctc tatctcctcc   6000
tcttacaaat acaggcttgg tgatctctga agatggcacc aacctgccat gaaatgaatc   6060
tgaggggttt tcccattttt ccctccatca aaatcgtaca aaaagctgga cgtggtggcc   6120
catgcctcta atcctagcat tttgggaggc cgaggtggga gaatcacttg acgccaagag   6180
ttcgagacca gcctgggcat cgtagtgaga ctccatctct gtctttttga aaataaaaaa   6240
tctttgaaaa ttgcacaaca ggcaggagac ctttacgtgt gcccatcctg gttgtacaca   6300
gtgccaccag tgctcctgca gtgcaaggcg gcatgcttct tgacatgggt cagattgtgt   6360
ccatcgtgtc tttgggaatc agccctagct cctaactggg ctgactactt cctccgcaaa   6420
cttatggggg ctcccagata ttccttgcca gccaggggcc agacacagtg caggcacagt   6480
ctgtgtcatt ggtgcacatg tgcgtgttta catgtgtacc tgggttcctt cccttgccca   6540
tgaatttgcc atgagcacag ccagaagcag cctcagcttg gcaaggtgtg gagatgactg   6600
ctgttccctt cgcatttggg gaaaacaggc tccctcggta gctcgatgat cctcttttga   6660
tcttgtgtga cctcctggag agtggatgaa gctggtggcc ttagcttttc tagacagtgt   6720
aagtggcact gggcaaggcc cccagagcag ggcaaggtct ctagagcggg tctcccacat   6780
gactggcttc acacaggcac ttccgctcgg gttgcatgct ctgtgtcatc ttaccggtcc   6840
agggttgcag gtaggaaatg tttgtaccct cttctgattg ccacctcctt cccatcgccc   6900
cttagggaca gggcttgagg gccagtgagg cgctggtcag gcaccccagg cctccttggg   6960
acctgcccag gggcaccctg agagctcctg aaaccccccac ttagcttcca gacctttctg  7020
caaaagctcc tcctggcttt cctccctccc ccaatctatg ggtcacagct aacagatctg   7080
agggcaactg ctgtgctagt ggccagggct gcacctgcca tccccggctc tgccacttta   7140
gggccttcta gaggcagtgt ccttaggaag tagctctgag gcatgggttt tctgctcctg   7200
tgcagggcag ctgatgggat aaggtgggga aggacggtca gtgcttgggc cccagctggc   7260
cagcctggcg atggggaaac caaaccatgt cccccagcga agggccagag tgggaacctg   7320
tcctcatgcc cttcgtcctg aggagccctg aggtgggcag caggggccag gggaagtttt   7380
caggccttca tcaaagagaa caacatcctc agctccgcac ccctcatcct gtatcagcac   7440
ttaccggtgt gtgactgccc ttgtcagcta gcatacggtg ggcccacctg gcccactggc   7500
tgtttatgcc actgatttat gatagggaat attatctttg aacccaatga agtgttttct   7560
cccccatcac aaaaaaaaaa attcttattt ttagtagaca tgtatttacc aaaaatatgt   7620
actcaattat tgtattttgg attttatcaa tttaaaaatt gtggaaattt gtttgctctt   7680
acgccaacat aatattgatt ttgcctcttg gctctgaaag cccaaaatat ttaccgtcta   7740
gcccgttaca gaaaaagtct gctgactact gagccagacc tccattacct ccatccctgt   7800
tggattattt aaagaaagcc tcagacagta agggcttttt taaaagaata aaatgacttg   7860
gtttgcgctt ggaagcaggg gaagcattca gatgagcggt ttctgcatta accctgccta   7920
tcacgcatct cgtgtcctgt gtggctggcg agcccccctt ggaaggttct ggtgcttcag   7980
ctggctcctg cagagtccac cccgcctcgt ggtgggaatg cagagccctt tgctttcctt   8040
cttgccgcct gcttcctgtt cctggggacc cgctgggcct ttggtctgca tcccctggcc   8100
aggtccctca gggttgatgc gtggagaagg actttgagca gtggtgggca gcagtggcct   8160
cctggccagc tcacactctt gtcctgggag gggcagcctg atctcacctc cacctagtac   8220
```

```
cttggggact gaggaccttt tggcttctct ggagcctgca agcctcttcc catgtgtcca   8280
gctgctcttc ctgctacaaa ggggactgct cacagtggcc tcagcttggt ggttttgagg   8340
ggccgccccc cggccctcca taagggtatc ctgggcctga gaattctgca tctgccattg   8400
gaggatggac agcctcaaat ggaaggagtc ccacgggaga tgggtccgag gtccggctgt   8460
ggccatccag ccccctgtgg cttgtccagc ctctgtgcac ccctggtgtc ttcactccag   8520
gggcagacag cagccactgc agttcctttc ttcgtgagta acagtagtga tagcagctgg   8580
ggctaacagg ctaggctttg tgttctgcgc atttggtcag cttctcactc gatcctccct   8640
aaagcaatgg ggaggccccc actagcccag ttttcaggaa gtcaactggg aggttagatg   8700
ggggccaggg tcccacagct actgatggcc cgagccaggt tgagcttcct ggtgtccagt   8760
ccggatccca cttgcagatc tcatgctctc agataggtgg gacaagttct tttgtcacag   8820
tgctggctct gtcctgaggc ctcattgctg gctgggtgtg ctctgctggg aaaagctttg   8880
cggggcttgc ttggttaacc acagaagaga aggggactgt ttggggtgcc tctctgcagc   8940
ctccccgtgc tgggtggaag cacggttact gtgttctcta atgttcatgt atttaaaatg   9000
atttctttct aaagatgtaa cctccacacc tttctccaga ttgggtgact cttttctaaa   9060
ggtggtggga gtatctgtcg gggtggtgtg gcccttggat gggtcaggtg ggtgtgagag   9120
gtcctgggga ggtgggcgtt gagctcaaag ttgtcctact gccatgtttt tgtacctgaa   9180
ataaagcata ttttgcactt gttactgtac catagtgcgg acgagaagtc tgtatgtggg   9240
atctgtgctt gggttagaat gcaaataaaa ctcacatttg taagaaaaaa aaaaaaaaaa   9300
aaaaaa                                                               9306
```

<210> SEQ ID NO 46
<211> LENGTH: 6564
<212> TYPE: DNA
<213> ORGANISM: Homo sapiens

<400> SEQUENCE: 46

```
atgcattaaa ctccaggtat tttcagggag gaatcatgaa gccgctcctg ttaaatcata     60
tccattttat tacgtctctc cttgtggatt acgtagaact ttggaaaatt aaacattaga    120
catcttcata gaaaatcatg tcactgattt ttaaagccag ctcaatttaa cctgccactg    180
attccctaac cagctcttct ctgactgtat cccgagggaa aatgtattga acgcagcaga    240
aggttaaggc agaggagttc ggctagaccg ggtagcagcc aatcagatgg ggagggtcca    300
aggatctgat gcctccaggc gagcagcgcc aagctgagct ggttagtctc cttttattgt    360
ggatgaacac cacgtacatg ccgtaaatgc tccctaggct ggctgcggct acaaggcaga    420
cccgggagct gagaatagag gaatacctgc ccaagcaact cattctgcac agcagccgac    480
aagacagcga ttttcctgtg ctggaatgtg cccatccaaa gccaaccaat ttgttggaaa    540
atcagtcaaa atctaatttt gatgttctgc aagttccctg gggccatga agcacctgac     600
acttggattg gacttaatct taaacctctg gagttcaaga ccttttaaaa agggctaaat    660
aaacaatctc tacatgtaaa aggccactga ctcctacttc ctctgtatag agcaactgtt    720
gaactcagct gcctgtagga aaactgaaga ctttaataac aaactctcca aggtgaaaat    780
gaacacagat agcggtgggt gtgctcgcaa acgtgccgcc atgtctgtta cgctaacatc    840
tgtgaagaga gtgcaaagtt ctccaaacct attggctgca gggcgtgatt ctcagtcacc    900
agactcagct tggagatctt acaatgatgg caatcaggag acactgaacg gagatgctac    960
```

-continued

```
atattcctct cttgcagcaa aaggttttag aagcgttcga ccaaacctac aagataaaag   1020
atcaccaact cagagccaga taacagtgaa tggaaactca ggaggtgccg tgagtcccat   1080
gagttactat cagaggccgt tttccccctc ggcatattct ctcccagcct cactcaactc   1140
cagcattgtc atgcagcacg gcacatccct cgattccaca gacacatatc cccagcatgc   1200
gcagtctctg gatggcacca ccagcagctc tatccccctg taccgatcct cagaggaaga   1260
gaagagagtg acagtcatca aagccccgca ttacccaggg atcgggcccg tggatgaatc   1320
cggaatcccc acagcaatta gaacgacagt cgaccggccc aaggactggt acaagacgat   1380
gtttaagcaa attcacatgg tgcacaagcc ggatgatgac acagacatgt ataatactcc   1440
ttatacatac aatgcaggtc tgtacaaccc accctacagt gctcagtcac accctgctgc   1500
aaagacccaa acctacagac ctctttccaa aagccactcc gacaacagcc ccaatgcctt   1560
taaggatgcg tcctccccag tgcctccccc acatgttcca cctccagtcc cgccgcttcg   1620
accaagagat cggtcttcaa cagaaaagca tgactgggat cctccagaca gaaaagtgga   1680
cacaagaaaa tttcggtctg agccaaggag tatttttgaa tatgaacctg gcaagtcatc   1740
aattcttcag catgaaagac cagcctcctt gtatcagtcc tctatagaca gaagcctgga   1800
aagacccatg agttctgcaa gcatggccag tgacttcagg aagcggagga agagcgagcc   1860
tgcagtgggt ccaccacggg gcttgggaga tcaaagtgcg agcaggacta gcccaggccg   1920
agtggacctc ccaggatcaa gcaccactct tacaaagtct ttcactagct cttctccttc   1980
ttccccatca agagcaaaag gtggggatga tagcaaaata tgtccatccc tttgcagtta   2040
ctcagggctc aacggcaacc cctccagtga gttagattac tgtagcactt acagacagca   2100
cttggatgtc cctcgggact caccaagagc cattagtttc aagaacggct ggcaaatggc   2160
ccggcaaaac gcagaaatct ggagcagcac ggaagaaacc gtctctccca aaatcaaatc   2220
ccggagctgt gacgatctcc taaacgacga ctgcgatagc ttcccggacc cgaaagtcaa   2280
gtcggaaagc atgggctccc tgttatgtga ggaggactcc aaggagagct gccccatggc   2340
gtgggggtcc ccctacgtcc cggaggttcg cagtaacggc agatcaagga tcagacacag   2400
gtcagcccgc aacgccccgg ggttcctgaa gatgtacaag aaaatgcacc gcatcaaccg   2460
caaggacctg atgaactccg aggtgatctg ctccgtgaag tccaggattc tgcagtacga   2520
gagcgagcag cagcacaagg acctgctgcg cgcctggagc cagtgctcca cggaggaggt   2580
gccccgggac atggtgccca cacgcatctc cgaattcgaa aagctgatcc agaagtccaa   2640
atccatgcca aatttagggg atgacatgct gtctcccgta accctagaac caccgcaaaa   2700
tggcctatgt cccaagaggc ggttttccat tgagtatttg ctggaggaag aaaatcaaag   2760
cggcccccccc gctcggggcc ggcgaggctg ccagtctaac gccctggtgc ccattcacat   2820
tgaagtcacc agcgatgagc agccccgagc acacgtggag ttttccgaca gcgaccagga   2880
cggggttgtg tccgaccaca gtgactacat tcacctagag gggtcatcct tctgcagtga   2940
aagtgacttt gatcactttt ccttcacatc ctccgaaagc ttttacggat ccagccacca   3000
ccaccaccat caccaccacc accaccaccg ccacctcatc agctcctgca aaggcaggtg   3060
cccggcctcc tacactcgat ttaccacaat gttaaaacac gaaagagcca gacacgaaaa   3120
caccgaggag cccagaaggc aagaaatgga ccctggcctt tctaaacttg cttttctagt   3180
cagtcctgtg cctttccgga ggaaaaaaaa ttcggctcct aagaaacaga ctgaaaaggc   3240
aaaatgtaaa gcatctgtgt ttgaggctct ggactctgcc cttaaagaca tctgtgacca   3300
aattaaagct gaaaagaaaa gggggagctt gccggacaac agcatcctgc accgcctcat   3360
```

-continued

```
cagtgagctg ctgccagatg ttcccgagag gaactcatcc ctgagagcgc tgaggaggag   3420
cccccctgcac cagcctctcc acccactgcc tcccgatggt gctattcatt gtccacccta   3480
ccagaatgac tgcgggagaa tgccccgcag tgcctctttc caagacgtgg acacagccaa   3540
cagcagctgc caccaccaag accgtggcgg tgcactccaa gaccgtgagt cccctagaag   3600
ttactcatcc actttgactg acatggggag aagtgcacca agggaaagaa gaggaactcc   3660
agaaaaagag aaattgcctg caaaagctgt ttatgatttt aaggctcaga catctaagga   3720
gttgtcattt aagaaaggag atactgtcta catcctcagg aaaattgatc aaaattggta   3780
tgagggagaa caccacggga gagtgggcat cttcccgatc tcatacgtag agaaactcac   3840
acctcctgag aaagcacagc ctgcaagacc acctccgcca gcccagcccg gagaaatcgg   3900
agaagctata gccaaataca acttcaacgc agacacaaat gtggagctgt cactgagaaa   3960
gggagataga gttattcttc ttaaaagagt tgatcaaaac tggtatgaag gtaaaatccc   4020
aggaaccaac agacaaggca tcttccctgt ttcctatgtg gaggtcgtca agaagaacac   4080
aaaaggtgct gaggactacc ctgaccctcc aataccccac agctattcta gtgataggat   4140
tcacagcttg agctcaaata agccacagcg tcctgtgttt actcatgaaa atattcaagg   4200
tgggggggaa ccgtttcagg ctctgtataa ctatactccc aggaatgaag atgagctgga   4260
gctcagagaa agtgatgtca ttgatgtcat ggaaaagtgt gatgacggct ggtttgtggg   4320
gacctcaaga agaaccaaat tctttggtac tttccccgga aactacgtca agaggctgtg   4380
aattgcgctc cctccttctg tagaggccgc ctgccagcca tgcacctgcg tcaacgcgcc   4440
tgaaacaccc cgcgggcctc ccgttgtcat gccttacggt ttccaatgcg ccgtcaccat   4500
ctccacctgc caccaaacca ccagcagagt agccgccgct gctgtgagcc tggggacgac   4560
atggcaggct ggtccccctc cgtgaaagtg tggattccta cttcctgctc taagctttga   4620
cacgtcaaaa tgtgggatca gaaagaaaaa aatcatgata tttaaaaatg gtcaaatatt   4680
tgaggcaaaa aaaaaaaaaa aaagtgtctc caggaggctg tccagcctcg tggctccatt   4740
tcaacatctc cccccaggcg atgttctccc ccaagacgac cagaaaattg tttattgggg   4800
aatgctgtgg tttgcatttt catattcttc gcttggcagt gtgtattctt ttcacaagtt   4860
tgcctagtgt cttggtttac acaatatgac aactgtaact gtactttagc tattgtttgc   4920
ctgcacatac atgttgtaat atgcacagtg attacaacct ttaaagcaag aggaggcgag   4980
ttaatttgga tgagtgtgat tttgctgatt gaatgtgagt tttcaaatag gagtcttttt   5040
ctgcaatttg tttgcatttt ttagaagtgc aaacagtaag taaataaaag ccttcggtaa   5100
taatcatgac aatacaagag gctgagctag gctacagggg aaaactattg tgttgtaaag   5160
ttgcatcgct attttatatt aaaatgtaat gatcagcatc atgaacaatg agctcttagt   5220
gttttattta tctgaaaaaa tgtaagtaaa agcagtgtta gtgagaggtg caaagaatta   5280
ttctaacaga cacctgaaag tatctgtaag caatactagt aggtaagatt tcactgtgtg   5340
tacacataca catttgagat tgtatgagaa catataatcc atatgatatg ttgtacattt   5400
tatggaaatg taatagaatc tcacacatta ttttatagaa atagagtaca gaagcatcac   5460
aagtattaaa gttggtttta gcaaggatta ggattactac aattattttt actataataa   5520
ttatttttct tctatggaac tcagaatcct ggctacattt gaggacagga atatgttgag   5580
cctgattttc ctggtgtgtg taaaatattt cctaggaata aattaggcac tttttagaag   5640
caatgttaaa tcattcaggt tttattttct gccctgaagc agaaatttaa aaaatgatat   5700
```

tgggacctgg aaggtttaat atggttcaca gtgcctgaat tacacctgct ccgaaaacta 5760
gctttgtatt tcttatgact ttgcataaga actgttcatc tttggatctt gagcacctta 5820
cagataaaac tttttatggc atctctttca tggacagtga tattgatctt ttcacaatgt 5880
acgtagcctc tagaattttg tacatatgtt tgctcttttt ttgtacagac tagttgttga 5940
gaaaacaggg gcgtttccta atttggtctt tatcctgcga caacactttc agcagactag 6000
cctctcctta tctcacagat cacaagcacc cctagatagt gtgattctgt cagatagcat 6060
ttatgcaaaa atctatgaag ttaaaagatc gtagaagcca aatgaaatgt acatatctac 6120
tgactgatga caagggaatt tcattaggaa gaaggtaaag aaacatcgtt gagtagccta 6180
ccttgatttc tgtcaagttc ataaccagct tcatatttta aaggcttcag gtttgaaatt 6240
aagtcaactg catgcagctt tgctgataaa tgaataattc tctttgatgc catttatgag 6300
aaaagacttc aatatctgtt gcctgtcata tttaagaaaa attactgttt ctactctctg 6360
tatctgattt taaaagaaaa aactattcat acctggcttc caggtaattg actttgaatt 6420
cttacaagca aaggtcattg tgtttttctt gaatagacat ctaataaatt ttgcttggaa 6480
gtatacttca gtttttcttc ttgacattta tctttataaa aattgtgtat tttattccaa 6540
cttgttaaac taagagaaaa tgca 6564

<210> SEQ ID NO 47
<211> LENGTH: 6398
<212> TYPE: DNA
<213> ORGANISM: Homo sapiens

<400> SEQUENCE: 47
gtggaatgac gggagggagt cccggcagct cctacctccc agcgatggcg tcgctgtgcc 60
gcgcccagtc cccagcctgc cggccggtac tcaccgctac ccggagttcg ctcagacggt 120
gagatttggg gcgggtccga ggcagcggcg ggacgctacc tgcgaccggg accatgagga 180
gctgccagac ccgtggggcc ggtaacgaga gcagtcgcgg cacctgctga gaggaaagag 240
ggagcggtcc ggcgcggctg gggcgcggca gaggcttgcc cgatcctcgg ccatgtcact 300
gctctgcgtg cgcgttaaaa gggccaaatt ccagggttca ccagataaat ttaacacata 360
tgtgaccctg aaagtacaga atgtgaagag cacaactgta gcagttcgtg gtgatcagcc 420
ttcctgggaa caggatttca tgtttgagat tagtcgcctg gacctgggtc taagtgtgga 480
ggtatggaac aaaggactga tctgggacac catggtgggg actgtgtgga ttgcgctgaa 540
gactattcgt cagtcggatg aggaagggcc tggggaatgg tccacattag aggcagagac 600
gttaatgaaa gacgatgaga tctgtggaac tagaaaccca actcctcata aaattttgct 660
tgatacaaga tttgagttgc cttttgatat cccagaggag gaagccagat attggaccta 720
caaatgggag caaatcaatg ccttgggagc tgacaatgag tattctagtc aagaagaaag 780
ccagaggaag ccattgccca ctgctgccgc ccagtgttct tttgaagacc ctgatagtgc 840
cgtcgatgac cgagatagtg actatcgcag tgagaccagc aacagcttcc cacctcctta 900
ccatacagct tcccagccca acgcttctgt gcaccagttc cctgtgccgg tgcgatcgcc 960
acagcagctg ctacttcaag gcagttcccg ggactcttgt aatgactcta tgcaaagtta 1020
tgaccttgat tatccagagc ggcgggctat cagcccccacc agcagcagta ggtatggctc 1080
ctcctgtaat gtgagtcaag gaagctctca gctaagtgaa ctagaccagt atcacgaaca 1140
agatgacgac catcgggaga cggactcgat tcattcttgc cacagctctc acagcctgtc 1200
cagagatggc caagcaggtt ttggagaaca agagaaaccc ttggaggtga caggtcaagc 1260
agagaaggag gcagcatgtg aacccaagga gatgaaagaa gatgccacaa cccaccctcc 1320
cccagatctg gtgctgcaaa aagaccactt cctaggtccc caggagagtt ttcctgagga 1380
gaatgcatct tcaccattta cccaagccag agcacattgg atccgagcag ttaccaaggt 1440
tcgactccag ctgcaggaga ttccagatga tggtgacccc tctctgcctc agtggctccc 1500
ggaagggcca gccggagggc tctatggcat tgacagcatg ccagatttac gcagaaagaa 1560
gccactgcca cttgtcagtg atctgtcact ggtccagtct cggaaggcag gaatcacttc 1620
tgcaatggct acacgcactt ctcttaagga cgaagagctg aaatcccacg tgtataagaa 1680
aaccctgcag gccttaatct accccatttc gtgcaccact cctcataact ttgaggtctg 1740
gacggccact accccaacct actgctatga gtgtgaaggc ctgctctggg gcattgcccg 1800
gcagggcatg cgctgcagcg aatgtggagt caagtgccat gagaagtgcc aggatctgct 1860
caatgctgac tgcctgcagc gggctgcaga aaagagctgt aaacatggag ctgaggaccg 1920
gacccagaac attatcatgg ccatgaagga ccgcatgaag atccgagagc gaaataagcc 1980
agagatcttt gaagttatcc gggacgtctt cacagtgaac aaagctgccc atgtgcagca 2040
gatgaaaaca gtgaagcaga gtgtactgga tggcacctcc aaatggtcag ccaagatcac 2100
cattactgtg gtgtgtgccc agggcctaca agccaaggac aaaacaggat ccagtgaccc 2160
ttacgtgact gtgcaagtca gcaaaactaa gaagcgtacc aagaccattt ttggaaactt 2220
gaatcctgtt tgggaggaga agttccattt tgagtgccac aactcctctg accgcattaa 2280
ggtgcgtgta tgggatgagg atgatgacat caagtcaaga gtaaagcaac gcctaaagcg 2340
agagtctgat gatttccttg gccaaaccat cattgaggtt cggaccctaa gtggcgagat 2400
ggacgtctgg tacaacttgg agaagaggac agacaaatca gccgtctcag gggctatccg 2460
actacaaatc agtgtggaga tcaaggggga ggagaaagta gccccatacc acgtgcagta 2520
tacatgtctc catgagaatc ttttccatta cctcacagac attcagggca gtggaggagt 2580
ccgcatccct gaagctcgag gagacgatgc ctggaaggtg tactttgatg agacagccca 2640
agaaattgtg gatgaatttg ccatgcgtta tggcattgag tccatatatc aggccatgac 2700
gcactttgca tgtttatcat ccaagtacat gtgtcctggt gtgccagcag tgatgagcac 2760
cttactggcc aacatcaacg cctactatgc ccacacaact gcctctacca atgtctctgc 2820
atctgatcgc tttgcagcct ccaactttgg gaaagagaga tttgtaaaac tgctggacca 2880
gctacacaac tcactgagga tcgacctctc tacatacagg aataatttcc ctgctgggag 2940
tcctgaacgg cttcaggact taaaatccac agtggatttg ctgaccagca ttactttctt 3000
cagaatgaag gtacaagaac tgcaaagccc tccaagagcc agccaggtgg taaaggattg 3060
tgtgaaggcc tgtttgaact ccacatatga atatatcttc aacaactgcc acgacttata 3120
cagccgccag taccagctga agcaggagct acctccagag gaacaagggc ccagcattcg 3180
gaacctggat ttctggccca agctcatcac actcatcgtg tcaatcatag aggaagataa 3240
gaattcctac acacctgttc tgaaccagtt tcctcaggag ttgaatgtgg gaaaagtcag 3300
cgcagaagtg atgtggcatt tgtttgccca agacatgaaa tatgcattgg aggagcatga 3360
gaaagaccac ctgtgtaaaa gtgctgacta catgaacctg cacttcaagg tgaagtggct 3420
ccacaatgaa tacgtgcggg atctgcctgt cctccagggg caggtgcctg agtacccagc 3480
gtggtttgag cagttcgtgc tacaatggct ggatgagaat gaggatgtat ccctggaatt 3540
cctgcgtggg gccctggaac gagataagaa ggatggattc cagcagacat cagagcatgc 3600

-continued

```
actcttttcc tgctctgtgg tggatgtctt cacacaactc aatcagagct ttgagatcat   3660
ccggaagctg gaatgcccag accccagcat ccttgcccac tacatgagga ggtttgctaa   3720
gaccatcggg aaggtgctga tgcagtatgc agacatcttg tcaaaggact tcccagccta   3780
ttgcacaaag gagaaactgc cctgcatcct gatgaacaac gtgcagcaac tgagggtcca   3840
gctggagaaa atgtttgagg ccatgggagg caaggagctg gaccttgaag ctgcagacag   3900
tctgaaggag ctgcaggtga aactgaatac ggttctggat gagctcagca tggtgtttgg   3960
aaacagtttc caggtacgga ttgatgagtg tgttcgacaa atggccgaca tcctgggcca   4020
ggttcggggc acagggaatg catctccaga cgccagggcc tcagcggctc aggatgcaga   4080
tagcgtactc cggcctctca tggacttcct ggatggcaac ctcaccctct ttgccactgt   4140
gtgtgagaag acggttctga agcgtgtact gaaggagctc tggcgcgtgg tgatgaacac   4200
aatggagagg atgattgttc tgccccccact cactgaccag acgggcaccc agctgatctt   4260
cactgctgcc aaggagctga gccatctttc caaactcaag gatcacatgg tacgagagga   4320
aacacggaat ctcactccaa agcagtgtgc agtccttgac ctcgccctgg acaccatcaa   4380
gcaatacttc catgcaggag gcaatgggct gaagaaaacc ttcctggaga agagcccaga   4440
tctgcagtct ctacgctatg ccctgtctct gtacacacag actactgaca ctctcatcaa   4500
gacctttgtg cgctcgcaga ccacccaagg gtctggtgtg gacgatcctg tgggagaagt   4560
ctctattcag gtggacttgt ttacacaccc tggtactggg gagcacaagg tcacagtgaa   4620
agtggtggct gccaatgacc tcaagtggca gacagcgggt atgttccggc ctttcgtgga   4680
ggtgactatg gttggcccac accaaagtga taagaagagg aagttcacaa ccaaatccaa   4740
aagcaacaac tgggcccccca agtacaatga gacattccac ttcctcctgg gaaatgagga   4800
ggggcccgag tcctatgagt tgcagatatg cgtgaaggat tactgctttg cccgggaaga   4860
tcgcgtgcta gggctggctg tgatgcctct gagggatgtc acagccaagg gcagctgtgc   4920
ctgctggtgc cccttgggcc ggaagatcca tatggatgag acaggcctga ccattctccg   4980
gattttatct cagaggagca atgacgaggt ggcccgagaa tttgtgaaac tcaaatcaga   5040
gtctcgttcc acggaggagg ggagctgaac accttcgact cctgtgccaa tcaggcagca   5100
gcaatttcac aaatcagggc cagtgggagt tagctgtgta accggcttag ggtctttgca   5160
gtcaagaggc tgaccccttc agttaaagat atttaaggaa aaatttgggg tggtgataat   5220
atggcttttc acagaaaggg tcatgaagcc ctggcccaac aggactgtgg tactaggggc   5280
tgggatgtgg ggttaccaca tggagagatt ttccattaag agagaaggac aaacatttct   5340
gagagtgtca gccattcttg gtagacacct ctccactcct catcccacct ctacccatct   5400
ccatgccaca ccttatccag ttagacacat acataccaat cattagaaga acaagtttag   5460
aaggtgtgga acttgtgcct ggctggctgg gtagtcagct gagcctgttg ctgagcccgg   5520
tggtctggat tggagtatgg ccagggcagg agtacacaga atagaattta gactgtccct   5580
tgagtagaat ccactgattt tctgtggctc cagtgagaac aaggctttga aactgaacaa   5640
gataacttct agaaatgaac tgtactaatc cctttcccca gattgtatca tgagtagaat   5700
caggttcacg tggtgcttca aagccctgag aagaatattt ctttggaccc caggcactag   5760
gggccacctg cctgggagtc tccctgcctc actcctctag gcaggggagt gatgcttcag   5820
gacgtgacag gctgttctaa catgtgtcta cctgagggct agttgaagga tccaggagta   5880
ttttcttctt gggtgggccc tgaacaaagc caaaaattgt agaaaccagt ctagaaaaag   5940
tcctgctcat ctgtggccac tgccttctag ccgtcctcca ccttgcagaa agaatctagc   6000
```

ctttggtctc tctctctctc atcggggtca tttgctattc ccctctgata ttcaacccta 6060
tagaaggagc ctggactctg atccctctgt acaggctgga tggaaggggc cctccacact 6120
tcctgggagg tcagagacaa actgtttcag agagtcagat ggacttccca agacttgttg 6180
agagatgtga catggttctt ggatttcctc tgtagcagcc tcctggactt cctgaggact 6240
cgacattgtc cacagatgta ctggccatta catgaaacaa gaaaccaagc atctttgctg 6300
ttgttaatta ttatatgtgc cattgttaca ggagattata ggctagtctg taataaatta 6360
tcttatagca aaaaaaaaaa aaaaaaaaaa aaaaaaaa 6398

<210> SEQ ID NO 48
<211> LENGTH: 3311
<212> TYPE: DNA
<213> ORGANISM: Homo sapiens

<400> SEQUENCE: 48
cgcccgggca ggtgaaaggt tttgtctatt tctgttcctt gttgaatctc tagtacctag 60
aaccatgtct ggtcctgatt aggcacttgg tgaatgtttt tgaatgaata ctctgagctg 120
ttctttaatc ggtcctcatg atcctcattg tacagatgag ggaactctgg gcgaacctgg 180
cctgggtctt gagctaatta cgggtaggtc aggttctgta cccaagtagt acacacagtg 240
atgggcgggg tggcctgggg ccgtggtttg tcaaccccta cgctggaggg tgatgttttg 300
gtacaagagg agaggtgccc caatgcgtcc tgtgtctgta attgatggcg ttgtctgtgt 360
ttccccagga tgtggttctg agacagtccc tgtccctgat ggcccacgga gcgactcggt 420
ggaaggaagt cccttccgtc ccccgtcaca ctccttctct gccgtcttcg atgaagacaa 480
gccgatagcc agcagtggga cttacaactt ggactttgac aacattgagc ttgtggatac 540
ctttcagacc ttggagcctc gtgcctcaga cgctaagaat caggagggca aagtgaacac 600
acggaggaag tccacggatt ccgtccccat ctctaagtct acactgtccc ggtcgctcag 660
cctgcaagcc agtgactttg atggtgcttc ttcctcaggc aatcccgagg ccgtggccct 720
tgccccagat gcatatagca cgggttccag cagtgcttct agtaccctta agcgaactaa 780
aaaaccgagg ccgccttcct taaaaaagaa acagaccacc aagaaaccca cagagacccc 840
cccagtgaag gagacgcaac aggagccaga tgaagagagc cttgtcccca gtggggagaa 900
tctagcatct gagacgaaaa cggaatctgc caagacggaa ggtcctagcc cagccttatt 960
ggaggagacg ccccttgagc ccgctgtggg gcccaaagct gcctgccctc tggactcaga 1020
gagtgcagaa ggggttgtcc ccccggcttc tggaggtggc agagtgcaga actcaccccc 1080
tgtcgggagg aaaacgctgc ctcttaccac ggccccggag gcaggggagg taaccccatc 1140
ggatagcggg gggcaagagg actctccagc caaagggctc tccgtaaggc tggagtttga 1200
ctattctgag gacaagagta gttgggacaa ccagcaggaa aacccccctc ctaccaaaaa 1260
gataggcaaa aagccagttg ccaaaatgcc cctgaggagg ccaaagatga aaaagacacc 1320
cgagaaactt gacaacactc ctgcctcacc tcccagatcc cctgctgaac ccaatgacat 1380
ccccattgct aaaggtactt acacctttga tattgacaag tgggatgacc ccaattttaa 1440
cccttttctt tccacctcaa aaatgcagga gtctcccaaa ctgccccaac aatcatacaa 1500
ctttgaccca gacacctgtg atgagtccgt tgaccccttt aagacatcct ctaagacccc 1560
cagctcacct tctaaatccc cagcctcctt tgagatccca gccagtgcta tggaagccaa 1620
tggagtggac ggggatgggc taaacaagcc cgccaagaag aagaagacgc ccctaaagac 1680

-continued

```
tgacacattt agggtgaaaa agtcgccaaa acggtctcct ctctctgatc caccttccca   1740
ggaccccacc ccagctgcta caccagaaac accaccagtg atctctgcgg tggtccacgc   1800
cacagatgag gaaaagctgg cggtcaccaa ccagaagtgg acgtgcatga cagtggacct   1860
agaggctgac aaacaggact acccgcagcc ctcggacctg tccacctttg taaacgagac   1920
caaattcagt tcacccactg aggagttgga ttacagaaac tcctatgaaa ttgaatatat   1980
ggagaaaatt ggctcctcct tacctcagga cgacgatgcc ccgaagaagc aggccttgta   2040
ccttatgttt gacacttctc aggagagccc tgtcaagtca tctcccgtcc gcatgtcaga   2100
gtccccgacg ccgtgttcag ggtcaagttt tgaagagact gaagcccttg tgaacactgc   2160
tgcgaaaaac cagcatcctg tcccacgagg actggcccct aaccaagagt cacacttgca   2220
ggtgccagag aaatcctccc agaaggagct ggaggccatg ggcttgggca ccccttcaga   2280
agcgattgaa attagagagg ctgctcaccc aacagacgtc tccatctcca aaacagcctt   2340
gtactcccgc atcgggaccg ctgaggtgga gaaacctgca ggccttctgt tccagcagcc   2400
cgacctggac tctgccctcc agatcgccag agcagagatc ataaccaagg agagagaggt   2460
ctcagaatgg aaagataaat atgaagaaag caggcgggaa gtgatggaaa tgaggaaaat   2520
agtggccgag tatgagaaga ccatcgctca gatgatagag gacgaacaga gagagaagtc   2580
agtctcccac cagacggtgc agcagctggt tctggagaag gagcaagccc tggccgacct   2640
gaactccgtg gagaagtctc tggccgacct cttcagaaga tatgagaaga tgaaggaggt   2700
cctagaaggc ttccgcaaga atgaagaggt gttgaagaga tgtgcgcagg agtacctgtc   2760
ccgggtgaag aaggaggagc agaggtacca ggccctgaag gtgcacgcgg aggagaaact   2820
ggacagggcc aatgctgaga ttgctcaggt tcgaggcaag gcccagcagg agcaagccgc   2880
ccaccaggcc agcctgcgga aggagcagct gcgagtggac gccctggaaa ggacgctgga   2940
gcagaagaat aaagaaatag aagaactcac caagatttgt gacgaactga ttgccaaaat   3000
ggggaaaagc taactctgaa ccgaatgttt tggacttaac tgttgcgtgc aatatgaccg   3060
tcggcacact gctgttcctc cagttccatg gacaggttct gttttcactt tttcgtatgc   3120
actactgtat ttcctttcta aataaaattg atttgattgt atgcagtact aaggagacta   3180
tcagaatttc ttgctattgg tttgcatttt cctagtataa ttcatagcaa gttgacctca   3240
gagttcctgt atcagggaga ttgtctgatt ctctaataaa agacacattg ctgaaaaaaa   3300
aaaaaaaaaa a                                                        3311
```

METHODS FOR SUBTYPING OF LUNG ADENOCARCINOMA

CROSS REFERENCE

This application is a continuation of U.S. application Ser. No. 16/302,167, filed on Nov. 16, 2018, which is a national phase of International Application No. PCT/US2017/033110, filed May 17, 2017, which claims priority from U.S. Provisional Application No. 62/337,591 filed May 17, 2016, U.S. Provisional Application No. 62/337,645 filed May 17, 2016, U.S. Provisional Application No. 62/396,587 filed Sep. 19, 2016, U.S. Provisional Application No. 62/420,836 filed Nov. 11, 2016, and U.S. Provisional Application No. 62/425,717 filed Nov. 23, 2016, each of which is incorporated by reference herein in its entirety for all purposes.

FIELD OF THE INVENTION

The present invention relates to methods for determining an adenocarcinoma subtype of a lung sample and for predicting the response to a treatment for a patient inflicted with specific subtypes of lung cancer.

STATEMENT REGARDING SEQUENCE LISTING

The Sequence Listing associated with this application is provided in text format in lieu of a paper copy, and is hereby incorporated by reference into the specification. The name of the text file containing the Sequence Listing is GNCN_009_02US_SeqList_ST25.txt. The text file is 194 KB, and was created on Jan. 22, 2021, and is being submitted electronically via EFS-Web.

BACKGROUND OF THE INVENTION

Lung cancer is the leading cause of cancer deaths in both the United States and worldwide. Approximately 172,000 tumors of the lung were diagnosed in 2005 with an estimated 163,000 deaths, more than colon, breast, and prostate combined. At least 75% of patients present with locally advanced disease. Although there has been much effort to improve screening using technology such as high-resolution CT, these methods often produce false positive results and usually do not change outcome. Thus, even small tumors detected early present a significant threat to patients with postoperative 5-year survival rates for stage I lung cancer estimated between 47 to 63 percent. For patients with advanced disease the prognosis is worse with median survivals well under a year. In general, palliative therapy is effective but not sustainable and the average impact on overall survival is approximately 3 months.

At the population level, the underlying cause of lung cancer is clearly tobacco use, with 90% of all lung cancers attributed directly to smoking. Smoking is so tightly correlated with lung cancer that it confounds definitive association with most other risk factors; although asbestos, radon, and a number of lung irritants are generally accepted as lung cancer risk factors. A genetic association is strongly suspected, however, the exact mechanism remains to be determined outside of a select group of rare Mendelian cancer syndromes. Despite many classification schemes and ongoing clinical trials, there has been overall disappointing progress in the field of clinical diagnostics and therapeutics.

Most lung cancers are classified as non-small cell lung carcinoma (NSCLC) (>85%), which is a diverse group with subtypes occurring throughout the respiratory tract. Adenocarcinoma (AD) and squamous cell carcinomas (SCC or SQ), the two main subtypes of NSCLC, are diagnosed at near equal frequency but are often found at different locations with SCC occurring more centrally. The 6th edition of the consensus classification of lung cancers developed by the World Health Organization (WHO) describes no fewer than 90 malignant morphologic classes and variants. There can often be heterogeneity, especially in larger tumors>1.5 cm, making morphological classification more difficult and leading to designations such as adeno-squamous carcinoma. Further, studies of histologic diagnosis reproducibility have shown limited intra-pathologist agreement and inter-pathologist agreement. Variability in morphology, limited tissue samples, and the need for assessment of a growing list of therapeutically targeted markers pose challenges to the current diagnostic standard. This is further highlighted by the idea that differentiation among various morphologic subtypes of lung cancer can be essential in guiding patient management and additional molecular testing can be used to identify specific therapeutic target markers.

Currently, gene expression based lung adenocarcinoma (AD) subtyping has been primarily restricted to a research protocol involving the extraction of RNA from fresh frozen lung tumors, followed by application of a nearest centroid predictor using quantitative gene expression of over 500 genes. Gene expression based adenocarcinoma subtyping has been shown to classify adenocarcinoma tumors into 3 biologically distinct subtypes (Terminal Respiratory Unit (TRU; formerly referred to as Bronchioid), Proximal Inflammatory (PI; formerly referred to as Squamoid), and Proximal Proliferative (PP; formerly referred to as Magnoid)) which can vary in their genomic profiles including gene expression, mutational spectrum, and copy number alterations. Further, these three subtypes can vary in their prognosis, in their distribution of smokers vs. nonsmokers, in their prevalence of EGFR alterations, ALK rearrangements, TP53 mutations, in their angiogenic features, and in their immunogenic response features. Despite evidence of prognostic and predictive benefits from AD subtyping, the requirement for gene expression of >500 genes in combination with complex bioinformatics analyses, has hindered the application of AD subtyping in drug development and/or in the clinic.

Cancer immunosurveillance is the principle that the immune system can identify precancerous and cancerous cells and kill these cells before they become clinically relevant, which has been demonstrated in immunodeficient mouse models. Innate and adaptive immune responses can work together to either promote or inhibit cancer growth, and evasion of immune destruction is an emerging hallmark of cancer. Historically, methods of immune stimulation were not effective for lung cancer patients in the clinic. Deficiencies in tumor antigen expression and presentation on antigen presenting cells (APCs), infiltration of immunosuppressive cells and cytokines, and ineffective T-cell activation can lead to immunosuppression at the tumor site. Advances in the understanding of cancer and the immune system have led to effective therapies that activate antitumor responses, even in tumors that have highly developed methods of immune evasion, such as lung cancer. However the high immunosuppressive effects caused by lung tumors limit the beneficial effects of these advances due to a delicate balance between immunoactivation and immunosuppression in a patient. For example, in NSCLC, the role of immunosuppressive cells hampering immune activation is high, which is suggested to be related to the type of tumor, advanced stage of the disease, and the tumor load.

Therefore, developing a method to effectively distinguish intrinsic lung adenocarcinoma subtypes is critical for clinical diagnosis and disease management. Accordingly, new methods are needed to further define populations that might be likely to respond to immunotherapy. The present invention addresses these and other needs in the field for determining a prognosis or disease outcome for adenocarcinoma patient populations based in part on the adenocarcinoma subtype (Terminal Respiratory Unit (TRU), Proximal Inflammatory (PI), Proximal Proliferative (PP)) of the patient. The methods of the invention provide a means for determining the cellular and molecular origins of lung cancer (e.g., subtyping AD) and can provide for more accurate diagnosis and applicable treatments as compared to diagnostic methods known in the art.

SUMMARY OF THE INVENTION

In one aspect, provided herein is a method for determining an adenocarcinoma (AD) subtype of a lung tissue sample obtained from a patient, the method comprising detecting an expression level of at least one classifier biomarker of Table 1, wherein the detection of the expression level of the classifier biomarker specifically identifies a Terminal Respiratory Unit (TRU), Proximal Proliferative (PP), or Proximal Inflammatory (PI) AD subtype. In some cases, the method further comprises comparing the detected levels of expression of the at least one classifier biomarkers of Table 1 to the expression of the at least one classifier biomarkers of Table 1 in at least one sample training set(s), wherein the at least one sample training set comprises expression data of the at least one classifier biomarkers of Table 1 from a reference AD TRU sample, expression data of the at least one classifier biomarkers of Table 1 from a reference AD PP sample, expression data of the at least one classifier biomarkers of Table 1 from a reference AD PI sample or a combination thereof; and classifying the sample as TRU, PP or PI subtype based on the results of the comparing step. In some cases, the comparing step comprises applying a statistical algorithm which comprises determining a correlation between the expression data obtained from the sample and the expression data from the at least one training set(s); and classifying the sample as a TRU, PP or PI subtype based on the results of the statistical algorithm. In some cases, the expression level of the classifier biomarker is detected at the nucleic acid level. In some cases, the nucleic acid level is RNA or cDNA. In some cases, the detecting an expression level comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques. In some cases, the expression level is detected by performing qRT-PCR. In some cases, the detection of the expression level comprises using at least one pair of oligonucleotide primers specific for at least one classifier biomarker of Table 1. In some cases, the sample is a formalin-fixed, paraffin-embedded (FFPE) lung tissue sample, fresh or a frozen tissue sample, an exosome, wash fluids, cell pellets, or a bodily fluid obtained from the patient. In some cases, the bodily fluid is blood or fractions thereof, urine, saliva, or sputum. In some cases, the at least one classifier biomarker comprises a plurality of classifier biomarkers. In some cases, the plurality of classifier biomarkers comprises at least two classifier biomarkers, at least 8 classifier biomarkers, at least 16 classifier biomarkers, at least 24 classifier biomarkers, at least 32 classifier biomarkers, at least 40 classifier biomarkers, or at least 48 classifier biomarkers of Table 1. In some cases, the at least one classifier biomarker comprises all the classifier biomarkers of Table 1.

In another aspect, provided herein is a method for determining an adenocarcinoma (AD) subtype of a lung tissue sample obtained from a patient comprising detecting an expression level of at least one nucleic acid molecule that encodes a classifier biomarker having a specific expression pattern in lung cancer cells, wherein the classifier biomarker is selected from the group consisting of the classifier genes set forth in Table 1, the method comprising: (a) isolating nucleic acid material from a lung tissue sample from a patient; (b) mixing the nucleic acid material with oligonucleotides that are substantially complementary to portions of nucleic acid molecule of the classifier biomarker; and (c) detecting expression of the classifier biomarker. In some cases, the method further comprises comparing the detected levels of expression of the at least one classifier biomarkers of Table 1 to the expression of the at least one classifier biomarkers of Table 1 in at least one sample training set(s), wherein the at least one sample training set comprises expression data of the at least one classifier biomarkers of Table 1 from a reference AD TRU sample, expression data of the at least one classifier biomarkers of Table 1 from a reference AD PP sample, expression data of the at least one classifier biomarkers of Table 1 from a reference AD PI sample or a combination thereof, and classifying the sample as TRU, PP or PI subtype based on the results of the comparing step. In some cases, the comparing step comprises applying a statistical algorithm which comprises determining a correlation between the expression data obtained from the sample and the expression data from the at least one training set(s); and classifying the sample as a TRU, PP or PI subtype based on the results of the statistical algorithm. In some cases, the detecting the expression level comprises performing qRT-PCR or any hybridization-based gene assays. In some cases, the expression level is detected by performing qRT-PCR. In some cases, the detection of the expression level comprises using at least one pair of oligonucleotide primers specific for at least one classifier biomarker of Table 1. In some cases, the method further comprises predicting the response to a therapy for treating a subtype of lung adenocarcinoma (AD) based on the detected expression level of the classifier biomarker. In some cases, the therapy is chemotherapy, angiogenesis inhibitors and/or immunotherapy. In some cases, the subtype of lung AD is TRU and the therapy is chemotherapy or angiogenesis inhibitor. In some cases, the subtype of lung AD is PP and the therapy is chemotherapy. In some cases, the subtype of lung AD is PI and the therapy is an immunotherapy. In some cases, the sample is a formalin-fixed, paraffin-embedded (FFPE) lung tissue sample, fresh or a frozen tissue sample, an exosome, wash fluids, cell pellets or a bodily fluid obtained from the patient. In some cases, the bodily fluid is blood or fractions thereof, urine, saliva, or sputum. In some cases, the at least one nucleic acid molecule that encodes a classifier biomarker comprises a plurality of nucleic acid molecules that encode a plurality of classifier biomarkers. In some cases, the plurality of classifier biomarkers comprises at least two classifier biomarkers, at least 5 classifier biomarkers, at least 10 classifier biomarkers, at least 20 classifier biomarkers or at least 30 classifier biomarkers of Table 1. In some cases, the at least one classifier biomarker comprises all the classifier biomarkers of Table 1.

In yet another aspect, provided herein is a method of detecting a biomarker in a lung tissue sample obtained from a patient, the method comprising measuring the expression level of a plurality of biomarker nucleic acids selected from Table 1 using an amplification, hybridization and/or sequencing assay. In some cases, the lung tissue sample was previously diagnosed as being adenocarcinoma. In some cases, the previous diagnosis was by histological examination. In some cases, the amplification, hybridization and/or sequencing assay comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques. In some cases, the expression level is detected by performing qRT-PCR. In some cases, the detection of the expression level comprises using at least one pair of oligonucleotide primers per each of the plurality of biomarker nucleic acids selected from Table 1. In some cases, the sample is a formalin-fixed, paraffin-embedded (FFPE) lung tissue sample, fresh or a frozen tissue sample, an exosome, wash fluids, cell pellets, or a bodily fluid obtained from the patient. In some cases, the bodily fluid is blood or fractions thereof, urine, saliva, or sputum. In some cases, the plurality of biomarker nucleic acids comprises, consists essentially of or consists of at least two biomarker nucleic acids, at least 10 biomarker nucleic acids, at least 20 biomarker nucleic acids, at least 30 biomarker nucleic acids, at least 40 biomarker nucleic acids, at least 50 biomarker nucleic acids, at least 60 biomarker nucleic acids, or at least 70 biomarker nucleic acids of Table 1. In some cases, the plurality of biomarker nucleic acids comprises, consists essentially of or consists of all the classifier biomarker nucleic acids of Table 1.

In one aspect, provided herein is a method of detecting a biomarker in a lung tissue sample obtained from a patient, the method consisting essentially of measuring the expression level of a plurality of biomarker nucleic acids selected from Table 1 using an amplification, hybridization and/or sequencing assay. In some cases, the lung tissue sample was previously diagnosed as being adenocarcinoma. In some cases, the previous diagnosis was by histological examination. In some cases, the amplification, hybridization and/or sequencing assay comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques. In some cases, the expression level is detected by performing qRT-PCR. In some cases, the detection of the expression level comprises using at least one pair of oligonucleotide primers per each of the plurality of biomarker nucleic acids selected from Table 1. In some cases, the sample is a formalin-fixed, paraffin-embedded (FFPE) lung tissue sample, fresh or a frozen tissue sample, an exosome, wash fluids, cell pellets, or a bodily fluid obtained from the patient. In some cases, the bodily fluid is blood or fractions thereof, urine, saliva, or sputum. In some cases, the plurality of biomarker nucleic acids comprises, consists essentially of or consists of at least two biomarker nucleic acids, at least 10 biomarker nucleic acids, at least 20 biomarker nucleic acids, at least 30 biomarker nucleic acids, at least 40 biomarker nucleic acids, at least 50 biomarker nucleic acids, at least 60 biomarker nucleic acids, or at least 70 biomarker nucleic acids of Table 1. In some cases, the plurality of biomarker nucleic acids comprises, consists essentially of or consists of all the classifier biomarker nucleic acids of Table 1.

In another aspect, provided herein is a method of detecting a biomarker in a lung tissue sample obtained from a patient, the method consisting of measuring the expression level of a plurality of biomarker nucleic acids selected from Table 1 using an amplification, hybridization and/or sequencing assay. In some cases, the lung tissue sample was previously diagnosed as being adenocarcinoma. In some cases, the previous diagnosis was by histological examination. In some cases, the amplification, hybridization and/or sequencing assay comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques. In some cases, the expression level is detected by performing qRT-PCR. In some cases, the detection of the expression level comprises using at least one pair of oligonucleotide primers per each of the plurality of biomarker nucleic acids selected from Table 1. In some cases, the sample is a formalin-fixed, paraffin-embedded (FFPE) lung tissue sample, fresh or a frozen tissue sample, an exosome, wash fluids, cell pellets, or a bodily fluid obtained from the patient. In some cases, the bodily fluid is blood or fractions thereof, urine, saliva, or sputum. In some cases, the plurality of biomarker nucleic acids comprises, consists essentially of or consists of at least two biomarker nucleic acids, at least 10 biomarker nucleic acids, at least 20 biomarker nucleic acids, at least 30 biomarker nucleic acids, at least 40 biomarker nucleic acids, at least 50 biomarker nucleic acids, at least 60 biomarker nucleic acids, or at least 70 biomarker nucleic acids of Table 1. In some cases, the plurality of biomarker nucleic acids comprises, consists essentially of or consists of all the classifier biomarker nucleic acids of Table 1.

In another aspect, provided herein is a method of determining whether an adenocarcinoma patient is likely to respond to immunotherapy, the method comprising, determining the adenocarcinoma subtype of a lung tissue sample from the patient, wherein the adenocarcinoma subtype is selected from the group consisting of squamoid (proximal inflammatory), bronchoid (terminal respiratory unit) and magnoid (proximal proliferative); and based on the subtype, assessing whether the patient is likely to respond to immunotherapy. In some cases, the immunotherapy comprises checkpoint inhibitor therapy. In some cases, the checkpoint inhibitor targets PD-1 or PD-L1. In some cases, the checkpoint inhibitor targets CTLA-4. In some cases, the checkpoint inhibitor is Pembrolizumab, Nivolumab or an antigen fragment binding fragment thereof. In some cases, the checkpoint inhibitor is Ipilimumab or an antigen binding fragment thereof. In some cases, the patient is initially determined to have adenocarcinoma via a histological analysis of a sample. In some cases, the patient's adenocarcinoma molecular subtype is selected from squamoid (proximal inflammatory), bronchoid (terminal respiratory unit) or magnoid (proximal proliferative), and is determined via a histological analysis of a sample obtained from the patient. In some cases, the sample is a formalin-fixed, paraffin-embedded (FFPE) lung tissue sample, fresh or a frozen tissue sample, an exosome, or a bodily fluid obtained from the patient. In some cases, the bodily fluid is blood or fractions thereof, urine, saliva, or sputum. In some cases, the determining the adenocarcinoma subtype comprises determining expression levels of a plurality of classifier biomarkers. In some cases, the determining the expression levels of the plurality of classifier biomarkers is at a nucleic acid level by performing RNA sequencing, reverse transcriptase polymerase chain reaction (RT-PCR) or hybridization based analyses. In some cases, the plurality of classifier biomarkers for determining the adenocarcinoma subtype is selected from a publically available lung adenocarcinoma dataset. In some cases, the publically available lung adenocarcinoma dataset is TCGA Lung AD RNAseq dataset. In some cases, the plurality of classifier biomarkers for determining the adenocarcinoma subtype is selected from Table 1. In some cases, the RT-PCR is quantitative real time reverse transcriptase polymerase chain reaction (qRT-PCR). In some cases, the RT-PCR is performed with primers specific to the plurality of classifier biomarkers of Table 1. In some cases, the method further comprises comparing the detected levels of expression of the plurality of classifier biomarkers of Table 1 to the expression of the plurality of classifier biomarkers of Table 1 in at least one sample training set(s), wherein the at least one sample training set comprises expression data of the plurality of classifier biomarkers of Table 1 from a reference adenocarcinoma TRU sample, expression data of the plurality of classifier biomarkers of Table 1 from a reference adenocarcinoma PP sample, expression data of the plurality of classifier biomarkers of Table 1 from a reference adenocarcinoma PI sample, or a combination thereof; and classifying the first sample as TRU, PP, or PI based on the results of the comparing step. In some cases, the comparing step comprises applying a statistical algorithm which comprises determining a correlation between the expression data obtained from the sample and the expression data from the at least one training set(s); and classifying the sample as a TRU, PP, or PI subtype based on the results of the statistical algorithm. In some cases, the plurality of the classifier biomarkers comprise each of the classifier biomarkers set forth in Table 1.

In yet another aspect, provided herein is a method for selecting an adenocarcinoma patient for immunotherapy, the method comprising, determining an adenocarcinoma subtype of a lung tissue sample from the patient, based on the subtype; and selecting the patient for immunotherapy. In some cases, the immunotherapy comprises checkpoint inhibitor therapy. In some cases, the checkpoint inhibitor targets PD-1 or PD-L1. In some cases, the checkpoint inhibitor targets CTLA-4. In some cases, the checkpoint inhibitor is Pembrolizumab, Nivolumab or an antigen fragment binding fragment thereof. In some cases, the checkpoint inhibitor is Ipilimumab or an antigen binding fragment thereof. In some cases, the patient is initially determined to have adenocarcinoma via a histological analysis of a sample. In some cases, the patient's adenocarcinoma molecular subtype is selected from squamoid (proximal inflammatory), bronchoid (terminal respiratory unit) or magnoid (proximal proliferative), and is determined via a histological analysis of a sample obtained from the patient. In some cases, the sample is a formalin-fixed, paraffin-embedded (FFPE) lung tissue sample, fresh or a frozen tissue sample, an exosome, or a bodily fluid obtained from the patient. In some cases, the bodily fluid is blood or fractions thereof, urine, saliva, or sputum. In some cases, the determining the adenocarcinoma subtype comprises determining expression levels of a plurality of classifier biomarkers. In some cases, the determining the expression levels of the plurality of classifier biomarkers is at a nucleic acid level by performing RNA sequencing, reverse transcriptase polymerase chain reaction (RT-PCR) or hybridization based analyses. In some cases, the plurality of classifier biomarkers for determining the adenocarcinoma subtype is selected from a publically available lung adenocarcinoma dataset. In some cases, the publically available lung adenocarcinoma dataset is TCGA Lung AD RNAseq dataset. In some cases, the plurality of classifier biomarkers for determining the adenocarcinoma subtype is selected from Table 1. In some cases, the RT-PCR is quantitative real time reverse transcriptase polymerase chain reaction (qRT-PCR). In some cases, the RT-PCR is performed with primers specific to the plurality of classifier biomarkers of Table 1. In some cases, the method further comprises comparing the detected levels of expression of the plurality of classifier biomarkers of Table 1 to the expression of the plurality of classifier biomarkers of Table 1 in at least one sample training set(s), wherein the at least one sample training set comprises expression data of the plurality of classifier biomarkers of Table 1 from a reference adenocarcinoma TRU sample, expression data of the plurality of classifier biomarkers of Table 1 from a reference adenocarcinoma PP sample, expression data of the plurality of classifier biomarkers of Table 1 from a reference adenocarcinoma PI sample, or a combination thereof, and classifying the first sample as TRU, PP, or PI based on the results of the comparing step. In some cases, the comparing step comprises applying a statistical algorithm which comprises determining a correlation between the expression data obtained from the sample and the expression data from the at least one training set(s); and classifying the sample as a TRU, PP, or PI subtype based on the results of the statistical algorithm. In some cases, the plurality of the classifier biomarkers comprise each of the classifier biomarkers set forth in Table 1.

In one aspect, provided herein is a method of treating lung cancer in a subject, the method comprising: measuring the expression level of at least one biomarker nucleic acid in a lung cancer sample obtained from the subject, wherein the at least one biomarker nucleic acid is selected from a set of biomarkers listed in Table 1, wherein the presence, absence and/or level of the at least one biomarker indicates a subtype of the lung cancer; and administering an immunotherapeutic agent based on the subtype of the lung cancer. In some cases, the lung cancer sample is an adenocarcinoma lung cancer sample, In some cases, the at least one biomarker nucleic acid selected from the set of biomarkers comprises, consists essentially of or consists of at least two biomarker nucleic acids, at least 8 biomarker nucleic acids, at least 16 biomarker nucleic acids, at least 32 biomarker nucleic acids, or all 48 biomarker nucleic acids of Table 1. In some cases, the lung tissue sample was previously diagnosed as being adenocarcinoma. In some cases, the previous diagnosis was by histological examination. In some cases, the method further comprises measuring the expression of at least one biomarker from an additional set of biomarkers. In some cases, the additional set of biomarkers comprise gene expression signatures of Innate Immune Cells (IIC), Adaptive Immune Cells (AIC), one or more individual immune biomarkers, one or more interferon (IFN) genes, one or more major histocompatibility complex, class II (MHCII) genes or a combination thereof. In some cases, the additional set of biomarkers comprises genes selected from Tables 4A, 4B, 5, 6, 7, or a combination thereof. In some cases, the gene expression signatures of AICs are selected from Table 4A. In some cases, the gene expression signature of IICs are selected from Table 413. In some cases, the one or more individual immune biomarkers are selected from Table 5. In some cases, the one or more IFN genes are selected from Table 6. In some cases, the one or more MHCII genes are selected from Table 7. In some cases, the measuring the expression level is conducted using an amplification, hybridization and/or sequencing assay. In some cases, the amplification, hybridization and/or sequencing assay comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques. In some cases, the expression level is detected by performing qRT-PCR. In some cases, the sample is a formalin-fixed, paraffin-embedded (FFPE) lung tissue sample, fresh or a frozen tissue sample, an exosome, wash fluids, cell pellets, or a bodily fluid obtained from the patient. In some cases, the bodily fluid is blood or fractions thereof, urine, saliva, or sputum. In some cases, the subject's adenocarcinoma subtype is selected from squamoid (proximal inflammatory), bronchoid (terminal respiratory unit) or magnoid (proximal proliferative). In some cases, the lung cancer subtype is proximal inflammatory and wherein the immunotherapeutic agent comprises a checkpoint inhibitor. In some cases, the checkpoint inhibitor targets PD-1 or PD-L1. In some cases, the checkpoint inhibitor targets CTLA-4. In some cases, the checkpoint inhibitor is Pembrolizumab, Nivolumab or an antigen fragment binding fragment thereof. In some cases, the checkpoint inhibitor is Ipilimumab or an antigen binding fragment thereof. In some cases, the at least one biomarker nucleic acid is a plurality of biomarker nucleic acids, wherein the plurality of biomarker nucleic acids comprises at least one biomarker nucleic acid listed in Table 1 in combination with one or more biomarker nucleic acids from a publically available lung adenocarcinoma dataset, wherein the presence, absence and/or level of the plurality of biomarker nucleic acids indicates a subtype of the lung cancer. In some cases, the at least one biomarker nucleic acid is a plurality of biomarker nucleic acids, wherein the plurality of biomarker nucleic acids comprises all of the biomarker nucleic acids listed in Table 1 in combination with one or more biomarker nucleic acids from a publically available lung adenocarcinoma dataset, wherein the presence, absence and/or level of the plurality of biomarker nucleic acids indicates a subtype of the lung cancer. In some cases, the publically available lung adenocarcinoma dataset is TCGA Lung AD RNAseq dataset.

BRIEF DESCRIPTION OF THE DRAWINGS

FIG. 2 illustrates the lung AD datasets used in the study described in Example 1.

FIGS. 7A-7B show survival associations of immune cell signatures and markers by AD subtype in the TCGA cohort (FIG. 7A) or the TGCA, Shedden and Tomida cohorts (FIG. 7B). Subtype specific immune marker hazard ratios and 95% confidence intervals were for 5 year overall survival in the TCGA cohort (n=515 AD) for FIG. 7A.

FIG. 13 illustrates agreement of AD subtype prediction by the 48 gene signature provided herein with the 506-gene classifier to define the gold standard subtype for multiple validation datasets. The agreement with the gold standard (TCGA) is 87%. The agreement with Shedden, Tomida, UNC, and FFPE is 87%, 79%, 92%, and 84%, respectively.

DETAILED DESCRIPTION OF THE INVENTION

Overview

Figure 1:
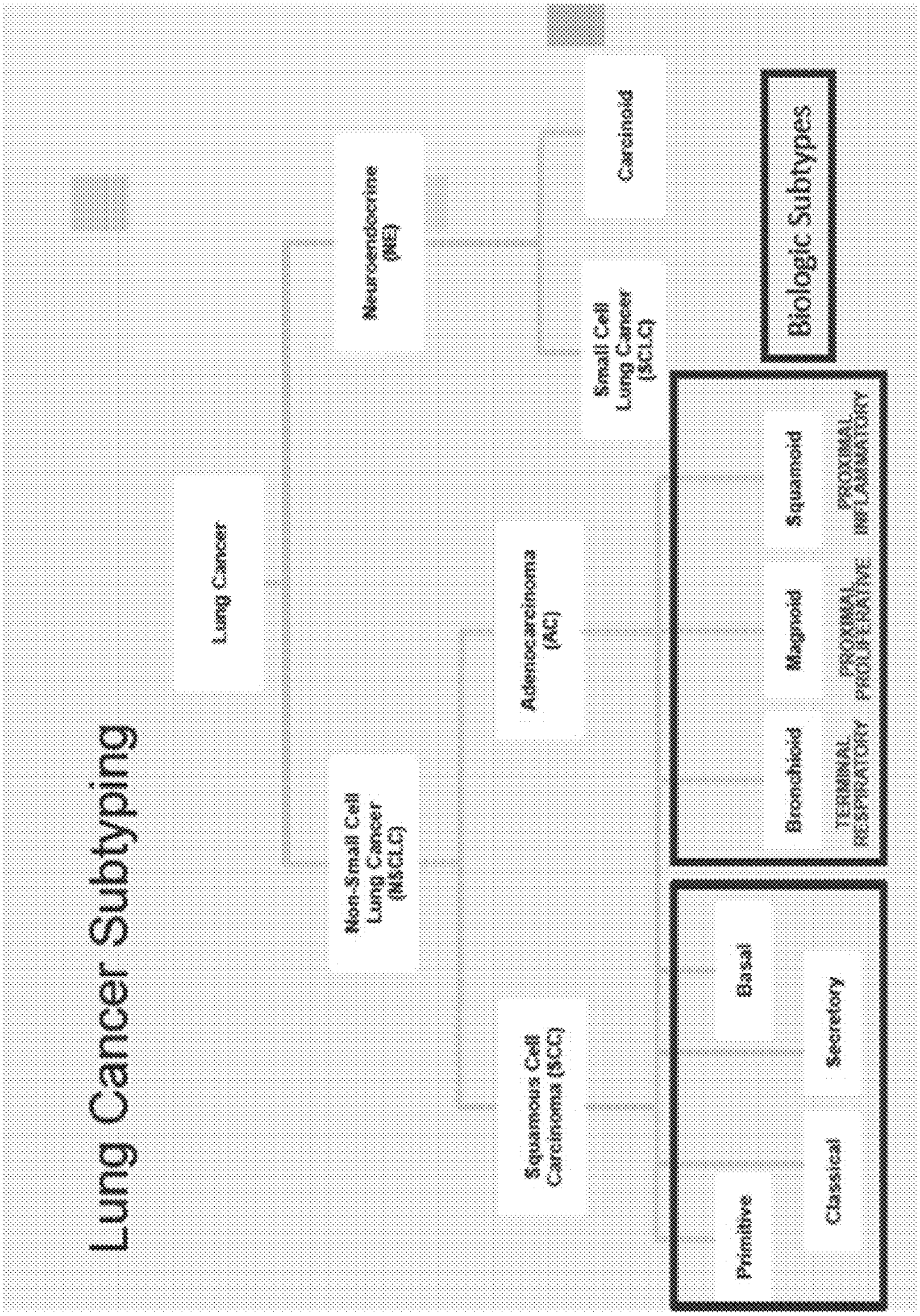
FIG. 1 illustrates lung cancer subtyping and the biologic subtypes of squamous cell carcinoma (SCC or SQ) and Adenocarcinoma (AC or AD).

The present invention provides kits, compositions and methods for identifying or diagnosing lung cancer. That is, the methods can be useful for molecularly defining subsets of lung cancer, specifically lung adenocarcinoma (AD). The methods provide a classification of lung cancer that can be prognostic and predictive for therapeutic response. While a useful term for epidemiologic purposes, "lung cancer" may not refer to a specific disease, but rather can represent a heterogeneous collection of tumors of the lung, bronchus, and pleura. For practical purposes, lung cancer can generally be divided into two histological subtypes-small cell lung cancer (SCLC) and non-small cell lung cancer (NSCLC). These main tumor types can present at different frequencies, can have different anatomic locations, can have different predilections for metastasis, may respond differently to therapy, and may likely be derived from different cell progenitors.

"Determining an adenocarcinoma subtype" can include, for example, diagnosing or detecting the presence and type of lung adenocarcinoma, monitoring the progression of the disease, and identifying or detecting cells or samples that are indicative of subtypes.

In one embodiment, lung cancer status is assessed through the evaluation of expression patterns, or profiles, of a plurality of classifier genes or biomarkers in one or more subject samples. For the purpose of discussion, the term subject, or subject sample, refers to an individual regardless of health and/or disease status. A subject can be a subject, a study participant, a control subject, a screening subject, or any other class of individual from whom a sample is obtained and assessed in the context of the invention. Accordingly, a subject can be diagnosed with lung adenocarcinoma (including subtypes, or grades thereof), can present with one or more symptoms of lung AD cancer, or a predisposing factor, such as a family (genetic) or medical history (medical) factor, for lung cancer, can be undergoing treatment or therapy for lung cancer, or the like. Alternatively, a subject can be healthy with respect to any of the aforementioned factors or criteria. It will be appreciated that the term "healthy" as used herein, is relative to lung cancer status, as the term "healthy" cannot be defined to correspond to any absolute evaluation or status. Thus, an individual defined as healthy with reference to any specified disease or disease criterion, can in fact be diagnosed with any other one or more diseases, or exhibit any other one or more disease criterion, including one or more other cancers.

As used herein, an "expression profile" or a "biomarker profile" or "gene signature" comprises one or more values corresponding to a measurement of the relative abundance, level, presence, or absence of expression of a discriminative or classifier gene or biomarker. An expression profile can be derived from a subject prior to or subsequent to a diagnosis of lung cancer, can be derived from a biological sample collected from a subject at one or more time points prior to or following treatment or therapy, can be derived from a biological sample collected from a subject at one or more time points during which there is no treatment or therapy (e.g., to monitor progression of disease or to assess development of disease in a subject diagnosed with or at risk for lung cancer), or can be collected from a healthy subject. The term subject can be used interchangeably with patient. The patient can be a human patient. The one or more biomarkers of the biomarker profiles provided herein are selected from one or more biomarkers of Table 1.

As used herein, the term "determining an expression level" or "determining an expression profile" or "detecting an expression level" or "detecting an expression profile" as used in reference to a biomarker or classifier means the application of a biomarker specific reagent such as a probe, primer or antibody and/or a method to a sample, for example a sample of the subject or patient and/or a control sample, for ascertaining or measuring quantitatively, semi-quantitatively or qualitatively the amount of a biomarker or biomarkers, for example the amount of biomarker polypeptide or mRNA (or cDNA derived therefrom). For example, a level of a biomarker can be determined by a number of methods including for example immunoassays including for example immunohistochemistry, ELISA, Western blot, immunoprecipitation and the like, where a biomarker detection agent such as an antibody for example, a labeled antibody, specifically binds the biomarker and permits for example relative or absolute ascertaining of the amount of polypeptide biomarker, hybridization and PCR protocols where a probe or primer or primer set are used to ascertain the amount of nucleic acid biomarker, including for example probe based and amplification based methods including for example microarray analysis, RT-PCR such as quantitative RT-PCR (qRT-PCR), serial analysis of gene expression (SAGE), Northern Blot, digital molecular barcoding technology, for example Nanostring Counter Analysis, and TaqMan quantitative PCR assays. Other methods of mRNA detection and quantification can be applied, such as mRNA in situ hybridization in formalin-fixed, paraffin-embedded (FFPE) tissue samples or cells. This technology is currently offered by the QuantiGene ViewRNA (Affymetrix), which uses probe sets for each mRNA that bind specifically to an amplification system to amplify the hybridization signals; these amplified signals can be visualized using a standard fluorescence microscope or imaging system. This system for example can detect and measure transcript levels in heterogeneous samples; for example, if a sample has normal and tumor cells present in the same tissue section. As mentioned, TaqMan probe-based gene expression analysis (PCR-based) can also be used for measuring gene expression levels in tissue samples, and this technology has been shown to be useful for measuring mRNA levels in FFPE samples. In brief, TaqMan probe-based assays utilize a probe that hybridizes specifically to the mRNA target. This probe contains a quencher dye and a reporter dye (fluorescent molecule) attached to each end, and fluorescence is emitted only when specific hybridization to the mRNA target occurs. During the amplification step, the exonuclease activity of the polymerase enzyme causes the quencher and the reporter dyes to be detached from the probe, and fluorescence emission can occur. This fluorescence emission is recorded and signals are measured by a detection system; these signal intensities are used to calculate the abundance of a given transcript (gene expression) in a sample.

In one embodiment, the "expression profile" or a "biomarker profile" or "gene signature" associated with the gene cassettes or classifier genes described herein (e.g., Tables 1 and 2) can be useful for distinguishing between normal and tumor samples. In another embodiment, the tumor samples are lung adenocarcinoma (AD). In another embodiment, AD can be further classified as bronchioid, squamoid, and magnoid based upon an expression profile determined using the methods provided herein. The characterization of bronchioid, squamoid, and magnoid adenocarcinomas using tumor biopsy tissue has been described in Hayes et al. (2006) *J. Clin Oncol.* 24(31):5079-90Expression profiles using the classifier genes disclosed herein (e.g., Table 1) can provide valuable molecular tools for specifically identifying lung adenocarcinoma subtypes, and for evaluating therapeutic efficacy in treating lung adenocarcinoma. Accordingly, the invention provides methods for screening and classifying a subject for molecular AD subtypes and methods for monitoring efficacy of certain therapeutic treatments for lung AD.

In some instances, a single classifier gene provided herein is capable of identifying subtypes of lung adenocarcinoma with a predictive success of at least about 70%, at least about 71%, at least about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, up to 100%.

In some instances, a single classifier gene as provided herein is capable of determining lung adenocarcinoma subtypes with a sensitivity or specificity of at least about 70%, at least about 71%, at least about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, up to 100%.

The present invention also encompasses a system capable of distinguishing various subtypes of lung adenocarcinoma not detectable using current methods. This system c an b e capable of processing a large number of subjects and subject variables such as expression profiles and other diagnostic criteria. The methods described herein can also be used for "pharmacometabonomics," in analogy to pharmacogenomics, e.g., predictive of response to therapy. In this embodiment, subjects could be divided into "responders" and "nonresponders" using the expression profile as evidence of "response," and features of the expression profile could then be used to target future subjects who would likely respond to a particular therapeutic course.

The expression profile can be used in combination with other diagnostic methods including histochemical, immunohistochemical, cytologic, immunocytologic, and visual diagnostic methods including histologic or morphometric evaluation of lung tissue.

In various embodiments of the present invention, the expression profile derived from a subject is compared to a reference expression profile. A "reference expression profile" can be a profile derived from the subject prior to treatment or therapy; can be a profile produced from the subject sample at a particular time point (usually prior to or following treatment or therapy, but can also include a particular time point prior to or following diagnosis of lung cancer); or can be derived from a healthy individual or a pooled reference from healthy individuals. A reference expression profile can be generic for lung cancer, or can be specific to different subtypes of lung adenocarcinoma.

The reference expression profile can be compared to a test expression profile. A "test expression profile" can be derived from the same subject as the reference expression profile except at a subsequent time point (e.g., one or more days, weeks or months following collection of the reference expression profile) or can be derived from a different subject. In summary, any test expression profile of a subject can be compared to a previously collected profile from a subject that has TRU, PP, or PI subtype.

The classifier biomarkers of the invention can include nucleic acids (RNA, cDNA, and DNA) and proteins, and variants and fragments thereof. Such biomarkers can include DNA comprising the entire or partial sequence of the nucleic acid sequence encoding the biomarker, or the complement of such a sequence. The biomarkers described herein can include RNA comprising the entire or partial sequence of any of the nucleic acid sequences of interest, or their non-natural cDNA products, obtained synthetically in vitro in a reverse transcription reaction. The biomarker nucleic acids can also include any expression product or portion thereof of the nucleic acid sequences of interest. A biomarker protein can be a protein encoded by or corresponding to a DNA biomarker of the invention. A biomarker protein can comprise the entire or partial amino acid sequence of any of the biomarker proteins or polypeptides. The biomarker nucleic acid can be extracted from a cell or can be cell free or extracted from an extracellular vesicular entity such as an exosome.

A "classifier biomarker" or "biomarker" or "classifier gene" can be any gene or protein whose level of expression in a tissue or cell is altered compared to that of a normal or healthy cell or tissue. For example, a "classifier biomarker" or "biomarker" or "classifier gene" can be any gene or protein whose level of expression in a tissue or cell is altered in a specific lung adenocarcinoma subtype. The detection of the biomarkers of the invention can permit the determination of the specific subtype. The "classifier biomarker" or "biomarker" or "classifier gene" may be one that is up-regulated (e.g. expression is increased) or down-regulated (e.g. expression is decreased) relative to a reference or control as provided herein. The reference or control can be any reference or control as provided herein. In some embodiments, the expression values of genes that are up-regulated or down-regulated in a particular subtype of lung adenocarcinoma can be pooled into one gene cassette. The overall expression level in each gene cassette is referred to herein as the "expression profile" and is used to classify a test sample according to the subtype of lung adenocarcinoma. However, it is understood that independent evaluation of expression for each of the genes disclosed herein can be used to classify tumor subtypes without the need to group up-regulated and down-regulated genes into one or more gene cassettes. In some cases, as shown in Table 2, a total of 48 biomarkers can be used for AD subtype determination. For each AD subtype, 8 of the 16 biomarkers can be negatively correlated genes while 8 can be positively correlated genes which can be selected as the gene signature of a specific AD subtype.

The classifier biomarkers of the invention include any gene or protein that is selectively expressed in lung adenocarcinoma, as defined herein above. Sample biomarker genes are listed in Table 1 or 2, below. In Table 2, the first column of the table represents the biomarker list selected for distinguishing Terminal Respiratory Unit (TRU). The middle column of the table represents the biomarker list selected for distinguishing Proximal Proliferative (PP). The last column of the table represents the biomarker list selected for distinguishing Proximal Inflammatory (PI).

The relative gene expression levels as represented by the tsat as described herein of the classifier biomarkers for lung AD subtyping are shown in Table 1. In one embodiment, the gene expression levels of the classifier biomarkers for lung adenocarcinoma subtyping are shown in Table 1. In one embodiment, all 48 genes can be used to classify the subtypes of AD. In one embodiment, the first 16 genes are the selected gene signature biomarkers for Terminal Respiratory Unit, with gene numbers 1-8 up-regulated and gene numbers 9-16 down-regulated compared to a non-TRU sample. In another embodiment, gene numbers 17-32 are the selected gene signature biomarkers specific for Proximal Proliferative (PP), with gene numbers 17-24 up-regulated and gene numbers 25-32 down-regulated compared to a non-PP sample. In yet another embodiment, gene numbers 33-48 are the selected gene signature biomarkers specific for Proximal Inflammatory (PI), with gene numbers 33-40 up-regulated and gene numbers 41-48 down-regulated compared to a non-PI sample.

TABLE 1

Gene Centroids of 48 Classifier Biomarkers for the Lung Adenocarcinoma (AD) Subtypes

| Gene # | Gene Symbol | Gene Name | Terminal Respiratory Unit (TRU) | Proximal Proliferative (PP) | Proximal Inflammatory (PI) | GenBank Acession Number* | SEQ ID NO: |
|---|---|---|---|---|---|---|---|
| 1 | FIGF | C-fos-induced growth factor | 2.129901586 | −1.173222174 | −1.545843019 | AY874421.1 | 1 |
| 2 | CTSH | Cathepsin H | 1.099895637 | −0.797376345 | −0.531006607 | NM_004390.4 | 2 |
| 3 | SCTR | Secretin receptor | 2.043898366 | −1.911062476 | −1.836386831 | NM_002980.2 | 3 |
| 4 | CYP4B1 | Cytochrome P450 family 4 subfamily B member 1 | 2.462733828 | −1.447070454 | −1.481195844 | NM_001319161.1 | 4 |
| 5 | GPR116 | G protein-coupled receptor 116 | 1.289460077 | −0.972597916 | −0.731487829 | AY140958.1 | 5 |
| 6 | ADH1B | Alcohol dehydrogenase 1B (class I) | 2.013525076 | −1.580299515 | −1.094580574 | NM_001286650.1 | 6 |
| 7 | CBX7 | Chromo box 7 | 0.728027298 | −0.698222051 | −0.243583657 | NM_175709.3 | 7 |
| 8 | HLF | Hepatic leukemia factor | 1.479193357 | −1.28826965 | −1.018563422 | M95585.1 | 8 |
| 9 | CEP55 | Centrosomal protein 55 | −1.524932169 | 0.5743319 | 0.580921528 | NM_0181314 | 9 |
| 10 | TPX2 | Tpx2, Microtubule-associated | −1.704080763 | 0.587761579 | 0.583674937 | NM_0121124 | 10 |
| 11 | BUB1B | BUB1 mitotic checkpoint serine/threonine kinase B | −1.531514951 | 0.769199954 | 0.543731288 | AF107297.1 | 11 |

TABLE 1-continued

Gene Centroids of 48 Classifier Biomarkers for the Lung Adenocarcinoma (AD) Subtypes

| Gene # | Gene Symbol | Gene Name | Terminal Respiratory Unit (TRU) | Proximal Proliferative (PP) | Proximal Inflammatory (PI) | GenBank Acession Number* | SEQ ID NO: |
|---|---|---|---|---|---|---|---|
| 12 | KIF4A | Kinesin family member 4A | −1.794045266 | 0.570328759 | 0.599399471 | NM_0123104 | 12 |
| 13 | CCNB2 | Cyclin B2 | −1.442466223 | 0.602807712 | 0.526093335 | NM_004701.3 | 13 |
| 14 | KIF14 | Kinesin family member 14 | −1.66445145 | 0.762295222 | 0.543132477 | NM_0148752 | 14 |
| 15 | MELK | Maternal embryonic leucine zipper kinase | −1.685012297 | 0.584181432 | 0.694064307 | NM_0147913 | 15 |
| 16 | KIF11 | Kinesin family member 11 | −1.183768087 | 0.693181955 | 0.481955763 | NM_004523.3 | 16 |
| 17 | FGL1 | Fibrinogen like 1 | −0.978882607 | 4.89751413 | −1.958269455 | NM_004467.3 | 17 |
| 18 | PBK | PDZ binding kinase | −1.407694417 | 1.278522857 | 0.404652088 | NM_018492.3 | 18 |
| 19 | HSPD1 | Heat shock protein family D (Hsp60) member 1 | −0.469703958 | 0.624572377 | 0.111400174 | NM_0021564 | 19 |
| 20 | TDG | Thymine DNA glycosylase | −0.351189471 | 0.60348929 | 0.076442589 | NM_003211.4 | 20 |
| 21 | PRC1 | Protein regulator of cytokinesis 1 | 1.159074285 | 0.797575854 | 0.461100041 | NM_003981.3 | 21 |
| 22 | DUSP4 | Dual specificity phosphatase 4 | 0.704273045 | 1.933259798 | −0.283343923 | NM_0013946 | 22 |
| 23 | GTPBP4 | GTP binding protein 4 | −0.467281005 | 0.543583167 | 0.038904486 | NM_012341.2 | 23 |
| 24 | ZWINT | ZW10 interacting kinetochore protein | −1.062801846 | 0.741405035 | 0.418738839 | NM_0070573 | 24 |
| 25 | TLR2 | Toll like receptor 2 | 0.672774085 | −1.389004155 | 0.098176794 | NM_001318787.1 | 25 |
| 26 | CD74 | CD74 molecule | 0.689011729 | −1.365243826 | 0.239872217 | NM_001025159.2 | 26 |
| 27 | HLA-DPB1 | Major histocompatibility complex, class II, DP beta 1 | 0.70548523 | −1.431001558 | 0.157288388 | M83664.1 | 27 |
| 28 | HLA-DPA1 | Major histocompatibility complex, class II, DP alpha 1 | 0.620746458 | −1.622212879 | 0.206805676 | NM_033554.3 | 28 |
| 29 | HLA-DRA | Major histocompatibility complex, class II, DR alpha | 0.47615106 | −1.517000712 | 0.209882138 | NM_0191114 | 29 |
| 30 | ITGB2 | Integrin subunit beta 2 | 0.227015125 | −1.489015066 | 0.473986644 | NM_000211.4 | 30 |
| 31 | FAS | Fas cell surface death receptor | 0.120924174 | −1.244937359 | 0.608312102 | KM114217.1 | 31 |
| 32 | HLA-DRB1 | Major histocompatibility complex, class II, DR beta 1 | 0.561088415 | −1.639812592 | 0.272965507 | NM_002124.3 | 32 |

TABLE 1-continued

Gene Centroids of 48 Classifier Biomarkers for the Lung Adenocarcinoma (AD) Subtypes

| Gene # | Gene Symbol | Gene Name | Terminal Respiratory Unit (TRU) | Proximal Proliferative (PP) | Proximal Inflammatory (PI) | GenBank Acession Number* | SEQ ID NO: |
|---|---|---|---|---|---|---|---|
| 33 | PLAU | Plasminogen activator, urokinase | 0.723116671 | −0.71054832 | 1.628730403 | NM_0026584 | 33 |
| 34 | GBP1 | Guanylate binding protein 1 | −0.302372654 | −0.688857626 | 1.204326606 | NM_002053.2 | 34 |
| 35 | DSE | Dermatan sulfate epimerase | −0.101374419 | −0.602077696 | 0.748133278 | NM_013352.3 | 35 |
| 36 | CCDC109B | Coiled-coil domain containing 109B | −0.13855818 | −0.703783616 | 0.7964386 | BC002633.2 | 36 |
| 37 | TGFBI | Transforming growth factor beta induced | −0.328357044 | −0.746331889 | 1.164873128 | NM_0003582 | 37 |
| 38 | CXCL10 | C—X—C motif chemokine ligand 10 | −0.434345777 | −0.62067894 | 1.70756508 | NM_001565.3 | 38 |
| 39 | LGALS1 | Lectin, galactoside binding soluble1 | −0.291230377 | −0.549722715 | 0.957730776 | NM_002305.3 | 39 |
| 40 | TUBB6 | Tubulin beta 6 class V | 0.153163739 | −0.328431543 | 0.781293298 | NM_0325252 | 40 |
| 41 | GJB1 | Gap junction protein beta 1 | 1.567852415 | 0.672938467 | −3.61601989 | NM_001097642.2 | 41 |
| 42 | RAP1GAP | RAP1 GTPase activating protein | 1.019990653 | 0.138302482 | −1.426817837 | NM_001145658.1 | 42 |
| 43 | CACNA2D2 | Calcium voltage-gated channel auxiliary subunit alpha2delta 2 | 1.610819757 | −0.126189977 | −2.357279793 | NM_001005505.2 | 43 |
| 44 | SELENBP1 | Selenium binding protein 1 | 1.0475958 | −0.331350331 | −1.209058454 | NM_003944.3 | 44 |
| 45 | TFCP2L1 | Transcription factor CP2-like 1 | 0.218606218 | 0.952552471 | −1.320932951 | NM_0145532 | 45 |
| 46 | SORBS2 | Sorbin and SH3 domain containing 2 | 0.603086366 | 0.462888705 | −1.412139816 | NM_001270771.1 | 46 |
| 47 | UNC13B | Unc-13 homolog B | 0.293706669 | 0.418115853 | −0.978505828 | NM_006377.3 | 47 |
| 48 | TACC2 | Transforming acidic coiled-coil containing protein 2 | 0.206302979 | 0.928437713 | −0.822332116 | AF220152.2 | 48 |

*Each GenBank Accession Number is a representative or exemplary GenBank Accession Number for the listed gene and is herein incorporated by reference in its entirety for all purposes. Further, each listed representative or exemplary accession number should not be construed to limit the claims to the specific accession number.

TABLE 2

Classifier Biomarkers Selected for Terminal Respiratory Unit, Proximal Proliferative, and Proximal Inflammatory

| Terminal Respiratory Unit (TRU) | Proximal Proliferative (PP) | Proximal Inflammatory (PI) |
|---|---|---|
| CEP55 | TLR2 | GJB1 |
| TPX2 | CD74 | RAP1GAP |
| BUB1B | HLA-DPB1 | CACNA2D2 |
| KIF4A | HLA-DPA1 | SELENBP1 |
| CCNB2 | HLA-DRA | TFCP2L1 |
| KIF14 | ITGB2 | SORBS2 |
| MELK | FAS | UNC13B |
| KIF11 | HLA-DRB1 | TACC2 |
| HLF | ZWINT | TUBB6 |
| CBX7 | GTPBP4 | LGALS1 |
| ADH1B | DUSP4 | CXCL10 |
| GPR116 | PRC1 | TGFBI |
| CYP4B1 | TDG | CCDC109B |
| SCTR | HSPD1 | DSE |
| CTSH | PBK | GBP1 |
| FIGF | FGL1 | PLAU |

Diagnostic Uses

In one embodiment, the methods and compositions provided herein allow for the differentiation of the three subtypes of adenocarcinoma: (1) Terminal Respiratory Unit (TRU), formerly referred to as bronchioid; (2) Proximal Proliferative (PP), formerly referred to as magnoid; and (3) Proximal Inflammatory (PI), formerly referred to as squamoid, with fewer genes needed that the molecular AD subtyping methods known in the art.

In general, the methods provided herein are used to classify a lung cancer sample as a particular lung cancer subtype (e.g. subtype of adenocarcinoma). In one embodiment, the method comprises measuring, detecting or determining an expression level of at least one of the classifier biomarkers of any publically available Lung AD expression dataset. In one embodiment, the method comprises detecting or determining an expression level of at least one of the classifier biomarkers of Table 1 in a lung cancer sample obtained from a patient or a subject. The lung cancer sample for the detection or differentiation methods described herein can be a sample previously determined or diagnosed as an adenocarcinoma sample. The previous diagnosis can be based on a histological analysis. The histological analysis can be performed by one or more pathologists.

In one embodiment, the measuring or detecting step is at the nucleic acid level by performing RNA-seq, a reverse transcriptase polymerase chain reaction (RT-PCR) or a hybridization assay with oligonucleotides that are substantially complementary to portions of cDNA molecules of the at least one classifier biomarker (such as the classifier biomarkers of Table 1) under conditions suitable for RNA-seq, RT-PCR or hybridization and obtaining expression levels of the at least one classifier biomarkers based on the detecting step. The expression levels of the at least one of the classifier biomarkers are then compared to reference expression levels of the at least one of the classifier biomarker (such as the classifier biomarkers of Table 1) from at least one sample training set. The at least one sample training set can comprise, (i) expression levels of the at least one biomarker from a sample that overexpresses the at least one biomarker, (ii) expression levels from a reference squamoid (proximal inflammatory), bronchioid (terminal respiratory unit) or magnoid (proximal proliferative) sample, or (iii) expression levels from an adenocarcinoma free lung sample, and classifying the lung tissue sample as a squamoid (proximal inflammatory), bronchioid (terminal respiratory unit) or a magnoid (proximal proliferative) subtype. The lung cancer sample can then be classified as a bronchioid, squamoid, or magnoid subtype of adenocarcinoma based on the results of the comparing step. In one embodiment, the comparing step can comprise applying a statistical algorithm which comprises determining a correlation between the expression data obtained from the lung tissue or cancer sample and the expression data from the at least one training set(s); and classifying the lung tissue or cancer sample as a squamoid (proximal inflammatory), bronchioid (terminal respiratory unit) or a magnoid (proximal proliferative) subtype based on the results of the statistical algorithm.

In one embodiment, the method comprises probing the levels of at least one of the classifier biomarkers provided herein, such as the classifier biomarkers of Table 1 at the nucleic acid level, in a lung cancer sample obtained from the patient. The lung cancer sample can be a sample previously determined or diagnosed as an adenocarcinoma sample. The previous diagnosis can be based on a histological analysis. The histological analysis can be performed by one or more pathologists. The probing step, in one embodiment, comprises mixing the sample with one or more oligonucleotides that are substantially complementary to portions of cDNA molecules of the at least one classifier biomarkers provided herein, such as the classifier biomarkers of Table 1 under conditions suitable for hybridization of the one or more oligonucleotides to their complements or substantial complements; detecting whether hybridization occurs between the one or more oligonucleotides to their complements or substantial complements; and obtaining hybridization values of the at least one classifier biomarkers based on the detecting step. The hybridization values of the at least one classifier biomarkers are then compared to reference hybridization value(s) from at least one sample training set. For example, the at least one sample training set comprises hybridization values from a reference TRU adenocarcinoma, PP adenocarcinoma, and/or PI adenocarcinoma sample. The lung cancer sample is classified, for example, as TRU, PP, or PI based on the results of the comparing step.

The lung tissue sample can be any sample isolated from a human subject or patient. For example, in one embodiment, the analysis is performed on lung biopsies that are embedded in paraffin wax. In one embodiment, the sample can be a fresh frozen lung tissue sample. In another embodiment, the sample can be a bodily fluid obtained from the patient. The bodily fluid can be blood or fractions thereof (i.e., serum, plasma), urine, saliva, sputum or cerebrospinal fluid (CSF). The sample can contain cellular as well as extracellular sources of nucleic acid for use in the methods provided herein. The extracellular sources can be cell-free DNA and/or exosomes. In one embodiment, the sample can be a cell pellet or a wash. This aspect of the invention provides a means to improve current diagnostics by accurately identifying the major histological types, even from small biopsies. The methods of the invention, including the RT-PCR methods, are sensitive, precise and have multianalyte capability for use with paraffin embedded samples. See, for example, Cronin et al. (2004) *Am. J Pathol.* 164 (1):35-42, herein incorporated by reference.

Formalin fixation and tissue embedding in paraffin wax is a universal approach for tissue processing prior to light microscopic evaluation. A major advantage afforded by formalin-fixed paraffin-embedded (FFPE) specimens is the preservation of cellular and architectural morphologic detail in tissue sections. (Fox et al. (1985) J Histochem Cytochem 33:845-853). The standard buffered formalin fixative in which biopsy specimens are processed is typically an aqueous solution containing 37% formaldehyde and 10-15% methyl alcohol. Formaldehyde is a highly reactive dipolar compound that results in the formation of protein-nucleic acid and protein-protein crosslinks in vitro (Clark et al. (1986) J Histochem Cytochem 34:1509-1512; McGhee and von Hippel (1975) Biochemistry 14:1281-1296, each incorporated by reference herein).

In one embodiment, the sample used herein is obtained from an individual, and comprises formalin-fixed paraffin-embedded (FFPE) tissue. However, other tissue and sample types are amenable for use herein. In one embodiment, the other tissue and sample types can be fresh frozen tissue, wash fluids, or cell pellets, or the like. In one embodiment, the sample can be a bodily fluid obtained from the individual. The bodily fluid can be blood or fractions thereof (e.g., serum, plasma), urine, sputum, saliva or cerebrospinal fluid (CSF). A biomarker nucleic acid as provided herein can be extracted from a cell or can be cell free or extracted from an extracellular vesicular entity such as an exosome.

Methods are known in the art for the isolation of RNA from FFPE tissue. In one embodiment, total RNA can be isolated from FFPE tissues as described by Bibikova et al. (2004) American Journal of Pathology 165:1799-1807, herein incorporated by reference. Likewise, the High Pure RNA Paraffin Kit (Roche) can be used. Paraffin is removed by xylene extraction followed by ethanol wash. RNA can be isolated from sectioned tissue blocks using the MasterPure Purification kit (Epicenter, Madison, Wis.); a DNase I treatment step is included. RNA can be extracted from frozen samples using Trizol reagent according to the supplier's instructions (Invitrogen Life Technologies, Carlsbad, Calif.). Samples with measurable residual genomic DNA can be resubjected to DNaseI treatment and assayed for DNA contamination. All purification, DNase treatment, and other steps can be performed according to the manufacturer's protocol. After total RNA isolation, samples can be stored at −80° C. until use.

General methods for mRNA extraction are well known in the art and are disclosed in standard textbooks of molecular biology, including Ausubel et al., ed., Current Protocols in Molecular Biology, John Wiley & Sons, New York 1987-1999. Methods for RNA extraction from paraffin embedded tissues are disclosed, for example, in Rupp and Locker (Lab Invest. 56:A67, 1987) and De Andres et al. (Biotechniques 18:42-44, 1995). In particular, RNA isolation can be performed using a purification kit, a buffer set and protease from commercial manufacturers, such as Qiagen (Valencia, Calif.), according to the manufacturer's instructions. For example, total RNA from cells in culture can be isolated using Qiagen RNeasy mini-columns. Other commercially available RNA isolation kits include MasterPure™. Complete DNA and RNA Purification Kit (Epicentre, Madison, Wis.) and Paraffin Block RNA Isolation Kit (Ambion, Austin, Tex.). Total RNA from tissue samples can be isolated, for example, using RNA Stat-60 (Tel-Test, Friendswood, Tex.). RNA prepared from a tumor can be isolated, for example, by cesium chloride density gradient centrifugation. Additionally, large numbers of tissue samples can readily be processed using techniques well known to those of skill in the art, such as, for example, the single-step RNA isolation process of Chomczynski (U.S. Pat. No. 4,843,155, incorporated by reference in its entirety for all purposes).

In one embodiment, a sample comprises cells harvested from a lung tissue sample, for example, an adenocarcinoma sample. Cells can be harvested from a biological sample using standard techniques known in the art. For example, in one embodiment, cells are harvested by centrifuging a cell sample and resuspending the pelleted cells. The cells can be resuspended in a buffered solution such as phosphate-buffered saline (PBS). After centrifuging the cell suspension to obtain a cell pellet, the cells can be lysed to extract nucleic acid, e.g, messenger RNA. All samples obtained from a subject, including those subjected to any sort of further processing, are considered to be obtained from the subject.

The sample, in one embodiment, is further processed before the detection of the biomarker levels of the combination of biomarkers set forth herein. For example, mRNA in a cell or tissue sample can be separated from other components of the sample. The sample can be concentrated and/or purified to isolate mRNA in its non-natural state, as the mRNA is not in its natural environment. For example, studies have indicated that the higher order structure of mRNA in vivo differs from the in vitro structure of the same sequence (see, e.g., Rouskin et al. (2014). Nature 505, pp. 701-705, incorporated herein in its entirety for all purposes).

mRNA from the sample in one embodiment, is hybridized to a synthetic DNA probe, which in some embodiments, includes a detection moiety (e.g., detectable label, capture sequence, barcode reporting sequence). Accordingly, in these embodiments, a non-natural mRNA-cDNA complex is ultimately made and used for detection of the biomarker. In another embodiment, mRNA from the sample is directly labeled with a detectable label, e.g., a fluorophore. In a further embodiment, the non-natural labeled-mRNA molecule is hybridized to a cDNA probe and the complex is detected.

In one embodiment, once the mRNA is obtained from a sample, it is converted to complementary DNA (cDNA) in a hybridization reaction or is used in a hybridization reaction together with one or more cDNA probes. cDNA does not exist in vivo and therefore is a non-natural molecule. Furthermore, cDNA-mRNA hybrids are synthetic and do not exist in vivo. Besides cDNA not existing in vivo, cDNA is necessarily different than mRNA, as it includes deoxyribonucleic acid and not ribonucleic acid. The cDNA is then amplified, for example, by the polymerase chain reaction (PCR) or other amplification method known to those of ordinary skill in the art. For example, other amplification methods that may be employed include the ligase chain reaction (LCR) (Wu and Wallace, Genomics, 4:560 (1989), Landegren et al., Science, 241:1077 (1988), incorporated by reference in its entirety for all purposes, transcription amplification (Kwoh et al., *Proc. Natl. Acad. Sci. USA,* 86:1173 (1989), incorporated by reference in its entirety for all purposes), self-sustained sequence replication (Guatelli et al., *Proc. Nat. Acad. Sci. USA,* 87:1874 (1990), incorporated by reference in its entirety for all purposes), incorporated by reference in its entirety for all purposes, and nucleic acid based sequence amplification (NASBA). Guidelines for selecting primers for PCR amplification are known to those of ordinary skill in the art. See, e.g., McPherson et al., PCR Basics: From Background to Bench, Springer-Verlag, 2000, incorporated by reference in its entirety for all purposes. The product of this amplification reaction, i.e., amplified cDNA is also necessarily a non-natural product. First, as mentioned above, cDNA is a non-natural molecule. Second, in the case of PCR, the amplification process serves to create hundreds of millions of cDNA copies for every individual cDNA molecule of starting material. The numbers of copies generated are far removed from the number of copies of mRNA that are present in vivo.

In one embodiment, cDNA is amplified with primers that introduce an additional DNA sequence (e.g., adapter, reporter, capture sequence or moiety, barcode) onto the fragments (e.g., with the use of adapter-specific primers), or mRNA or cDNA biomarker sequences are hybridized directly to a cDNA probe comprising the additional sequence (e.g., adapter, reporter, capture sequence or moiety, barcode). Amplification and/or hybridization of mRNA to a cDNA probe therefore serves to create non-natural double stranded molecules from the non-natural single stranded cDNA, or the mRNA, by introducing additional sequences and forming non-natural hybrids. Further, as known to those of ordinary skill in the art, amplification procedures have error rates associated with them. Therefore, amplification introduces further modifications into the cDNA molecules. In one embodiment, during amplification with the adapter-specific primers, a detectable label, e.g., a fluorophore, is added to single strand cDNA molecules. Amplification therefore also serves to create DNA complexes that do not occur in nature, at least because (i) cDNA does not exist in vivo, (i) adapter sequences are added to the ends of cDNA molecules to make DNA sequences that do not exist in vivo, (ii) the error rate associated with amplification further creates DNA sequences that do not exist in vivo, (iii) the disparate structure of the cDNA molecules as compared to what exists in nature, and (iv) the chemical addition of a detectable label to the cDNA molecules.

In some embodiments, the expression of a biomarker of interest is detected at the nucleic acid level via detection of non-natural cDNA molecules.

In some embodiments, the method for lung cancer AD subtyping includes detecting expression levels of a classifier biomarker set. In some embodiments, the detecting includes all of the classifier biomarkers of Table 1 at the nucleic acid level or protein level. In another embodiment, a single or a subset of the classifier biomarkers of Table 1 are detected, for example, from about 8 to about 16. For example, in one embodiment, from about 5 to about 10, from about 5 to about 15, from about 5 to about 20, from about 5 to about 25, from about 5 to about 30, from about 5 to about 35, from about 5 to about 40, from about 5 to about 45, from about 5 to about 48 of the biomarkers in Table 1 are detected in a method to determine the lung cancer AD subtype. In another embodiment, each of the biomarkers from Table 1 is detected in a method to determine the lung cancer subtype. In another embodiment, 16 of the biomarkers from Table 1 are selected as the gene signatures for a specific lung cancer AD subtype.

The detecting can be performed by any suitable technique including, but not limited to, RNA-seq, a reverse transcriptase polymerase chain reaction (RT-PCR), a microarray hybridization assay, or another hybridization assay, e.g., a NanoString assay for example, with primers and/or probes specific to the classifier biomarkers, and/or the like. In some cases, the primers useful for the amplification methods (e.g., RT-PCR or qRT-PCR) are any forward and reverse primers suitable for binding to a classifier gene provided herein, such as the classifier biomarkers listed in Table 1.

The biomarkers described herein include RNA comprising the entire or partial sequence of any of the nucleic acid sequences of interest, or their non-natural cDNA product, obtained synthetically in vitro in a reverse transcription reaction. The term "fragment" is intended to refer to a portion of the polynucleotide that generally comprise at least 10, 15, 20, 50, 75, 100, 150, 200, 250, 300, 350, 400, 450, 500, 550, 600, 650, 700, 800, 900, 1,000, 1,200, or 1,500 contiguous nucleotides, or up to the number of nucleotides present in a full-length biomarker polynucleotide disclosed herein. A fragment of a biomarker polynucleotide will generally encode at least 15, 25, 30, 50, 100, 150, 200, or 250 contiguous amino acids, or up to the total number of amino acids present in a full-length biomarker protein of the invention.

In some embodiments, overexpression, such as of an RNA transcript or its expression product, is determined by normalization to the level of reference RNA transcripts or their expression products, which can be all measured transcripts (or their products) in the sample or a particular reference set of RNA transcripts (or their non-natural cDNA products). Normalization is performed to correct for or normalize away both differences in the amount of RNA or cDNA assayed and variability in the quality of the RNA or cDNA used. Therefore, an assay typically measures and incorporates the expression of certain normalizing genes, including well known housekeeping genes, such as, for example, GAPDH and/or β-Actin. Alternatively, normalization can be based on the mean or median signal of all of the assayed biomarkers or a large subset thereof (global normalization approach).

Isolated mRNA can be used in hybridization or amplification assays that include, but are not limited to, Southern or Northern analyses, PCR analyses and probe arrays, NanoString Assays. One method for the detection of mRNA levels involves contacting the isolated mRNA or synthesized cDNA with a nucleic acid molecule (probe) that can hybridize to the mRNA encoded by the gene being detected. The nucleic acid probe can be, for example, a cDNA, or a portion thereof, such as an oligonucleotide of at least 7, 15, 30, 50, 100, 250, or 500 nucleotides in length and sufficient to specifically hybridize under stringent conditions to the non-natural cDNA or mRNA biomarker of the present invention.

As explained above, in one embodiment, once the mRNA is obtained from a sample, it is converted to complementary DNA (cDNA) in a hybridization reaction. Conversion of the mRNA to cDNA can be performed with oligonucleotides or primers comprising sequence that is complementary to a portion of a specific mRNA. Conversion of the mRNA to cDNA can be performed with oligonucleotides or primers comprising random sequence. Conversion of the mRNA to cDNA can be performed with oligonucleotides or primers comprising sequence that is complementary to the poly(A) tail of an mRNA. cDNA does not exist in vivo and therefore is a non-natural molecule. In a further embodiment, the cDNA is then amplified, for example, by the polymerase chain reaction (PCR) or other amplification method known to those of ordinary skill in the art. PCR can be performed with the forward and/or reverse primers comprising sequence complementary to at least a portion of a classifier gene provided herein, such as the classifier biomarkers in Table 1. The product of this amplification reaction, i.e., amplified cDNA is necessarily a non-natural product. As mentioned above, cDNA is a non-natural molecule. Second, in the case of PCR, the amplification process serves to create hundreds of millions of cDNA copies for every individual cDNA molecule of starting material. The number of copies generated is far removed from the number of copies of mRNA that are present in vivo.

In one embodiment, cDNA is amplified with primers that introduce an additional DNA sequence (adapter sequence) onto the fragments (with the use of adapter-specific primers). The adaptor sequence can be a tail, wherein the tail sequence is not complementary to the cDNA. For example, the forward and/or reverse primers comprising sequence complementary to at least a portion of a classifier gene provided herein, such as the classifier biomarkers from Table 1 can comprise tail sequence. Amplification therefore serves to create non-natural double stranded molecules from the non-natural single stranded cDNA, by introducing barcode, adapter and/or reporter sequences onto the already non-natural cDNA. In one embodiment, during amplification with the adapter-specific primers, a detectable label, e.g., a fluorophore, is added to single strand cDNA molecules. Amplification therefore also serves to create DNA complexes that do not occur in nature, at least because (i) cDNA does not exist in vivo, (ii) adapter sequences are added to the ends of cDNA molecules to make DNA sequences that do not exist in vivo, (iii) the error rate associated with amplification further creates DNA sequences that do not exist in vivo, (iv) the disparate structure of the cDNA molecules as compared to what exists in nature, and (v) the chemical addition of a detectable label to the cDNA molecules.

In one embodiment, the synthesized cDNA (for example, amplified cDNA) is immobilized on a solid surface via hybridization with a probe, e.g., via a microarray. In another embodiment, cDNA products are detected via real-time polymerase chain reaction (PCR) via the introduction of fluorescent probes that hybridize with the cDNA products. For example, in one embodiment, biomarker detection is assessed by quantitative fluorogenic RT-PCR (e.g., with TaqMan® probes). For PCR analysis, well known methods are available in the art for the determination of primer sequences for use in the analysis.

Biomarkers provided herein in one embodiment, are detected via a hybridization reaction that employs a capture probe and/or a reporter probe. For example, the hybridization probe is a probe derivatized to a solid surface such as a bead, glass or silicon substrate. In another embodiment, the capture probe is present in solution and mixed with the patient's sample, followed by attachment of the hybridization product to a surface, e.g., via a biotin-avidin interaction (e.g., where biotin is a part of the capture probe and avidin is on the surface). The hybridization assay, in one embodiment, employs both a capture probe and a reporter probe. The reporter probe can hybridize to either the capture probe or the biomarker nucleic acid. Reporter probes e.g., are then counted and detected to determine the level of biomarker(s) in the sample. The capture and/or reporter probe, in one embodiment contain a detectable label, and/or a group that allows functionalization to a surface.

For example, the nCounter gene analysis system (see, e.g., Geiss et al. (2008) Nat. Biotechnol. 26, pp. 317-325, incorporated by reference in its entirety for all purposes, is amenable for use with the methods provided herein.

Hybridization assays described in U.S. Pat. Nos. 7,473,767 and 8,492,094, the disclosures of which are incorporated by reference in their entireties for all purposes, are amenable for use with the methods provided herein, i.e., to detect the biomarkers and biomarker combinations described herein.

Biomarker levels may be monitored using a membrane blot (such as used in hybridization analysis such as Northern, Southern, dot, and the like), or microwells, sample tubes, gels, beads, or fibers (or any solid support comprising bound nucleic acids). See, for example, U.S. Pat. Nos. 5,770,722, 5,874,219, 5,744,305, 5,677,195 and 5,445,934, each incorporated by reference in their entireties.

In one embodiment, microarrays are used to detect biomarker levels. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning hybridization intensities for each probe on the array are determined and converted to a quantitative value representing relative gene expression levels. See, for example, U.S. Pat. Nos. 6,040,138, 5,800,992 and 6,020,135, 6,033,860, and 6,344,316, each incorporated by reference in their entireties. High-density oligonucleotide arrays are particularly useful for determining the gene expression profile for a large number of RNAs in a sample.

Techniques for the synthesis of these arrays using mechanical synthesis methods are described in, for example, U.S. Pat. No. 5,384,261. Although a planar array surface is generally used, the array can be fabricated on a surface of virtually any shape or even a multiplicity of surfaces. Arrays can be nucleic acids (or peptides) on beads, gels, polymeric surfaces, fibers (such as fiber optics), glass, or any other appropriate substrate. See, for example, U.S. Pat. Nos. 5,770,358, 5,789,162, 5,708,153, 6,040,193 and 5,800,992, each incorporated by reference in their entireties. Arrays can be packaged in such a manner as to allow for diagnostics or other manipulation of an all-inclusive device. See, for example, U.S. Pat. Nos. 5,856,174 and 5,922,591, each incorporated by reference in their entireties.

Serial analysis of gene expression (SAGE) in one embodiment is employed in the methods described herein. SAGE is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. See, Velculescu et al. Science 270:484-87, 1995; Cell 88:243-51, 1997, incorporated by reference in its entirety.

An additional method of biomarker level analysis at the nucleic acid level is the use of a sequencing method, for example, RNAseq, next generation sequencing, and massively parallel signature sequencing (MPSS), as described by Brenner et al. (Nat. Biotech. 18:630-34, 2000, incorporated by reference in its entirety). This is a sequencing approach that combines non-gel-based signature sequencing with in vitro cloning of millions of templates on separate 5 μm diameter microbeads. First, a microbead library of DNA templates is constructed by in vitro cloning. This is followed by the assembly of a planar array of the template-containing microbeads in a flow cell at a high density (typically greater than $3.0\times10^6$ microbeads/$cm^2$). The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a yeast cDNA library.

Another method of biomarker level analysis at the nucleic acid level is the use of an amplification method such as, for example, RT-PCR or quantitative RT-PCR (qRT-PCR). Methods for determining the level of biomarker mRNA in a sample may involve the process of nucleic acid amplification, e.g., by RT-PCR (the experimental embodiment set forth in Mullis, 1987, U.S. Pat. No. 4,683,202), ligase chain reaction (Barany (1991) Proc. Natl. Acad. Sci. USA 88:189-193), self-sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (Lizardi et al., U.S. Pat. No. 5,854,033) or any other nucleic acid amplification method, followed by the detection of the amplified molecules using techniques well known to those of skill in the art. Numerous different PCR or qRT-PCR protocols are known in the art and can be directly applied or adapted for use using the presently described compositions for the detection and/or quantification of expression of discriminative genes in a sample. See, for example, Fan et al. (2004) Genome Res. 14:878-885, herein incorporated by reference. Generally, in PCR, a target polynucleotide sequence is amplified by reaction with at least one oligonucleotide primer or pair of oligonucleotide primers. The primer(s) hybridize to a complementary region of the target nucleic acid and a DNA polymerase extends the primer(s) to amplify the target sequence. Under conditions sufficient to provide polymerase-based nucleic acid amplification products, a nucleic acid fragment of one size dominates the reaction products (the target polynucleotide sequence which is the amplification product). The amplification cycle is repeated to increase the concentration of the single target polynucleotide sequence. The reaction can be performed in any thermocycler commonly used for PCR.

Quantitative RT-PCR (qRT-PCR) (also referred as real-time RT-PCR) is preferred under some circumstances because it provides not only a quantitative measurement, but also reduced time and contamination. As used herein, "quantitative PCR" (or "real time qRT-PCR") refers to the direct monitoring of the progress of a PCR amplification as it is occurring without the need for repeated sampling of the reaction products. In quantitative PCR, the reaction products may be monitored via a signaling mechanism (e.g., fluorescence) as they are generated and are tracked after the signal rises above a background level but before the reaction reaches a plateau. The number of cycles required to achieve a detectable or "threshold" level of fluorescence varies directly with the concentration of amplifiable targets at the beginning of the PCR process, enabling a measure of signal intensity to provide a measure of the amount of target nucleic acid in a sample in real time. A DNA binding dye (e.g., SYBR green) or a labeled probe can be used to detect the extension product generated by PCR amplification. Any probe format utilizing a labeled probe comprising the sequences of the invention may be used.

Immunohistochemistry methods are also suitable for detecting the levels of the biomarkers of the present invention. Samples can be frozen for later preparation or immediately placed in a fixative solution. Tissue samples can be fixed by treatment with a reagent, such as formalin, gluteraldehyde, methanol, or the like and embedded in paraffin. Methods for preparing slides for immunohistochemical analysis from formalin-fixed, paraffin-embedded tissue samples are well known in the art.

In one embodiment, the levels of the biomarkers provided herein, such as the classifier biomarkers of Table 1 (or subsets thereof, for example 8 to 16, 16 to 32, or 32 to 48 biomarkers), are normalized against the expression levels of all RNA transcripts or their non-natural cDNA expression products, or protein products in the sample, or of a reference set of RNA transcripts or a reference set of their non-natural cDNA expression products, or a reference set of their protein products in the sample.

In one embodiment, lung adenocarcinoma subtypes can be evaluated using levels of protein expression of one or more of the classifier genes provided herein, such as the classifier biomarkers listed in Table 1. The level of protein expression can be measured using an immunological detection method. Immunological detection methods which can be used herein include, but are not limited to, competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, and the like. Such assays are routine and well known in the art (see, e.g., Ausubel e t al, eds, 1994*, Current Protocols in Molecular Biology*, Vol. I, John Wiley & Sons, Inc., New York, which is incorporated by reference herein in its entirety).

In one embodiment, antibodies specific for biomarker proteins are utilized to detect the expression of a biomarker protein in a body sample. The method comprises obtaining a body sample from a patient or a subject, contacting the body sample with at least one antibody directed to a biomarker that is selectively expressed in lung cancer cells, and detecting antibody binding to determine if the biomarker is expressed in the patient sample. A preferred aspect of the present invention provides an immunocytochemistry technique for diagnosing lung cancer subtypes. One of skill in the art will recognize that the immunocytochemistry method described herein below may be performed manually or in an automated fashion.

As provided throughout, the methods set forth herein provide a method for determining the lung cancer AD subtype of a patient. Once the biomarker levels are determined, for example by measuring non-natural cDNA biomarker levels or non-natural mRNA-cDNA biomarker complexes, the biomarker levels are compared to reference values or a reference sample, for example with the use of statistical methods or direct comparison of detected levels, to make a determination of the lung cancer molecular AD subtype. Based on the comparison, the patient's lung cancer sample is AD classified, e.g., as TRU, PP, or PI.

In one embodiment, expression level values of the at least one classifier biomarkers provided herein, such as the classifier biomarkers of Table 1 are compared to reference expression level value(s) from at least one sample training set, wherein the at least one sample training set comprises expression level values from a reference sample(s). In a further embodiment, the at least one sample training set comprises expression level values of the at least one classifier biomarkers provided herein, such as the classifier biomarkers of Table 1 from a proximal inflammatory (squamoid), proximal proliferative (magnoid), a terminal respiratory unit (bronchioid) sample, or a combination thereof.

In a separate embodiment, hybridization values of the at least one classifier biomarkers provided herein, such as the classifier biomarkers of Table 1 are compared to reference hybridization value(s) from at least one sample training set, wherein the at least one sample training set comprises hybridization values from a reference sample(s). In a further embodiment, the at least one sample training set comprises hybridization values of the at least one classifier biomarkers provided herein, such as the classifier biomarkers of Table 1 from a proximal inflammatory (squamoid), proximal proliferative (magnoid), a terminal respiratory unit (bronchioid) sample, or a combination thereof. Methods for comparing detected levels of biomarkers to reference values and/or reference samples are provided herein. Based on this comparison, in one embodiment a correlation between the biomarker levels obtained from the subject's sample and the reference values is obtained. An assessment of the lung cancer AD subtype is then made.

Various statistical methods can be used to aid in the comparison of the biomarker levels obtained from the patient and reference biomarker levels, for example, from at least one sample training set.

In one embodiment, a supervised pattern recognition method is employed. Examples of supervised pattern recognition methods can include, but are not limited to, the nearest centroid methods (Dabney (2005) Bioinformatics 21(22):4148-4154 and Tibshirani et al. (2002) Proc. Natl. Acad. Sci. USA 99(10):6576-6572); soft independent modeling of class analysis (SIMCA) (see, for example, Wold, 1976); partial least squares analysis (PLS) (see, for example, Wold, 1966; Joreskog, 1982; Frank, 1984; Bro, R., 1997); linear descriminant analysis (LDA) (see, for example, Nillson, 1965); K-nearest neighbour analysis (KNN) (see, for example, Brown et al., 1996); artificial neural networks (ANN) (see, for example, Wasserman, 1989; Anker et al., 1992; Hare, 1994); probabilistic neural networks (PNNs) (see, for example, Parzen, 1962; Bishop, 1995; Speckt, 1990; Broomhead et al., 1988; Patterson, 1996); rule induction (RI) (see, for example, Quinlan, 1986); and, Bayesian methods (see, for example, Bretthorst, 1990a, 1990b, 1988). In one embodiment, the classifier for identifying tumor subtypes based on gene expression data is the centroid based method described in Mullins et al. (2007) Clin Chem. 53(7):1273-9, each of which is herein incorporated by reference in its entirety.

In other embodiments, an unsupervised training approach is employed, and therefore, no training set is used.

Referring to sample training sets for supervised learning approaches again, in some embodiments, a sample training set(s) can include expression data of a plurality or all of the classifier biomarkers (e.g., all the classifier biomarkers of Table 1) from an adenocarcinoma sample. The plurality of classifier biomarkers can comprise at least two classifier biomarkers, at least 8 classifier biomarkers, at least 16 classifier biomarkers, at least 24 classifier biomarkers, at least 32 classifier biomarkers, at least 40 classifier biomarkers, or at least 48 classifier biomarkers of Table 1. In some embodiments, the sample training set(s) are normalized to remove sample-to-sample variation.

In some embodiments, comparing can include applying a statistical algorithm, such as, for example, any suitable multivariate statistical analysis model, which can be parametric or non-parametric. In some embodiments, applying the statistical algorithm can include determining a correlation between the expression data obtained from the human lung tissue sample and the expression data from the adenocarcinoma training set(s). In some embodiments, cross-validation is performed, such as (for example), leave-one-out cross-validation (LOOCV). In some embodiments, integrative correlation is performed. In some embodiments, a Spearman correlation is performed. In some embodiments, a centroid based method is employed for the statistical algorithm as described in Mullins et al. (2007) Clin Chem. 53(7):1273-9, and based on gene expression data, which is herein incorporated by reference in its entirety.

Results of the gene expression performed on a sample from a subject (test sample) may be compared to a biological sample(s) or data derived from a biological sample(s) that is known or suspected to be normal ("reference sample" or "normal sample", e.g., non-adenocarcinoma sample). In some embodiments, a reference sample or reference gene expression data is obtained or derived from an individual known to have a particular molecular subtype of adenocarcimona, i.e., squamoid (proximal inflammatory), bronchioid (terminal respiratory unit) or magnoid (proximal proliferative).

The reference sample may be assayed at the same time, or at a different time from the test sample. Alternatively, the biomarker level information from a reference sample may be stored in a database or other means for access at a later date.

The biomarker level results of an assay on the test sample may be compared to the results of the same assay on a reference sample. In some cases, the results of the assay on the reference sample are from a database, or a reference value(s). In some cases, the results of the assay on the reference sample are a known or generally accepted value or range of values by those skilled in the art. In some cases the comparison is qualitative. In other cases the comparison is quantitative. In some cases, qualitative or quantitative comparisons may involve but are not limited to one or more of the following: comparing fluorescence values, spot intensities, absorbance values, chemiluminescent signals, histograms, critical threshold values, statistical significance values, expression levels of the genes described herein, mRNA copy numbers.

In one embodiment, an odds ratio (OR) is calculated for each biomarker level panel measurement. Here, the OR is a measure of association between the measured biomarker values for the patient and an outcome, e.g., lung adenocarcinoma subtype. For example, see, *J. Can. Acad. Child Adolesc. Psychiatry* 2010; 19(3): 227-229, which is incorporated by reference in its entirety for all purposes.

In one embodiment, a specified statistical confidence level may be determined in order to provide a confidence level regarding the lung cancer subtype. For example, it may be determined that a confidence level of greater than 90% may be a useful predictor of the lung cancer subtype. In other embodiments, more or less stringent confidence levels may be chosen. For example, a confidence level of about or at least about 50%, 60%, 70%, 75%, 80%, 85%, 90%, 95%, 97.5%, 99%, 99.5%, or 99.9% may be chosen. The confidence level provided may in some cases be related to the quality of the sample, the quality of the data, the quality of the analysis, the specific methods used, and/or the number of gene expression values (i.e., the number of genes) analyzed. The specified confidence level for providing the likelihood of response may be chosen on the basis of the expected number of false positives or false negatives. Methods for choosing parameters for achieving a specified confidence level or for identifying markers with diagnostic power include but are not limited to Receiver Operating Characteristic (ROC) curve analysis, binormal ROC, principal component analysis, odds ratio analysis, partial least squares analysis, singular value decomposition, least absolute shrinkage and selection operator analysis, least angle regression, and the threshold gradient directed regularization method.

Determining the lung adenocarcinoma subtype in some cases can be improved through the application of algorithms designed to normalize and or improve the reliability of the gene expression data. In some embodiments of the present invention, the data analysis utilizes a computer or other device, machine or apparatus for application of the various algorithms described herein due to the large number of individual data points that are processed. A "machine learning algorithm" refers to a computational-based prediction methodology, also known to persons skilled in the art as a "classifier," employed for characterizing a gene expression profile or profiles, e.g., to determine the lung adenocarcinoma subtype. The biomarker levels, determined by, e.g., microarray-based hybridization assays, sequencing assays, NanoString assays, etc., are in one embodiment subjected to the algorithm in order to classify the profile. Supervised learning generally involves "training" a classifier to recognize the distinctions among subtypes such as squamoid (proximal inflammatory) positive, bronchioid (terminal respiratory unit) positive or magnoid (proximal proliferative) positive, and then "testing" the accuracy of the classifier on an independent test set. Therefore, for new, unknown samples the classifier can be used to predict, for example, the class (e.g., squamoid vs bronchioid vs magnoid) in which the samples belong.

In some embodiments, a robust multi-array average (RMA) method may be used to normalize raw data. The RMA method begins by computing background-corrected intensities for each matched cell on a number of microarrays. In one embodiment, the background corrected values are restricted to positive values as described by Irizarry et al. (2003). Biostatistics April 4 (2): 249-64, incorporated by reference in its entirety for all purposes. After background correction, the base-2 logarithm of each background corrected matched-cell intensity is then obtained. The background corrected, log-transformed, matched intensity on each microarray is then normalized using the quantile normalization method in which for each input array and each probe value, the array percentile probe value is replaced with the average of all array percentile points, this method is more completely described by Bolstad et al. Bioinformatics 2003, incorporated by reference in its entirety. Following quantile normalization, the normalized data may then be fit to a linear model to obtain an intensity measure for each probe on each microarray. Tukey's median polish algorithm (Tukey, J. W., Exploratory Data Analysis. 1977, incorporated by reference in its entirety for all purposes) may then be used to determine the log-scale intensity level for the normalized probe set data.

Various other software programs may be implemented. In certain methods, feature selection and model estimation may be performed by logistic regression with lasso penalty using glmnet (Friedman et al. (2010). *Journal of statistical software* 33(1): 1-22, incorporated by reference in its entirety). Raw reads may be aligned using TopHat (Trapnell et al. (2009). *Bioinformatics* 25(9): 1105-11, incorporated by reference in its entirety). In methods, top features (N ranging from 10 to 200) are used to train a linear support vector machine (SVM) (Suykens J A K, Vandewalle J. Least Squares Support Vector Machine Classifiers. *Neural Processing Letters* 1999; 9(3): 293-300, incorporated by reference in its entirety) using the e1071 library (Meyer D. Support vector machines: the interface to libsvm in package e1071. 2014, incorporated by reference in its entirety). Confidence intervals, in one embodiment, are computed using the pROC package (Robin X, Turck N, Hainard A, et al. pROC: an open-source package for R and S+ to analyze and compare ROC curves. *BMC bioinformatics* 2011; 12: 77, incorporated by reference in its entirety).

In addition, data may be filtered to remove data that may be considered suspect. In one embodiment, data derived from microarray probes that have fewer than about 4, 5, 6, 7 or 8 guanosine+cytosine nucleotides may be considered to be unreliable due to their aberrant hybridization propensity or secondary structure issues. Similarly, data deriving from microarray probes that have more than about 12, 13, 14, 15, 16, 17, 18, 19, 20, 21, or 22 guanosine+cytosine nucleotides may in one embodiment be considered unreliable due to their aberrant hybridization propensity or secondary structure issues.

In some embodiments of the present invention, data from probe-sets may be excluded from analysis if they are not identified at a detectable level (above background).

In some embodiments of the present disclosure, probe-sets that exhibit no, or low variance may be excluded from further analysis. Low-variance probe-sets are excluded from the analysis via a Chi-Square test. In one embodiment, a probe-set is considered to be low-variance if its transformed variance is to the left of the 99 percent confidence interval of the Chi-Squared distribution with (N−1) degrees of freedom. (N−1)*Probe-set Variance/(Gene Probe-set Variance). Chi-Sq(N−1) where N is the number of input CEL files, (N−1) is the degrees of freedom for the Chi-Squared distribution, and the "probe-set variance for the gene" is the average of probe-set variances across the gene. In some embodiments of the present invention, probe-sets for a given mRNA or group of mRNAs may be excluded from further analysis if they contain less than a minimum number of probes that pass through the previously described filter steps for GC content, reliability, variance and the like. For example in some embodiments, probe-sets for a given gene or transcript cluster may be excluded from further analysis if they contain less than about 1, 2, 3, 4, 5, 6, 7, 8, 9, 10, 11, 12, 13, 14, 15, or less than about 20 probes.

Methods of biomarker level data analysis in one embodiment, further include the use of a feature selection algorithm as provided herein. In some embodiments of the present invention, feature selection is provided by use of the LIMMA software package (Smyth, G. K. (2005). Limma: linear models for microarray data. In: Bioinformatics and Computational Biology Solutions using R and Bioconductor, R. Gentleman, V. Carey, S. Dudoit, R. Irizarry, W. Huber (eds.), Springer, New York, pages 397-420, incorporated by reference in its entirety for all purposes).

Methods of biomarker level data analysis, in one embodiment, include the use of a pre-classifier algorithm. For example, an algorithm may use a specific molecular fingerprint to pre-classify the samples according to their composition and then apply a correction/normalization factor. This data/information may then be fed in to a final classification algorithm which would incorporate that information to aid in the final diagnosis.

Methods of biomarker level data analysis, in one embodiment, further include the use of a classifier algorithm as provided herein. In one embodiment of the present invention, a diagonal linear discriminant analysis, k-nearest neighbor algorithm, support vector machine (SVM) algorithm, linear support vector machine, random forest algorithm, or a probabilistic model-based method or a combination thereof is provided for classification of microarray data. In some embodiments, identified markers that distinguish samples (e.g., of varying biomarker level profiles, and/or varying molecular subtypes of adenocarcinoma (e.g., squamoid, bronchioid, magnoid)) are selected based on statistical significance of the difference in biomarker levels between classes of interest. In some cases, the statistical significance is adjusted by applying a Benjamin Hochberg or another correction for false discovery rate (FDR).

In some cases, the classifier algorithm may be supplemented with a meta-analysis approach such as that described by Fishel and Kaufman et al. 2007 Bioinformatics 23(13): 1599-606, incorporated by reference in its entirety for all purposes. In some cases, the classifier algorithm may be supplemented with a meta-analysis approach such as a repeatability analysis.

Methods for deriving and applying posterior probabilities to the analysis of biomarker level data are known in the art and have been described for example in Smyth, G. K. 2004 *Stat. Appi. Genet. Mol. Biol.* 3: Article 3, incorporated by reference in its entirety for all purposes. In some cases, the posterior probabilities may be used in the methods of the present invention to rank the markers provided by the classifier algorithm.

A statistical evaluation of the results of the biomarker level profiling may provide a quantitative value or values indicative of one or more of the following: molecular subtype of adenocarcinoma (squamoid, bronchioid or magnoid); the likelihood of the success of a particular therapeutic intervention, e.g., angiogenesis inhibitor therapy, chemotherapy, or immunotherapy. In one embodiment, the data is presented directly to the physician in its most useful form to guide patient care, or is used to define patient populations in clinical trials or a patient population for a given medication. The results of the molecular profiling can be statistically evaluated using a number of methods known to the art including, but not limited to: the students T test, the two sided T test, Pearson rank sum analysis, hidden Markov model analysis, analysis of q-q plots, principal component analysis, one way ANOVA, two way ANOVA, LIMMA and the like.

In some cases, accuracy may be determined by tracking the subject over time to determine the accuracy of the original diagnosis. In other cases, accuracy may be established in a deterministic manner or using statistical methods. For example, receiver operator characteristic (ROC) analysis may be used to determine the optimal assay parameters to achieve a specific level of accuracy, specificity, positive predictive value, negative predictive value, and/or false discovery rate.

In some cases, the results of the biomarker level profiling assays, are entered into a database for access by representatives or agents of a molecular profiling business, the individual, a medical provider, or insurance provider. In some cases, assay results include sample classification, identification, or diagnosis by a representative, agent or consultant of the business, such as a medical professional. In other cases, a computer or algorithmic analysis of the data is provided automatically. In some cases the molecular profiling business may bill the individual, insurance provider, medical provider, researcher, or government entity for one or more of the following: molecular profiling assays performed, consulting services, data analysis, reporting of results, or database access.

In some embodiments of the present invention, the results of the biomarker level profiling assays are presented as a report on a computer screen or as a paper record. In some embodiments, the report may include, but is not limited to, such information as one or more of the following: the levels of biomarkers (e.g., as reported by copy number or fluorescence intensity, etc.) as compared to the reference sample or reference value(s); the likelihood the subject will respond to a particular therapy, based on the biomarker level values and the lung adenocarcinoma subtype and proposed therapies.

In one embodiment, the results of the gene expression profiling may be classified into one or more of the following: squamoid (proximal inflammatory) positive, bronchioid (terminal respiratory unit) positive, magnoid (proximal proliferative) positive, squamoid (proximal inflammatory) negative, bronchioid (terminal respiratory unit) negative, magnoid (proximal proliferative) negative; likely to respond to angiogenesis inhibitor, immunotherapy or chemotherapy; unlikely to respond to angiogenesis inhibitor, immunotherapy or chemotherapy; or a combination thereof.

In some embodiments of the present invention, results are classified using a trained algorithm. Trained algorithms of the present invention include algorithms that have been developed using a reference set of known gene expression values and/or normal samples, for example, samples from individuals diagnosed with a particular molecular subtype of adenocarcinoma. In some cases, a reference set of known gene expression values are obtained from individuals who have been diagnosed with a particular molecular subtype of adenocarcinoma, and are also known to respond (or not respond) to angiogenesis inhibitor therapy. In some cases, a reference set of known gene expression values are obtained from individuals who have been diagnosed with a particular molecular subtype of adenocarcinoma, and are also known to respond (or not respond) to immunotherapy. In some cases, a reference set of known gene expression values are obtained from individuals who have been diagnosed with a particular molecular subtype of adenocarcinoma, and are also known to respond (or not respond) to chemotherapy.

Algorithms suitable for categorization of samples include but are not limited to k-nearest neighbor algorithms, support vector machines, linear discriminant analysis, diagonal linear discriminant analysis, updown, naive Bayesian algorithms, neural network algorithms, hidden Markov model algorithms, genetic algorithms, or any combination thereof.

When a binary classifier is compared with actual true values (e.g., values from a biological sample), there are typically four possible outcomes. If the outcome from a prediction is p (where "p" is a positive classifier output, such as the presence of a deletion or duplication syndrome) and the actual value is also p, then it is called a true positive (TP); however if the actual value is n then it is said to be a false positive (FP). Conversely, a true negative has occurred when both the prediction outcome and the actual value are n (where "n" is a negative classifier output, such as no deletion or duplication syndrome), and false negative is when the prediction outcome is n while the actual value is p. In one embodiment, consider a test that seeks to determine whether a person is likely or unlikely to respond to angiogenesis inhibitor therapy. A false positive in this case occurs when the person tests positive, but actually does respond. A false negative, on the other hand, occurs when the person tests negative, suggesting they are unlikely to respond, when they actually are likely to respond. The same holds true for classifying a lung cancer subtype.

The positive predictive value (PPV), or precision rate, or post-test probability of disease, is the proportion of subjects with positive test results who are correctly diagnosed as likely or unlikely to respond, or diagnosed with the correct lung cancer subtype, or a combination thereof. It reflects the probability that a positive test reflects the underlying condition being tested for. Its value does however depend on the prevalence of the disease, which may vary. In one example the following characteristics are provided: FP (false positive); TN (true negative); TP (true positive); FN (false negative). False positive rate $(a)=FP/(FP+TN)-specificity$; False negative rate $(\beta)=FN/(TP+FN)-sensitivity$; $Power=sensitivity=1-\beta$; Likelihood-ratio $positive=sensitivity/(1-specificity)$; Likelihood-ratio negative=(1−sensitivity)/specificity. The negative predictive value (NPV) is the proportion of subjects with negative test results who are correctly diagnosed.

In some embodiments, the results of the biomarker level analysis of the subject methods provide a statistical confidence level that a given diagnosis is correct. In some embodiments, such statistical confidence level is at least about, or more than about 85%, 90%, 91%, 92%, 93%, 94%, 95%, 96%, 97%, 98%, 99% 99.5%, or more.

In some embodiments, the method further includes classifying the lung tissue sample as a particular lung cancer subtype based on the comparison of biomarker levels in the sample and reference biomarker levels, for example present in at least one training set. In some embodiments, the lung tissue sample is classified as a particular subtype if the results of the comparison meet one or more criterion such as, for example, a minimum percent agreement, a value of a statistic calculated based on the percentage agreement such as (for example) a kappa statistic, a minimum correlation (e.g., Pearson's correlation) and/or the like.

It is intended that the methods described herein can be performed by software (stored in memory and/or executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including Unix utilities, C, C++, Java™, Ruby, SQL, SAS®, the R programming language/software environment, Visual Basic™, and other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

Some embodiments described herein relate to devices with a non-transitory computer-readable medium (also can be referred to as a non-transitory processor-readable medium or memory) having instructions or computer code thereon for performing various computer-implemented operations and/or methods disclosed herein. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

In some embodiments, a single biomarker, or from about 5 to about 10, from about 8 to about 16, from about 5 to about 15, from about 5 to about 20, from about 5 to about 25, from about 5 to about 30, from about 5 to about 35, from about 5 to about 40, from about 5 to about 45, from about 5 to about 48 biomarkers (e.g., as disclosed in Table 1) is capable of classifying subtypes of lung adenocarcinoma with a predictive success of at least about 70%, at least about 71%, at least about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, up to 100%, and all values in between. In some embodiments, any combination of biomarkers disclosed herein (e.g., in Table 1) can be used to obtain a predictive success of at least about 70%, at least about 71%, at least about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, up to 100%, and all values in between.

In some embodiments, a single biomarker, or from about 5 to about 10, from about 8 to about 16, from about 5 to about 15, from about 5 to about 20, from about 5 to about 25, from about 5 to about 30, from about 5 to about 35, from about 5 to about 40, from about 5 to about 45, from about 5 to about 48 biomarkers (e.g., as disclosed in Table 1) is capable of classifying lung adenocarcinoma subtypes with a sensitivity or specificity of at least about 70%, at least about 71%, at least about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, up to 100%, and all values in between. In some embodiments, any combination of biomarkers disclosed herein can be used to obtain a sensitivity or specificity of at least about 70%, at least about 71%, at least about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, up to 100%, and all values in between.

Classifier Gene Selection

Figure 8:
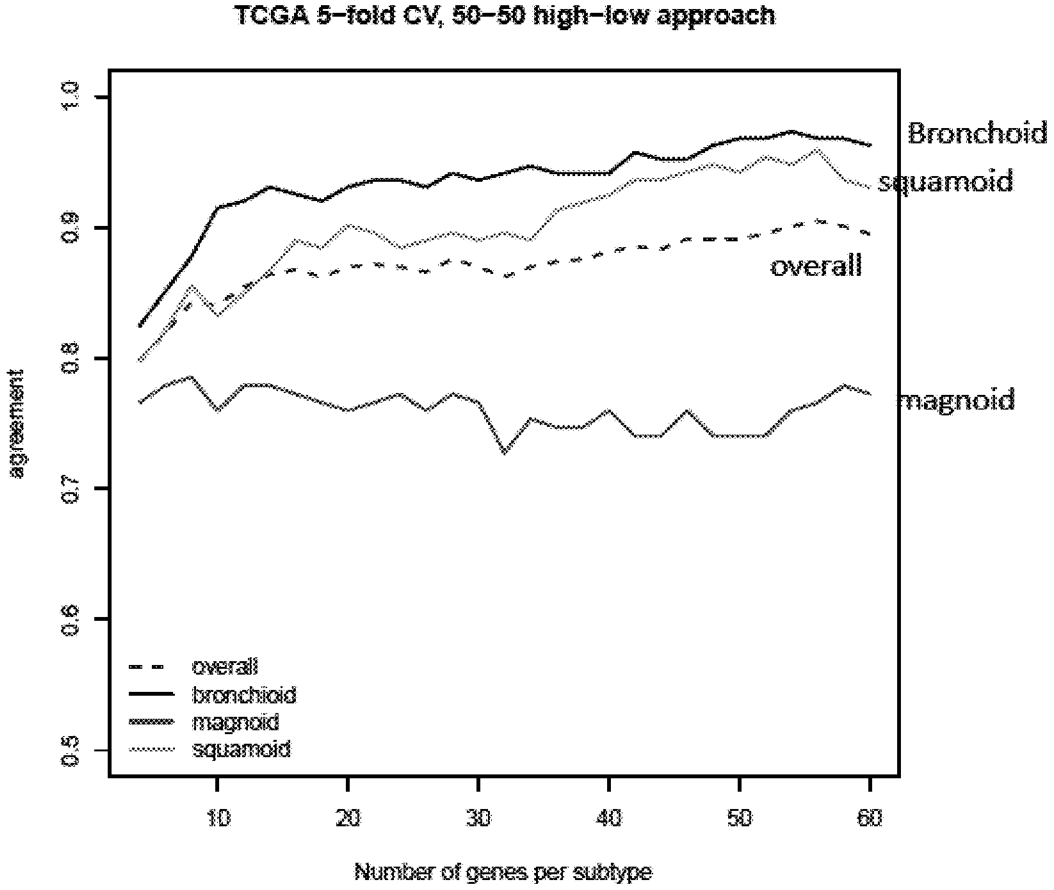
FIG. 8 illustrates a five-fold cross validation study performed from the Cancer Genome Atlas (TCGA) on an RNASeq lung adenocarcinoma (AD) dataset. For determining an optimal number of genes to include for subtyping AD. Terminal Respiratory Unit (TRU) is formerly referred to as bronchioid. Proximal Proliferative (PP) is formerly referred to as magnoid. Proximal Inflammatory (PI) is formerly referred to as squamoid.
Figure 9:
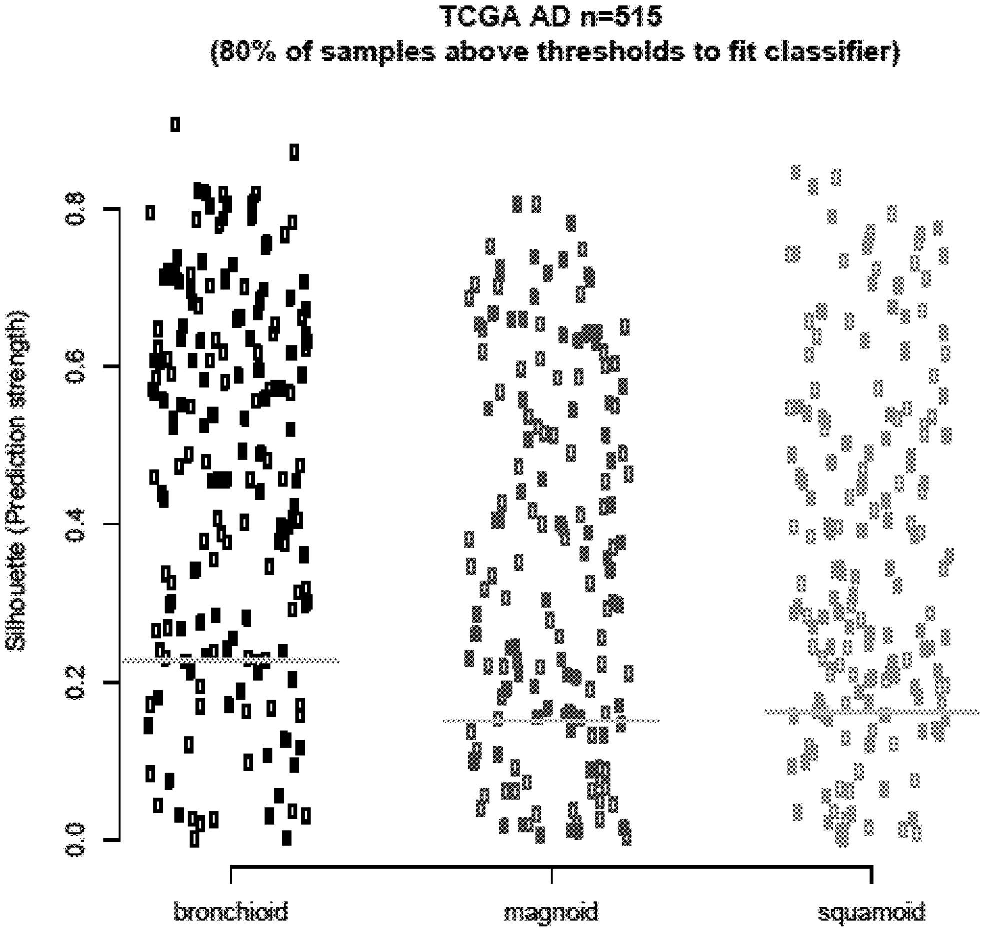
FIG. 9 illustrates the selection of prototype samples by silhouette score for gene signature training of the AD predictor described herein.

In one embodiment, the methods and compositions provided herein are useful for determining the AD subtype of a sample (e.g., lung tissue sample) from a patient by analyzing the expression of a set of biomarkers, whereby the set of biomarkers comprise a fewer number of biomarkers that methods known in the art for molecularly classifying lung AD subtype. In some cases, the set of biomarkers is less than 250, 240, 230, 220, 210, 200, 150, 100, 95 or 90 biomarkers. In some cases, the set of biomarkers is less than 50 biomarkers. In some cases, the set of biomarkers is the set of 48 biomarkers listed in Table 1. In some cases, the set of biomarkers is a sub-set of biomarkers listed Table 1. The biomarkers or classifier genes useful in the methods and compositions provided herein can be selected from one or more lung adenocarcinoma datasets from one or more databases. The databases can be public databases. In one embodiment, classifier genes (e.g., one or more genes listed in Table 1 and Table 2) useful in the methods and compositions provided herein for detecting or diagnosing lung adenocarcinoma subtypes were selected from a lung adenocarcinoma RNAseq dataset from The Cancer Genome Atlas (TCGA). In one embodiment, classifier genes useful for the methods and compositions provided herein such as those in Table 1 are selected by subjecting a large set of classifier genes to an in silico based process in order to determine the minimum number of genes whose expression profile can be used to determine an AD subtype of sample obtained from a subject. In some cases, the large set of classifier genes can be a lung AD RNAseq dataset such as, for example, from TCGA. In some cases, the large set of classifier genes can be 506-gene classifier described herein, whereby the 506-gene classifier can serve to define gold standard subtype. The in silico process for selecting a gene cassette as provided herein for determining lung AD subtype of a sample from a patient can comprise, applying or using a Classifying arrays to Nearest Centroid (CLaNC) algorithm with modification on the standard 506 classifier genes to choose an equal number of negatively and positively correlated genes for each subtype. For determination of the optimal number of genes (e.g, 16 per subtype as shown in Table 1) to include in the signature, the process can further comprise performing a 5-fold cross validation using TCGA lung adenocarcinoma dataset as provided herein to produce cross-validation curves as shown in FIG. 8. To get the final list of gene classifiers, the method can further comprise applying the Classifying arrays to Nearest Centroid (CLaNC) to the entire TCGA data set minus 20% of samples with the lowest gold standard subtype prediction strength, and removing an equal number from each subtype such as shown in FIG. 9.

In one embodiment, the method further comprises validating the gene classifiers. Validation can comprise testing the expression of the classifiers in several fresh frozen publicly available array and RNAseq datasets and calling the subtype based on said expression levels and subsequently comparing the expression with the gold standard subtype calls as defined by the previously published 506-gene signature. Final validation of the gene signature (e.g., Table 1) can then be performed in a newly collected RNAseq dataset of archived formalin-fixed paraffin-embedded (FFPE) adenocarcinoma samples to assure comparable performance in the FFPE samples. In one embodiment, the classifier biomarkers of Table 1 were selected based on the in silico CLaNC process described herein. The gene symbols and official gene names are listed in column 2 and column 3, respectively.

In one embodiment, the methods of the invention require the detection of at least 1, at least 2, at least 3, at least 4, at least 5, at least 6, at least 7, at least 8, at least 9, at least 10, at least 11, at least 12, at least 13, at least 14, at least 15, or up to 16 classifier biomarkers in a lung cancer cell sample obtained from a patient which expression is altered in order to identify a TRU, a PP, or a PI lung adenocarcinoma subtype. The same applies for other classifier gene expression datasets as provided herein.

In another embodiment, the methods of the invention require the detection of a total of at least 1, at least 2, at least 5, at least 8, at least 10, at least 16, at least 20, at least 30, at least 32, or up to 48 classifier biomarkers out of the 48 gene biomarkers of Table 1 in a lung cancer cell sample (e.g., lung AD sample) obtained from a patient in order to identify a TRU, a PP, or a PI lung adenocarcinoma subtype. The same applies for other classifier gene expression datasets as provided herein.

In one embodiment, at least 1, at least 2, at least 3, at least 4, at least 5, at least 6, at least 7, or up to 8 biomarkers of Table 1 are "up-regulated" in a specific subtype of lung adenocarcinoma. In another embodiment, at least 1, at least 2, at least 3, at least 4, at least 5, at least 6, at least 7, or up to 8 biomarkers of Table 1 are "down-regulated" in a specific subtype of lung adenocarcinoma. The same applies for other classifier gene expression datasets as provided herein.

In one embodiment, the expression level of an "up-regulated" biomarker as provided herein is increased by about 0.5-fold, about 1-fold, about 1.5-fold, about 2-fold, about 2.5-fold, about 3-fold, about 3.5-fold, about 4-fold, about 4.5-fold, about 5-fold, and any values in between. In another embodiment, the expression level of a "down-regulated" biomarker as provided herein is decreased by about 0.8-fold, about 1.4-fold, about 2-fold, about 2.6-fold, about 3.2-fold, about 3.6-fold, about 4-fold, and any values in between.

It is recognized that additional genes or proteins can be used in the practice of the invention. For example, vimentin, a member of the intermediate filament family of proteins can be used to identify the adenocarcinoma subtype Proximal Proliferative (magnoid), and SMA can be used to identify Proximal Inflammatory (squamoid) subtype. In general, genes useful in classifying the subtypes of lung adenocarcinoma, include those that are independently capable of distinguishing between normal versus tumor, or between different classes or grades of lung cancer. A gene is considered to be capable of reliably distinguishing between subtypes if the area under the receiver operator characteristic (ROC) curve is approximately 1.

Clinical/Therapeutic Uses

In one embodiment, a method is provided herein for determining a disease outcome or prognosis for a patient suffering from cancer. In some cases, the cancer is lung cancer. The disease outcome or prognosis can be measured by examining the overall survival for a period of time or intervals (e.g., 0 to 36 months or 0 to 60 months). In one embodiment, survival is analyzed as a function of subtype (e.g., for lung cancer, adenocarcinoma (TRU, PI, and PP)). Relapse-free and overall survival can be assessed using standard Kaplan-Meier plots as well as Cox proportional hazards modeling.

In one embodiment, upon determining a patient's lung cancer subtype, the patient is selected for suitable therapy, for example chemotherapy or drug therapy with an angiogenesis inhibitor or immunotherapy. In one embodiment, upon determining a patient's lung cancer subtype, the patient is administered a suitable therapeutic agent, for example chemotherapeutic agent(s) or an angiogenesis inhibitor or immunotherapeutic agent(s). In one embodiment, the therapy is immunotherapy, and the immunotherapeutic agent is a checkpoint inhibitor, monoclonal antibody, biological response modifier, therapeutic vaccine or cellular immunotherapy.

The methods of present invention are also useful for evaluating clinical response to therapy, as well as for endpoints in clinical trials for efficacy of new therapies. The extent to which sequential diagnostic expression profiles move towards normal can be used as one measure of the efficacy of the candidate therapy.

In one embodiment, the methods of the invention also find use in predicting response to different lines of therapies based on the subtype of lung adenocarcinoma (AD). For example, chemotherapeutic response can be improved by more accurately assigning tumor subtypes. Likewise, treatment regimens can be formulated based on the tumor subtype. For example, clinical trials have shown convincing evidence that the VEGF inhibitor, bevacizumab, can be effective in the treatment of NSCLC.

In one embodiment, the Terminal Respiratory Unit (TRU) subtype may have enhanced response to EGFR inhibitors and Pemetrexed. In another embodiment, Proximal Proliferative (PP) can have enhanced response to chemotherapy. In another embodiment, Proximal Inflammatory (PI) can have enhanced response to immunotherapy. In another embodiment, all subtypes can have enhanced response to chemotherapies, angiogenesis inhibitor treatments, and immunotherapies.

Angiogenesis Inhibitors

In one embodiment, upon determining a patient's lung adenocarcinoma subtype, the patient is selected for drug therapy with an angiogenesis inhibitor.

In one embodiment, the angiogenesis inhibitor is a vascular endothelial growth factor (VEGF) inhibitor, a VEGF receptor inhibitor, a platelet derived growth factor (PDGF) inhibitor or a PDGF receptor inhibitor.

Each biomarker panel can include one, two, three, four, five, six, seven, eight or more biomarkers usable by a classifier (also referred to as a "classifier biomarker") to assess whether an adenocarcinoma patient is likely to respond to angiogenesis inhibitor therapy; to select an adenocarcinoma patient for angiogenesis inhibitor therapy; to determine a "hypoxia score" and/or to subtype an adenocarcinoma sample as squamoid (also referred to as proximal inflammatory), bronchioid (also referred to as terminal respiratory unit) or magnoid (also referred to as proximal proliferative) molecular subtype. As used herein, the term "classifier" can refer to any algorithm for statistical classification, and can be implemented in hardware, in software, or a combination thereof. The classifier can be capable of 2-level, 3-level, 4-level, or higher, classification, and can depend on the nature of the entity being classified. One or more classifiers can be employed to achieve the aspects disclosed herein.

In general, methods of determining whether an adenocarcinoma patient is likely to respond to angiogenesis inhibitor therapy, or methods of selecting an adenocarcinoma patient for angiogenesis inhibitor therapy are provided herein. In one embodiment, the method comprises assessing whether the patient's adenocarcinoma subtype is squamoid (proximal inflammatory), bronchioid (terminal respiratory unit) or magnoid (proximal proliferative) using the methods described herein (e.g., assessing the expression of one or more classifier biomarkers of Table 1) and probing an adenocarcinoma sample from the patient for the levels of at least five biomarkers selected from the group consisting of RRAGD, FABP5, UCHL1, GAL, PLOD, DDIT4, VEGF, ADM, ANGPTL4, NDRG1, NP, SLC16A3, and C14ORF58 (see Table 3) at the nucleic acid level. In a further embodiment, the probing step comprises mixing the sample with five or more oligonucleotides that are substantially complementary to portions of nucleic acid molecules of the at least five biomarkers under conditions suitable for hybridization of the five or more oligonucleotides to their complements or substantial complements, detecting whether hybridization occurs between the five or more oligonucleotides to their complements or substantial complements; and obtaining hybridization values of the sample based on the detecting steps. The hybridization values of the sample are then compared to reference hybridization value(s) from at least one sample training set, wherein the at least one sample training set comprises (i) hybridization value(s) of the at least five biomarkers from a sample that overexpresses the at least five biomarkers, or overexpresses a subset of the at least five biomarkers, (ii) hybridization values of the at least five biomarkers from a reference squamoid (proximal inflammatory), bronchioid (terminal respiratory unit) or magnoid (proximal proliferative) sample, or (iii) hybridization values of the at least five biomarkers from an adenocarcinoma free lung sample. A determination of whether the patient is likely to respond to angiogenesis inhibitor therapy, or a selection of the patient for angiogenesis inhibitor is then made based upon (i) the patient's adenocarcinoma subtype and (ii) the results of comparison.

TABLE 3

Biomarkers for hypoxia profile

| Name | Abbreviation | GenBank Accession No. |
|---|---|---|
| RRAGD | Ras-related GTP binding D | BC003088 |
| FABP5 | fatty acid binding protein 5 | M94856 |
| UCHL1 | ubiquitin carboxyl-terminal esterase L1 | NM_004181 |
| GAL | Galanin | BC030241 |
| PLOD | procollagen-lysine, 2-oxoglutarate 5-dioxygenase lysine hydroxylase | M98252 |
| DDIT4 | DNA-damage-inducible transcript 4 | NM_019058 |
| VEGF | vascular endothelial growth factor | M32977 |
| ADM | Adrenomedullin | NM_001124 |
| ANGPTL4 | angiopoietin-like 4 | AF202636 |
| NDRG1 | N-myc downstream regulated gene 1 | NM_006096 |
| NP | nucleoside phosphorylase | NM_000270 |
| SLC16A3 | solute carrier family 16 monocarboxylic acid transporters, member 3 | NM_004207 |
| C14ORF58 | chromosome 14 open reading frame 58 | AK000378 |

The aforementioned set of thirteen biomarkers, or a subset thereof, is also referred to herein as a "hypoxia profile".

In one embodiment, the method provided herein includes determining the levels of at least five biomarkers, at least six biomarkers, at least seven biomarkers, at least eight biomarkers, at least nine biomarkers, or at least ten biomarkers, or five to thirteen, six to thirteen, seven to thirteen, eight to thirteen, nine to thirteen or ten to thirteen biomarkers selected from RRAGD, FABP5, UCTBL1, GAL, PLOD, DDJT4, VEGF, ADM, ANGPTL4, NDRG1, NP, SLC16A3, and C140RF58 in an adenocarcinoma sample obtained from a subject. Biomarker expression in some instances may be normalized against the expression levels of all RNA transcripts or their expression products in the sample, or against a reference set of RNA transcripts or their expression products. The reference set as explained throughout, may be an actual sample that is tested in parallel with the adenocarcinoma sample, or may be a reference set of values from a database or stored dataset. Levels of expression, in one embodiment, are reported in number of copies, relative fluorescence value or detected fluorescence value. The level of expression of the biomarkers of the hypoxia profile together with adenocarcinoma subtype as determined using the methods provided herein can be used in the methods described herein to determine whether a patient is likely to respond to angiogenesis inhibitor therapy.

In one embodiment, the levels of expression of the thirteen biomarkers (or subsets thereof, as described above, e.g., five or more, from about five to about 13), are normalized against the expression levels of all RNA transcripts or their non-natural cDNA expression products, or protein products in the sample, or of a reference set of RNA transcripts or a reference set of their non-natural cDNA expression products, or a reference set of their protein products in the sample.

In one embodiment, angiogenesis inhibitor treatments include, but are not limited to an integrin antagonist, a selectin antagonist, an adhesion molecule antagonist, an antagonist of intercellular adhesion molecule (ICAM)-1, ICAM-2, ICAM-3, platelet endothelial adhesion molecule (PCAM), vascular cell adhesion molecule (VCAM)), lymphocyte function-associated antigen 1 (LFA-1), a basic fibroblast growth factor antagonist, a vascular endothelial growth factor (VEGF) modulator, a platelet derived growth factor (PDGF) modulator (e.g., a PDGF antagonist).

In one embodiment of determining whether a subject is likely to respond to an integrin antagonist, the integrin antagonist is a small molecule integrin antagonist, for example, an antagonist described by Paolillo et al. (Mini Rev Med Chem, 2009, volume 12, pp. 1439-1446, incorporated by reference in its entirety), or a leukocyte adhesion-inducing cytokine or growth factor antagonist (e.g., tumor necrosis factor-α (TNF-α), interleukin-1β (IL-1β), monocyte chemotactic protein-1 (MCP-1) and a vascular endothelial growth factor (VEGF)), as described in U.S. Pat. No. 6,524,581, incorporated by reference in its entirety herein.

The methods provided herein are also useful for determining whether a subject is likely to respond to one or more of the following angiogenesis inhibitors: interferon gamma 1β, interferon gamma 1β (Actimmune®) with pirfenidone, ACUHTR028, αVβ5, aminobenzoate potassium, amyloid P, ANG1122, ANG1170, ANG3062, ANG3281, ANG3298, ANG4011, anti-CTGF RNAi, Aplidin, *Astragalus membranaceus* extract with *salvia* and *Schisandra chinensis*, atherosclerotic plaque blocker, Azol, AZX100, BB3, connective tissue growth factor antibody, CT140, danazol, Esbriet, EXC001, EXC002, EXC003, EXC004, EXC005, F647, FG3019, Fibrocorin, Follistatin, FT011, a galectin-3 inhibitor, GKT137831, GMCT01, GMCT02, GRMD01, GRMD02, GRN510, Heberon Alfa R, interferon α-2β, ITMN520, JKB119, JKB121, JKB122, KRX168, LPA1 receptor antagonist, MGN4220, MIA2, microRNA 29a oligonucleotide, MMI0100, noscapine, PB1I4050, PB1I4419, PDGFR inhibitor, PF-06473871, PGN0052, Pirespa, Pirfenex, pirfenidone, plitidepsin, PRM151, Px102, PYN17, PYN22 with PYN17, Relivergen, rhPTX2 fusion protein, RXI109, secretin, STX100, TGF-β Inhibitor, transforming growth factor, β-receptor 2 oligonucleotide, VA999260, XV615 or a combination thereof.

In another embodiment, a method is provided for determining whether a subject is likely to respond to one or more endogenous angiogenesis inhibitors. In a further embodiment, the endogenous angiogenesis inhibitor is endostatin, a 20 kDa C-terminal fragment derived from type XVIII collagen, angiostatin (a 38 kDa fragment of plasmin), a member of the thrombospondin (TSP) family of proteins. In a further embodiment, the angiogenesis inhibitor is a TSP-1, TSP-2, TSP-3, TSP-4 and TSP-5. Methods for determining the likelihood of response to one or more of the following angiogenesis inhibitors are also provided a soluble VEGF receptor, e.g., soluble VEGFR-1 and neuropilin 1 (NPR1), angiopoietin-1, angiopoietin-2, vasostatin, calreticulin, platelet factor-4, a tissue inhibitor of metalloproteinase (TIMP) (e.g., TIMP1, TIMP2, TIMP3, TIMP4), cartilage-derived angiogenesis inhibitor (e.g., peptide troponin I and chrondomodulin I), a disintegrin and metalloproteinase with thrombospondin motif 1, an interferon (IFN), (e.g., IFN-α, IFN-β, IFN-γ), a chemokine, e.g., a chemokine having the C-X-C motif (e.g., CXCL10, also known as interferon gamma-induced protein 10 or small inducible cytokine B10), an interleukin cytokine (e.g., IL-4, IL-12, IL-18), prothrombin, antithrombin III fragment, prolactin, the protein encoded by the TNFSF15 gene, osteopontin, maspin, canstatin, proliferin-related protein.

In one embodiment, a method for determining the likelihood of response to one or more of the following angiogenesis inhibitors is provided is angiopoietin-1, angiopoietin-2, angiostatin, endostatin, vasostatin, thrombospondin, calreticulin, platelet factor-4, TIMP, CDAI, interferon α, interferon β, vascular endothelial growth factor inhibitor (VEGI) meth-1, meth-2, prolactin, VEGI, SPARC, osteopontin, maspin, canstatin, proliferin-related protein (PRP), restin, TSP-1, TSP-2, interferon gamma 1β, ACUHTR028, αVβ5, aminobenzoate potassium, amyloid P, ANG1122, ANG1170, ANG3062, ANG3281, ANG3298, ANG4011, anti-CTGF RNAi, Aplidin, *Astragalus membranaceus* extract with *salvia* and *schisandra chinensis*, atherosclerotic plaque blocker, Azol, AZX100, BB3, connective tissue growth factor antibody, CT140, danazol, Esbriet, EXC001, EXC002, EXC003, EXC004, EXC005, F647, FG3019, Fibrocorin, Follistatin, FT011, a galectin-3 inhibitor, GKT137831, GMCT01, GMCT02, GRMDO1, GRMD02, GRN510, Heberon Alfa R, interferon α-2β, ITMN520, JKB119, JKB121, JKB122, KRX168, LPA1 receptor antagonist, MGN4220, MIA2, microRNA 29a oligonucleotide, MMI0100, noscapine, PB1I4050, PB1I4419, PDGFR inhibitor, PF-06473871, PGN0052, Pirespa, Pirfenex, pirfenidone, plitidepsin, PRM151, Px102, PYN17, PYN22 with PYN17, Relivergen, rhPTX2 fusion protein, RXI109, secretin, STX100, TGF-β Inhibitor, transforming growth factor, β-receptor 2 oligonucleotide, VA999260, XV615 or a combination thereof.

In yet another embodiment, the angiogenesis inhibitor can include pazopanib (Votrient), sunitinib (Sutent), sorafenib (Nexavar), axitinib (Inlyta), ponatinib (Iclusig), vandetanib (Caprelsa), cabozantinib (Cometrig), ramucirumab (Cyramza), regorafenib (Stivarga), ziv-aflibercept (Zaltrap), motesanib, or a combination thereof. In another embodiment, the angiogenesis inhibitor is a VEGF inhibitor. In a further embodiment, the VEGF inhibitor is axitinib, cabozantinib, aflibercept, brivanib, tivozanib, ramucirumab or motesanib. In yet a further embodiment, the angiogenesis inhibitor is motesanib.

In one embodiment, the methods provided herein relate to determining a subject's likelihood of response to an antagonist of a member of the platelet derived growth factor (PDGF) family, for example, a drug that inhibits, reduces or modulates the signaling and/or activity of PDGF-receptors (PDGFR). For example, the PDGF antagonist, in one embodiment, is an anti-PDGF aptamer, an anti-PDGF antibody or fragment thereof, an anti-PDGFR antibody or fragment thereof, or a small molecule antagonist. In one embodiment, the PDGF antagonist is an antagonist of the PDGFR-α or PDGFR-β. In one embodiment, the PDGF antagonist is the anti-PDGF-β aptamer E10030, sunitinib, axitinib, sorefenib, imatinib, imatinib mesylate, nintedanib, pazopanib HCl, ponatinib, MK-2461, dovitinib, pazopanib, crenolanib, PP-121, telatinib, imatinib, KRN 633, CP 673451, TSU-68, Ki8751, amuvatinib, tivozanib, masitinib, motesanib diphosphate, dovitinib dilactic acid, linifanib (ABT-869).

Upon making a determination of whether a patient is likely to respond to angiogenesis inhibitor therapy, or selecting a patient for angiogenesis inhibitor therapy, in one embodiment, the patient is administered the angiogenesis inhibitor. The angiogenesis in inhibitor can be any of the angiogenesis inhibitors described herein.

Immunotherapy

In one embodiment, provided herein is a method for determining whether an adenocarcinoma (AD) lung cancer patient is likely to respond to immunotherapy by determining the subtype of AD of a sample obtained from the patient and, based on the AD lung cancer subtype, assessing whether the patient is likely to respond to immunotherapy. In another embodiment, provided herein is a method of selecting a patient suffering from AD for immunotherapy by determining an AD subtype of a sample from the patient and, based on the AD subtype, selecting the patient for immunotherapy. The determination of the AD subtype of the sample obtained from the patient can be performed using any method for subtyping AD known in the art. In one embodiment, the sample obtained from the patient has been previously diagnosed as being AD, and the methods provided herein are used to determine the AD subtype of the sample. The previous diagnosis can be based on a histological analysis. The histological analysis can be performed by one or more pathologists. In one embodiment, the AD subtyping is performed via gene expression analysis of a set or panel of biomarkers or subsets thereof in order to generate an expression profile. The gene expression analysis can be performed on a lung cancer sample (e.g., lung cancer AD sample) obtained from a patient in order to determine the presence, absence or level of expression of one or more biomarkers selected from a publically available lung cancer database described herein and/or Table 1 provided herein. The AD subtype can be selected from the group consisting of squamoid (proximal inflammatory), bronchioid (terminal respiratory unit) and magnoid (proximal proliferative). The immunotherapy can be any immunotherapy provided herein. In one embodiment, the immunotherapy comprises administering one or more checkpoint inhibitors. The checkpoint inhibitors can be any checkpoint inhibitor provided herein such as, for example, a checkpoint inhibitor that targets PD-1, PD-LI or CTLA4.

As disclosed herein, the biomarkers panels, or subsets thereof, can be those disclosed in any publically available AD gene expression dataset or datasets. In one embodiment, the lung cancer is AD and the biomarker panel or subset thereof is, for example, the cancer genome atlas (TCGA) lung AD RNAseq gene expression dataset (n=515). In one embodiment, the lung cancer is AD and the biomarker panel or subset thereof is, for example, the AD gene expression dataset (n=442) disclosed in Shedden et al. (Nat Med 2008; 14(8): 822-827), the contents of which are herein incorporated by reference in its entirety. In one embodiment, the lung cancer is AD and the biomarker panel or subset thereof is, for example, the AD gene expression dataset (n=117) disclosed in Tomida et al. (J Clin Oncol 2009; 27(17):2793-2799), the contents of which are herein incorporated by reference in its entirety. In one embodiment, the lung cancer is AD and the biomarker panel or subset thereof is, for example, the AD gene expression dataset (n=116) disclosed in Wilkerson et al. (PLoS One 2012; 7(5):e36530), the contents of which are herein incorporated by reference in its entirety. In one embodiment, the lung cancer is AD and the biomarker panel or subset thereof is, for example, the AD gene expression dataset disclosed in Table 1. In one embodiment, the lung cancer is AD and the biomarker panel or subset thereof is, for example, the AD gene expression dataset disclosed in Table 1 in combination with one or more biomarkers from a publically available AD expression dataset. In Table 2, the first column of the table represents the biomarker list for distinguishing Terminal Respiratory Unit (TRU). The middle column of the table represents the biomarker list for distinguishing Proximal Proliferative (PP). The last column of the table represents the biomarker list for distinguishing Proximal Inflammatory (PI). In some cases, as shown in Table 2, a total of 48 biomarkers can be used for AD subtype determination. For each AD subtype, 8 of the 16 biomarkers can be negatively correlated genes, while 8 can be positively correlated genes which can be selected as the gene signature of a specific AD subtype.

In some embodiments, the method for lung cancer subtyping (e.g., AD subtyping) includes detecting expression levels of a classifier biomarker set. The classifier biomarker set can be a set of biomarkers from a publically available database such as, for example, TCGA lung AD RNASeq gene expression dataset(s) or any other dataset provided herein. In some embodiments, the detecting includes all of the classifier biomarkers of Table 1 or any other dataset provided herein at the nucleic acid level or protein level. In another embodiment, a single classifier biomarker of Table 1 or a subset of the classifier biomarkers of Table 1 or any other dataset provided herein are detected, for example, from about five to about twenty. In another embodiment, a single classifier biomarker of Table 1 or a subset of the classifier biomarkers of Table 1 and/or any other dataset provided herein are detected, for example, from about 16 to about 48. In another embodiment, all of the classifier biomarkers of Table 1 or any other dataset provided herein are detected. In another embodiment, at least one or all of the classifier biomarkers of Table 1 in combination with one or more classifier biomarkers of any other AD dataset provided herein are detected. The detecting can be performed by any suitable technique including, but not limited to, RNA-seq, a reverse transcriptase polymerase chain reaction (RT-PCR), a microarray hybridization assay, or another hybridization assay, e.g., a NanoString assay for example, with primers and/or probes specific to the classifier biomarkers, and/or the like. In some cases, the primers useful for the amplification methods (e.g., RT-PCR or qRT-PCR) are any forward and reverse primers suitable for binding to a classifier gene from a dataset provided herein alone or in combination.

In one embodiment, from about 1 to about 5, about 5 to about 10, from about 5 to about 15, from about 5 to about 20, from about 5 to about 25, from about 5 to about 30, from about 5 to about 35, from about 5 to about 40, from about 5 to about 45, from about 5 to about 50, from about 5 to about 55, from about 5 to about 60, from about 5 to about 65, from about 5 to about 70, from about 5 to about 75, or from about 5 to about 80 of the biomarkers in any of the AD gene expression datasets provided herein, including, for example, Table 1 for an AD lung sample are detected in a method to determine the lung cancer subtype as provided herein. In another embodiment, each of the biomarkers from any one of the AD gene expression datasets provided herein, including, for example, Table 1 for an AD lung sample are detected in a method to determine the lung cancer subtype as provided herein.

In one embodiment, the methods provided herein further comprise determining the presence, absence or level of immune activation in an AD subtype. The presence or level of immune cell activation can be determined by creating an expression profile or detecting the expression of one or more biomarkers associated with innate immune cells and/or adaptive immune cells associated with each AD subtype in a sample (e.g., lung cancer sample) obtained from a patient. In one embodiment, immune cell activation associated with an AD subtype is determined by monitoring the immune cell signatures of Bindea et al (Immunity 2013; 39(4); 782-795), the contents of which are herein incorporated by reference in its entirety. In one embodiment, the method further comprises measuring single gene immune biomarkers, such as, for example, CTLA4, PDCD1 and CD274 (PD-LI), PDCDLG2(PD-L2) and/or IFN gene signatures. The presence or a detectable level of immune activation (Innate and/or Adaptive) associated with an AD subtype can indicate or predict that a patient with said AD subtype may be amendable to immunotherapy. The immunotherapy can be treatment with a checkpoint inhibitor as provided herein. In one embodiment, the PI subtype of AD has immune expression. In one embodiment, a method is provided herein for detecting the expression of at least one classifier biomarker provided herein in a sample (e.g., lung cancer AD sample) obtained from a patient further comprises administering an immunotherapeutic agent following detection of immune activation as provided herein in said sample.

In one embodiment, the method comprises determining a subtype of a lung cancer AD sample and subsequently determining a level of immune cell activation of said subtype. In one embodiment, the subtype is determined by determining the expression levels of one or more classifier biomarkers using sequencing (e.g., RNASeq), amplification (e.g., qRT-PCR) or hybridization assays (e.g., microarray analysis) as described herein. The one or more biomarkers can be selected from a publically available database (e.g., TCGA lung AD RNASeq gene expression datasets or any other publically available AD gene expression datasets provided herein). In some embodiments, the biomarkers of Table 1 can be used to specifically determine the subtype of an AD lung sample obtained from a patient. In one embodiment, the level of immune cell activation is determined by measuring gene expression signatures of immunomarkers. The immunomarkers can be measured in the same and/or different sample used to subtype the lung cancer sample as described herein. The immunomarkers that can be measured can comprise, consist of, or consistently essentially of innate immune cell (IIC) and/or adaptive immune cell (AIC) gene signatures, interferon (IFN) gene signatures, individual immunomarkers, major histocapability complex class II (MHC class II) genes or a combination thereof. The gene expression signatures for both IICs and AICs can be any known gene signatures for said cell types known in the art. For example, the immune gene signatures can be those from Bindea et al. (Immunity 2013; 39(4); 782-795). In one embodiment, the immunomarkers for use in the methods provided herein are selected from Table 4A and/or Table 4B. The individual immunomarkers can be CTLA4, PDCD1 and CD274 (PD-L1). In one embodiment, the individual immunomarkers for use in the methods provided herein are selected from Table 5. The immunomarkers can be one or more interferon (INF) genes. In one embodiment, the immunomarkers for use in the methods provided herein are selected from Table 6. The immunomarkers can be one or more MHCII genes. In one embodiment, the immunomarkers for use in the methods provided herein are selected from Table 7. In yet another embodiment, the immunomarkers for use in the methods provided herein are selected from Tables 4A, 4B, 5, 6, 7, or a combination thereof.

| | Cell Type | | | | | |
|---|---|---|---|---|---|---|
| | B cells | T cells | T helper cells | Tcm | Tem | Th1 cells |
| Human Gene (Gene Name; GenBank Accession No.*) | ABCB4 (ATP binding cassette subfamily B member 4; NM_000443) | BCL11B (B-cell lymphoma/leukaemia 11B; AJ404614.1) | ANP32B (acidic nuclear phosphoprotein 32 family member B; NM_006401.2) | AQP3 (aquaporine 3; NM_004925.4) | AKT3 (AKT serine/threonine kinase 3; NM_005465.4) | APBB2 (amyloid beta precursor protein binding family B member 2; NM_001166054.1) |
| | BACH2 (BTB domain and CNC homolog 2; NM_021813.3) | CD2 (CD2 molecule; NM_001328609.1) | ASF1A (anti-silencing function 1A histone chaperone; NM_014034.2) | ATF7IP (activating transcription factor 7 interacting protein; NM_181352.1) | C7orf54 (staphylococcalnuclease and tudor domain containing 1 (SND1); NG_051199.1) | APOD (apolipoprotein D; NM_001647.3) |
| | BCL11A (B-cell CLL/lymphoma 11A; NM_022893.3) | CD28 (CD28 molecule; NM_001243078.1) | ATF2 (activating transcription factor 2; NM_001256093.1) | ATM (ATM serine/threonine kinase; NM_000051.3) | CCR2 (C—C motif chemokine receptor 2; NM_001123396.1) | ATP9A (ATPase phospholipid transporting 9A; NM_006045.2) |
| | BLK (BLK proto-oncogene, Src family tyrosine kinase; NM_001715.2) | CD3D (CD3d molecule; NM_000732.4) | BATF (basic leucine zipper ATF-like transcription factor; NM_006399.3) | CASP8 (caspase 8; NM_001228.4) | DDX17 (DEAD-box helicase 17; NM_006386.4) | BST2 (bone marrow stromal cell antigen 2; NM_004335.3) |
| | BLNK (B-cell linker; NM_013314.3) | CD3E (CD3e molecule; NM_000733.3) | C13orf34 (aurora borealis; EU834129.1) | CDC14A (cell division cycle 14A; NM_003672.3) | EWSR1 (EWS RNA binding protein 1; NM_013986.3) | BTG3 (BTG anti-proliferation factor 3; NM_001130914.1) |
| | CCR9 (C—C motif chemokine receptor 9; NM_031200.2) | CD3G (CD3g molecule; NM_000073.2) | CD28 (CD28 molecule; NM_006139.3) | CEP68 (centrosomal protein 68; NM_015147.2) | FLI1 (Fli-1 proto-oncogene, ETS transcription factor; NM_002017.4) | CCL4 (C—C motif chemokine ligand 4; NM_002984.3) |
| | CD19 (CD19 molecule; NM_001178098.1) | CD6 (CD6 molecule; NM_006725.4) | DDX50 (DEAD-box helicase 50; NM_024045.1) | CG030 (BRCA2 region, mRNA sequence CG030; U50531.1) | GDPD5 (glycerophosphodiester phosphodiesterase domain containing 5; NM_030792.6) | CD38 (CD38 molecule; NM_001775.3) |
| | CD72 (CD72 molecule; NM_001782.2) | CD96 (CD96 molecule; NM_198196.2) | FAM111A (family with sequence similarity 111 member A; NM_022074.3) | CLUAP1 (clusterin associated protein 1; NM_015041.2) | LTK (leukocyte receptor tyrosine kinase; NM_002344.5) | CD70 (CD70 molecule; NM_001252.4) |
| | COCH (cochlin; NM_001135058.1) | GIMAP5 (GTPase, IMAP family member 5; NM_018384.4) | FRYL (FRY like transcription coactivator; NM_015030.1) | CREBZF (CREB/ATF bZIP transcription factor; NM_001039618.2) | MEFV (Mediterranean fever; NM_000243.2) | CMAH (cytidine monophospho-N-acetylneuraminic acid hydroxylase, pseudogene; NR_002174.2) |
| | CR2 (complement C3d receptor 2; NM_001006658.2) | ITM2A (integral membrane protein 2A; NM_004867.4) | FUSIP1 (serine and arginine rich splicing factor 10; NM_006625.5) | CYLD (CYLD lysine 63 deubiquitinase; NM_015247.2) | NFATC4 (nuclear factor of activated T-cells 4; NM_001136022.2) | CSF2 (colony stimulating factor 2; NM_000758.3) |

-continued

| Cell Type | | | | | |
|---|---|---|---|---|---|
| DTNB (dystrobrevin beta; NM_021907.4) | LCK (LCK proto-oncogene, Src family tyrosine kinase; NM_001042771.2) | GOLGA8A (golgin A8 family member A; NM_181077.3) | CYorf15B (taxilin gamma pseudogene, Y-linked; NR_045128.1) | PRKY (protein kinase, Y-linked, pseudogene; NR_028062.1) | CTLA4 (cytotoxic T-lymphocyte associated protein 4; NM_005214.4) |
| FAM30A (family with sequence similarity 30, member A; NR_026800.2) | NCALD (neurocalcin delta; NM_001040624.1) | ICOS (inducible T-cell costimulator; NM_012092.3) | DOCK9 (dedicator of cytokinesis 9; NM_015296.2) | TBC1D5 (TBC1 domain family member 5; NM_001134381.1) | DGKI (diacylglycerol kinase iota; NM_004717.3) |
| FCRL2 (Fc receptor like 2; NM_030764.3) | PRKCQ (protein kinase C theta; NM_006257.4) | ITM2A (integral membrane protein 2A; NM_004867.4) | FOXP1 (forkhead box P1; NM_032682.5) | TBCD (tubulin folding cofactor D; NM_005993.4) | DOK5 (docking protein 5; NM_018431.4) |
| GLDC (glycine decarboxylase; NM_000170.2) | SH2D1A (SH2 domain containing 1A; NM_002351.4) | LRBA (LPS responsive beige-like anchor protein; NM_001199282.2) | FYB (FYN binding protein; NM_001465.4) | TRA (T cell receptor alpha delta locus; NG_001332.3) | DPP4 (dipeptidyl peptidase 4; NM_001935.3) |
| GNG7 (G protein subunit gamma 7; NM_052847.2) | SKAP1 (src kinase associated phosphoprotein 1; NM_001075099.1) | NAP1L4 (nucleosome assembly protein 1 like 4; NM_005969.3) | HNRPH1 (heterogeneous nuclear ribonucleoprotein H1 (H); NM_001257293.1) | VIL2 (ezrin; NM_003379.4) | DUSP5 (dual specificity phosphatase 5; NM_004419.3) |
| HLA-DOB (major histocompatibility complex, class II, DO beta; NM_002120.3) | TRA (T cell receptor alpha delta locus; NG_001332.3) | NUP107 (nucleoporin 107; NM_020401.3) | INPP4B (inositol polyphosphate-4-phosphatase type II B; NM_003866.3) | | EGFL6 (EGF like domain multiple 6; NM_015507.3) |
| HLA-DQA1 (major histocompatibility complex, class II, DQ alpha 1; NM_002122.3) | TRAC (nuclear receptor corepressor 2; NM_006312.5) | PHF10 (PHD finger protein 10; NM_018288.3) | KLF12 (Kruppel like factor 12; NM_007249.4) | | GGT1 (gamma-glutamyltransferase 1; NM_013421.2) |
| IGHA1 (immunoglobulin heavy locus; NG_001019.6) | TRAT1 (T cell receptor associated transmembrane adaptor 1; NM_016388.3) | PPP2R5C (protein phosphatase 2 regulatory subunit B', gamma; NM_001161725.1) | LOC202134 (family with sequence similarity 153 member B; NM_001265615.1) | | HBEGF (heparin binding EGF like growth factor; NM_001945.2) |
| IGHG1 (immunoglobulin heavy locus; NG_001019.6) | TRBC1 (T cell receptor beta locus; NG_001333.2) | RPA1 (replication protein A1; NM_002945.3) | MAP3K1 (mitogen-activated protein kinase kinase kinase 1, E3 ubiquitin protein ligase; NM_005921.1) | | IFNG (interferon gamma; NM_000619.2) |
| IGHM (immunoglobulin heavy locus; NG_001019.6) | | SEC24C (SEC24 homolog C, COPII coat complex component; NM_004922.3) | MLL (lysine (K)-specific methyltransferase 2A; NM_005933.3) | | IL12RB2 (interleukin 12 receptor subunit beta 2; NM_001319233.1) |

-continued

| Cell Type | | | |
|---|---|---|---|
| | | | |
| IGKC (immunoglobulin kappa locus, proximal V-cluster and J-C cluster; NG_000834.1) | SLC25A12 (solute carrier family 25 member 12; NM_003705.4) | NEFL (neurofilament, light polypeptide; NM_006158.4) | IL22 (interleukin 22; NM_020525.4) |
| IGL (immunoglobulin lambda locus; NG_000002.1) | TRA (T cell receptor alpha delta locus; NG_001332.3) | NFATC3 (nuclear factor of activated T-cells 3; NM_173165.2) | LRP8 (LDL receptor related protein 8; NM_017522.4) |
| KIAA0125 (family with sequence similarity 30, member A; NR_026800.2) | UBE2L3 (ubiquitin conjugating enzyme E2 L3; NM_003347.3) | PCM1 (pericentriolar material 1; NM_001315507.1) | LRRN3 (leucine rich repeat neuronal 3; NM_018334.4) |
| MEF2C (myocyte enhancer factor 20; NM_001308002.1) | YME1L1 (YME1 like 1 ATPase; NM_001253866.1) | PCNX (pecanex homolog 1; NM_014982.2) | LTA (lymphotoxin alpha; NM_000595.3) |
| MICAL3 (microtubule associated monooxygenase, calponin and LIM domain containing 3; NM_001136004.3) | | PDXDC2 (pyridoxal dependent decarboxylase domain containing 2, pseudogene; NR_003610.1) | SGCB (sarcoglycan, beta (43 kDa dystrophin-associated glycoprotein); NM_000232.4) |
| MS4A1 (membrane spanning 4-domains A1; NM_021950.3) | | PHC3 (polyhomeotic homolog 3; NM_001308116.1) | SYNGR3 (synaptogyrin 3; NM_004209.5) |
| OSBPL10 (oxysterol binding protein like 10; NM_017784.4) | | POLR2J2 (RNA polymerase II subunit J2; NM_032959.5) | ZBTB32 (zinc finger and BTB domain containing 32; NM_014383.2) |
| PNOC (prepronociceptin; NM_001284244.1) | | PSPC1 (paraspeckle component 1; NM_001042414.2) | |
| QRSL1 (glutaminyl-tRNA synthase (glutamine-hydrolyzing)-like 1; NM_018292.4) | | REPS1 (RALBP1 associated Eps domain containing 1; NM_001128617.2) | |
| SCN3A (sodium voltage-gated channel alpha subunit 3; NM_001081677.1) | | RP11-74E24.2 (zinc finger CCCH-type domain-containing-like; NM_001271675.1) | |
| SLC15A2 (solute carrier family 15 member 2; XM_017007074.1) | | RPP38 (ribonuclease P/MRP subunit p38; NM_001265601.1) | |

-continued

| | Cell Type | | | | | | |
|---|---|---|---|---|---|---|---|
| | SPIB (Spi-B transcription factor; NM_001244000.1) | | | SLC7A6 (solute carrier family 7 member 6; NM_003983.5) | | | |
| | TCL1A (T-cell leukemia/lymphoma 1A; NM_001098725.1) | | | SNRPN (small nuclear ribonucleoprotein polypeptide N; NM_022807.3) | | | |
| | TNFRSF17 (TNF receptor superfamily member 17; NM_001192.2) | | | ST3GAL1 (ST3 beta-galactoside alpha-2,3-sialyltransferase 1; NM_173344.2) | | | |
| | | | | STX16 (syntaxin 16; NM_001204868.1) | | | |
| | | | | TIMM8A (translocase of inner mitochondrial membrane 8 homolog A; NM_001145951.1) | | | |
| | | | | TRAF3IP3 (TRAF3 interacting protein 3; NM_001320144.1) | | | |
| | | | | TXK (TXK tyrosine kinase; NM_003328.2) | | | |
| | | | | USP9Y (ubiquitin specific peptidase 9, Y-linked; NG_008311.1) | | | |
| | Th2 cells | TFH | Th17 cells | TReg | CD8 T cells | Tgd | Cytotoxic cells |
| Human Gene (Gene Name; GenBank Accession No.*) | ADCY1 (adenylate cyclase 1; NM_001281768.1) | B3GAT1 (beta-1,3-glucuronyltransferase 1; NM_018644.3) | IL17A (interleukin 17A; NM_002190.2) | FOXP3 (forkhead box P3; NM_014009.3) | ABT1 (activator of basal transcription 1; NM_013375.3) | C1orf61 (chromosome 1 open reading frame 61; NM_006365.2) | APBA2 (amyloid beta precursor protein binding family A member 2; NM_005503.3) |
| | AHI1 (Abelson helper integration site 1; NM_001134831.1) | BLR1 (c—x—c chemokine receptor type 5; EF444957.1) | IL17RA (interleukin 17 receptor A; NM_014339.6) | | AES (amino-terminal enhancer of split; NM_198969.1) | CD160 (CD160 molecule; NM_007053.3) | APOL3 (apolipoprotein L3; NM_014349.2) |
| | AI582773 (tn17d08.x1 NCI_CGAP_Brn25 *Homo sapiens* cDNA clone; AI582773.1) | C18orf1 (low density lipoprotein receptor class A domain containing 4; NM_181481.4) | RORC (RAR related orphan receptor C; NM_001001523.1) | | APBA2 (amyloid beta precursor protein binding family A member 2; NM_001130414.1) | FEZ1 (Fasciculation And Elongation Protein Zeta 1; AF123659.1) | CTSW (cathepsin W; NM_001335.3) |

-continued

| Cell Type | | | | |
|---|---|---|---|---|
| ANK1 (ankyrin 1; NM_020476.2) | CDK5R1 (cyclin dependent kinase 5 regulatory subunit 1; NM_003885.2) | ARHGAP8 (Rho GTPase activating protein 8; NM_001198726.1) | TARP (TCR gamma alternate reading frame protein; NM_001003806.1) | DUSP2 (dual specificity phosphatase 2; NM_004418.3) |
| BIRC5 (baculoviral IAP repeat containing 5; NM_001012271.1) | CHGB (chromogranin B; NM_001819.2) | C12orf47 (MAPKAPK5 antisense RNA 1; NR_015404.1) | TRD (T cell receptor alpha delta locus; NG_001332.3) | GNLY (granulysin; NM_012483.3) |
| CDC25C (cell division cycle 25C; NM_001318098.1) | CHI3L2 (chitinase 3 like 2; NM_001025199.1) | C19orf6 (transmembrane protein 259; NM_001033026.1) | TRGV9 (T cell receptor gamma V region 9; X69385.1) | GZMA (granzyme A; NM_006144.3) |
| CDC7 (cell division cycle 7; NM_001134420.1) | CXCL13 (C—X—C motif chemokine ligand 13; NM_006419.2) | C4orf15 (HAUS augmin like complex subunit 3; NM_001303143.1) | | GZMH (granzyme H; NM_001270781.1) |
| CENPF (centromere protein F; NM_016343.3) | HEY1 (hes related family bHLH transcription factor with YRPW motif 1; NM_001282851.1) | CAMLG (calcium modulating ligand; NM_001745.3) | | KLRB1 (killer cell lectin like receptor B1; NM_002258.2) |
| CXCR6 (killer cell lectin like receptor B1; NM_002258.2) | HIST1H4K (histone cluster 1 H4 family member k; NM_003541.2) | CD8A (CD8a molecule; NM_001768.6) | | KLRD1 (killer cell lectin like receptor D1; NM_001114396.1) |
| DHFR (dihydrofolate reductase; NM_001290354.1) | ICA1 (islet cell autoantigen 1; NM_001136020.2) | CD8B (CD8b molecule; NM_001178100.1) | | KLRF1 (killer cell lectin like receptor F1; NM_001291822.1) |
| EVI5 (ecotropic viral integration site 5; NM_001308248.1) | KCNK5 (potassium two pore domain channel subfamily K member 5; NM_003740.3) | CDKN2AIP (CDKN2A interacting protein; NM_001317343.1) | | KLRK1 (killer cell lectin like receptor K1; NM_007360.3) |
| GATA3 (GATA binding protein 3; NM_001002295.1) | KIAA1324 (KIAA1324; NM_001284353.1) | DNAJB1 (DnaJ heat shock protein family (Hsp40) member B1; NM_001313964.1) | | NKG7 (natural killer cell granule protein 7; NM_005601.3) |
| GSTA4 (glutathione S-transferase alpha 4; NM_001512.3) | MAF (MAF bZIP transcription factor; NM_001031804.2) | FLT3LG (fms related tyrosine kinase 3 ligand; NM_001278638.1) | | RORA (RAR related orphan receptor A; NM_134262.2) |
| HELLS (helicase, lymphoid-specific; NM_001289074.1) | MAGEH1 (MAGE family member H1; NM_014061.4) | GADD45A (growth arrest and DNA damage inducible alpha; NM_001199742.1) | | RUNX3 (runt related transcription factor 3; NM_004350.2) |
| IL26 (interleukin | MKL2 | GZMM (granzyme | | SIGIRR (single lg |

-continued

| Cell Type | | | |
| --- | --- | --- | --- |
| 26; NM_018402.1) | (MKL1/myocardin like 2; NM_014048.4) | M; NM_001258351.1) | and TIR domain containing; NM_001135054.1) |
| LAIR2 (leukocyte associated immunoglobulin like receptor 2; NM_021270.4) | MYO6 (myosin VI; NM_001300899.1) | KLF9 (Kruppel like factor 9; NM_001206.2) | WHDC1L1 (WAS protein homolog associated with actin, golgi membranes and microtubules pseudogene 3; NR_003521.1) |
| LIMA1 (LIM domain and actin binding 1; NM_001243775.1) | MYO7A (myosin VIIA; NM_001127179.2) | LEPROTL1 (leptin receptor overlapping transcript-like 1; NM_001128208.1) | ZBTB16 (zinc finger and BTB domain containing 16; NM_001018011.1) |
| MB (myoglobin; NM_203377.1) | PASK (PAS domain containing serine/threonine kinase; NM_001252119.1) | LIME1 (Lck interacting transmembrane adaptor 1; NM_017806.3) | |
| MICAL2 (microtubule associated monooxygenase, calponin and LIM domain containing 2; NM_001282663.1) | PDCD1 (programmed cell death 1; NM_005018.2) | MYST3 (MYST histone acetyltransferase (monocytic leukemia) 3; NM_006766.4) | |
| NEIL3 (nei like DNA glycosylase 3; NM_018248.2) | POMT1 (protein O-mannosyltransferase 1; NM_001136114.1) | PF4 (platelet factor 4; NM_002619.3) | |
| PHEX (phosphate regulating endopeptidase homolog, X-linked; NM_000444.5) | PTPN13 (protein tyrosine phosphatase, non-receptor type 13; NM_080685.2) | PPP1R2 (protein phosphatase 1 regulatory inhibitor subunit 2; NM_001291504.1) | |
| PMCH (pro-melanin concentrating hormone; NM_002674.3) | PVALB (parvalbumin; NM_001315532.1) | PRF1 (perforin 1; NM_005041.4) | |
| PTGIS (12 synthase; NM_000961.3) | SH3TC1 (SH3 domain and tetratricopeptide repeats 1; NM_018986.4) | PRR5 (proline rich 5; NM_181333.3) | |
| SLC39A14 (solute | SIRPG (signal | RBM3 (RNA binding | |

-continued

| Cell Type | | |
|---|---|---|
| carrier family 39 member 14; NM_001135153.1) | regulatory protein gamma; NM_018556.3) | motif (RNP1, RRM) protein 3; NM_006743.4) |
| SMAD2 (SMAD family member 2; NM_001135937.2) | SLC7A10 (solute carrier family 7 member 10; NM_019849.2) | SF1 (splicing factor 1; NM_004630.3) |
| SNRPD1 (small nuclear ribonucleoprotein D1 polypeptide; NM_001291916.1) | SMAD1 (SMAD family member 1; NM_001003688.1) | SFRS7 (serine and arginine rich splicing factor 7; NM_001031684.2) |
| WDHD1 (WD repeat and HMG-box DNA binding protein 1; NM_001008396.2) | ST8SIA1 (ST8 alpha-N-acetyl-neuraminide alpha-2,8-sialyltransferase 1; NM_001304450.1) | SLC16A7 (solute carrier family 16 member 7; NM_001270622.1) |
| | STK39 (serine/threonine kinase 39; NM_013233.2) | TBCC (tubulin folding cofactor C; NM_003192.2) |
| | THADA (THADA, armadillo repeat containing; NM_001271644.1) | THUMPD1 (THUMP domain containing 1; NM_017736.4) |
| | TOX (thymocyte selection associated high mobility group box; NM_014729.2) | TMC6 (transmembrane channel like 6; NM_001321185.1) |
| | TSHR (thyroid stimulating hormone receptor; NM_000369.2) | TSC22D3 (TSC22 domain family member 3; NM_001318470.1) |
| | ZNF764 (zinc finger protein 764; NM_001172679.1) | VAMP2 (vesicle associated membrane protein 2; NM_014232.2) |
| | | ZEB1 (zinc finger E-box binding homeobox 1; NM_001128128.2) |
| | | ZFP36L2 (ZFP36 ring finger protein like 2; |

-continued

| Cell Type | |
|---|---|
| | NM_006887.4)<br>ZNF22 (zinc finger<br>protein 22;<br>NM_006963.4)<br>ZNF609 (zinc finger<br>protein 609;<br>NM_015042.1)<br>ZNF91 (zinc finger<br>protein 91;<br>NM_001300951.1) |

*Each GenBank Accession Number is a representative or exemplary GenBank Accession Number for the listed gene and is herein incorporated by reference in its entirety for all purposes. Further, each listed representative or exemplary accession number should not be construed to limit the claims to the specific accession number.

TABLE 4B

Innate immune cell (IIC) gene signature immunomarkers for use in the methods provided herein.

| | Cell Type | | | | |
|---|---|---|---|---|---|
| | NK cells | NK CD56dim cells | NK CD56bright cells | DC | iDC |
| Human Gene (Gene Name; GenBank Accession No.*) | ADARB1 (adenosine deaminase, RNA specific B1; NM_001112) | EDG8 (sphingosine-1-phosphate receptor 5; NM_001166215.1) | BG255923 (lysophosphatidyl-choline acyltransferase 4; NM_153613.2) | CCL13 (C-C motif ligand chemokine 13; NM_005408.2) | ABCG2 (ATP-binding cassette, sub-family G (WHITE), member 2 (Junior blood group); NM_001257386.1) |
| | AF107846 (neuroendocrine-specific Golgi protein p55; AF107846.1) | FLJ20699 (cDNA FLJ20699 fis, clone KAIA2372; AK000706.1) | DUSP4 (dual specificity phosphatase 4; NM_057158.3) | CCL17 (C-C motif chemokine ligand 17; NM_002987.2) | BLVRB (biliverdin reductase B; NM_000713.2) |
| | AL080130 (cDNA DKFZp434E033 (from clone DKFZp434E033); AL080130.1) | GTF3C1 (general transcription factor IIIC subunit 1; NM_001286242.1) | FOXJ1 (forkhead box J1; NM_001454.3) | CCL22 (C-C motif chemokine ligand 22; NM_002990.4) | CARD9 (caspase recruitment domain family member 9; NM_052814.3) |
| | ALDH1B1 (aldehyde dehydrogenase 1 family member B1; NM_000692.4) | GZMB (granzyme B; NM_004131.4) | MADD (MAP kinase activating death domain; NM_ 001135944.1) | CD209 (CD209 molecule; NM_ 001144899.1) | CD1A (CD1a molecule; NM_001763.2) |
| | ARL6IP2 (atlastin GTPase 2; NM_001330461.1) | IL21R (interleukin 21 receptor; NM_181079.4) | MPPED1 (metallo-phosphoesterase domain containing 1, mRNA; NM_ 001044370.1) | HSD11B1 (hydroxysteroid 11-beta dehydrogenase 1; NM_ 001206741.1) | CD1B (CD1b molecule; NM_001764.2) |
| | BCL2 (apoptosis regulator (BCL2); NM_000633.2) | KIR2DL3 (killer cell immunoglobulin like receptor, two Ig domains and long cytoplasmic tail 3; NM_015868.2) | MUC3B (mucin 3B cell surface associated; JQ511939.1) | NPR1 (natriuretic peptide receptor 1; NM_000906.3) | CD1C (CD1c molecule; NM_001765.2) |
| | CDC5L (cell division cycle 5 like; NM_001253.3) | KIR2DS1 (killer cell immunoglobulin like receptor, two Ig domains and short cytoplasmic tail 1; NM_014512.1) | NIBP (NIK and IKKbetta-binding protein; AY630619.1) | PPFIBP2 (PPFIA binding protein 2; XR_930917.2) | CD1E (CD1e molecule; NM_001185115.1) |
| | FGF18 (fibroblast growth factor 18; NM_003862.2) | KIR2DS2 (killer cell immunoglobulin like receptor, two Ig domains and short cytoplasmic tail 2; NM_001291700.1) | PLA2G6 (phospholipase A2 group VI; NM_ 001004426.1) | | CH25H (cholesterol 25-hydroxylase; NM_003956.3) |
| | FUT5 (fucosyltransferase 5; NM_002034.2) | KIR2DS5 (killer cell immunoglobulin like receptor, two Ig domains and short cytoplasmic tail 5; NM_014513.2) | RRAD (Ras related glycolysis inhibitor and calcium channel regulator; NM_001128850.1) | | CLEC10A (C-type lectin domain family 10 member A; NM_001330070.1) |
| | FZR1 (fizzy/cell division cycle 20 related 1; XM_005259573.4) | KIR3DL1 (killer cell immunoglobulin like receptor, three Ig domains and long cytoplasmic tail 1; NM_013289.2) | SEPT6 (septin 6; NM_145802.3) | | CSF1R (colony stimulating factor 1 receptor; NM_001288705.1) |
| | GAGE2 (G antigen 2; NM_001127212.1) | KIR3DL2 (killer cell immunoglobulin like receptor, three Ig domains and long cytoplasmic tail 2; NM_006737.3) | XCL1 (X-C motif chemokine ligand 1; NM_002995.2) | | CTNS (cystinosin, lysosomal cystine transporter; NM_001031681.2) |
| | IGFBP5 (insulin like growth factor binding protein 5; NM_000599.3) | KIR3DL3 (killer cell immunoglobulin like receptor, three Ig domains and long cytoplasmic tail 3; NM_153443.4) | | | F13A1 (factor XIII a subunit; AH002691.2) |
| | LDB3 (LIM domain binding 3; NM_001171611.1) | KIR3DS1 (killer cell immunoglobulin like receptor, three Ig domains and short cytoplasmic tail 1; NM_001083539.2) | | | FABP4 (fatty acid binding protein 4; NM_001442.2) |

TABLE 4B-continued

Innate immune cell (IIC) gene signature immunomarkers for use in the methods provided herein.

Cell Type

| | | | |
|---|---|---|---|
| LOC643313 (similar to hypothetical protein LOC284701; XM_933043.1) | SPON2 (spondin 2; NM_001199021.1) | | FZD2 (frizzled class receptor 2; NM_001466.3) |
| LOC730096 (hypothetical protein LOC730096; NC_000022.9) | TMEPAI (prostate transmembrane protein, androgen induced 1; NM_199169.2) | | GSTT1 (glutathione S-transferase theta 1; NM_001293814.1) |
| MAPRE3 (microtubule associated protein RP/EB family member 3; NM_001303050.1) | | | GUCA1A (guanylate cyclase activator 1A; NM_001319062.1) |
| MCM3AP (minichromosome maintenance complex component 3 associated protein; NM_003906.4) | | | HS3ST2 (heparan sulfate (glucosamine) 3-O-sulfotransferase 2; NM_006043.1) |
| MRC2 (mannose receptor C type 2; NM_006039.4) | | | LMAN2L (lectin, mannose binding 2 like; NM_001322355.1) |
| NCR1 (natural cytotoxicity triggering receptor 1; NM_001242357.2) | | | MMP12 (matrix metallopeptidase 12; NM_002426.5) |
| NM_014114 (PRO0097 protein; NM_014114.1) | | | MS4A6A (membrane spanning 4-domains A6A; NM_001330275.1) |
| NM_014274 (transient receptor potential cation channel, subfamily V, member 6; NM_014274.3) | | | NM_021941 (chromosome 21 open reading frame 97; NM_021941.1) |
| NM_017616 (KN motif and ankyrin repeat domains 2; NM_015493.6) | | | NUDT9 (nudix hydrolase 9; NM_001248011.1) |
| PDLIM4 (PDZ and LIM domain 4; NM_003687.3) | | | PPARG (peroxisome proliferator activated receptor gamma; NM_005037.5) |
| PRX (periaxin; NM_020956.2) | | | PREP (prolyl endopeptidase; NM_002726.4) |
| PSMD4 (proteasome 26S subunit, non-ATPase 4; NM_001330692.1) | | | RAP1GAP (RAP1 GTPase activating protein; NM_001330383.1) |
| RP5-886K2.1 (neuronal thread protein AD7c-NTP; AF010144.1) | | | SLC26A6 (solute carrier family 26 member 6; NM_001281733.1) |
| SLC30A5 (solute carrier family 30 member 5; NM_001251969.1) | | | SLC7A8 (solute carrier family 7 member 8; NR_049767.1) |
| SMEK1 (protein phosphatase 4 regulatory subunit 3A; NM_001284280.1) | | | SYT17 (synaptotagmin 17; NM_001330509.1) |
| SPN (sialophorin; NM_003123.4) | | | TACSTD2 (tumor-associated calcium signal transducer 2; NM_002353.2) |
| TBXA2R (thromboxane A2 receptor; NM_001060.5) | | | TM7SF4 (dendrocyte expressed seven transmembrane protein; NM_001257317.1) |
| TCTN2 (tectonic family member 2; NM_001143850.2) | | | VASH1 (vasohibin 1; NM_014909.4) |
| TINAGL1 (tubulointerstitial nephritis antigen like | | | |

TABLE 4B-continued

Innate immune cell (IIC) gene signature immunomarkers for use in the methods provided herein.
Cell Type

| | |
|---|---|
| | 1; NM_001204415.1) |
| | XCL1 (X-C motif chemokine ligand 1; NM_002995.2) |
| | XCL2 (X-C motif chemokine ligand 2; NM_003175.3) |
| | ZNF205 (zinc finger protein 205; NM_001278158.1) |
| | ZNF528 (zinc finger protein 528; NM_032423.2) |
| | ZNF747 (zinc finger protein 747; NM_023931.3) |

| | aDC | pDC | Eosinophils | Macrophages | Mast cells | Neutrophils |
|---|---|---|---|---|---|---|
| Human Gene (Gene Name; GenBank Accession No.*) | CCL1 (Chemokine (C_C motif) ligand 1; NM_002981) | IL3RA (interleukin 3 receptor subunit alpha; NM_001267713.1) | ABHD2 (abhydrolase domain containing 2; NM_007011.7) | APOE (apolipoprotein E; NM_ 001302691.1) | ABCC4 (ATP binding cassette subfamily C member 4; NM_001301829.1) | ALPL (alkaline phosphatase, liver/bone/kidney; NM_001127501.3) |
| | EBI3 (Epstein-Barr virus induced 3; NM_005755.2) | | ACACB (acetyl-CoA carboxylase beta; NM_001093.3) | ATG7 (autophagy related 7; NM_ 001144912.1) | ADCYAP1 (adenylate cyclase activating polypeptide 1; NM_001117.4) | BST1 (bone marrow stromal cell antigen 1; NM_004334.2) |
| | INDO (indoleamine-pyrrole 2,3 dioxygenase; AY221100.1) | | C9orf156 (tRNA methyltransferase O; NM_ 001330725.1) | BCAT1 (branched chain amino acid transaminase 1; NM_ 001178094.1) | CALB2 (calbindin 2; NM_001740.4) | CD93 (CD93 molecule; NM_012072.3) |
| | LAMP3 (lysosomal associated membrane protein 3; NM_014398.3) | | CAT (catalase; NM_001752.3) | CCL7 (C-C motif chemokine ligand 7; NM_006273.3) | CEACAM8 (carcinoembryonic antigen related cell adhesion molecule 8; NM_001816.3) | CEACAM3 (carcinoembryonic antigen related cell adhesion molecule 3; NM_001277163.2) |
| | OAS3 (2'-5'-oligoadenylate synthetase 3; NM_006187.3) | | CCR3 (C-C motif chemokine receptor 3; NM_ 178329.2) | CD163 (CD163 molecule; NM_203416.3) | CMA1 (chymase 1, mast cell; NM_001308083.1) | CREB5 (cAMP responsive element binding protein 5; NM_001011666.2) |
| | | | CLC (Charcot-Leyden crystal galectin; NM_001828.5) | CD68 (CD68 molecule; NM_ 001040059.1) | CPA3 (carboxypeptidase A3; NM_001870.3) | CRISPLD2 (cysteine rich secretory protein LCCL domain containing 2; NM_031476.3) |
| | | | CYSLTR2 (cysteinyl leukotriene receptor 2; NM_001308471.1) | CD84 (CD84 molecule; NM_ 001184881.1) | CTSG (cathepsin G; NM_001911.2) | CSF3R (colony stimulating factor 3 receptor; NM_172313.2) |
| | | | EMR1 (EGF-like module containing mucin-like hormone receptor-like 1; DQ217942.1) | CHI3L1 (chitinase 3 like 1; NM_001276.2) | ELA2 (neutrophil elastase; EU617980.1) | CYP4F3 (cytochrome P450 family 4 subfamily F member 3; NM_001199209.1) |
| | | | EPN2 (epsin 2; NM_001102664.1) | CHIT1 (chitinase 1; NM_ 001270509.1) | GATA2 (GATA binding protein 2; NM_001145661.1) | DYSF (dysferlin; NM_001130455.1) |
| | | | GALC (galacto-sylceramidase; NM_000153.3) | CELC5A (C-type lectin domain family 5 member A; NM_ 001301167.1) | HDC (histidine decarboxylase; NM_002112.3) | FCAR (Fc fragment of IgA receptor; NM_133278.3 |
| | | | GPR44 (orphan G protein-coupled receptor; AF118265.1) | COL8A2 (collagen type VII alpha 2 chain; NM_ 001294347.1) | HPGD (hydroxyprostaglandin dehydrogenase 15-(NAD); NM_001256307.1) | FCGR3B (Fc fragment of IgG receptor IIIb; NM_001271035.1) |
| | | | HES1 (hes family bHLH transcription | COLEC12 (collectin | KIT (KIT proto-oncogene receptor | FLJ11151 (hypothetical |

TABLE 4B-continued

Innate immune cell (IIC) gene signature immunomarkers for use in the methods provided herein.
Cell Type

| | | | |
|---|---|---|---|
| factor 1; NM_005524.3) | subfamily member 12; NM_130386.2) | tyrosine kinase; NM_000222.2) | protein FLJ11151; BC006289.2) |
| HIST1H1C (histone cluster 1 H1 family member c; NM_005319.3) | CTSK (cathepsin K; NM_000396.3) | LOC339524 (long intergenic non-protein coding RNA 1140; NR_026985.1) | FPR1 (formyl peptide receptor 1; NM_001193306.1) |
| HRH4 (histamine receptor H4; NM_001143828.1) | CXCL5 (C-X-C motif chemokine ligand 5; NM_002994.4) | LOH11CR2A (BCSC-1 isoform; AY366508.1) | FPRL1 (formyl peptide receptor-like receptor; M84562.1) |
| IGSF2 (immunoglobulin superfamily, member 2; BC130327.1) | CYBB (cytochrome b-245 beta chain; NM_000397.3) | MOAB (monoamine oxidase B; NM_000898.4) | G0S2 (G0/G1 switch 2; NM_015714.3) |
| IL5RA (interleukin 5 receptor subunit alpha; NM_001243099.1) | DNASE2B (de-oxyribonuclease 2 beta; NM_058248.1) | MLPH (melanophilin; NM_001042467.2) | HIST1H2BC (histone cluster 1 H2B family member c; NM_03526.2) |
| KBTBD11 (kelch repeat and BTB domain containing 11; NM_014867.2) | EMP1 (epithelial membrane protein 1; NM_001423.2) | MPO (myeloperoxidase; NM_000250.1) | HPSE (heparanase; NM_001098540.2) |
| KCNH2 (potassium voltage-gated channel, subfamily H (eag-related), member 2; NM_000238.3) | FDX1 (ferredoxin 1; NM_004109.4) | MS4A2 (membrane spanning 4-domains A2; NM_001256916.1) | IL8RA (interleukin 8 receptor alpha; L19591.1) |
| LRP5L (LDL receptor related protein 5 like; NM_001135772.1) | FN1 (fibronectin 1; NM_ 001306131.1) | NM_003293 (tryptase alpha/beta 1; NM_003294.3) | IL8RB (interleukin-8 receptor type B; U11878.1) |
| MYO15B (myosin XVB; NM_001309242.1) | GM2A (GM2 ganglioside activator; NM_000405.4) | NR0B1 (nuclear receptor subfamily 0 group B member 1; NM_000475.4) | KCNJ15 (potassium voltage-gated channel subfamily J member 15; NM_001276438.1) |
| RCOR3 (REST corepressor 3; NM_001136224.2) | GPC4 (glypican 4; NM_001448.2) | PGDS (hematopoietic prostaglandin D synthase; NM_014485.2) | KIAA0329 (tectonin beta-propeller repeat containing 2; NM_014844.4) |
| RNASE2 (ribonuclease A family member 2; NM_002934.2 | KAL1 (anosmin 1; NM_000216.3) | PPM1H (protein phosphatase, Mg2+/Mn2+ dependent 1H; NM_020700.1) | LILRB2 (leukocyte immunoglobulin like receptor B2; NR_103521.2) |
| RNU2 (U2 snRNA; U57614.1) | MARCO (macrophage receptor with collagenous structure; NM_006770.3) | PRG2 (proteoglycan 2, pro eosinophil major basic protein; NM_001302927.1) | MGAM (maltase-glucoamylase; NM_004668.2) |
| RRP12 (ribosomal RNA processing 12 homolog; NM_001284337.1) | ME1 (malic enzyme 1; NM_002395.5) | PTGS1 (prostaglandin-endoperoxide synthase 1; NM_000962.3) | MME (membrane metalloendo-peptidase; NM_007289.2) |
| SIAH1 (siah E3 ubiquitin protein ligase 1; NM_003031.3) | MS4A4A (membrane spanning 4-domains A4A; NM_ 001243266.1) | SCG2 (secretogranin II; NM_003469.4) | PDE4B (phosphodiesterase 4B; NM_ 001297440.1) |
| SMPD3 (sphingomyelin phosphodiesterase 3; NM_018667.3) | MSR1 (macrophage scavenger receptor 1; NM_138716.2) | SIGLEC6 (sialic acid binging Ig like lectin 6; NM_198845.5) | S100A12 (S100 calcium binding protein A12; NM_005621.1) |
| SYNJ1 (synaptojanin 1; NM_001160302.1) | PCOLCE2 (procollagen C-endopeptidase enhancer 2; NM_013363.3) | SLC18A2 (solute carrier family 18 member A2; NM_003054.4) | SIGLEC5 (sialic acid binding Ig like lectin 5; NM_003830.3) |

TABLE 4B-continued

Innate immune cell (IIC) gene signature immunomarkers for use in the methods provided herein.

| Cell Type | | | | |
|---|---|---|---|---|
| | TGIF1 (TGFB induced factor homeobox 1; NM_174886.2) | PTGDS (prostaglandin D2 synthase; NM_000954.5) | SLC24A3 (solute carrier family 24 member 3; NM_020689.3) | SLC22A4 (solute carrier family 22 member 4; NM_003059.2) |
| | THBS1 (thrombospondin 1; NM_003246.3) | RAI14 (retinoic acid induced 14; NM_ 001145525.1) | TAL1 (T-cell acute lymphocytic leukemia 1; X51990.1) | SLC25A37 (solute carrier family 25 member 37; NM_001317812.1) |
| | THBS4 (thrombospondin 4; NM_ 001306213.1) | SCARB2 (scavenger receptor class B member 2; NM_ 001204255.1) | TPSAB1 (tryptase alpha/beta 1; NM_003294.3) | TNFRSF10C (TNF receptor superfamily member 10c; NM_003841.3) |
| | TIPARP (TCDD inducible poly (ADP-ribose) polymerase; NM_001184718.1) | SCG5 (secretogranin V; NM_ 001144757.2) | TPSB2 (tryptase beta 2; NM_024164.5) | VNN3 (vanin 3; NM_001291703.1) |
| | TKTL1 (transketolase like 1; NM_001145934.1) | SGMS1 (sphingomyelin synthase 1; NM_147156.3) | | |
| | | SULT1C2 (sulfotransferase family 1C member 2; NM_176825.2) | | |

*Each GenBank Accession Number is a representative or exemplary GenBank Accession Number for the listed gene and is herein incorporated by reference in its entirety for all purposes. Further, each listed representative or exemplary accession number should not be construed to limit the claims to the specific accession number.

TABLE 5

Individual Immunomarkers for use in the methods provided herein.

| Gene Name | Abbreviation | GenBank Accession No.* |
|---|---|---|
| Programmed Death Ligand 1 | PDL1 | NM_014143 |
| programmed death ligand 2 | PDL2 | AY254343 |
| programmed cell death 1 | PDCD1 | NM_005018 |
| cytotoxic T-lymphocyte associated protein 4 | CTLA4 | NM_005214 |

*Each GenBank Accession Number is a representative or exemplary GenBank Accession Number for the listed gene and is herein incorporated by reference in its entirety for all purposes. Further, each listed representative or exemplary accession number should not be construed to limit the claims to the specific accession number.

TABLE 6

Interferon (IFN) Genes for use in the methods provided herein.

| Gene Name | Abbreviation | GenBank Accession No.* |
|---|---|---|
| Chemokine (C-X-C Motif) Ligand 10 | CXCL10 | NM_001565 |
| C-X-C motif chemokine ligand 9 | CXCL9 | NM_002416 |
| interferon alpha inducible protein 27 | IFI27 | NM_001130080 |
| interferon induced protein with tetratricopeptide repeats 1 | IFIT1 | NM_001548 |
| interferon induced protein with tetratricopeptide repeats 2 | IFIT2 | NM_001547 |
| interferon induced protein with tetratricopeptide repeats 3 | IFIT3 | NM_001549 |
| MX dynamin like GTPase 1 | MX1 | NM_001144925 |
| MX dynamin like GTPase 2 | MX2 | XM_005260983 |
| 2'-5'-oligoadenylate synthetase 1 | OAS1 | NM_016816 |

TABLE 6-continued

Interferon (IFN) Genes for use in the methods provided herein.

| Gene Name | Abbreviation | GenBank Accession No.* |
|---|---|---|
| 2'-5'-oligoadenylate synthetase 2 | OAS2 | NM_016817 |
| signal transducer and activator of transcription 1 | STAT1 | NM_007315 |
| signal transducer and activator of transcription 2 | STAT2 | NM_005419 |

*Each GenBank Accession Number is a representative or exemplary GenBank Accession Number for the listed gene and is herein incorporated by reference in its entirety for all purposes. Further, each listed representative or exemplary accession number should not be construed to limit the claims to the specific accession number.

TABLE 7

MHC class II genes for use in the methods provided herein.

| Name | Abbreviation | GenBank Accession No.* |
|---|---|---|
| CD74 | *Homo sapiens* CD74 molecule (CD74) | NM_001025159 |
| CIITA | class II major histocompatibility complex transactivator | NM_001286402 |
| CTSH | cathepsin H | NM_004390 |
| HLA-DMA | *Homo sapiens* major histocompatibility complex, class II, DM alpha | NM_006120 |
| HLA-DPA1 | *Homo sapiens* major histocompatibility complex, class II, DP alpha 1 | NM_033554 |
| HLA-DPB1 | Human MHC class II lymphocyte antigen (HLA-DP) beta chain | M83664 |
| HLA-DQA1 | *Homo sapiens* major histocompatibility complex, class II, DQ alpha 1 | NM_002122 |
| HLA-DRB1 | *Homo sapiens* major histocompatibility complex, class II, DR beta 1 | NM_002124 |
| HLA-DRB5 | *Homo sapiens* major histocompatibility complex, class II, DR beta 5 | NM_002125 |

TABLE 7-continued

MHC class II genes for use in the methods provided herein.

| Name | Abbreviation | GenBank Accession No.* |
|---|---|---|
| HLA-DRB6 | *Homo sapiens* major histocompatibility complex, class II, DR beta 6 | NR_001298 |
| NCOA1 | *Homo sapiens* nuclear receptor coactivator 1 | NM_003743 |

*Each GenBank Accession Number is a representative or exemplary GenBank Accession Number for the listed gene and is herein incorporated by reference in its entirety for all purposes. Further, each listed representative or exemplary accession number should not be construed to limit the claims to the specific accession number.

In one embodiment, upon determining a patient's AD lung cancer subtype using any of the methods and classifier biomarkers panels or subsets thereof as provided herein alone or in combination with determining expression of one or more immune cell markers as provided herein, the patient is selected for treatment with or administered an immunotherapeutic agent. The immunotherapeutic agent can be a checkpoint inhibitor, monoclonal antibody, biological response modifiers, therapeutic vaccine or cellular immunotherapy.

In another embodiment, the immunotherapeutic agent is a checkpoint inhibitor. In some cases, a method for determining the likelihood of response to one or more checkpoint inhibitors is provided. In one embodiment, the checkpoint inhibitor is a PD-1/PD-LI checkpoint inhibitor. The PD-1/PD-LI checkpoint inhibitor can be nivolumab, pembrolizumab, atezolizumab, durvalumab, lambrolizumab, or avelumab. In one embodiment, the checkpoint inhibitor is a CTLA-4 checkpoint inhibitor. The CTLA-4 checkpoint inhibitor can be ipilimumab or tremelimumab. In one embodiment, the checkpoint inhibitor is a combination of checkpoint inhibitors such as, for example, a combination of one or more PD-1/PD-LI checkpoint inhibitors used in combination with one or more CTLA-4 checkpoint inhibitors.

In one embodiment, the immunotherapeutic agent is a monoclonal antibody. In some cases, a method for determining the likelihood of response to one or more monoclonal antibodies is provided. The monoclonal antibody can be directed against tumor cells or directed against tumor products. The monoclonal antibody can be panitumumab, matuzumab, necitumunab, trastuzumab, amatuximab, bevacizumab, ramucirumab, bavituximab, patritumab, rilotumumab, cetuximab, immu-132, or demcizumab.

In yet another embodiment, the immunotherapeutic agent is a therapeutic vaccine. In some cases, a method for determining the likelihood of response to one or more therapeutic vaccines is provided. The therapeutic vaccine can be a peptide or tumor cell vaccine. The vaccine can target MAGE-3 antigens, NY-ESO-1 antigens, p53 antigens, survivin antigens, or MUC1 antigens. The therapeutic cancer vaccine can be GVAX (GM-CSF gene-transfected tumor cell vaccine), belagenpumatucel-L (allogeneic tumor cell vaccine made with four irradiated NSCLC cell lines modified with TGF-beta2 antisense plasmid), MAGE-A3 vaccine (composed of MAGE-A3 protein and adjuvant AS15), (1)-BLP-25 anti-MUC-1 (targets MUC-1 expressed on tumor cells), CimaVax EGF (vaccine composed of human recombinant Epidermal Growth Factor (EGF) conjugated to a carrier protein), WT1 peptide vaccine (composed of four Wilms' tumor suppressor gene analogue peptides), CRS-207 (live-attenuated *Listeria monocytogenes* vector encoding human mesothelin), Bec2/BCG (induces anti-GD3 antibodies), GV1001 (targets the human telomerase reverse transcriptase), tergenpumatucel-L (consists of human lung cancer cells genetically modified to include a mouse gene to which the immune system responds strongly), TG4010 (targets the MUC1 antigen), racotumomab (anti-idiotypic antibody which mimicks the NGcGM3 ganglioside that is expressed on multiple human cancers), tecemotide (liposomal BLP25; liposome-based vaccine made from tandem repeat region of MUC1) or DRibbles (a vaccine made from nine cancer antigens plus TLR adjuvants).

In one embodiment, the immunotherapeutic agent is a biological response modifier. In some cases, a method for determining the likelihood of response to one or more biological response modifiers is provided. The biological response modifier can trigger inflammation such as, for example, PF-3512676 (CpG 7909) (a toll-like receptor 9 agonist), CpG-ODN 2006 (downregulates Tregs), *Bacillus* Calmette-Guerin (BCG), *mycobacterium* vaccae (SRL172) (nonspecific immune stimulants now often tested as adjuvants). The biological response modifier can be cytokine therapy such as, for example, IL-2+ tumor necrosis factor alpha (TNF-alpha) or interferon alpha (induces T-cell proliferation), interferon gamma (induces tumor cell apoptosis), or Mda-7 (IL-24) (Mda-7/IL-24 induces tumor cell apoptosis and inhibits tumor angiogenesis). The biological response modifier can be a colony-stimulating factor such as, for example granulocyte colony-stimulating factor. The biological response modifier can be a multi-modal effector such as, for example, multi-target VEGFR: thalidomide and analogues such as lenalidomide and pomalidomide, cyclophosphamide, cyclosporine, denileukin diftitox, talactoferrin, trabecetedin or all-trans-retinmoic acid.

In one embodiment, the immunotherapy is cellular immunotherapy. In some cases, a method for determining the likelihood of response to one or more cellular therapeutic agents. The cellular immunotherapeutic agent can be dendritic cells (DCs) (ex vivo generated DC-vaccines loaded with tumor antigens), T-cells (ex vivo generated lymphokine-activated killer cells; cytokine-induce killer cells; activated T-cells; gamma delta T-cells), or natural killer cells.

In some cases, specific subtypes of AD have different levels of immune activation (e.g., innate immunity and/or adaptive immunity) such that subtypes with elevated or detectable immune activation (e.g., innate immunity and/or adaptive immunity) are selected for treatment with one or more immunotherapeutic agents described herein. In one embodiment, the PP subtype of AD has low immune activation (e.g., innate immunity and/or adaptive immunity) as compared to other AD subtypes or lung cancer subtypes. In some cases, specific subtypes of AD have high or elevated levels of immune activation. In some cases, the PI subtype of AD has elevated levels of immune activation (e.g., innate immunity and/or adaptive immunity) as compared to other AD subtypes or lung cancer subtypes. In one embodiment, AD subtypes with low levels of or no immune activation (e.g., innate immunity and/or adaptive immunity) are not selected for treatment with one or more immunotherapeutic agents described herein.

Detection Methods

In one embodiment, the methods and compositions provided herein allow for the detection of at least one nucleic acid in a lung cancer sample (e.g. adenocarcinoma lung cancer sample) obtained from a subject. The at least one nucleic acid can be a classifier biomarker provided herein. In one embodiment, the at least one nucleic acid detected using the methods and compositions provided herein are selected from Table 1. In one embodiment, the methods of detecting the nucleic acid(s) (e.g., classifier biomarkers) in the lung cancer sample obtained from the subject comprises, consists essentially of, or consists of measuring the expression level of at least one or a plurality of biomarkers using any of the methods provided herein. The biomarkers can be selected from Table 1. In some cases, the plurality of biomarker nucleic acids comprises, consists essentially of or consists of at least two biomarker nucleic acids, at least 8 biomarker nucleic acids, at least 16 biomarker nucleic acids, at least 24 biomarker nucleic acids, at least 32 biomarker nucleic acids, or all 48 biomarkers nucleic acids of Table 1. The detection can be at the nucleic acid level. The detection can be by using any amplification, hybridization and/or sequencing assay disclosed herein.

In another embodiment, the methods and compositions provided herein allow for the detection of at least one nucleic acid or a plurality of nucleic acids in a lung cancer sample (e.g. adenocarcinoma lung cancer sample) obtained from a subject such that the at least one nucleic acid is or the plurality of nucleic acids are selected from the biomarkers listed in Table 1 and the detection of at least one biomarker from a set of biomarkers whose presence, absence and/or level of expression is indicative of immune activation. The set of biomarkers for indicating immune activation can be gene expression signatures of and/or Adaptive Immune Cells (AIC) (e.g., Table 4A) and/or Innate Immune Cells (IIC) (e.g., Table 4B), individual immune biomarkers (e.g., Table 5), interferon genes (e.g., Table 6), major histocompatibility complex, class II (MHC II) genes (e.g., Table 7) or a combination thereof. The gene expression signatures of both IC and AIC can be any gene signatures known in the art such as, for example, the gene signature listed in Bindea et al. (Immunity 2013; 39(4); 782-795). The detection can be at the nucleic acid level. The detection can be by using any amplification, hybridization and/or sequencing assay disclosed herein.

Kits

Kits for practicing the methods of the invention can be further provided. By "kit" can encompass any manufacture (e.g., a package or a container) comprising at least one reagent, e.g., an antibody, a nucleic acid probe or primer, etc., for specifically detecting the expression of a biomarker of the invention. The kit may be promoted, distributed, or sold as a unit for performing the methods of the present invention. Additionally, the kits may contain a package insert describing the kit and methods for its use.

In one embodiment, kits for practicing the methods of the invention are provided. Such kits are compatible with both manual and automated immunocytochemistry techniques (e.g., cell staining). These kits comprise at least one antibody directed to a biomarker of interest, chemicals for the detection of antibody binding to the biomarker, a counterstain, and, optionally, a bluing agent to facilitate identification of positive staining cells. Any chemicals that detect antigen-antibody binding may be used in the practice of the invention. The kits may comprise at least 2, at least 3, at least 4, at least 5, at least 6, at least 7, at least 8, at least 9, at least 10, or more antibodies for use in the methods of the invention.

EXAMPLES

The present invention is further illustrated by reference to the following Examples. However, it should be noted that these Examples, like the embodiments described above, are illustrative and are not to be construed as restricting the scope of the invention in any way.

Example 1—Immune Cell Activation Differences Among Lung Adenocarcinoma

Intrinsic Subtypes and Variable Correlation with CD274 (PD-L1) Expression.

INTRODUCTION

Gene expression based subtyping in Lung Adenocarcinoma (AD) classifies AD tumors into distinct subtypes with variable biologic and clinical features. Gene expression based subtyping has consistently identified 3 distinct biologic types in Lung AD, Terminal Respiratory Unit (TRU), formerly Bronchioid, Proximal Proliferative (PP), formerly Magnoid, and Proximal Inflammatory (PI), formerly Squamoid (1,2)) (see FIG. 1). AD subtypes demonstrate key differences in genomic alterations, tumor drivers, prognosis, and likely response to various therapies (1-2).

Methods

Using previously published Bindea et al. (3) immune cell gene signatures (24 in total) and AD subtyping gene expression signatures (1-2), several publically available lung AD datasets (2, 4 and 5) and 1 recently collected gene expression dataset (see FIG. 2), were examined for immune cell features in relation to AD subtypes. This investigation of immune differences by subtype used the 24 immune cell gene signatures from Bindea et al [3] that each had a varying number of genes and were classified as adaptive or innate immunity cell signatures (see Table 4A-4B). Adaptive Immune Cell (AIC) signatures (Table 4A) included Tcells, Central Memory T cells (Tcm), Effector Memory T cells (Tem), T helper cell (Th), Type 1 T helper cells (Th1), Type 2 T helper cells (Th2), T follicular helper cells (Tfh), T helper 17 cells (Th17), T Regulatory Cells (Treg), Gamma Delta T cells (Tgd), CD8 Tcells, Cytotoxic T cells, B cells, and Innate Immune Cell (IIC) signatures (Table 4B) included Natural Killer (NK), NK CD56dim cells, NK CD56bright cells, Dendritic cells (DC), Immature Dendritic Cells (iDC), Dendritic Cells (pDC), Activated Dendritic Cells (aDC), Mast cells, Eosinophils, Macrophages, and Neutrophils. In addition to the gene expression signatures of both Innate Immune Cells (IIC) and Adaptive Immune Cells (AIC), a 13 gene IFN signature (IFN; Table 6), a 13-gene MHC class II signature score (Forero [6]; Table 7) as well as single gene immune biomarkers in Table 5 (CTLA4, PDCD1, CD274 (PD-L1), and PDCDLG2 (PD-L2)) were examined in the 3 AD subtypes (TRU, PP, and PI)

The AD datasets included several publically available lung cancer gene expression data sets as described above and a newly collected adenocarcinoma dataset of Formalin Fixed Paraffin Embedded (FFPE) lung tumor samples (n=88). The newly collected AD dataset of 88 formalin fixed paraffin embedded (FFPE) samples were archived residual lung tumor samples collected under an approved IRB protocol at the University of North Carolina at Chapel Hill (UNC-CH). FFPE sample sections (3 10 um sections) were macrodissected prior to RNA extraction. Transcriptome-enriched RNAseq was performed using Illumina's RNA-Access kits (San Diego, CA) with input of 100 ng/sample. Sequence data was aligned using hg19 as reference and the transcriptome was built using cufflinks (Trapnell 2010). Cuff compare was used to annotate the transcriptome and gene expression counts were calculated.

For AD, 4 published and 1 recently collected gene expression data sets (i.e., GeneCentric expression data set) of lung adenocarcinoma samples with a total of 1278 patient samples were used. The published data sets included TCGA [2], Shedden et al [4], Tomida et al [5], and Wilkerson et al [1], derived from fresh frozen specimens. The GeneCentric expression data set was derived from Formalin Fixed Paraffin Embedded (FFPE) specimens. For TCGA, upper quantile normalized RSEM data was downloaded from Firehose and log 2 transformed. Affymetrix Cel files from Shedden et al [4] were downloaded from the caIntegrator website and robust multi-array average expression measures were generated using the Affy package in R. Normalized Agilent array data was downloaded from the Gene Expression Omnibus (GEO) website for Tomida et al [5] (GSE13213) and Wilkerson et al [1] (GSE26939).

To determine adenocarcinoma subtype (TRU, PP, and PI), the published 506-gene nearest centroid classifier as described previously in Wilkerson et al [1] was used. After median centering of genes in the signature, each sample was assigned the subtype corresponding to the centroid with which it was maximally correlated. (Pearson)

Figure 3:
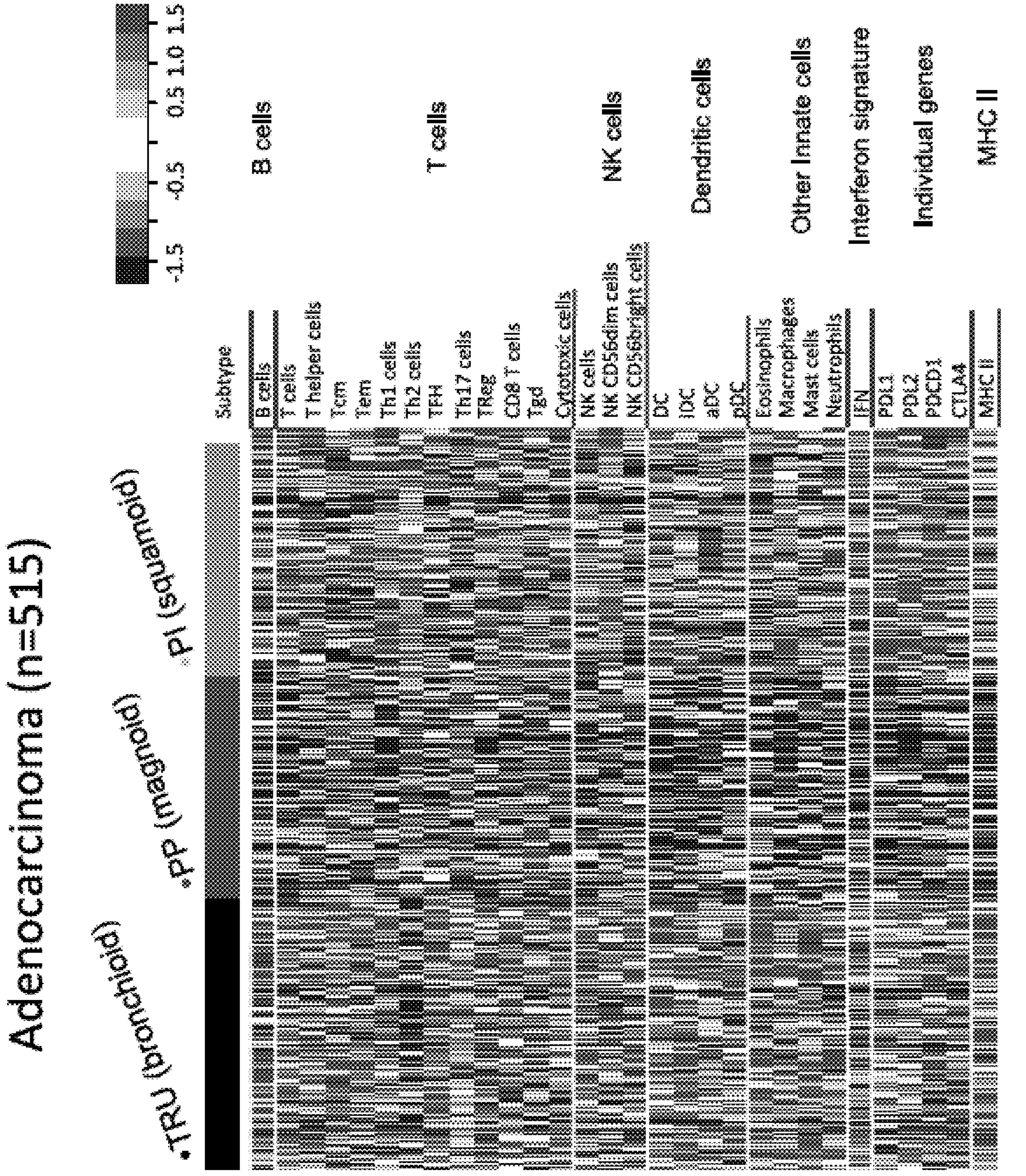
FIG. 3 illustrates a heatmap of immune cell signatures expression (i.e., Bindea et al reference from Example 1), other immune markers and individual immune markers in the Cancer Genome Atlas (TCGA) Lung AD dataset. TRU=Terminal Respiratory Unit, PP=Proximal Proliferative, PI=Proximal Inflammatory.
Figure 4:
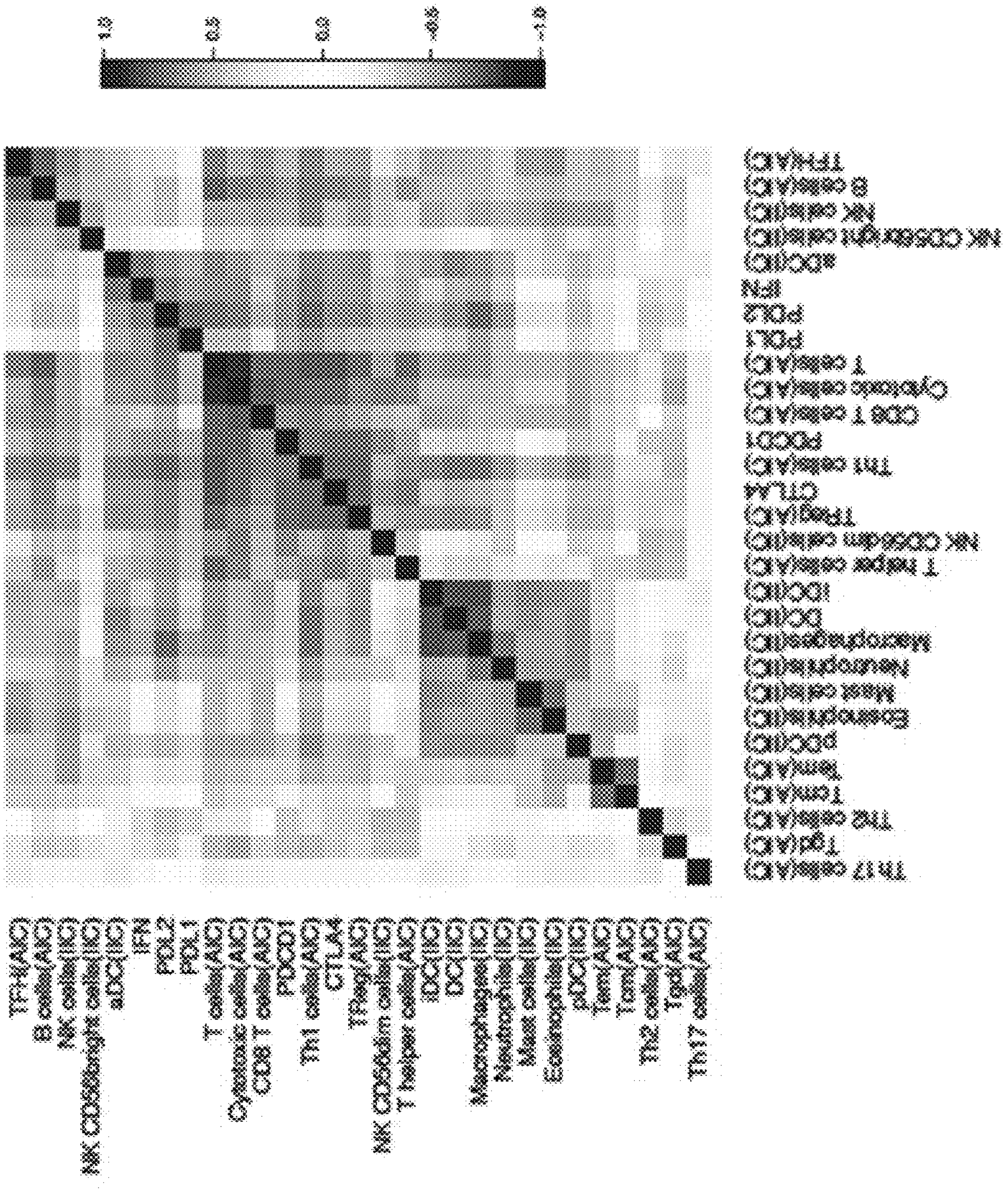
FIG. 4 illustrates correlation matrices of immune cell signatures in the TCGA AD dataset where signatures were arranged by hierarchical clustering. White means no correlation.

Using the TCGA data for adenocarcinoma, correlations were assessed among the 30 markers by plotting matrices of pairwise Spearman rank correlation coefficients where markers were ordered by hierarchical clustering (see FIG. 4). To investigate overall immunity marker trends by subtype, expression heatmaps were plotted where samples were arranged by subtype and markers were grouped according to ordering in Bindea et al [3] (see FIG. 3). To evaluate the reproducibility of immunity marker differences among the subtypes, normalized T cell signatures were plotted by subtype for each data set (see FIG. 5).

Immune cell signature associations with tumor subtype and with CD274 expression were evaluated using linear regression. More specifically, to assess the prediction strength of subtype as a predictor of immune markers relative to that of PD-L1, a linear regression model of each signature with subtype the sole predictor, and again with PD-L1 the sole predictor, was fitted in the TCGA dataset. PD-L1 expression was treated as a low/medium/high categorical variable with equal proportions in each group. Scatter plots of adjusted R-squared when subtype was the predictor against adjusted R-squared when PD-L1 was the predictor were inspected for overall trends (see FIG. 6).

Using non-silent mutation burden per Mb data, available in the supplementary information from TCGA adenocarcinoma (Lawrence 2013), mutation burden-Tcell expression associations was investigated using the Kruskal Wallis test and the Spearman correlation coefficients, respectively. For TCGA adenocarcinoma, STK11 CNV and mutation status were downloaded from Firehose, and STK11 inactivation-subtype association was evaluated using Fisher's exact test. Here, a sample was called inactive when it was reported as deleted and/or mutated. To test whether STK11 in AD showed evidence of association after adjusting for subtype, a linear model for Tcell expression was fit with inactive STK11 in AD as sole predictors and again following adjustment for subtype.

Subtype and immune signature associations with a 13-gene MHC class II signature [Forero [6]; Table 7], calculated as an average of all genes in the list (Table 7), were investigated using the Kruskal-Wallis test. For immune signature-MHC class II associations, Spearman correlation coefficients were calculated.

Hierarchical clustering of immune signatures and pairwise signature correlations were also analyzed. Survival signature associations of Stages I-III samples were evaluated with stratified cox proportional hazard models allowing for different baseline hazards in each dataset. More specifically, immune marker-survival associations in the TCGA data sets were tested, overall and separately within each subtype, using Cox proportional hazards models. Immune markers were centered and scaled to have mean 0 and variance 1, and stage IV patients were excluded. Evaluations within a specific subtype adjusted for stage, and overall evaluations adjusted for both stage and subtype. Forest plots showing hazard ratios and confidence intervals for each signature were made (see FIGS. 7A and 7B). All statistical analyses were conducted using R 3.2.0 software (http://www.R-project.org).

Results

Figure 18:
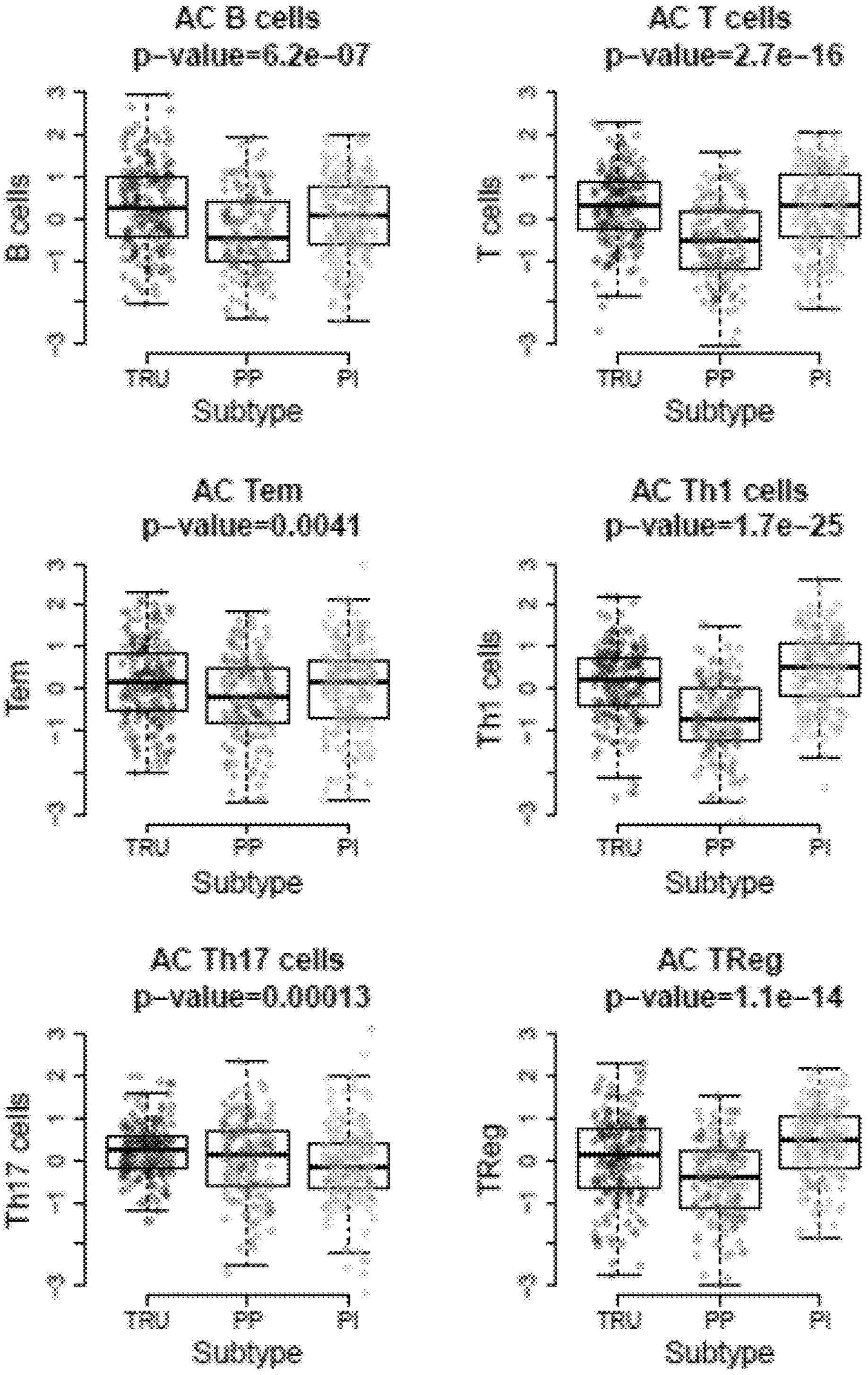
FIG. 18 illustrates box plots of all the immune cells and immunomarkers (i.e., IFN genes, MHCII genes and individual immunomarkers PDL1, PDL2, PDCD1 and CTLA4) by AD. TRU=Terminal Respiratory Unit, PP=Proximal Proliferative, PI=Proximal Inflammatory. AC=adenocarcinoma.
Figure 18:
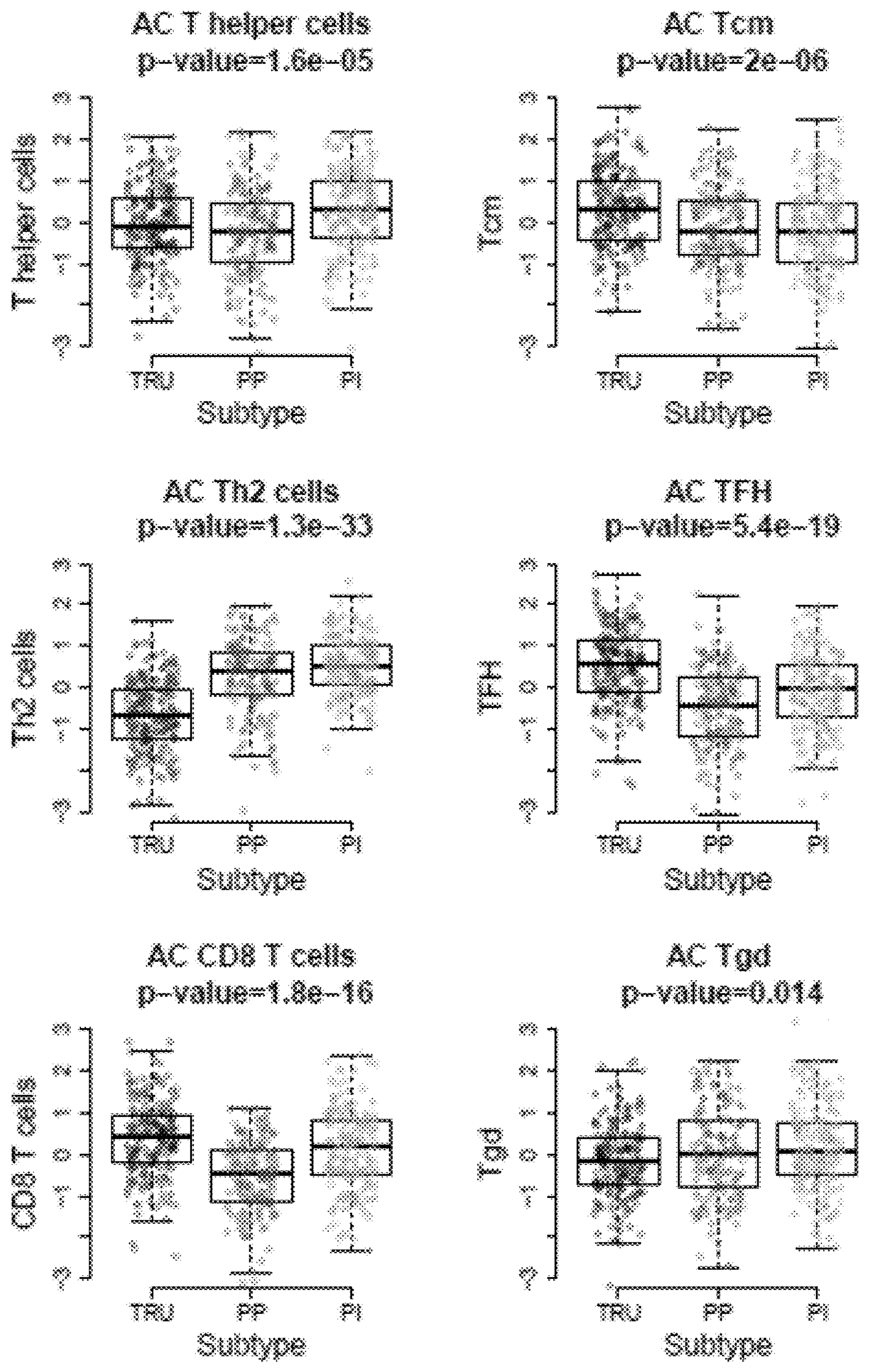
Figure 18:
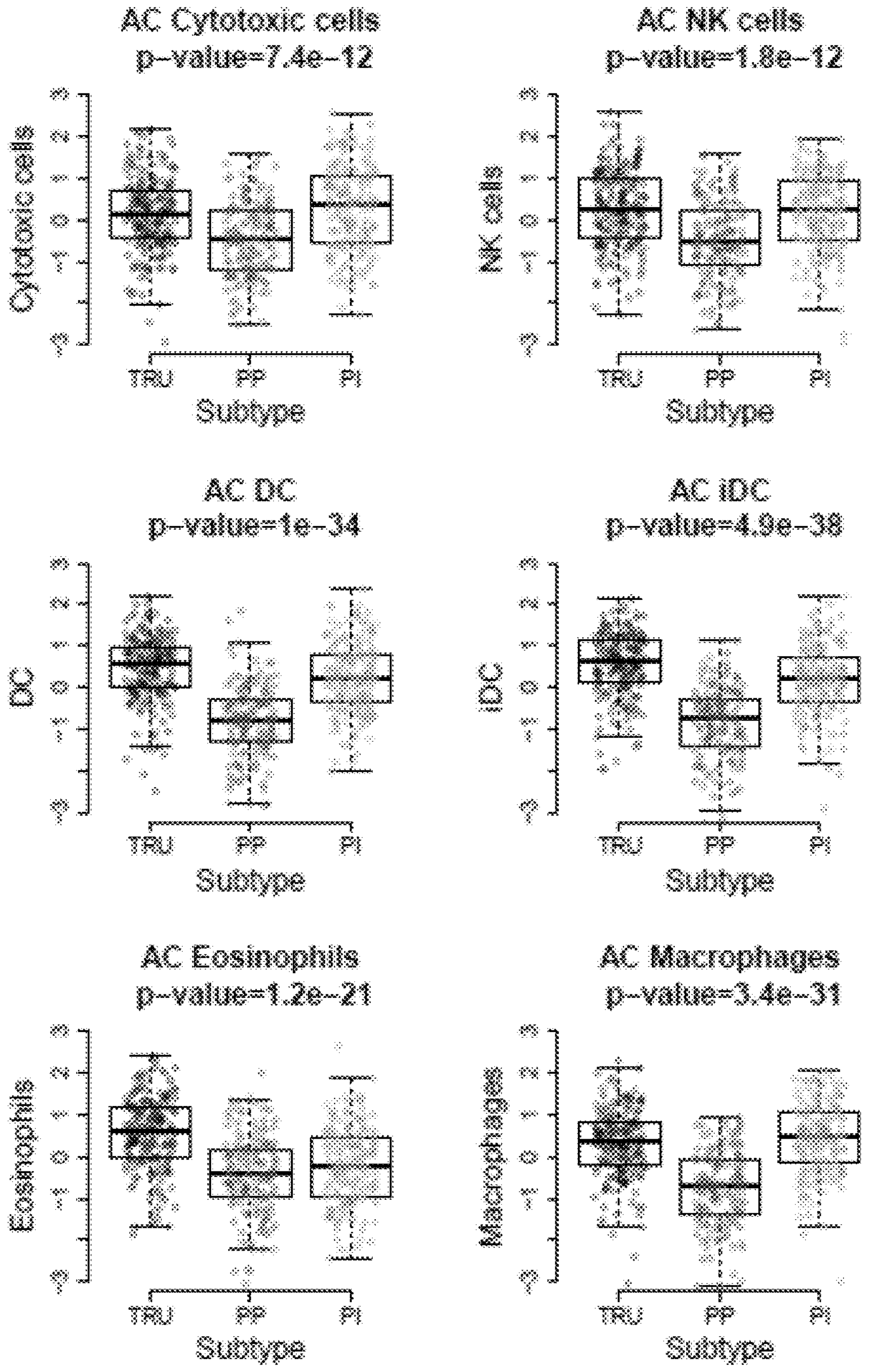
Figure 18:
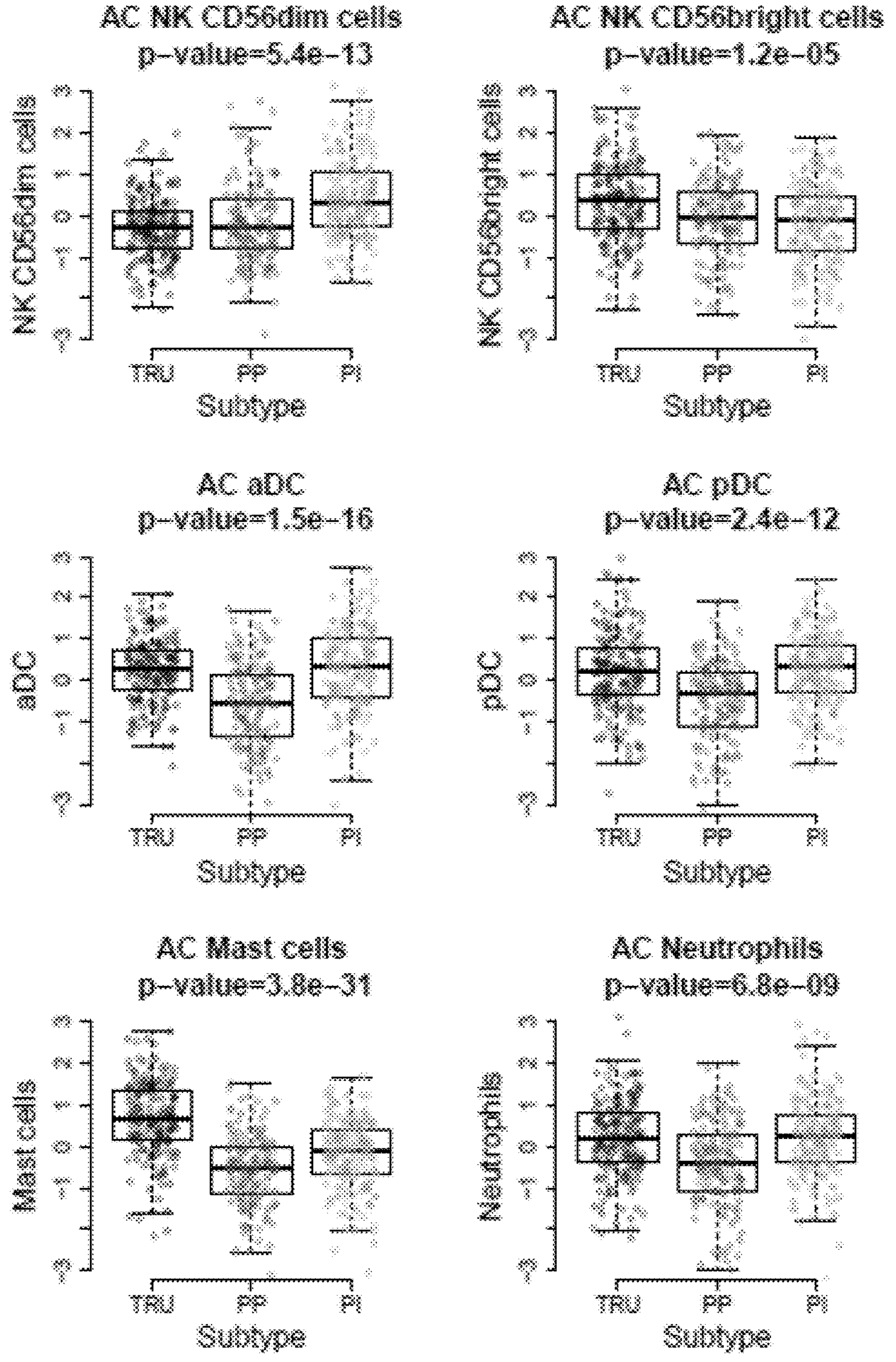
Figure 18:
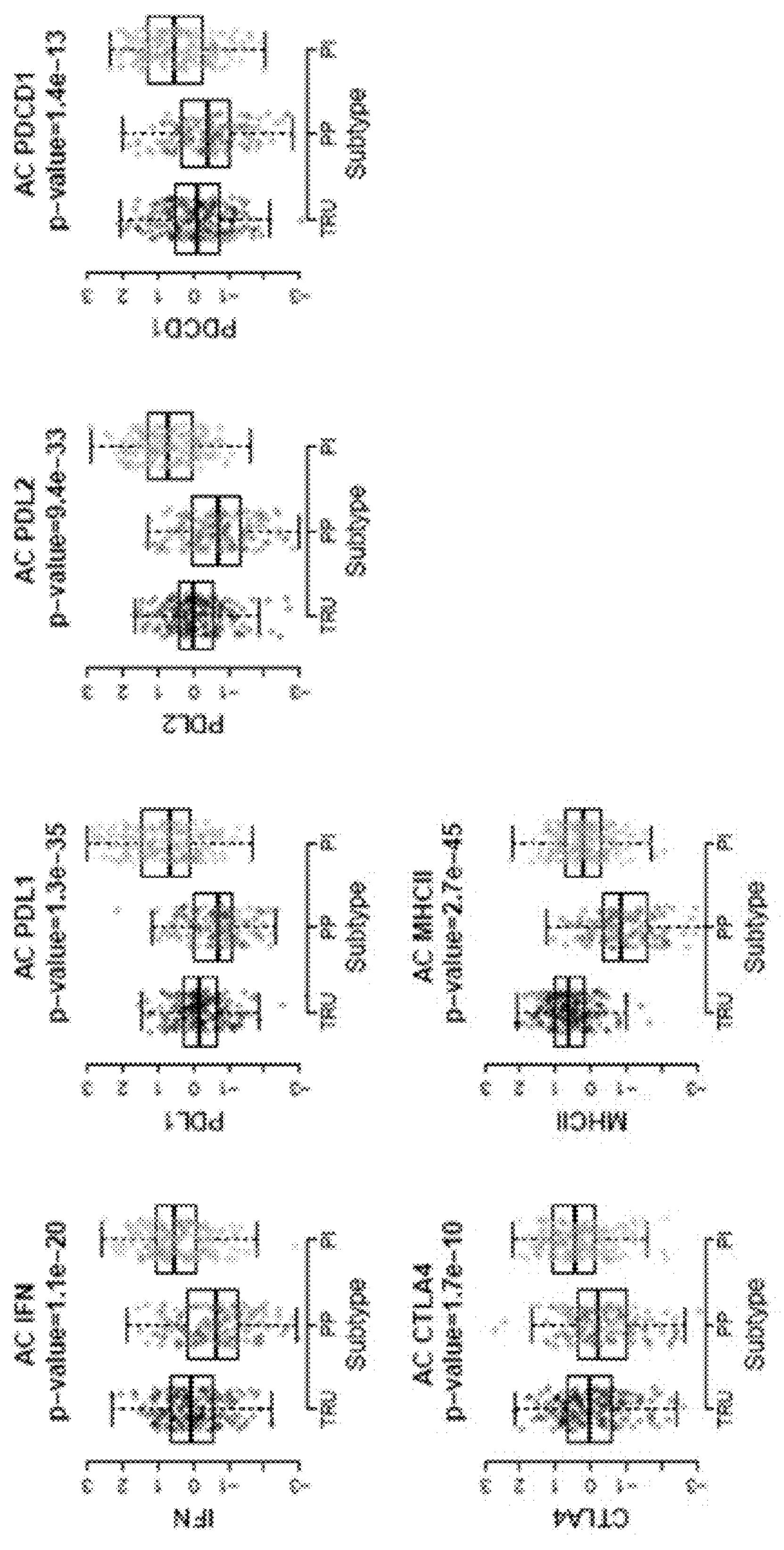

Heatmap analysis and unsupervised hierarchical clustering of immune cell gene signatures provided separation of intrinsic subtypes of AD (see FIGS. 3 and 4). Examination of Immune cell gene signatures (both AIC and IIC) as well as individual immune gene markers revealed clear differences among the AD subtypes (see FIG. 3). In AD, immune expression was consistently lower in the PP subtype for most cell types examined. Expression was similar in TRU and PI for most T cells but could be differentiated between TRU and PI by greater expression of some innate immune cells (dendritic cells, NK CD56bright, mast cells, eosinophils) and several adaptive immune cells (Bcells, TFH, Tcm, Th17, CD8 Tcells) in the TRU subtype, while the PI subtype showed higher expression of Th1 and Th2, Treg, cytotoxic Tcells and NKCD56dim cells (box plots of all the immune cells and markers by AD subtype can be found in FIG. 18). Immunotherapy targets, CTLA4 and CD274 (PD-L1), demonstrated consistently higher expression in the PI subtype across multiple datasets (box plot supplemental FIG. 18). In the PP tumors, both adaptive and innate immune cells expression as well as immunotherapy target expression was depressed relative to other AD. (FIG. 18).

Overall, immune activation was most prominent in the PI subtype of AD demonstrating activation of both innate as well as adaptive immune cells. In contrast, the PP subtype of AD demonstrated lower immune activation.

Using hierarchical clustering, correlation matrices revealed clustering of adaptive immune cells and innate immune cells (see FIG. 4). In AD, adaptive immune features such as T cells, cytotoxic cells, CD8 cells, Th1 cells, PDCD1, CTLA4, and Tregs had high pairwise correlations and similarly for innate immune cells, including iDC, DC, macrophages, neutrophils, mast cells, and eosinophils are correlated (FIG. 4).

Figure 6:
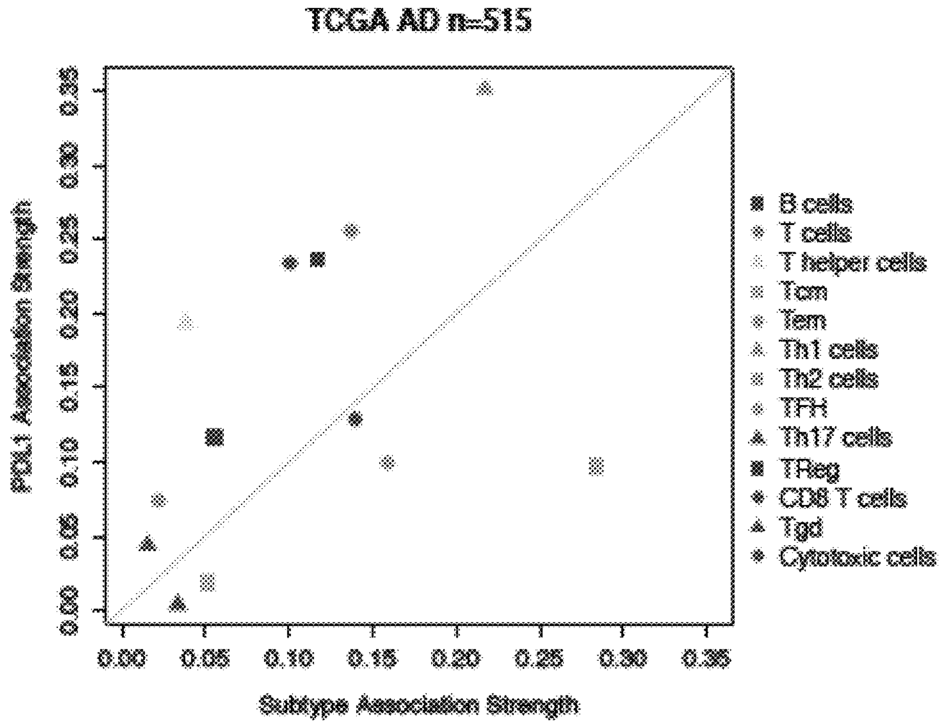
FIG. 6 illustrates association (adjusted R-squared) between CD274 (PD-L1) expression and adaptive immune cell (AIC) signatures in an Adenocarcinoma (AD) evaluation of the TCGA dataset. Association was consistently greater for subtypes than for PD-L1. Tcm=:central memory T cells, Tem==Effector Memory T cells, Th1==Type 1 T helper cells, Th2=Type 2 T helper cells, TFH=T follicular helper cells, Th17=T helper 17 cells, Treg=Tregulatory cells, Tgd===Gamma Delta Tcells.

Strength of association of CD274 (PD-L1) expression with adaptive immune cell signatures, as compared to AD subtype was conducted. As shown in FIG. 6, for AD subtypes, association strengths (adjusted R squared) were mixed showing CD274 association greater for some cells (Bcells, Tcells, Th1, Treg, cytotoxic cells, Thelper, Tem, Tgd) while AD subtype association greater for others (TFH, Th2, CD8, Th17, and Tcm).

Figure 5:
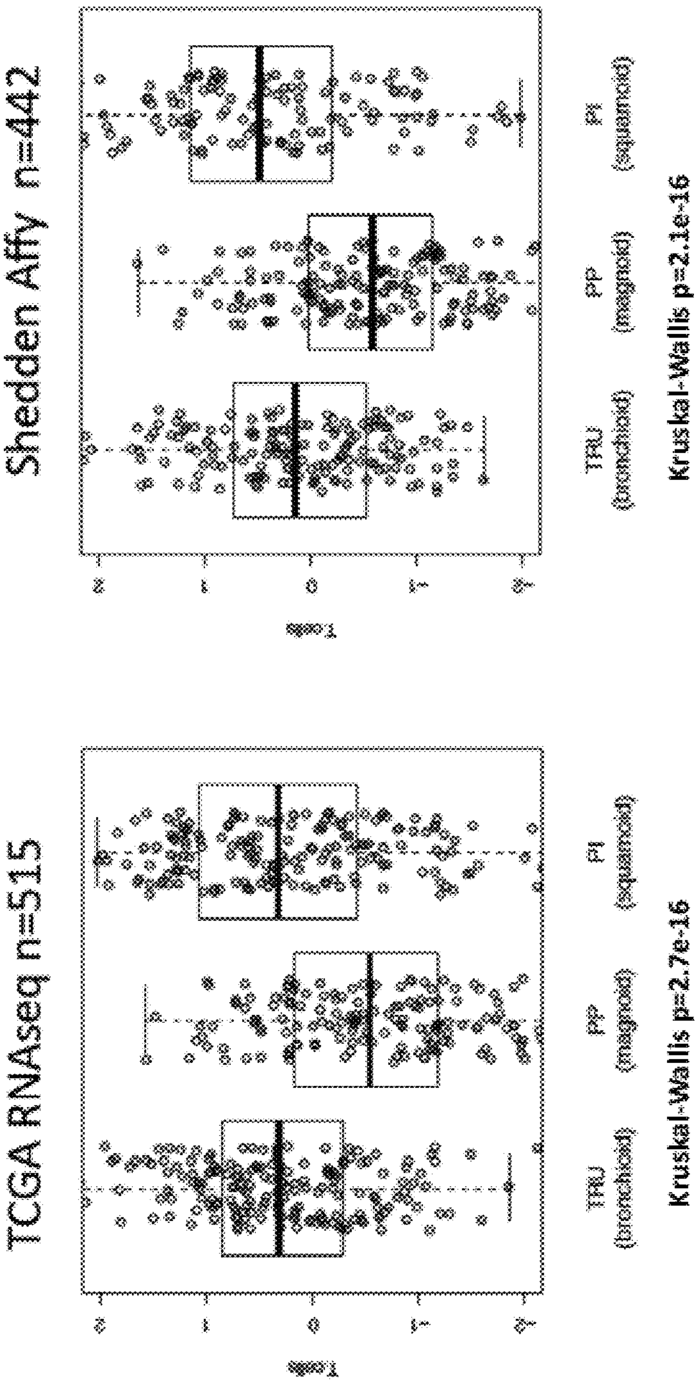
FIG. 5 illustrates reproducibility of T cell signature gene expression subtype patterns across multiple AD datasets as described in Example 1. TRU=Terminal Respiratory Unit, PP=Proximal Proliferative, PI=Proximal Inflammatory. RNAseq (Illumina, San Diego, CA) and microarrays from both Affymetrix (Santa Clara, CA) and Agilent (Santa Clara, CA).
Figure 5:
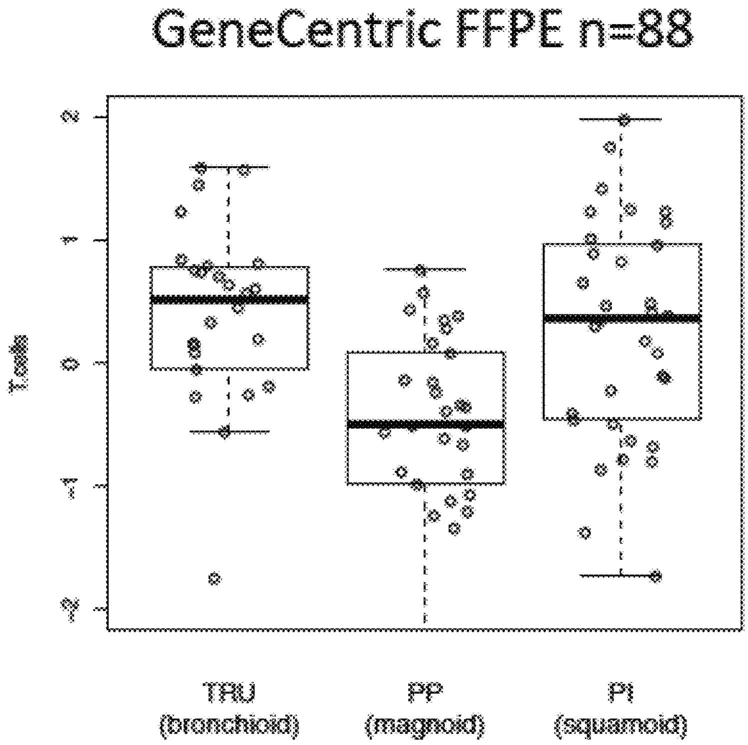

Immune cell signatures were primarily evaluated in the TCGA datasets, however AD subtype immune differences, as measured by the immune cell signatures, were found to be very reproducible across multiple datasets (see FIG. 5). T cell immune cell signature expression subtype differences in AD subtypes were remarkably reproducible across a variety of gene expression datasets derived from both frozen and FFPE samples and involving a variety of gene expression platforms including RNAseq (Illumina, San Diego, CA) and microarrays from both Affymetrix (Santa Clara, CA) and Agilent (Santa Clara, CA). Overall, immune cell signature gene expression patterns were consistent across multiple AD (see FIG. 5) datasets.

Figure 19:
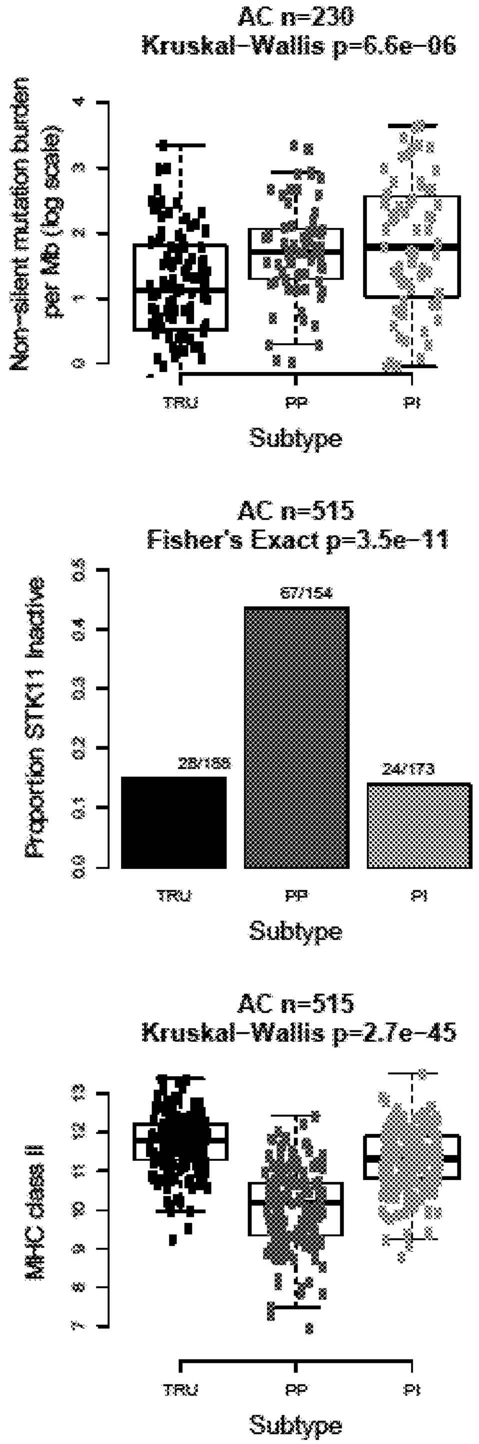
FIG. 19 illustrates Adenocarcinoma (AD) subtype non-silent mutation burden, STK11 inactivation (mutation and/or deletion) in AD, and MHC class II signature, with Kruskal-Wallis association test p-values. TRU=Terminal Respiratory Unit, PP=Proximal Proliferative, PI=Proximal Inflammatory, MHC II=Major Histocompatibility Class II gene signature.

Non-silent mutation burden in the TCGA AD data differed by subtype with PI showing the highest burden and TRU the lowest burden (FIG. 19). The PI subtype, which is enriched for TP53 mutations, was associated with elevated immune cell expression, however, TRU had the lowest mutation burden despite having relatively high immune expression. Mutation burden was not strongly correlated with Tcell immune cell expression in AD datasets (Spearman correlation=−0.07 in AD).

Several other genomic features such as loss of STK11 in AD (Cao [7], Shabath [8], Koyama [9]) have been suggested as possible contributors to reduced immune response in NSCLC. STK11 inactivation was enriched in the low immune response adenocarcinoma PP subtype. STK11 inactivation in AD were associated with lower immune cell expression, however after adjustment for subtype using linear regression, STK11 was not a significant predictor (STK11 in AD p=0.0007 to p=0.43 following adjustment for subtype).

The association of immune cell expression in AD lung cancer with MHC class II genes was investigated using a published 13 gene MHC class II signature (Forero [6]). MHC class II gene expression was strongly correlated with several immune cells in AD including T-cell expression (Spearman correlation=0.66 in AD), B-cell expression (Spearman correlation=0.5 in AD) and DC expression (Spearman correlation=0.69 in AD). MHC class 11 gene expression was significantly higher in tumor adjacent normal lung tissue as compared with tumor and was differentially expressed across tumor subtypes (FIG. 19), In a linear model of the MHC class II signature as a predictor of T-cell immune cell expression, MHC class II remained significant following adjustment for AD subtype (p<1E-50 for MHC II).

Figure 7A:
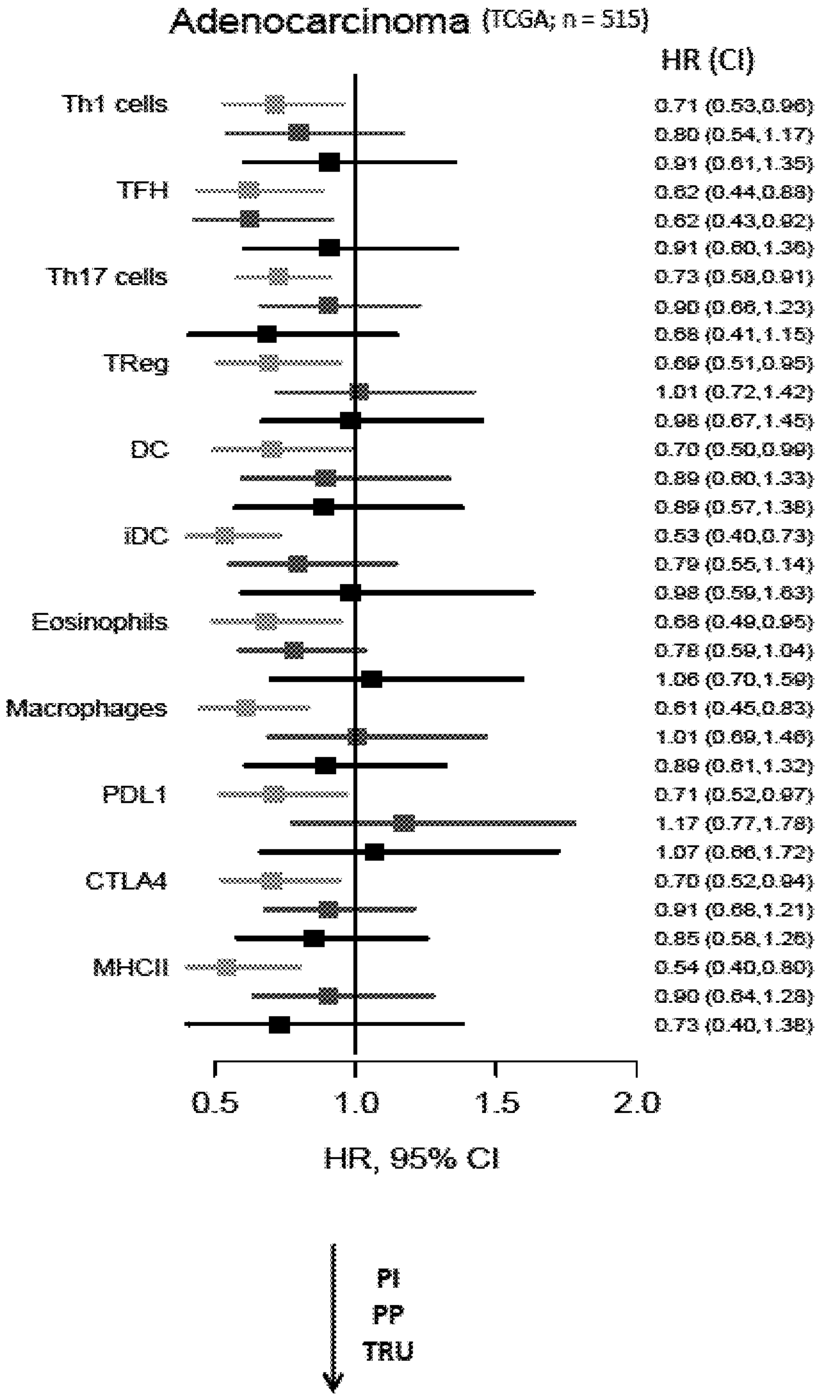
FIGS. 7A-7B illustrate signature-survival associations overall and by subtype as described in Example 1. Hazard Ratios (HR) and confidence intervals (CI) calculated from stratified cox models correspond to a unit increase in the normalized immune marker and were adjusted for pathological stage. Subtype specific HR's were adjusted for stage (overall adjusted by stage and subtype) and only immune features with significant associations (nominal $p<0.05$) for at least one subtype are shown. AD=Adenocarcinoma, TRU=Terminal Respiratory Unit, PP=Proximal Proliferative, PI=Proximal Inflammatory, MHC II=Major Histocompatibility Class II gene signature, Th1==Type 1 T helper cells, Th2=Type 2 T helper cells, TFH=T follicular helper cells, Th17=T helper 17 cells, Treg=Tregulatory cells, DC=Dendritic cells, iDC=Immature Dendritic Cells.
Figure 7B:
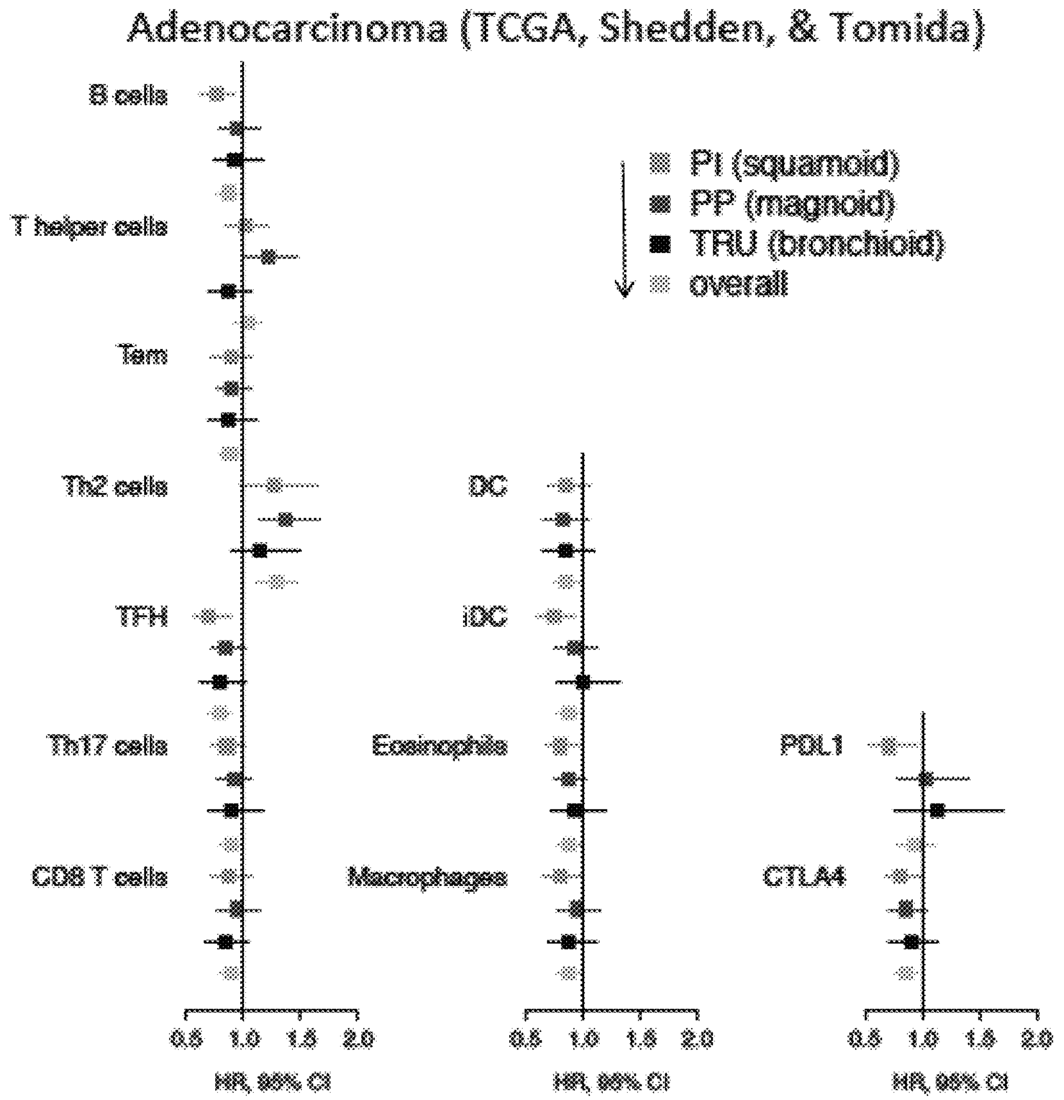

Using cox proportional hazard models, subtype specific hazard ratios (HRs) for one unit of increased expression were calculated. Subtype specific HRs were adjusted for pathologic stage and confidence intervals (CI) were calculated. Hazard ratios and confidence intervals for markers that were significant (nominal p-value<0.05) for at least one subtype are shown in FIGS. 7A-7B. The HR and CI for cell signatures or genes showing significant survival associations for one or more of the subtypes are shown in FIGS. 7A-7B. For AD subtypes, a unit increase in expression of many innate and adaptive immune cells, CD274 (PD-L1) MHC class II signature, and CTLA4 was significantly associated with improved survival in the PI subtype of AD but not in other subtypes (FIGS. 7A-7B). Overall, survival analysis of immune cell signatures suggested T Helper 17 and T Follicular Helper immune cells predicted improved survival in AD (p<0.001) (see FIG. 7A-7B).

Conclusion

Lung AD gene expression subtypes vary in their immune landscape. Intrinsic biologic subtypes of AD reveal key differences in immune cell activation, which were not always correlated with CD274 expression and demonstrated variable association with survival AD PP subtype showed minimal immune infiltration (depressed immune cell expression) suggesting reduced response to immunoRX. The AD PI subtype showed immune feature expression associated with improved survival. Further, non-silent mutation burden was not correlated with immune cell expression across subtypes; however, MHC class I gene expression was highly correlated. Increased immune and MHC II gene expression was associated with improved survival in the TRU and PI subtype of AD.

INCORPORATION BY REFERENCE

The following references are incorporated by reference in their entireties for all purposes.

1.) Wilkerson M D, et al. PLoS One 2012; 7(5): e36530. PMID 22590557

2.) TCGA Lung AdenoC. Nature 2014; 511(7511): 543-550. PMID 25079552

3.) Bindea et al., Immunity 2013; 39(4): 782-95. PMID 24138885

4.) Shedden K. et al. Nat Med 2008; 14(8): 822-827. PMID 18641660

5.) Tomida S, et al. J Clin Oncol 2009; 27(17): 2793-99. PMID 19414676

6.) Forero A, Li Y, Dongquan C, et al. Expression of the MHC class II pathway in triple negative breast cancer tumor cells is associated with a good prognosis and infiltrating lymphocytes. Cancer Immunol Res 2016; 4(5): 390-399.

7.) Cao C, Gao R, Zhang M, er al. Role of LKB1-CRTC1 on glycosylated COX-2 and response yto COX-2 inhibition in lung cancer. J Natl Cancer Inst. 2015; 107(1):1-11.

8.) Shabath M B, Welsh E A, Fultp W J, et al. Differential association of STK11 and TP53 with KRAS mutation-associated gene expression, proliferation, and immune surveillance in lung adenocarcinoma. Oncogene. 2015:1-8.

9.) Koyama S, Akbey E A, Li Y, et al. STK11/LKB1 deficiency promotes neutrophil recruitment and proinflammatory cytokine production to suppress T-cell activity in the lung tumor microenvironment. Cancer Res 2016; 76(5): 999-1008.

Example 2—Development and Validation of the Lung Adenocarcinoma Subtyping Signature Background Several genomic studies have demonstrated three distinct intrinsic lung adenocarcinoma subtypes that can vary in their genomic profiles including gene expression, mutational spectrum, and copy number alterations [1-3]. The three biologic AD subtypes TRU, PP, and PI differ not only in their genomic features, but also demonstrate potentially important differences in clinical features [1-4]. The gene expression subtypes of AD can demonstrate significant differences in tumor differentiation, likelihood of distant recurrence, stage specific survival, underlying tumor drivers and inflammatory response [1-4] and may not be readily distinguishable by standard morphology-based techniques (microscopy & immunohistochemistry). Potential response differences to chemotherapy [2], Pemetrexed [5], and/or EGFR inhibitor therapies have also been suggested [2]. Enrichment for EGFR over-expression was demonstrated in the terminal respiratory unit (TRU) subtype [2, 3]. Greater frequency of KRAS mutations, in combination with LKB1/STK11 deletions, are more likely in the proximal proliferative (PP) subtype [2, 3]. TP53 mutations and immune gene activation are hallmarks of the proximal inflammatory (PI) subtype [2-4]. Preliminary data may demonstrate potential for enhanced response to EGFR inhibitors in the TRU subtype, enhanced response to chemotherapy in the PP subtype, enhanced Pemetrexed response in the TRU subtype, and potential response to immunotherapy in the PI subtype [2-6].

The emerging data suggests that AD classification by gene expression subtype may provide valuable information complementing drug target mutation testing and informing lung cancer patient management.

Objective

Lung Adenocarcinoma (AD) subtyping has been primarily restricted to a research protocol involving the extraction of RNA from Fresh Frozen lung tumors, followed by application of a nearest centroid predictor using quantitative gene expression of over 500 genes. Despite evidence of prognostic and predictive benefits from adenocarcinoma subtyping, the need for Fresh Frozen tissue, the requirement for gene expression of >500 genes in combination with complex bioinformatic analyses, has hindered the application of AD subtyping in drug development and/or the clinic. The goal of this study was to develop a robust and efficient gene signature (with fewer genes needed) for differentiating the three subtypes of adenocarcinoma (Terminal Respiratory Unit (TRU); formerly referred to as Bronchioid, Proximal Proliferative (PP); formerly referred to as Magnoid, and Proximal Inflammatory (PI); formerly referred to as Squamoid). The new efficient gene signature may serve to reliably subtype AD from fresh frozen or FFPE tumor samples, making it amenable for diagnostic applications and/or drug development using any of the available quantitative RNA platforms (qRT-PCR, RNAseq, Affymetrix or Agilent Arrays). Development of the 48 gene signature for differentiating the subtypes of adenocarcinoma was performed as described in the methods herein.

Methods

Using the 515 lung adenocarcinoma The Cancer Genome Atlas (TCGA) RNAseq dataset for training and the 506-gene classifier to define gold standard subtype, a 48-gene signature was developed that maintains low misclassification rates when applied to several independent test sets. Starting with the standard 506 classifier genes, the Classifying arrays to Nearest Centroid (CLaNC) [7] algorithm was used with modification to select an equal number of negatively and positively correlated genes for each subtype. The optimal number of genes (16 per subtype) to include in the signature was chosen based on 5-fold cross validation curves was performed using the TCGA lung adenocarcinoma dataset (see FIG. 8). Selection of prototype samples for training of the predictor is shown in FIG. 9, whereby to get the final list of 48 genes, the CLaNC was applied to the entire TCGA data set minus 20% of samples with the lowest gold standard subtype prediction strength, removing an equal number from each subtype (FIG. 9). The 48-gene signature was then tested in several Fresh Frozen publicly available array and RNAseq datasets [2, 8, 9] and results were compared with the gold standard subtype calls as defined by the previously published 506-gene signature [2]. Final validation of the 48-gene signature (Table 1) was then performed in a newly collected RNAseq dataset of archived FFPE adenocarcinoma samples to assure comparable performance in FFPE samples.

In order to validate the consistent performance of the selected 48 gene signature, the newly collected FFPE samples were lung adenocarcinoma (AD) residual archived samples (primarily surgical samples) that had been collected under an IRB approved protocol at the University of North Carolina in Chapel Hill, NC. The samples were reviewed by a pathologist for tumor cells and three 10 μm tissue sections were macrodissected prior to extraction to enrich for tumor cells. RNA was quantitated and 100 ng was input per sample. Sequencing libraries were constructed using Illumina RNA-Access kits that enrich for the transcriptome. Sequencing libraries were under quality control by using a BA analyzer and quantified using qPCR. Sequence data was generated on an Illumina HiSeq platform (50 bp PE, 20-30 million reads) and was under quality control by using fastQC. Sequence results were aligned against hg19 reference sequence using STAR aligner and the transcriptome was built using Cufflinks [10]. Cuffcompare was used to annotate the transcriptome and counts of various expressed genes were calculated. RSEM expression count estimates were upper quartile normalized and log 2 transformed following the approach used in the Cancer Genome Atlas lung adenocarcinoma analysis [3, 11].

Results

Figure 10:
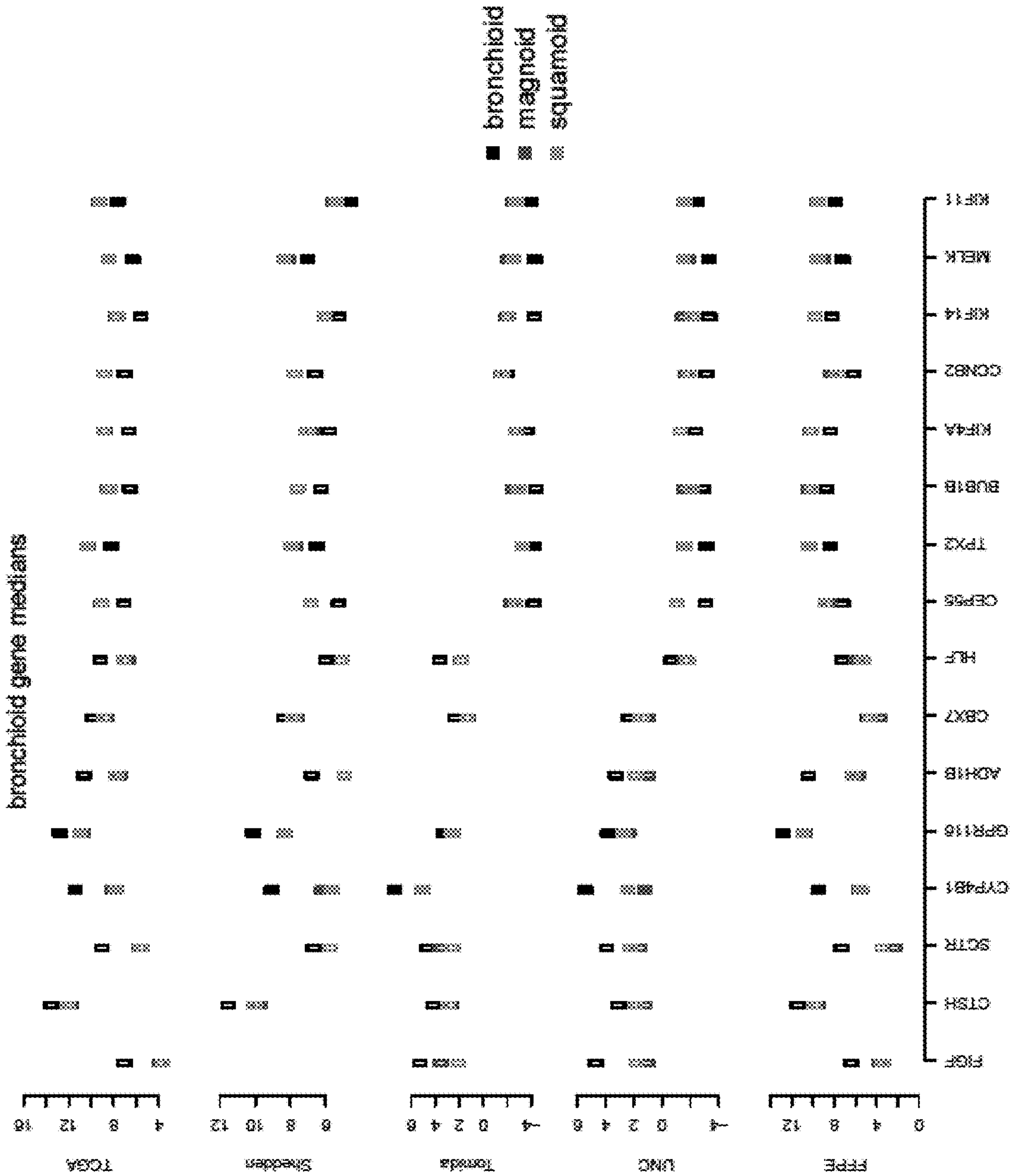
FIG. 10 illustrates the median gene expression of a subset of 16 genes from the 48 gene classifier selected for differentiating bronchioid samples (Terminal Respiratory Unit).
Figure 11:
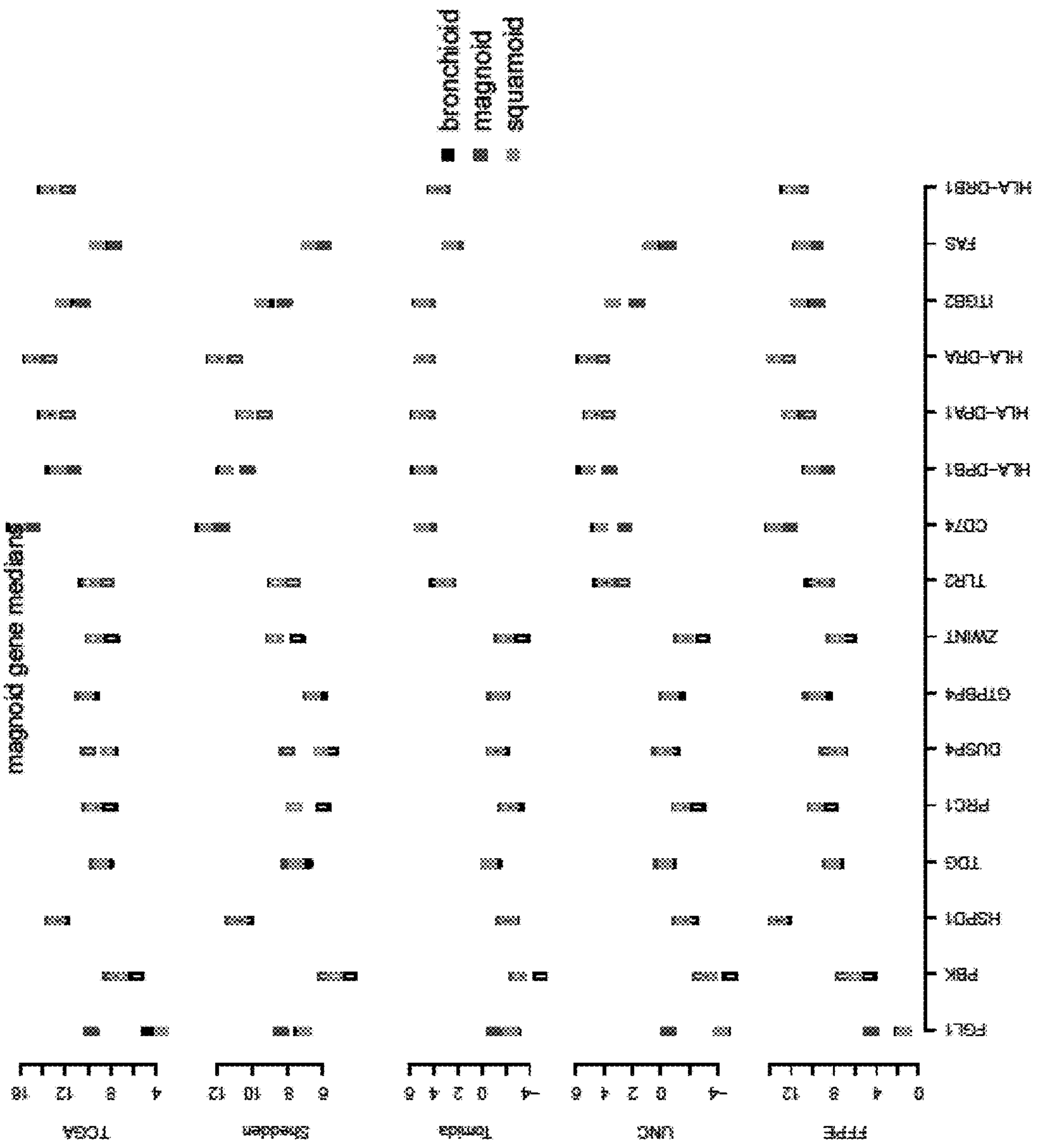
FIG. 11 illustrates the median gene expression of a subset of 16 genes from the 48 gene classifier selected for differentiating magnoid samples (Proximal Proliferative).
Figure 12:
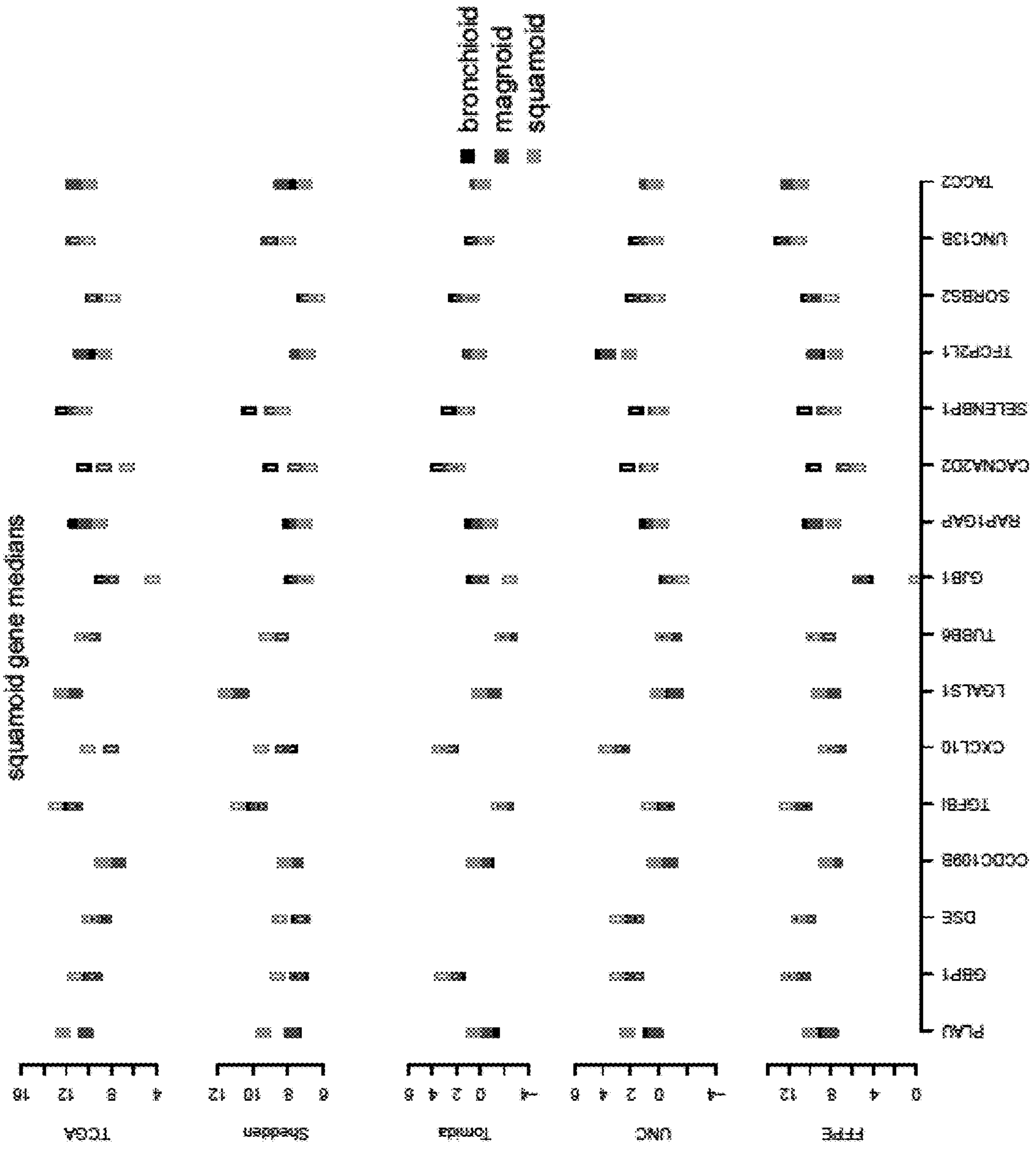
FIG. 12 illustrates the median gene expression of a subset of 16 genes from the 48 gene classifier selected for differentiating squamoid samples (Proximal Inflammatory).

The 48 gene signature gene list developed in this study is shown in Table 2, while the T statistics for the 48 gene signature gene list for each AD subtype can be found in Table 1. The median gene expression of the 16 genes selected for each AD subtype (bronchioid, magnoid, squamoid) is shown in FIGS. 10, 11, and 12, respectively. Agreement of subtype calls using the 48 gene signature with the published 506 gene signature subtype call in several different test datasets is shown in FIG. 13. The newly developed 48 gene signature demonstrated agreement of 0.84 in the newly collected FFPE dataset and a range of 0.79-0.92 in the other 3 Fresh Frozen test datasets. Below is a summary of the test datasets, the types of the RNA platforms, and the numbers of the adenocarcinoma samples used.

| Reference | RNA Platform | Adenocarcinoma Samples |
|---|---|---|
| TCGA Adenocarcinoma | RNAseq | 515 |
| Shedden et al. | Affymetrix Arrays | 442 |
| Tomida et al. | Agilent Arrays | 117 |
| Newly collected UNC FFPE samples | RNAseq | 88 |

Conclusion

Development and validation of an efficient 48 gene signature for AD subtyping was described. The resulting 48 gene signature maintains low misclassification rates when applied to several independent test sets. Thus, the new signature reliably subtypes AD from fresh frozen or FFPE tumor samples and can perform reliably using gene expression data generated from a variety of platforms including RNAseq and Arrays.

INCORPORATION BY REFERENCE

The following references are incorporated by reference in their entireties for all purposes.

1.) Hayes D N, Monti S, Parmigiani G, et al. Gene expression profiling reveals reproducible human lung adenocarcinoma subtypes in multiple independent patient cohorts. J Clin Oncol 2006. 24(31): 5079-5090.

2.) Wilkerson M, Yin X, Walter V, et al. Differential pathogenesis of lung adenocarcinoma subtypes involving sequence mutations, copy number, chromosomal instability, and methylation. PLoS ONE. 2012; 7(5) e36530. Doi:10.1371/journal.pone.0036530.

3.) Cancer Genome Atlas Research Network. Comprehensive molecular profiling of lung adenocarcinoma. Nature 511.7511 (2014): 543-550.

4.) Ringner M, Jonsson G, Staaf J. Prognostic and Chemotherapy Predictive Value of Gene-Expression Phenotypes in Primary Lung Adenocarcinoma. Clin Cancer Research 2016; 22(1): 218-29.

5.) Fennell D A, Myrand S P, Nguyen T S, Ferry D, Kerr K M, et al. Association between Gene Expression Profile and Clinical Outcome of Pemetrexed-Based Treatment in Patients with Advanced Non-Small Cell Lung Cancer: Exploratory Results from a Phase II study. PLOS one 2014; September 14 9(9): e107455.

6.) Skoulidis F, Byers L A, Diao L, Papadimitrakopoulou V A, Tong P, et al. Co-occurring genomic alterations define major subsets of KRAS-mutant lung adenocarcinoma with distinct biology, immune profiles, and therapeutic vulnerabilities. Cancer Discov 2015 Aug. 5(8): 860-77.

7.) Dabney A R. ClaNC: Point-and-click software for classifying microarrays to nearest centroids. Bioinformatics. 2006; 22: 122-123. doi:10.1093/bioinformatics/bti756

8.) Shedden K, Taylor J M G, Enkemann S A, et al. Gene expression-based survival prediction in lung adenocarcinoma: a multi-site, blinded validation study: director's challenge consortium for the molecular classification of lung adenocarcinoma. Nat Med 2008. 14(8): 822-827. doi: 10.1038/nm.1790.

9.) Tomida S, Takeuchi T, Shimada Y, Arima C, Maatsuo K, et al. Relapse-Related Molecular Signature Identifies Patients With Dismal Prognosis. J Clin Oncol 2009; 27(17): 2793-99.

10.) Trapnell C, Williams B A, Pertea Q Mortazavi A, Kwan Q van Baren M J, et al. Transcript assembly and quantification by RNA-Seq reveals unannotated transcripts and isoform switching during cell differentiation. Nature biotechnology 2010; 28(5):511-5.

11.) Li B, and Dewey C N. RSEM: accurate transcript quantification from RNA-Seq data with or without a reference genome. BMC Bioinformatics 2011, 12:323 doi:10.1186/1471-2105-12-323

Example 3—Immune Cell Activation Differences Among Lung Adenocarcinoma Intrinsic Subtypes as Determined Using Lung Adenocarcinoma Subtyping 48 Gene Signature from Example 2

Methods

Using previously published Bindea et al. (3) immune cell gene signatures (24 in total) and the Lung AD subtyping gene signature described in Example 2 for subtyping AD, several publically available lung AD datasets (1-2, 4-5; see FIG. 2), were examined for immune cell features in relation to AD subtypes as determined using the lung AD) gene signature described in Example 2. Gene expression signatures of both Innate Immune Cells (IIC) and Adaptive Immune Cells (AIC), a 13 gene IFN signature (IFN), as well as single gene immune biomarkers (CTLA4, PDCD1, and CD274 (PD-L1), PDCDLG2 (PD-L2)) were examined in the 3 AD subtypes (TRU, PP, and PI). Immune cell signature associations with tumor subtype and with CD274 expression were evaluated using linear regression. Hierarchical clustering of immune signatures and pairwise signature correlations were also analyzed. Survival signature associations of Stages I-II samples were evaluated with stratified cox proportional hazard models allowing for different baseline hazards in each dataset.

Results

Figure 14:
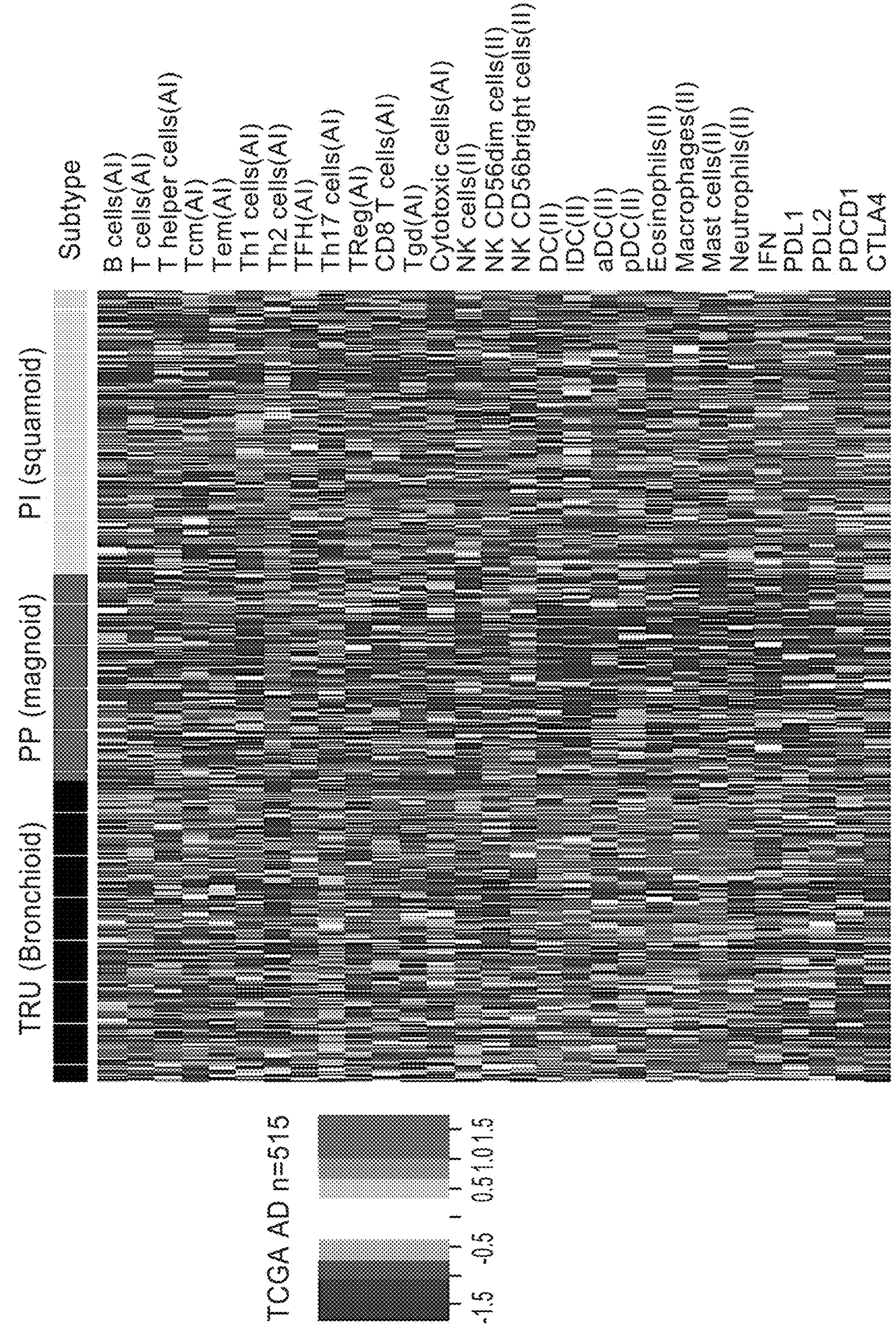
FIG. 14 illustrates a heatmap of immune cell signatures (i.e., Bindea et al reference from Example 3) and other immune markers in the Cancer Genome Atlas (TCGA) Lung AD datasets.
Figure 15:
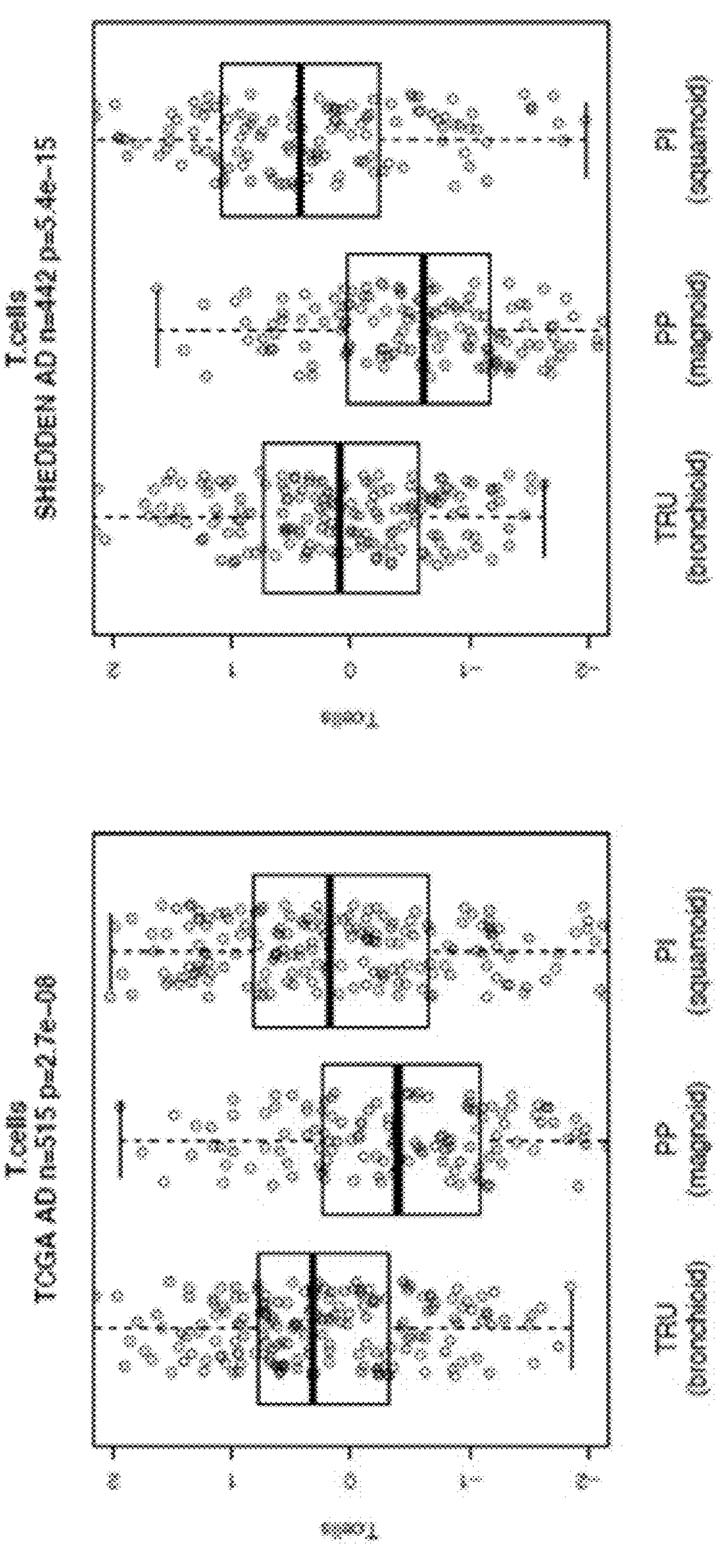
FIG. 15 illustrates reproducibility of T cell signature gene expression subtype patterns across multiple AD datasets as described in Example 3.
Figure 15:
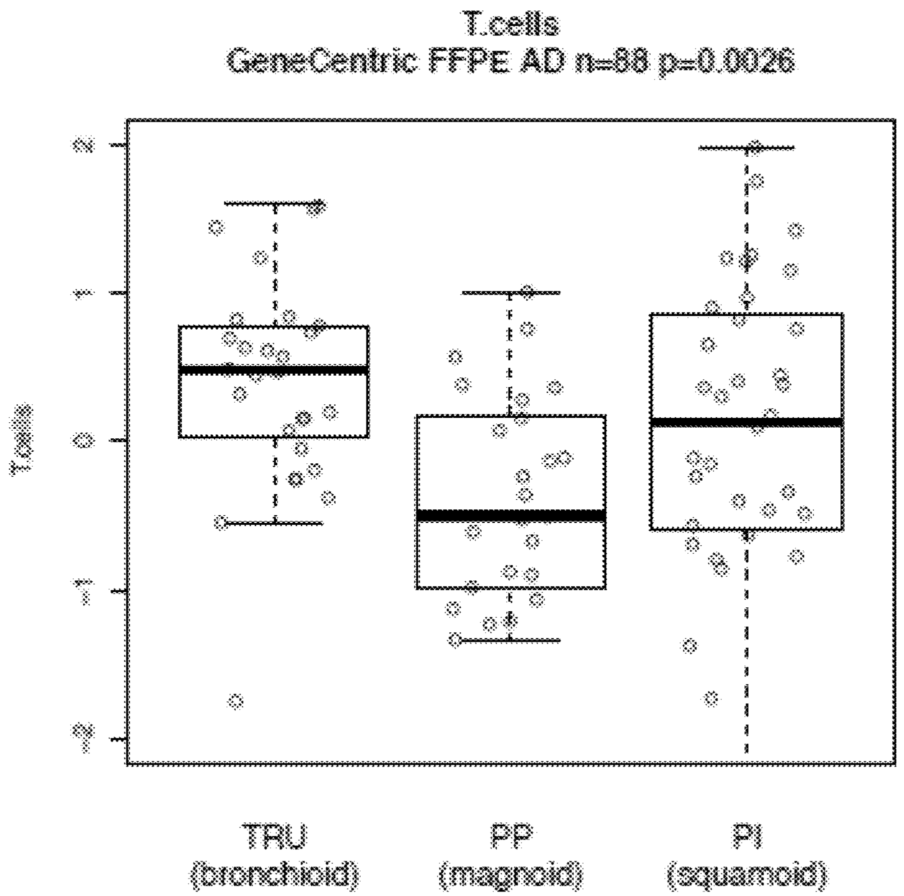
Figure 16:
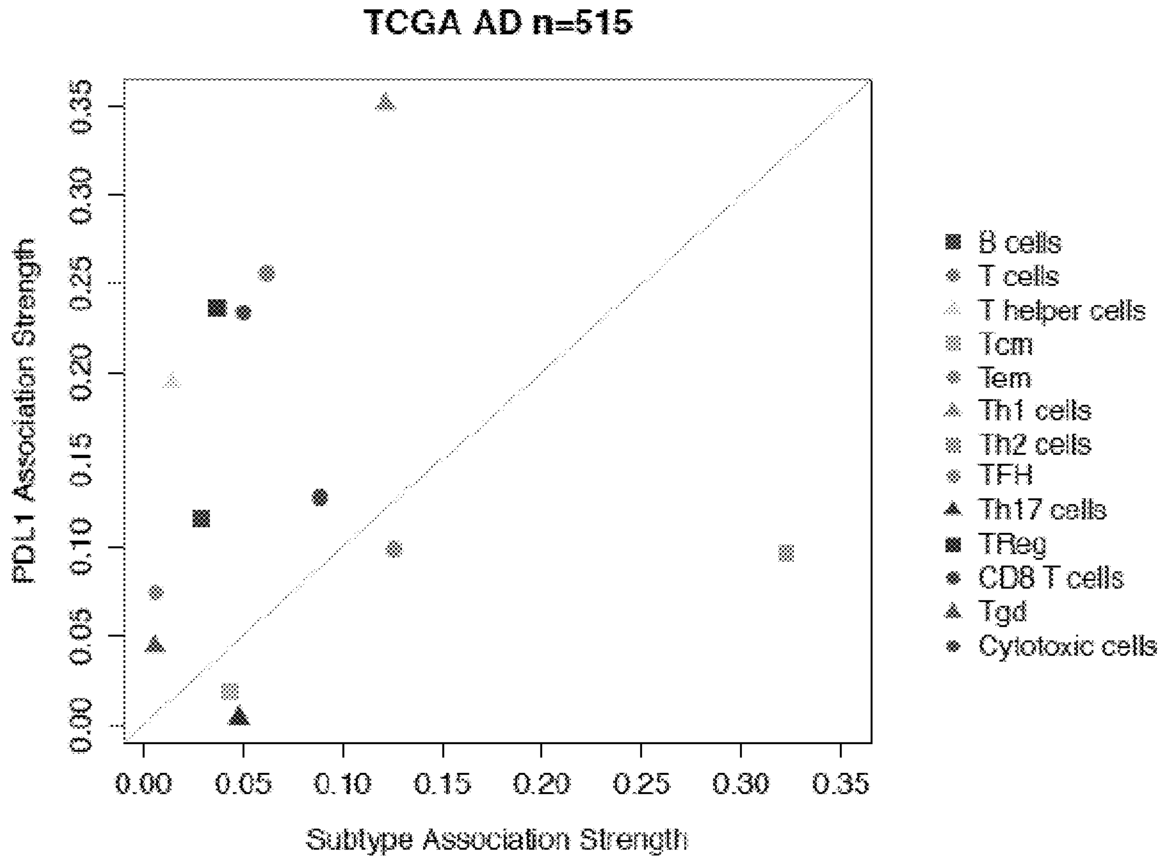
FIG. 16 illustrates an association (adjusted R-squared) between CD274 (PD-L1) expression and adaptive immune cell (AIC) signatures versus subtype and AIC signatures as described in Example 3. Tcm==central memory T cells, Tem:=Effector Memory T cells, Th1=Type 1 T helper cells, Th2=Type 2 T helper cells, TFH=T follicular helper cells, Th17=T helper 17 cells, Treg=Tregulatory cells, Tgd=Gamma. Delta Tcells.

Using the TCGA AD dataset and the 48 gene AD subtyping signature of Example 2, heatmap analysis and unsupervised hierarchical clustering of immune cell gene signatures provided separation of intrinsic subtypes of AD in a similar fashion as to what was observed in Example 1 (see FIG. 3 and FIG. 14). Further, immune cell signature gene expression patterns were consistent across multiple AD (see FIG. 15) datasets similar to that observed in Example 1 (see FIG. 5). Strength of association of CD274 (PD-L1) expression with adaptive immune cell signatures, as compared to AD subtype was conducted. As shown in FIG. 16 (like in FIG. 6 of Example 1), for AD subtypes, association strengths (adjusted R squared) were mixed showing CD274 association greater for some cells (Bcells, Tcells, Th1, Treg, cytotoxic cells, Thelper, Tem, Tgd), while AD subtype association greater for others (TFH, Th2, CD8, Th17, and Tcm). As in Example 1, immune activation was most prominent in the PI subtype of AD, while the PP subtype of AD demonstrated lower immune activation, and AD subtype and CD274 expression were similarly predictive of AIC expression (see FIG. 6 and FIG. 16).

Figure 17:
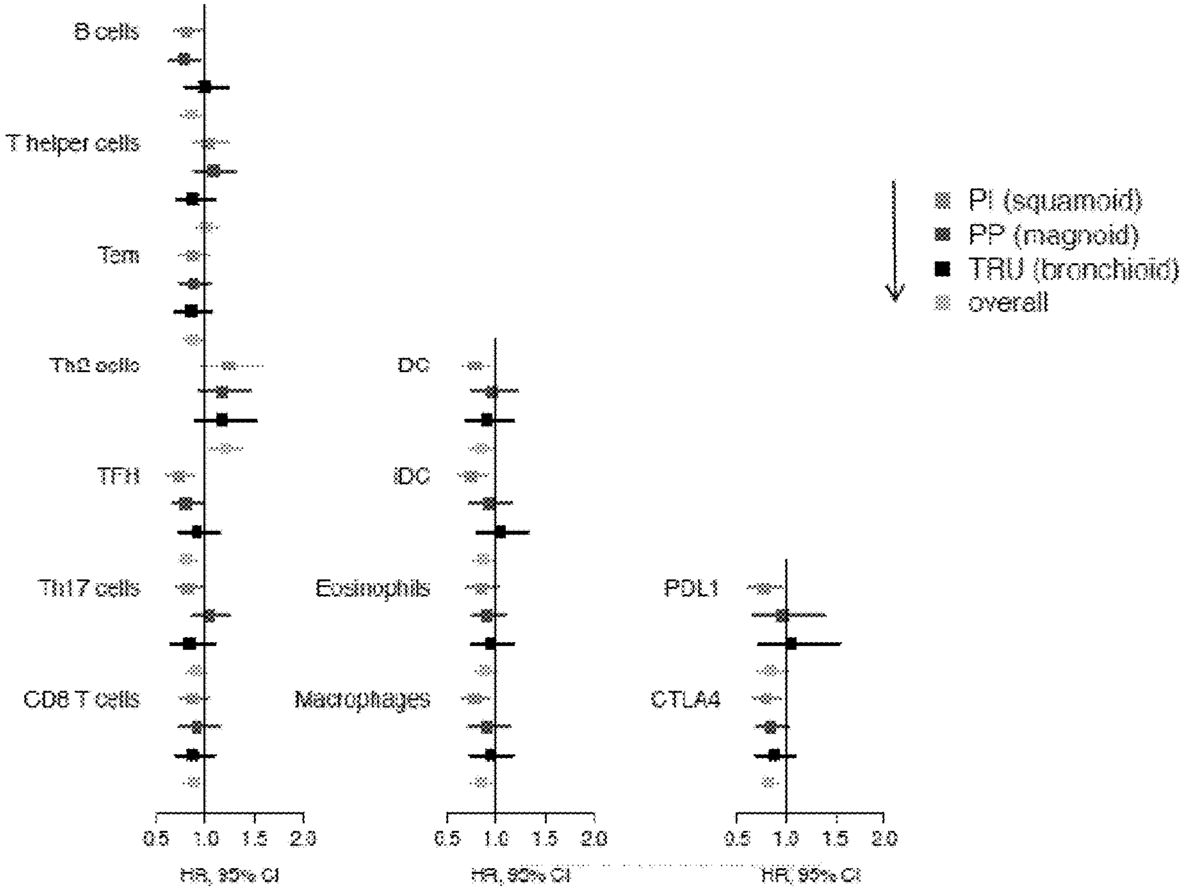
FIG. 17 illustrates for AD signature-survival associations overall and by subtype as described in Example 3. Hazard Ratios (HR) and confidence intervals calculated from stratified cox models. Subtype specific HR's were adjusted for stage (overall adjusted by stage and subtype) and only immune features with significant associations ($p<0.05$) are shown.

Using cox proportional hazard models, subtype specific hazard ratios for one unit of increased expression were calculated. Subtype specific HR's were adjusted for pathologic stage and confidence intervals were calculated. The HR and CI for cell signatures or genes showing significant survival associations for one or more of the subtypes are shown in FIG. 17. For AD subtypes, like in Example 1, a unit increase in expression of many innate and adaptive immune cells, CD274 (PD-L1) and CTLA4 was significantly associated with improved survival in the PI subtype of AD but not in other subtypes (see FIGS. 7A-7B and 17). Overall, like in Example 1, survival analysis of immune cell signatures suggested T Helper 17 and T Follicular Helper immune cells predicted improved survival in AD ($p<0.001$) (see FIGS. 7A-7B and 17).

Conclusion

The 48 gene signature for AD subtyping described in Example 2 shows similar results to the AD subtyping gene signature(s) used in Example 1 in terms of showing how Lung AD subtypes vary in their immune landscape. In agreement with the AD subtyping gene signatures of Example 1, the AD subtyping gene signature used in this example shows that Lung AD gene expression subtypes vary in their immune landscape. Intrinsic biologic subtypes of AD revealed key differences in immune cell activation, which were not always correlated with CD274 expression and demonstrated variable association with survival. AD PP subtype showed minimal immune infiltration suggesting reduced response to immunoRX, AD PI subtype showed immune feature expression associated with improved survival.

INCORPORATION BY REFERENCE

The following references are incorporated by reference in their entireties for all purposes.

1.) Wilkerson M D, et al. PLoS One 2012; 7(5): e36530. PMID 22590557

2.) TCGA Lung AdenoC. Nature 2014; 511(7511): 543-550. PMID 25079552

3.) Bindea et al., Immunity 2013; 39(4): 782-95. PMID 24138885

4.) Shedden K. et al. Nat Med 2008; 14(8): 822-827. PMID 18641660

5.) Tomida S, et al. J Clin Oncol 2009; 27(17): 2793-99. PMID 19414676

6.) Lee E S, et al. Cancer Res 2008; 14(22): 7397-7404. PMID 19010856

7.) Raponi M, et al. Cancer Res 2006; 66(7): 466-72. PMID 16885343

Example 4—Expression Subtypes of Lung Adenocarcinoma Reveal a Varied Immune Landscape and Unique Somatic Genetic Features Suggesting Differential Response to Multiple Drug Targets Introduction: Gene expression based subtyping in Lung Adenocarcinoma (AD) classifies AD tumors into distinct subtypes with variable outcomes and potential response to therapy. Gene expression based subtyping has consistently identified 3 distinct biologic types in Lung AD, Terminal Respiratory Unit (TRU), formerly Bronchioid, Proximal Proliferative (PP), formerly Magnoid, and Proximal Inflammatory (PI), formerly Squamoid (1,2) (see FIG. 1). AD subtypes demonstrate key differences in genomic alterations, tumor drivers, prognosis, and likely response to various therapies (1-2).

Methods: As a follow up to the experiments conducted in Example 1, differential drug target gene expression was evaluated in the lung AD subtypes from Example 1 that were determined using the TCGA lung cancer gene expression dataset (AD n=515)[2] shown in FIG. 2. Previously published AD subtypes (TRU, PP and PI) were defined in Example 1 using gene expression patterns. In this example, the variable expression of genes from a clinical oncology solid tumor mutation panel (322 genes, see Table 8),[3] was examined in relation to AD subtypes from Example 1 as a supplement to the examination of the immune cell gene signatures (Bindea et al. 24 immune cell types),[4] expression of single immune gene biomarkers (CTLA4, PDCD1 (PD-1), and CD274 (PD-L1)), proliferation (11 gene signature; see Table 9),[5] and non-silent mutation burden done in Example 1. Differential gene expression was assessed using the Kruskal-Wallis (KW) test with Bonferroni correction, while linear regression and Spearman correlations were used to evaluate association of non-silent mutation burden, tumor subtype, and CD274 (PD-L1) expression with immune cell expression.

Figure 20:
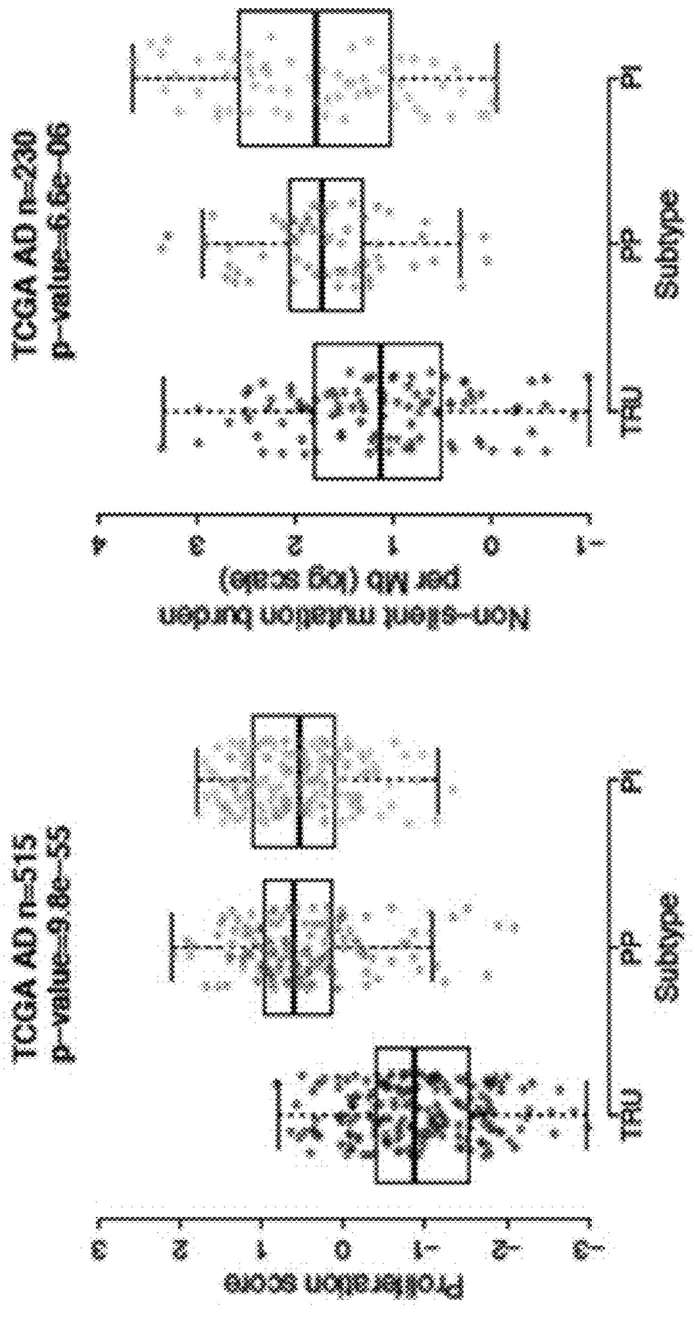
FIG. 20 illustrates significant Adenocarcinoma (AD) subtype differences in proliferation, non-silent mutation burden, and key drug targets: CD274 (PD-L1), PDCD1 (PD-1), and CTLA4. AD was determined as described in Example 4.
Figure 20:
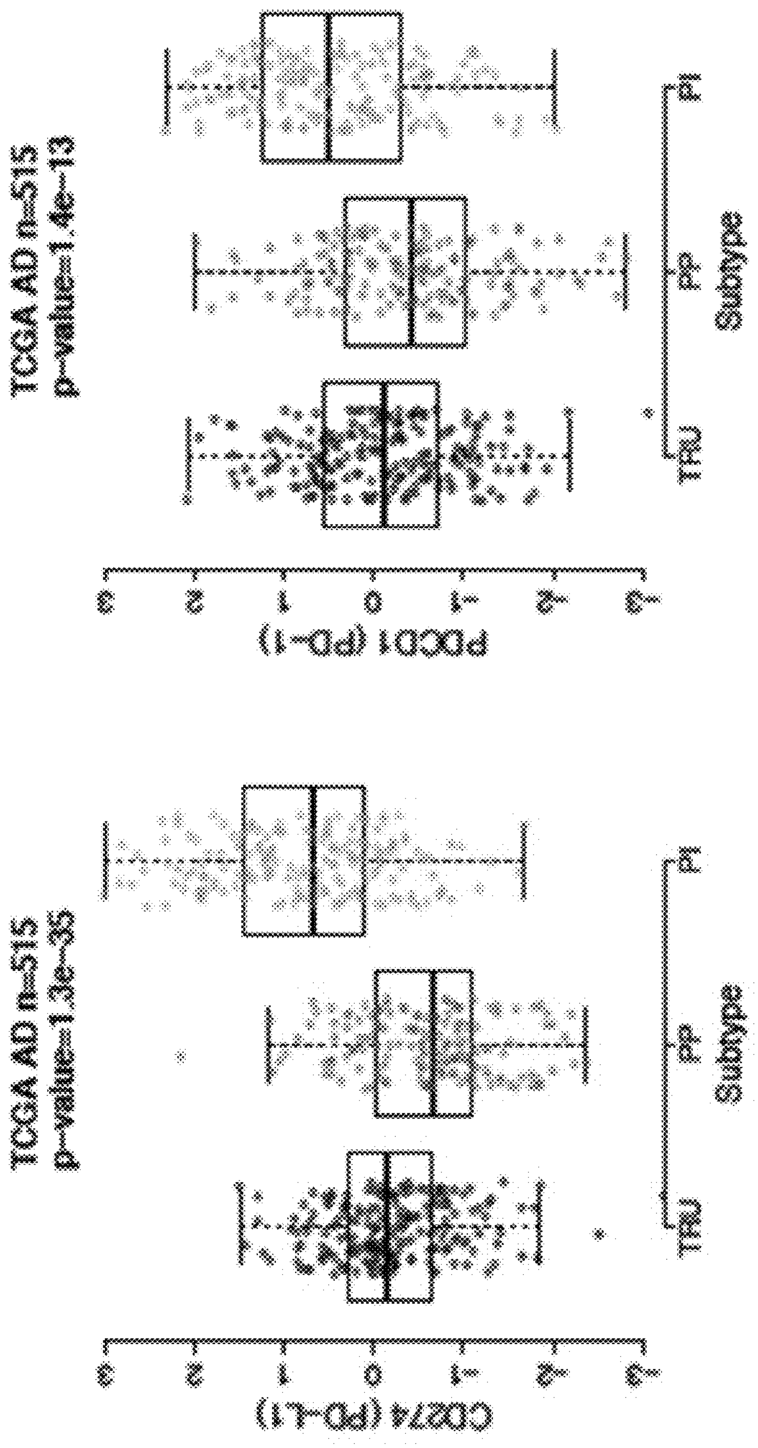
Figure 20:
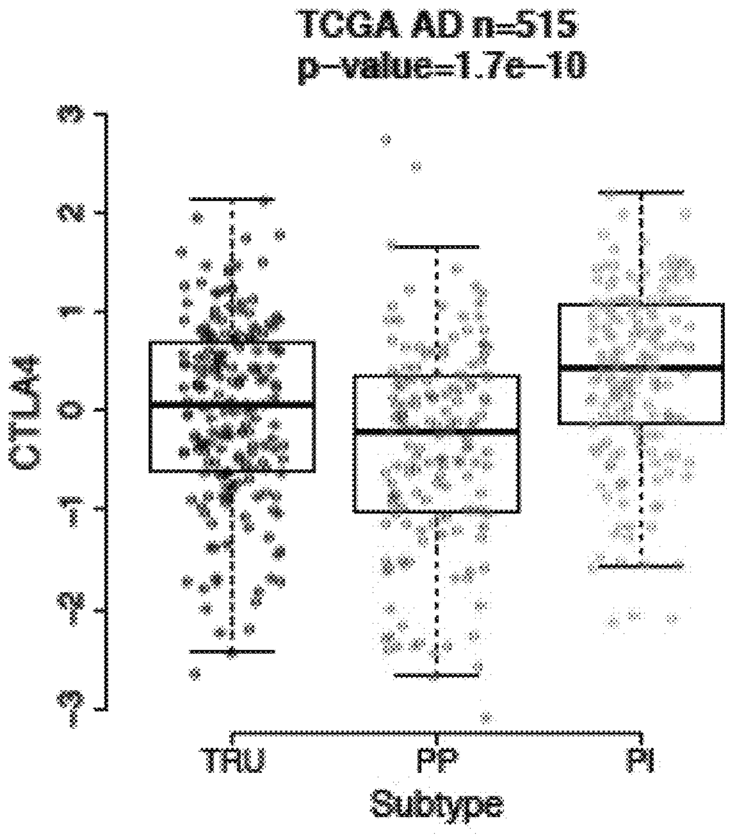
Figure 21:
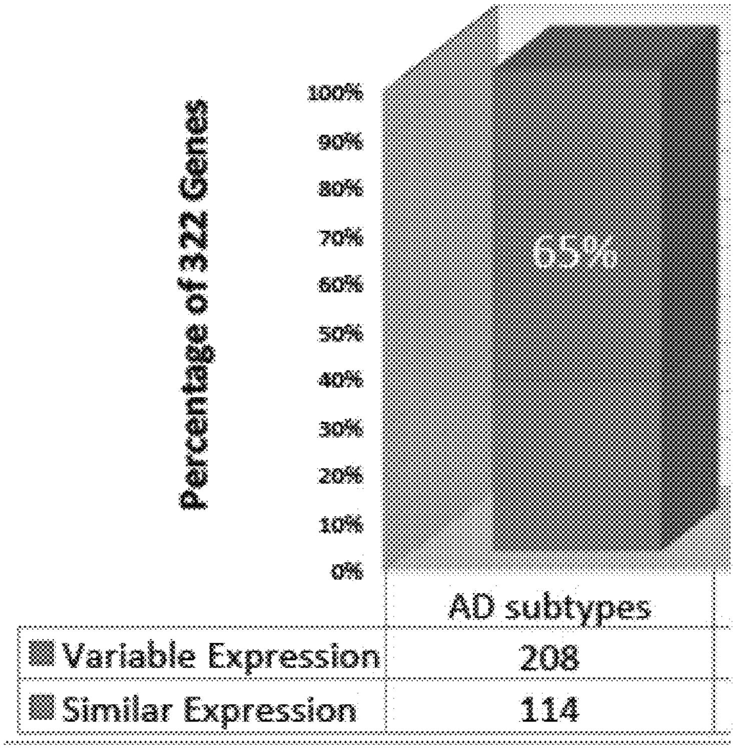
FIG. 21 illustrates significant drug target gene expression differences of AD subtypes for the majority of genes in a clinical solid tumor mutation panel (322 genes disclosed in Table 8). In AD subtypes, 65% of panel genes showed significantly variable expression (KW Bonferroni threshold $p<0.000155$). AD subtyping was determined as described in Example 4.

Results: As shown in FIG. 21, variable expression of 208/322 tumor panel genes (65%) in AD subtypes were observed (KW Bonferroni threshold $p<0.000155$). Most drug target genes, including but not limited to AURKA, CHEK1, ROS1, CD274 (PD-L1), CSF1R and ERBB4 in AD exhibited strong differential expression across the subtypes ($p<1E-28$). Further, the top 25 genes from the 322 genes of the clinical oncology solid tumor mutation panel showing differential gene expression across the AD subtypes can be seen in Table 10. Immune cell expression was also highly variable across subtypes (see FIG. 3). The PI subtype of AD demonstrated the greatest immune cell expression while the PP subtype of AD demonstrated low expression of immune cells (see FIG. 3). Non-silent mutation burden was not strongly correlated with immune cell expression (Spearman correlation=−0.07 in AD) however, the PI subtype of AD, which is enriched for TP53 mutations, was associated with elevated immune cell expression and a high mutation burden (see FIG. 20). Overall, as shown in FIG. 20, there were significant AD subtype differences in proliferation, non-silent mutation burden, and key drug targets CD274 (PD-L1), PDCD1 (PD-1), and CTLA4.

Conclusion: Molecular subtypes of lung AD vary in expression of the majority of key drug target genes included in a clinical solid tumor sequencing panel. Molecular subtypes of lung AD revealed differential expression of host immune response and immune targets. Evaluation of subtypes as potential biomarkers for drug sensitivity should be investigated alone, and in combination with immune cell features and key mutation targets.

INCORPORATION BY REFERENCE

The following references are incorporated by reference in their entireties for all purposes.

1.) Wilkerson M D, et al. PLoS One 2012; 7(5): e36530. PMID 22590557
2.) TCGA Lung AdenoC. Nature 2014; 511(7511): 543-550. PMID 25079552
3.) Foundation Medicine Solid Tumor Mutation Panel accessed October 2014.
4.) Bindea et al., Immunity 2013; 39(4): 782-95. PMID 24138885
5.) Neilson T O, et al. Clin Cancer Res 2010; 16(21): 522-5232. PMID 20837693.

Example 5: Expression Subtypes of Lung Adenocarcinoma Reveal a Varied Immune Landscape and Unique Somatic Genetic Features Suggesting Differential Response to Multiple Drug Targets Introduction: Just like in Example 4, the purpose of this Example was to assess the differential expression of clinically important genes across previously defined gene expression subtypes of Adenocarcinoma (AD). In contrast to Example 4 where the AD and gene expression based subtyping was performed using the TCGA lung cancer gene expression dataset (AD n=515)[2] as described in Example 1, gene expression based AD subtyping in this Example was performed using the 48 gene sets described in Example 2. Further, the clinically important genes were 322 genes (see Table 8) that constituted a clinical solid tumor mutation sequencing panel used in the management of oncology patients to identify genomic alterations impacting therapeutic management and/or to determine eligibility for targeted drug clinical trials. Just like in Example 4, differences in tumor proliferation were also assessed across the AD subtypes using an 11 gene proliferation signature (see Table 9).

Methods: Using the TCGA lung cancer gene expression dataset (Adenocarcinoma (AD) n=515),[1] differential drug target gene expression was evaluated in lung AD subtypes. Subtype was defined in AD using the Clanc48 AD subtyper (see Example 2 and described herein) as previously described (nearest centroid prediction).[2] AD subtypes Terminal Respiratory Unit (TRU), Proximal Proliferative (PP), and Proximal Inflammatory (PI) were examined. Variable expression of genes from a clinical oncology solid tumor mutation panel (322 genes),[3] was examined in relation to AD. Differential gene expression was assessed using the Kruskal-Wallis (KW) test with Bonferroni correction. Further, a proliferation score was calculated as the average expression (log 2(RSEM+1)) of available genes in the 11-gene PAM50 proliferation signature[4]. Subtype-proliferation association was tested using the Kruskal-Wallis test.

Figure 22:
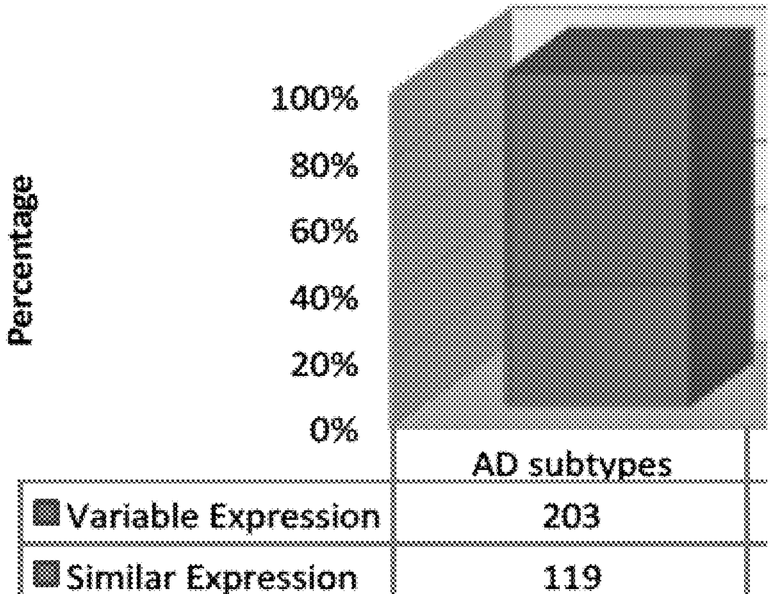
FIG. 22 illustrates significant drug target gene expression differences of AD for the majority of genes in a clinical solid tumor mutation panel (322 genes disclosed in Table 8). In AD subtypes, 63% of panel genes showed significantly variable expression (KW Bonferroni threshold $p<0.000155$). AD subtyping was determined as described in Example 5.
Figure 23:
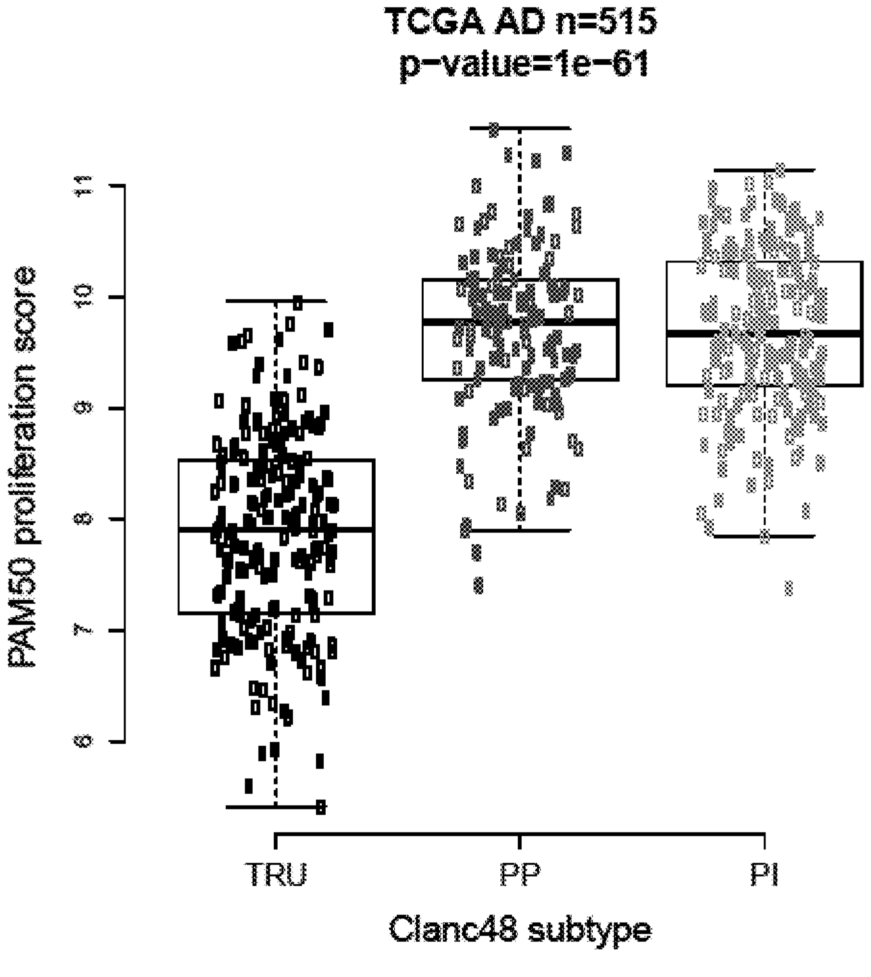
FIG. 23 illustrates significant Adenocarcinoma (AD) subtype differences in proliferation. AD subtyping was determined as described in Example 5.

Results: Similar to FIG. 21, FIG. 22 showed variable expression of 203/322 tumor panel genes (63%) across the AD subtypes observed (KW Bonferroni threshold $p<0.000155$). Further, just like in FIG. 20 in Example 4, there were significant AD subtype differences in proliferation (see. FIG. 23). Moreover, the top 25 genes from the 322 genes of the clinical oncology solid tumor mutation panel showing differential gene expression across the AD subtypes seen in Table 11 are very similar to those found in Table 10.

Conclusion: Just like in Example 4, molecular subtypes of lung AD vary in expression of the majority of key drug target genes included in a clinical solid tumor sequencing panel. Molecular subtypes of lung AD revealed differential expression of host immune response and immune targets.

INCORPORATION BY REFERENCE

The following references are incorporated by reference in their entireties for all purposes.

1.) TCGA Lung AD. Nature 2014; 511(7511): 543-550. PMID 25079552

2.) Wilkerson M I D, et al. PLoS One 2012; 7(5): e36530. PMTD 22590557

3.) Foundation Medicine Solid Tumor Mutation Panel accessed Oct. 6, 2014.

4.) Neilson T O, Parker J S, Leung J S, et al. Clin Cancer Res 2010; 16(21): 5222-5232. PMID 20837693

TABLE 8

| 322 genes of a clinical solid tumor mutation sequencing panel[3] | | | | | | | | |
|---|---|---|---|---|---|---|---|---|
| ABL1 | C11orf30 (EMSY) | DDR2 | FGFR4 | IL7R | MET | PIK3CA | SDHD | TSHR |
| ABL2 | CARD11 | DICER1 | FH | INHBA | MITF | PIK3CB | SETD2 | U2AF1 |
| ACVR1B | CBFB | DNMT3A | FLCN | INPP4B | MLH1 | PIK3CG | SF3B1 | VEGFA |
| AKT1 | CBL | DOTIL | FLT1 | IRF2 | MPL | PIK3R1 | SLIT2 | VHL |
| AKT2 | CCND1 | EGFR | FLT3 | IRF4 | MRE11A | PIK3R2 | SMAD2 | WISP3 |
| AKT3 | CCND2 | EP300 | FLT4 | IRS2 | MSH2 | PLCG2 | SMAD3 | WT1 |
| ALK | CCND3 | EPHA3 | FOXL2 | JAK1 | MSH6 | PMS2 | SMAD4 | XPO1 |
| AMER1 (FAM123B) | CCNE1 | EPHA5 | FOXP1 | JAK2 | MTOR | POLD1 | SMARCA4 | ZBTB2 |
| APC | CD274 | EPHA7 | FRS2 | JAK3 | MUTYH | POLE | SMARCB1 | ZNF217 |
| AR | CD79A | EPHB1 | FUBP1 | JUN | MYC | PPP2R1A | SMO | ZNF703 |
| ARAF | CD79B | ERBB2 | GABRA6 | KAT6A (MYST3) | MYCL (MYCL1) | PRDM1 | SNCAIP | ETV4 |
| ARFRP1 | CDC73 | ERBB3 | GATA1 | KDM5A | MYCN | PREX2 | SOCS1 | ETV5 |
| ARIDIA | CDH1 | ERBB4 | GATA2 | KDM5C | MYD88 | PRKAR1A | SOX10 | ETV6 |
| ARID1B | CDK12 | ERG | GATA3 | KDM6A | NF1 | PRKCI | SOX2 | ETV1 |
| ARID2 | CDK4 | ERRFI1 | GATA4 | KDR | NF2 | PRKDC | SOX9 | NFKBIA |
| ASXL1 | CDK6 | ESR1 | GATA6 | KEAP1 | NFE2L2 | PRSS8 | SPEN | |
| ATM | CDK8 | EZH2 | GID4 (C17orf39) | KEL | NFKBIA | PTCH1 | SPOP | |
| ATR | CDKN1A | FAM46C | GLI1 | KIT | NKX2-1 | PTEN | SPTA1 | |
| ATRX | CDKN1B | FANCA | GNA11 | KLHL6 | NOTCH1 | PTPN11 | SRC | |
| AURKA | CDKN2A | FANCC | GNA13 | KMT2A (MLL) | NOTCH2 | QKI | STAG2 | |
| AURKB | CDKN2B | FANCD2 | GNAQ | KMT2C (MLL3) | NOTCH3 | RAC1 | STAT3 | |
| AXIN1 | CDKN2C | FANCE | GNAS | KMT2D (MLL2) | NPM1 | RAD50 | STAT4 | |
| AXL | CEBPA | FANCF | GPR124 | KRAS | NRAS | RAD51 | STK11 | |
| BAP1 | CHD2 | FANCG | GRIN2A | LMO1 | NSD1 | RAF1 | SUFU | |
| BARD1 | CHD4 | FANCL | GRM3 | LRP1B | NTRK1 | RANBP2 | SYK | |
| BCL2 | CHEK1 | FAS | GSK3B | LYN | NTRK2 | RARA | TAF1 | |
| BCL2L1 | CHEK2 | FAT1 | H3F3A | LZTR1 | NTRK3 | RB1 | TBX3 | |
| BCL2L2 | CIC | FBXW7 | HGF | MAGI2 | NUP93 | RBM10 | TERC | |
| BCOR | CREBBP | FGF10 | HNF1A | MAP2K1 | PAK3 | RET | TERT (promoter only) | |
| BCORL1 | CRKL | FGF14 | HRAS | MAP2K2 | PALB2 | RICTOR | TET2 | |
| BLM | CRLF2 | FGF19 | HSD3B1 | MAP2K4 | PARK2 | RNF43 | TGFBR2 | |
| BRAF | CSF1R | FGF23 | HSP90AA1 | MAP3K1 | PAX5 | ROS1 | TNFAIP3 | |
| BRCA1 | CTCF | FGF3 | IDH1 | MCL1 | PBRM1 | RPTOR | TNFRSF14 | |
| BRCA2 | CTNNA1 | FGF4 | IDH2 | MDM2 | PDCD1LG2 | RUNX1 | TOP1 | |
| BRD4 | CTNNB1 | FGF6 | IGF1R | MDM4 | PDGFRA | RUNX1T1 | TOP2A | |
| BRIP1 | CUL3 | FGFR1 | IGF2 | MED12 | PDGFRB | SDHA | TP53 | |
| BTG1 | CYLD | FGFR2 | IKBKE | MEF2B | PDK1 | SDHB | TSC1 | |
| BTK | DAXX | FGFR3 | IKZF1 | MEN1 | PIK3C2B | SDHC | TSC2 | |

TABLE 9

| 11 gene proliferation gene signature | | | |
|---|---|---|---|
| BIRC5 | CDCA1 (NUF2) | MKI67 | TYMS |
| CCNB1 | CEP55 | PTTG1 | UBE2C |
| CDC20 | KNTC2 (NDC80) | RRM2 | |

TABLE 10

Top 25 differentiated genes of the 322 tumor panel[3] for the AD expression subtypes as determined in Example 4.

| AD Genes | KW p value |
|---|---|
| AURKA | 1.40E−50 |
| AURKB | 1.06E−49 |
| TOP2A | 1.88E−46 |
| RAD51 | 2.28E−46 |
| CHEK1 | 3.40E−44 |
| BLM | 1.40E−43 |
| TMPRSS2 | 6.34E−40 |
| FAS | 9.42E−39 |
| ROS1 | 1.07E−37 |
| EZH2 | 2.18E−37 |
| BRCA1 | 1.16E−36 |
| CD274 | 1.26E−35 |
| CCNE1 | 4.95E−35 |
| BRIP1 | 2.50E−34 |
| ERBB4 | 2.16E−33 |
| CSF1R | 2.97E−33 |
| PDCD1LG2 | 9.44E−33 |
| FANCG | 1.22E−32 |
| BTK | 3.48E−32 |
| CHEK2 | 3.13E−30 |
| CEBPA | 4.87E−30 |
| AXL | 2.12E−29 |
| FANCD2 | 3.93E−29 |
| ETV1 | 1.66E−27 |
| DNMT3A | 5.53E−26 |

TABLE 11

Top 25 differentiated genes of the 322 tumor panel[3] for the AD expression subtypes as determined in Example 5.

| AD Genes | KW p value |
|---|---|
| AURKA | 9.48E−57 |
| AURKB | 1.81E−56 |
| TOP2A | 1.74E−54 |
| RAD51 | 6.87E−53 |
| CHEK1 | 6.77E−49 |
| BLM | 2.08E−48 |
| BRCA1 | 3.25E−44 |
| CCNE1 | 7.10E−42 |
| EZH2 | 2.19E−41 |
| TMPRSS2 | 4.67E−41 |
| BRIP1 | 4.52E−39 |
| FANCG | 1.34E−35 |
| CHEK2 | 1.83E−35 |
| FAS | 3.16E−34 |
| FANCD2 | 1.54E−33 |
| ROS1 | 3.42E−32 |
| CEBPA | 6.55E−31 |
| ERBB4 | 1.05E−30 |
| FANCA | 2.63E−29 |
| MSH6 | 5.67E−29 |
| BRCA2 | 4.75E−27 |
| CD274 | 4.95E−27 |
| TGFBR2 | 1.12E−26 |
| POLE | 2.82E−26 |
| ETV1 | 2.32E−25 |

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of assaying a lung sample obtained from a human patient, the method comprising measuring in a lung sample obtained from the human patient, a nucleic acid expression level of each and every biomarker in a set of biomarkers consisting of C-fos-induced growth factor (FIGF), Cathepsin H (CTSH), Secretin receptor (SCTR), Cytochrome P450 family 4 subfamily B member 1 (CYP4B1), G protein-coupled receptor 116 (GPR116), Alcohol dehydrogenase 1B (class I) (ADH1B), Chromobox 7 (CBX7), Hepatic leukemia factor (HLF), Centrosomal protein 55 (CEP55), Tpx2, Microtubule-associated (TPX2), BUB1 mitotic checkpoint serine/threonine kinase B (BUB1B), Kinesin family member 4A (KIF4A), Cyclin B2 (CCNB2), Kinesin family member 14 (KIF14), Maternal embryonic leucine zipper kinase (MELK), and Kinesin family member 11 (KIF11), wherein the method measures the nucleic acid expression level of only the biomarkers in set of biomarkers.

2. The method of claim 1, wherein the lung sample was previously diagnosed as being adenocarcinoma.

3. The method of claim 1, wherein the measuring is performed by an amplification, hybridization and/or sequencing assay, wherein the amplification, hybridization and/or sequencing assay comprises quantitative real time reverse transcriptase polymerase chain reaction (qRT-PCR), RNAseq, microassay analysis, gene chip analysis, Serial Analysis of Gene Expression (SAGE), Rapid Analysis of Gene Expression (RAGE), nuclease protection assays, or Northern blotting.

4. The method of claim 1, wherein the lung sample is a formalin-fixed, paraffin-embedded (FFPE) lung tissue sample, fresh or a frozen lung tissue sample, an exosome, wash fluids, cell pellets, or a bodily fluid obtained from the human patient.

5. The method of claim 1, further comprising measuring the nucleic acid expression level of each and every biomarker in the set of biomarkers in a normal lung sample, a reference squamoid (proximal inflammatory) sample, a reference bronchoid (terminal respiratory unit) sample or reference magnoid (proximal proliferative) sample.

* * * * *

UNITED STATES PATENT AND TRADEMARK OFFICE

CERTIFICATE OF CORRECTION

PATENT NO. : 12,139,763 B2
APPLICATION NO. : 17/156024
DATED : November 12, 2024
INVENTOR(S) : Hawazin Faruki et al.

It is certified that error appears in the above-identified patent and that said Letters Patent is hereby corrected as shown below:

In the Claims

At Column 227, Claim number 1, Line number 67, reads:
“set of biomarkers.”
Should read:
--the set of biomarkers.--

At Column 228, Claim number 3, Line number 57, reads:
“RNAseq, microassay analysis, gene chip analysis, Serial”
Should read:
--RNAseq, microarray analysis, gene chip analysis, Serial--

Signed and Sealed this
Nineteenth Day of August, 2025

Coke Morgan Stewart
*Acting Director of the United States Patent and Trademark Office*